United States Patent
Lopez Siles et al.

(10) Patent No.: US 11,299,788 B2
(45) Date of Patent: Apr. 12, 2022

(54) **METHOD FOR THE QUANTIFICATION OF *FAECALIBACTERIUM PRAUSNITZII* PHYLOGROUP I AND/OR PHYLOGROUP II MEMBERS AND THE USE THEREOF AS BIOMARKERS**

(71) Applicants: Universitat de Girona, Girona (ES); Fundado Institut D'Investigacio Biomedica de Girona Dr. Josep Trueta, Salt (ES); Goodgut S.L., Girona (ES)

(72) Inventors: Mireia Lopez Siles, San Hilari de Sacalm (ES); Librado Jesus Garcia Gil, Fontcuberta (ES); Xavier Aldeguer Mante, Girona (ES); Margarita Martinez Medina, Santa Cristina d'Aro (ES)

(73) Assignees: Universitat de Girona, Girona (ES); Fundacio Institut D'Investigacio Biomedica de Girona Dr. Josep Trueta, Salt (ES); Goodgut S.L., Girona (ES)

( * ) Notice: Subject to any disclaimer, the term of this patent is extended or adjusted under 35 U.S.C. 154(b) by 554 days.

(21) Appl. No.: 15/751,805

(22) PCT Filed: Aug. 11, 2016

(86) PCT No.: PCT/EP2016/069188
§ 371 (c)(1),
(2) Date: Feb. 9, 2018

(87) PCT Pub. No.: WO2017/025617
PCT Pub. Date: Feb. 16, 2017

(65) Prior Publication Data
US 2019/0024146 A1    Jan. 24, 2019

(30) Foreign Application Priority Data
Aug. 11, 2015  (EP) .................................... 15382427

(51) Int. Cl.
*C12Q 1/689* (2018.01)
*C12Q 1/6883* (2018.01)
*C12Q 1/6886* (2018.01)

(52) U.S. Cl.
CPC ........... *C12Q 1/689* (2013.01); *C12Q 1/6883* (2013.01); *C12Q 1/6886* (2013.01); *C12Q 2600/106* (2013.01); *C12Q 2600/112* (2013.01); *C12Q 2600/118* (2013.01); *C12Q 2600/158* (2013.01)

(58) Field of Classification Search
CPC .... C12Q 1/689; C12Q 1/6883; C12Q 1/6886; C12Q 2600/112; C12Q 2600/118; C12Q 2600/158
See application file for complete search history.

(56) References Cited

U.S. PATENT DOCUMENTS

| | | |
|---|---|---|
| 7,670,829 B2 | 3/2010 | Spagnoli et al. |
| 7,696,334 B1 | 4/2010 | Bentwich |
| 8,906,610 B2 | 12/2014 | Brodie et al. |
| 2006/0051769 A1 | 3/2006 | Barts |
| 2008/0113351 A1 | 5/2008 | Naito et al. |
| 2012/0213772 A1 | 8/2012 | Jansson et al. |
| 2012/0238468 A1 | 9/2012 | Tuk et al. |
| 2015/0038352 A1 | 2/2015 | Cao et al. |

FOREIGN PATENT DOCUMENTS

| | | | |
|---|---|---|---|
| EP | 2 876 167 A1 | | 5/2015 |
| WO | 02/061109 A2 | | 8/2002 |
| WO | 2005/116204 A1 | | 12/2005 |
| WO | 2008/021290 A2 | | 2/2008 |
| WO | 2012/170478 A2 | | 12/2012 |
| WO | 2014/137211 A1 | | 9/2014 |
| WO | 2014/138999 A1 | | 9/2014 |
| WO | 2014/197607 A1 | | 12/2014 |
| WO | WO 2014/197607 | * | 12/2014 |
| WO | 2015/132273 A1 | | 9/2015 |

OTHER PUBLICATIONS

Jia et al. (2010), "Is the abundance of Faecalibacterium prausnitzii relevant to Crohn's disease?", FEMS Microbiol Let 310(2): 138-144. (Year: 2010).*
Lopez-Siles et al. (2011), "Cultured Representatives of Two Major Phylogroups of Human Colonic Faecalibacterium prausnitzii Can Utilize Pectin, Uronic Acids, and Host-Derived Substrates for Growth", Appl Environ Microbiol 78(2): 420-428. (Year: 2011).*
Hold et al. (2003),"Oligonucleotide Probes That Detect Quantitatively Significant Groups of Butyrate-Producing Bacteria in Human Feces", Appl Environ Microbiol 69(7): 4320-4324. (Year: 2003).*

(Continued)

*Primary Examiner* — Jehanne S Sitton
*Assistant Examiner* — Daniel W Nielsen
(74) *Attorney, Agent, or Firm* — Seed IP Law Group LLP

(57) ABSTRACT

The present invention relates to a novel method for an accurate quantification in intestinal samples of *Faecalibacterium prausnitzii* phylogroup I members (PHGI) and/or *Faecalibacterium prausnitzii* phylogroup II members (PHGII). It further relates to a method for detecting intestinal diseases, including the screening, diagnosis, differential diagnosis, and/or monitoring of disease activity or progression in a human subject comprising determining the abundance of PHGI and/or PHGII in an intestinal sample from said subject. Moreover, it relates to a method for the prediction of the efficacy of a drug in the therapeutic treatment of an intestinal disease in a human subject comprising determining the abundance of PHGI and/or PHGII in an intestinal sample from said subject.

15 Claims, 36 Drawing Sheets
Specification includes a Sequence Listing.

(56) References Cited

OTHER PUBLICATIONS

Biassoni and Raso (2013), "Quantitative Real-Time PCR: Methods and Protocols", Methods in Mole Biol 1160: pp. v (Year: 2013).*
Lopez-Siles et al. (2014), "Mucosa-associated Faecalibacterium prausnitzii and Escherichia coli co-abundance can distinguish Irritable Bowel Syndrome and Inflammatory Bowel Disease phenotypes", Int J Med Microbiol 304:464-475 (Year: 2014).*
"Hit details for GSN:BBS66643", Dec. 11, 2014, XP055585694, Retrieved from the Internet: URL:http://ibis/exam/hitDetails.jsp?id=214662113. (1 page).
"Hit details for GS_NUC_ALERT:US2011166037.34252", Jul. 7, 2011, XP055585691, Retrieved from the Internet: URL:http://ibis/exam/hitDetails.jsp?id=214545658. (1 page).
"Hit details for GS_NUC_ALERT:WO2014068408.30855", May 8, 2014, XP055584468, Retrieved from the Internet: URL:http://ibis.internal.epo.org/exam/hitDetails.jsp?id=214543524. (1 page).
"EM_STD:JN067863", Jun. 1, 2012, XP055585700, Retrieved from the Internet: URL:http://ibis/exam/dbfetch.jsp?id=EM_STD:JN067863. (1 page).
Office Action, dated May 10, 2019, for European Application No. 16754468.3, 7 pages.
Altschul et al., "Gapped BLAST and PSI-BLAST: a new generation of protein database search programs," Nucleic Acids Research 25(17):3389-3402, 1997.
Andoh et al., "Recent Advances in Molecular Approaches to Gut Microbiota in Inflammatory Bowel Disease," Current Pharmaceutical Design 15:2066-2073, 2009.
Arumugam et al., "Enterotypes of the human gut microbiome," Nature 473:174-180, 2011 (9 pages).
Bach et al., "Enumeration of total bacteria and bacteria with genes for proteolytic activity in pure cultures and in environmental samples by quantitative PCR mediated amplification," Journal of Microbiological Methods 49:235-245, 2002.
Balamurugan et al., "Real-time polymerase chain reaction quantification of specific butyrate-producing bacteria, Desulfovibrio and Enterococcus faecalis in the feces of patients with colorectal cancer," Journal of Gastroenterology and Hepatology 23:1298-1303, 2008.
Barcenilla et al., "Phylogenetic Relationships of Butyrate-Producing Bacteria from the Human Gut," Applied and Environmental Microbiology 66(4):1654-1661, 2000.
Baumgart et al., "Culture independent analysis of ileal mucosa reveals a selective increase in invasive Escherichia coli of novel phylogeny relative to depletion of Clostridiales in Crohn's disease involving the ileum," The ISME Journal 1:403-418, 2007.
Bernstein et al., "Inflammatory bowel disease: a global perspective," World Gastroenterology Organisation Global Guidelines, Jun. 2009, 24 pages.
Best et al., "Development of a Crohn's Disease Activity Index," Gastroenterology 70:439-444, 1976.
Busquets et al., "Anti-tumour Necrosis Factor Treatment with Adalimumab Induces Changes in the Microbiota of Crohn's Disease," J. Crohns Colitis 9(10):899-906, 2015.
Carlsson et al., "Faecalibacterium prausnitzii supernatant improves intestinal barrier function in mice DSS colitis," Scandinavian Journal of Gastroenterology 48:1136-1144, 2013.
Cheifetz et al., "The Diagnosis and Treatment of Pouchitis in Inflammatory Bowel Disease," J. Clin. Gastroenterol. 38(Supp. 1):S44-S50, 2004.
Corless et al., "Contamination and Sensitivity Issues with a Real-Time Universal 16S rRNA PCR," Journal of Clinical Microbiology 38(5):1747-1752, 2000.
Duncan et al., "Growth requirements and fermentation products of Fusobacterium prausnitzii, and a proposal to reclassify it as Faecalibacterium prausnitzii gen. nov., comb, nov.," International Journal of Systematic and Evolutionary Microbiology 52:2141-2146, 2002.
Eckburg et al., "Diversity of the Human Intestinal Microbial Flora," Science 308(5728):1635-1638, 2005 (8 pages).
Eeckhaut et al., "Butyricicoccus pullicaecorum in inflammatory bowel disease," Gut 62:1745-1752, 2013. (9 pages).
Extended European Search Report, dated Oct. 30, 2015, for European Application No. 15382427.1-1404, 10 pages.
Farmer et al., "The Importance of Diagnostic Accuracy in Colonic Inflammatory Bowel Disease," The American Journal of Gastroenterology 95(11):3184-3188, 2000.
Flekna et al., "Real-time PCR method with statistical analysis to compare the potential of DNA isolation methods to remove PCR inhibitors from samples for diagnostic PCR," Molecular and Cellular Probes 21:282-287, 2007.
Florkowski, "Sensitivity, Specificity, Receiver-Operating Characteristic (ROC) Curves and Likelihood Ratios: Communicating the Performance of Diagnostic Tests," Clin. Biochem. Rev. 29(Supp. i):S83-S87, 2008.
Frank et al., "Molecular-phylogenetic characterization of microbial community imbalances in human inflammatory bowel diseases," PNAS 104(34):13780-13785, 2007.
Furet et al., "Comparative assessment of human and farm animal faecal microbiota using real-time quantitative PCR," FEMS Microbiol. Ecol. 65:351-362, 2009.
Geboes et al., "Terminology for the diagnosis of colitis," J. Clin. Pathol. 55(11):1133-1134, 2005.
Ghoshal et al., "The Gut Microbiota and Irritable Bowel Syndrome: Friend or Foe?" International Journal of Inflammation 2012:151085, 14 pages.
Giulietti et al., "An Overview of Real-Time Quantitative PCR: Applications to Quantify Cytokine Gene Expression," Methods 25:386-401, 2001.
Greiner et al., "Principles and practical application of the receiver-operating characteristic analysis for diagnostic tests," Preventive Veterinary Medicine 45:23-41, 2000.
GS nuc alert:US2015038352.149432 standard; peptide; 25 AA, Feb. 5, 2015, retrieved from http://ibis.internal.epo.org/exam/dbfetch.jsp?id=GS NUCALERT:US2015038352.149432, 1 page.
Hansen et al., "Microbiota of De-Novo Pediatric IBD: Increased Faecalibacterium Prausnitzii and Reduced Bacterial Diversity in Crohn's But Not in Ulcerative Colitis," The American Journal of Gastroenterology 107:1913-1922, 2012.
Harmsen et al., "Extensive Set of 16S rRNA-Based Probes for Detection of Bacteria in Human Feces," Applied and Environmental Microbiology 65(6):2982-2990, 2002.
Harvey et al., "A Simple Index of Crohn's-Disease Activity," The Lancet 375(8167):514, 1980.
Hold et al., "Oligonucleotide Probes That Detect Quantitatively Significant Groups of Butyrate-Producing Bacteria in Human Feces," Applied and Environmental Microbiology 69(7):4320-4324, 2003.
International Search Report and Written Opinion of the International Searching Authority, dated Dec. 1, 2016, for International Application No. PCT/EP2016/069188, 26 pages.
Jia et al., "Is the abundance of Faecalibacterium prausnitzii relevant to Crohn's disease?" FEMS Microbiol. Lett. 310:138-144, 2010.
Johnson et al., "NCBI BLAST: a better web interface," Nucleic Acids Research 36:W5-W9, 2008.
Kabeerdoss et al., "Clostridium leptum group bacteria abundance and diversity in the fecal microbiota of patients with inflammatory bowel disease: a case-control study in India," BMC Gastroenterology 13:20, 2013, 8 pages.
Kalliomaki et al., "Distinct patterns of neonatal gut microflora in infants in whom atopy was and was not developing," J. Allergy Clin. Immunol. 707(1):129-134, 2001.
Kennedy et al., "The Impact of Different DNA Extraction Kits and Laboratories upon the Assessment of Human Gut Microbiota Composition by 16S rRNA Gene Sequencing," PLoS One 9(2):e88982, 2014, 9 pages.
Konikoff et al., "Role of Fecal Calprotectin as a Biomarker of Intestinal Inflammation in Inflammatory Bowel Disease," Inflamm. Bowel Dis. 12(6):524-534, 2006.
López Siles, "Ecophysiology and Phylogeny of Faecalibacterium prausnitzii in Healthy and Diseased Gut. Application in Inflammatory Bowel Disease Diagnostics," doctoral thesis, Universitat de Girona, Girona, Spain, 2015, 211 pages.

(56) References Cited

OTHER PUBLICATIONS

Lopez-Siles et al., "Changes in the Abundance of *Faecalibacterium prausnitzii* Phylogroups I and II in the Intestinal Mucosa of Inflammatory Bowel Disease and Patients with Colorectal Cancer," *Inflamm. Bowel Dis.* 22(1):28-41, 2016.

Lopez-Siles et al., "Cultured Representatives of Two Major Phylogroups of Human Colonic *Faecalibacterium prausnitzii* Can Utilize Pectin, Uronic Acids, and Host-Derived Substrates for Growth," *Applied and Environmental Microbiology* 78(2):420-428, 2012.

Lopez-Siles et al., "Mucosa-associated *Faecalibacterium prausnitzii* and *Escherichia coli* co-abundance can distinguish Irritable Bowel Syndrome and Inflammatory Bowel Disease phenotypes," *Int. J. Med. Microbiol.* 304(3-4):464-475, 2014 (45 pages).

Lopez-Siles et al., "Mucosa-Associated *Faecalibacterium prausnitzii* Phylotype Richness Is Reduced in Patients with Inflammatory Bowel Disease," *Applied and Environmental Microbiology* 81(21):7582-7592, 2015.

Louis et al., "Diversity, metabolism and microbial ecology of butyrate-producing bacteria from the human large intestine," *FEMS Microbiol. Lett.* 294:1-8, 2009.

M'Koma, "Diagnosis of inflammatory bowel disease: Potential role of molecular biometrics," *World Journal of Gastrointestinal Surgery* 6(11):208-219, 2014 (13 pages).

Maidak et al., "The RDP (Ribosomal Database Project) continues," *Nucleic Acids Research* 28(1):173-174, 2000.

Manichanh et al., "The gut microbiota in IBD," *Nature Reviews Gastroenterology & Hepatology* 9:599-608, 2012.

Martinez-Medina et al., "Abnormal Microbiota Composition in the Ileocolonic Mucosa of Crohn's Disease Patients as Revealed by Polymerase Chain Reaction-Denaturing Gradient Gel Electrophoresis," *Inflamm. Bowel Dis.* 12(12):1136-1145, 2006.

McLaughlin et al., "The bacterial pathogenesis and treatment of pouchitis," *Therapeutic Advances in Gastroenterology* 3(6):335-348, 2010.

McOrist et al., "A comparison of five methods for extraction of bacterial DNA from human faecal samples," *Journal of Microbiological Methods* 50:131-139, 2002.

Miquel et al., "*Faecalibacterium prausnitzii* and human intestinal health," *Current Opinion in Microbiology* 16:1-7, 2013.

Mowat et al., "Guidelines for the management of inflammatory bowel disease in adults," *Gut* 60(5):571-607, 2011 (38 pages).

Nadkarni et al., "Determination of bacterial load by real-time PCR using abroad-range (universal) probe and primers set," *Microbiology* 148:257-266, 2002.

Nagalingam et al., "Role of the Microbiota in Inflammatory Bowel Diseases," *Inflamm. Bowel Dis.* 18(5):968-980, 2012.

Nava et al., "Diversity of the autochthonous colonic microbiota," *Gut Microbes* 2(2):99-104, 2011.

Pineton de Chambrun et al., "Clinical implications of mucosal healing for the management of IBP," *Nature Reviews Gastroenterology & Hepatology* 7:15-29, 2010.

Rajilić-Stojanović et al., "Global and Deep Molecular Analysis of Microbiota Signatures in Fecal Samples From Patients With Irritable Bowel Syndrome," *Gastroenterology* 747:1792-1801, 2011.

Roux et al., "Comparison of 16S rRNA and protein-coding genes as molecular markers for assessing microbial diversity (*Bacteria* and *Archaea*) in ecosystems," *FEMS Microbiol. Ecol.* 78:617-628, 2011.

Satsangi et al., "The Montreal classification of inflammatory bowel disease: controversies, consensus, and implications," *Gut* 55:749-753, 2006.

Schwiertz et al., "Microbiota in Pediatric Inflammatory Bowel Disease," *The Journal of Pediatrics* 157(2):240-244, 2010 (6 pages).

Sequence ID:AFE87984 standard; DNA; 25 BP., sequence 214698, Mar. 9, 2006, retrieved from http://ibis.internal.epo.org/exam/dbfetch.jsp?id=GSN:AFE87984, 1 page.

Sequence ID:BBS66443 standard; DNA; 70 BP., sequence 21170, Dec. 11, 2014, retrieved from http://ibis.internal.epo.org/exam/dbfetch.jsp?id=GSN:BBS66443, 1 page.

Sequence ID:BCM17194 standard; DNA; 20 BP., sequence 4, Jul. 1, 2015, retrieved from http://ibis.internal.epo.org/exam/dbfetch.jsp?id=GSN:BCM17194, 1 page.

Sequence ID:HK237957; SV 1; linear; genomic DNA; PAT; UNC; 25 BP., Sequence 2240, Dec. 9, 2014, retrieved from http://ibis.internal.epo.org/exam/dbfetch.jsp?id=EM_PAT:HK237957, 1 page.

Silverberg et al., "Toward an integrated clinical, molecular and serological classification of inflammatory bowel disease: Report of a Working Party of the 2005 Montreal World Congress of Gastroenterology," *Can. J. Gastroenterol.* 19(Suppl. A):5A-36A, 2005.

Smith et al., "Advantages and limitations of quantitative PCR(Q-PCR)-based approaches in microbial ecology," *FEMS Microbiol. Ecol.* 67:6-20, 2009.

Sokol et al., "*Faecalibacterium prausnitzii* is an anti-inflammatory commensal bacterium identified by gut microbiota analysis of Crohn disease patients," *PNAS* 105(43):16731-16736, 2008.

Sokol et al., "Low Counts of *Faecalibacterium prausnitzii* in Colitis Microbiota," *Inflamm. Bowel Dis.* 75(8):1183-1189, 2009.

Sostegni et al., "Review article: Crohn's disease: monitoring disease activity," *Aliment. Pharmacol. Ther.* 17(Suppl. 2):11-17, 2003.

Spiller, "Inflammation as a basis for functional GI disorders," *Best Practice & Research Clinical Gastroenterology* 18(4):641-661, 2004.

Stange et al., "European evidence-based Consensus on the diagnosis and management of ulcerative colitis: Definitions and diagnosis," *Journal of Crohn's and Colitis* 2:1-23, 2008.

Suau et al., "*Fusobacterium prausnitzii* and Related Species Represent a Dominant Group Within the Human Fecal Flora," *System. Appl. Microbiol.* 24:139-145, 2001.

Sutherland et al., "5-Aminosalicylic Acid Enema in the Treatment of Distal Ulcerative Colitis, Proctosigmoiditis, and Proctitis," *Gastroenterology* 92:1894-1898, 1987.

Suzuki et al., "Quantitative Analysis of Small-Subunit rRNA Genes in Mixed Microbial Populations via 5'-Nuclease Assays," *Applied and Environmental Microbiology* 66(11):4605-4614, 2000.

Swidsinski et al., "Active Crohn's Disease and Ulcerative Colitis Can Be Specifically Diagnosed and Monitored Based on the Biostructure of the Fecal Flora," *Inflamm. Bowel Dis.* 14(2):147-161, 2008.

Swidsinski et al., "Spatial organization of bacterial flora in normal and inflamed intestine: A fluorescence in situ hybridization study in mice," *World J. Gastroenterol.* 11(8):1131-1140, 2005.

Thompson et al., "Clustal W: improving the sensitivity of progressive multiple sequence alignment through sequence weighting, position-specific gap penalties and weight matrix choice," *Nucleic Acids Research* 22(22):4673-4680, 1994.

van Rheenen et al., "Faecal calprotectin for screening of patients with suspected inflammatory bowel disease: diagnostic meta-analysis," *BMJ* 341:c3369, 2010 (11 pages).

Vermeiren et al., "Decreased colonization of fecal *Clostridium coccoides/Eubacterium rectale* species from ulcerative colitis patients in and in vitro dynamic gut model with mucin environment," *FEMS Microbiol. Ecol.* 79:685-696, 2012.

Walker et al., "Dominant and diet-responsive groups of bacteria within the human colonic microbiota," *The ISME Journal* 5:220-230, 2011.

Weinstock, "Genomic approaches to studying the human microbiota," *Nature* 489(7415):250-256, 2012 (16 pages).

Weisburg et al., "16S Ribosomal DNA Amplification for Phylogenetic Study," *Journal of Bacteriology* 173(2):697-703, 1991.

Whitney et al., "Enhanced Retrieval of DNA from Human Fecal Samples Results in Improved Performance of Colorectal Cancer Screening Test," *Journal of Molecular Diagnostics* 6(4):386-395, 2004.

Willing, "Twin studies reveal specific imbalances in the mucosa-associated microbiota of patients with ileal Crohn's disease," *Inflamm. Bowell Dis.* 15(5):653-660, 2009 (28 pages).

Wrzosek et al., "*Bacteroides thetaiotaomicron* and *Faecalibacterium prausnitzii* influence the production of mucus glycans and the development of goblet cells in the colonic epithelium of a gnotobiotic model rodent," *BMC Biology* 11:61, 2013 (13 pages).

Zweig et al., "Receiver-Operating Characteristic (ROC) Plots: A Fundamental Evaluation Tool in Clinical Medicine," *Clin. Chem.* 39(4):561-577, 1993.

(56) References Cited

OTHER PUBLICATIONS

Sobhani et al., "Microbial Dysbiosis in Colorectal Cancer (CRC) Patients," *PLoS One* 6(1):1-7, e16393, Jan. 2011.

* cited by examiner

SEQUENCE LISTING

<160> NUMBER OF SEQ ID NOS: 16

<210> SEQ ID NO 1
<211> LENGTH: 22
<212> TYPE: DNA
<213> ORGANISM: Faecalibacterium prausnitzii
<220> FEATURE:
<221> NAME/KEY: misc_feature
<222> LOCATION: (1)..(22)
<223> OTHER INFORMATION: Fpra 136F; F. prausnitzii phylogroups forward
      primer

<400> SEQUENCE: 1
ctcaaagagg gggacaacag tt                                              22

<210> SEQ ID NO 2
<211> LENGTH: 19
<212> TYPE: DNA
<213> ORGANISM: Faecalibacterium prausnitzii
<220> FEATURE:
<221> NAME/KEY: misc_feature
<222> LOCATION: (1)..(19)
<223> OTHER INFORMATION: Fpra 232R; F. prausnitzii phylogroups reverse
      primer

<400> SEQUENCE: 2
gccatctcaa agcggattg                                                  19

<210> SEQ ID NO 3
<211> LENGTH: 21
<212> TYPE: DNA
<213> ORGANISM: Faecalibacterium prausnitzii
<220> FEATURE:
<221> NAME/KEY: misc_feature
<222> LOCATION: (1)..(21)
<223> OTHER INFORMATION: PHG1 180PR oligont; Phylogroup I probe
      (unmodified oligonucleotide)

<400> SEQUENCE: 3
taagcccacg acccggcatc g                                               21

<210> SEQ ID NO 4
<211> LENGTH: 20
<212> TYPE: DNA
<213> ORGANISM: Faecalibacterium prausnitzii
<220> FEATURE:
<221> NAME/KEY: misc_feature
<222> LOCATION: (1)..(20)
<223> OTHER INFORMATION: PHG2 180PR oligont; Phylogroup II probe
      (unmodified oligonucleotide)

<400> SEQUENCE: 4
taagcccacr gctcggcatc                                                 20

<210> SEQ ID NO 5
<211> LENGTH: 28
<212> TYPE: DNA
<213> ORGANISM: Faecalibacterium prausnitzii
<220> FEATURE:
<221> NAME/KEY: misc_feature
<222> LOCATION: (1)..(28)
<223> OTHER INFORMATION: Fpra 428 F;  F. prausnitzii total forward
      primer

<400> SEQUENCE: 5
tgtaaactcc tgttgttgag gaagataa                                        28

<210> SEQ ID NO 6

```
<211> LENGTH: 18
<212> TYPE: DNA
<213> ORGANISM: Faecalibacterium prausnitzii
<220> FEATURE:
<221> NAME/KEY: misc_feature
<222> LOCATION: (1)..(18)
<223> OTHER INFORMATION: Fpra 583 R; F. prausnitzii total reverse primer

<400> SEQUENCE: 6
gcgctccctt tacaccca                                                       18

<210> SEQ ID NO 7
<211> LENGTH: 29
<212> TYPE: DNA
<213> ORGANISM: Faecalibacterium prausnitzii
<220> FEATURE:
<221> NAME/KEY: misc_feature
<222> LOCATION: (1)..(29)
<223> OTHER INFORMATION: Fpra 493 PR oligont; F. prausnitzii total probe
      (unmodified oligonucleotide)

<400> SEQUENCE: 7
caaggaagtg acggctaact acgtgccag                                           29

<210> SEQ ID NO 8
<211> LENGTH: 18
<212> TYPE: DNA
<213> ORGANISM: Artificial Sequence
<220> FEATURE:
<223> OTHER INFORMATION: Bacterial DNA
<220> FEATURE:
<221> NAME/KEY: misc_feature
<222> LOCATION: (1)..(18)
<223> OTHER INFORMATION: F_Bact 1369; Total bacteria forward primer

<400> SEQUENCE: 8
cggtgaatac gttcccgg                                                       18

<210> SEQ ID NO 9
<211> LENGTH: 22
<212> TYPE: DNA
<213> ORGANISM: Artificial Sequence
<220> FEATURE:
<223> OTHER INFORMATION: Bacterial DNA
<220> FEATURE:
<221> NAME/KEY: misc_feature
<222> LOCATION: (1)..(22)
<223> OTHER INFORMATION: R_Prok_1492; Total bacteria reverse primer

<400> SEQUENCE: 9
tacggctacc ttgttacgac tt                                                  22

<210> SEQ ID NO 10
<211> LENGTH: 19
<212> TYPE: DNA
<213> ORGANISM: Artificial Sequence
<220> FEATURE:
<223> OTHER INFORMATION: Bacterial DNA
<220> FEATURE:
<221> NAME/KEY: misc_feature
<222> LOCATION: (1)..(19)
<223> OTHER INFORMATION: P_TM_1389F oligont; Total bacteria probe
      (unmodified oligonucleotide)

<400> SEQUENCE: 10
cttgtacaca ccgcccgtc                                                      19

<210> SEQ ID NO 11
<211> LENGTH: 22
```

```
<212> TYPE: DNA
<213> ORGANISM: Artificial Sequence
<220> FEATURE:
<223> OTHER INFORMATION: Internal Amplification Control (IAC)
<220> FEATURE:
<221> NAME/KEY: misc_feature
<222> LOCATION: (1)..(22)
<223> OTHER INFORMATION: IAC F; IAC forward primer

<400> SEQUENCE: 11
tacggatgag gaggacaaag ga                                            22

<210> SEQ ID NO 12
<211> LENGTH: 21
<212> TYPE: DNA
<213> ORGANISM: Artificial Sequence
<220> FEATURE:
<223> OTHER INFORMATION: Internal Amplification Control (IAC)
<220> FEATURE:
<221> NAME/KEY: misc_feature
<222> LOCATION: (1)..(21)
<223> OTHER INFORMATION: IAC R; IAC reverse primer

<400> SEQUENCE: 12
cacttcgctc tgatccattg g                                             21

<210> SEQ ID NO 13
<211> LENGTH: 19
<212> TYPE: DNA
<213> ORGANISM: Artificial Sequence
<220> FEATURE:
<223> OTHER INFORMATION: Internal Amplification Control (IAC)
<220> FEATURE:
<221> NAME/KEY: misc_feature
<222> LOCATION: (1)..(19)
<223> OTHER INFORMATION: IAC PR oligont; IAC probe (unmodified
      oligonucleotide)

<400> SEQUENCE: 13
cgccgctatg ggcatcgca                                                19

<210> SEQ ID NO 14
<211> LENGTH: 20
<212> TYPE: DNA
<213> ORGANISM: Artificial Sequence
<220> FEATURE:
<223> OTHER INFORMATION: E.coli 395 F; E.coli forward primer
<220> FEATURE:
<221> NAME/KEY: misc_feature
<222> LOCATION: (1)..(20)

<400> SEQUENCE: 14
catgccgcgt gtatgaagaa                                               20

<210> SEQ ID NO 15
<211> LENGTH: 21
<212> TYPE: DNA
<213> ORGANISM: Artificial Sequence
<220> FEATURE:
<223> OTHER INFORMATION: E.coli 490 R; E.coli reverse primer
<220> FEATURE:
<221> NAME/KEY: misc_feature
<222> LOCATION: (1)..(21)

<400> SEQUENCE: 15
cgggtaacgt caatgagcaa a                                             21

<210> SEQ ID NO 16
<211> LENGTH: 31
```

```
<212> TYPE: DNA
<213> ORGANISM: Artificial Sequence
<220> FEATURE:
<223> OTHER INFORMATION: E.coli 437 PR; E.coli probe (unmodified
      oligonucleotide)
<220> FEATURE:
<221> NAME/KEY: misc_feature
<222> LOCATION: (1)..(31)

<400> SEQUENCE: 16 tattaactttt actcccttcc tccccgctga a                              31
```

METHOD FOR THE QUANTIFICATION OF *FAECALIBACTERIUM PRAUSNITZII* PHYLOGROUP I AND/OR PHYLOGROUP II MEMBERS AND THE USE THEREOF AS BIOMARKERS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 370081_401USPC_SEQUENCE_LISTING.txt. The text file is 6 KB, was created on Feb. 9, 2018, and is being submitted electronically via EFS-Web.

BACKGROUND

Technical Field

The present invention relates to the field of diagnosis and classification of intestinal diseases and personalized medicine in general. It further relates to the field of microbiology and molecular biology, more particularly it relates to the relationship between intestinal microbiota composition and intestinal disease, e.g., in inflammatory bowel disease (IBD). Specifically it relates to a novel method for an accurate quantification in intestinal samples of *Faecalibacterium prausnitzii* phylogroup I members (PHGI) and/or *Faecalibacterium prausnitzii* phylogroup II members (PHGII). It further relates to a method for detecting intestinal diseases, including the screening, diagnosis, differential diagnosis, determining disease activity and/or monitoring of disease activity and/or progression in a human subject comprising determining the abundance of PHGI and/or PHGII members in an intestinal sample from said subject. Moreover, it relates to a method for the prediction of the efficacy of a drug in the therapeutic treatment of an intestinal disease in a human subject comprising determining the abundance of PHGI and/or PHGII in an intestinal sample from said subject.

Description of the Related Art

Inflammatory bowel disease (IBD) represents a group of idiopathic chronic inflammatory intestinal conditions. The two main disease categories the term covers are Crohn's disease (CD) and ulcerative colitis (UC), with both overlapping and distinct clinical and pathological features (World Gastroenterology Organisation Global Guidelines, Inflammatory bowel disease: a global perspective, June 2009; and Silverberg et al., Can J Gastroenterol. 2005, 19 Suppl A:5-36).

IBD affects as many as 1.6 million persons in the United States and 2.2 million in Europe. The incidence is increasing worldwide. In spite of advances in IBD-therapy, IBD hospitalizations and surgery rates in the United States have increased significantly since 1990. IBD is one of the five most prevalent gastrointestinal disease burdens in the United States, with annual overall health care costs of more than $1.7 billion. One to two of every 1000 people in developed countries are affected with IBD, and global rates seem to be increasing, attributable to the rapid modernization and to the adoption of the Western world lifestyle. These chronic diseases result in significant morbidity and mortality, compromising quality of life and life expectancies. (M'Koma A. E., World J Gastrointest Surg 2014; 6(11), 208-219).

An association between the increased incidence of IBD and environmental factors linked to socioeconomic development has been persistently detected in different parts of the world, and it seems that the lifestyle in developed countries might impair the natural patterns of microbial colonization of the human gut. In IBD, mucosal lesions are generally associated to an excessive or dysregulated immune response against commensal microbes in the gut, and studies using molecular methods for intestinal microbiota analysis indicate that dysbiosis (that is, abnormal microbiota composition) and decreased complexity of the gut microbial ecosystem are common features in patients with CD or UC (Manichanh et al., Nat. Rev. Gastroenterol. Hepatol. 2012; 9, 599-608).

*Faecalibacterium prausnitzii* (Ruminococcaceae) is one of the three most abundant bacterial species found in the gut, representing between 2-20% of the fecal microbiota in healthy individuals, according to diversity studies of the human gut microbiome based on 16S rRNA gene analysis (Arumugam et al. Nature. 2011; 473:174-180; Eckburg et al. Science. 2005; 308:1635-1638; Hold et al. Appl Environ Microbiol. 2003; 69:4320-4324; Schwiertz et al. J Pediatr. 2010; 157:240-244; Suau et al. Systematic and Applied Microbiology. 2001; 24:139-145; Walker et al. ISME J. 2011:220-230). On the other hand, it has been reported to represent 6% of bacteria in mucosa-associated microbial communities (Swidsinski et al. World J Gastroenterol. 2005; 11:1131-1140), although some studies have indicated that these values can increase to around 20-50% in some individuals (Nava G M, Stappenbeck T S. Gut Microbes. 2011; 2: 99-104; Baumgart et al. ISME J. 2007; 1:403-418).

In recent years, there has been increasing interest in *F. prausnitzii* given its potentially important role in promoting gut health (Louis et al. FEMS Microbiol Lett. 2009; 294:1-8; Sokol et al. Proc Natl Acad Sci USA. 2008; 105:16731-16736) through the formation of anti-inflammatory compounds (Louis et al. FEMS Microbiol Lett. 2009; 294:1-8; Sokol et al. Proc Natl Acad Sci USA. 2008; 105:16731-16736; Barcenilla et al. Appl Environ Microbiol. 2000; 66:1654-1661; Duncan et al. Int J Syst Evol Microbiol 2002; 52:2141-2146; Lopez-Siles et al. Appl Environ Microbiol. 2012; 78:420-428) and enhancement of intestinal barrier function (Carlsson et al. Scand J Gastroenterol. 2013; 48:1136-1144; Wrzosek et al. BMC Biol. 2013; 11:61).

Many studies have shown that *F. prausnitzii* prevalence and abundance is reduced in different intestinal disorders (Miguel et al. Curr Opin Microbiol. 2013; 16:255-261), in particular the depletion in *F. prausnitzii* numbers has been most extensively reported in inflammatory bowel disease (IBD). Low counts of this species have been observed in both fecal and mucosa-associated communities of adult CD patients (Sokol et al. Proc Natl Acad Sci USA. 2008; 105:16731-16736; Lopez-Siles et al. International Journal of Medical Microbiology. 2014; 304:464-475; Sokol et al. Inflamm Bowel Dis. 2009; 15:1183-1189; Swidsinski et al. Inflamm Bowel Dis. 2008; 14:147-161; Willing et al. Inflamm Bowel Dis. 2009; 15:653-660).

Variable populations have been reported in UC patients (Swidsinski et al. World J Gastroenterol. 2005; 11:1131-1140; Lopez-Siles et al. International Journal of Medical Microbiology. 2014; 304:464-475; Sokol et al. Inflamm Bowel Dis. 2009; 15:1183-1189; Hansen et al. Am J Gastroenterol. 2012; 107:1913-1922; Jia et al. FEMS Microbiol Lett. 2010; 310:138-144; Kabeerdoss et al. BMC Gastroenterol. 2013; 13:20; Machiels et al. Gut. 2013; McLaughlin et al. Therap Adv Gastroenterol. 2010; 3:335-348; Vermeiren et al. FEMS Microbiol Ecol. 2012; 79:685-696), despite the reduction of Firmicutes having been repeatedly observed in this disorder (Machiels et al. Gut. 2013; Frank et al. Proc Natl Acad Sci USA. 2007; 104:13780-13785; Nagalingam N A, Lynch S V. Inflamm Bowel Dis. 2012; 18:968-984). A recent study conducted on 127 UC subjects points out that a reduction in *F. prausnitzii* is also involved in UC dysbiosis (Machiels et al. Gut. 2013).

Interestingly, lower counts of *Faecalibacterium*-related bacteria have also been observed in functional gut disorders such as irritable bowel syndrome (IBS) of alternating type (Rajilic-Stojanovic et al. Gastroenterology. 2011; 141:1792-1801), that in turn shares some features with IBD patients (Ghoshal et al. Int J Inflam. 2012; 2012:151085; Spiller R C. Best Practice & Research Clinical Gastroenterology. 2004; 18:641-661), and in more severe intestinal disorders as colorectal cancer (CRC) (Balamurugan et al. J Gastroenterol Hepatol. 2008; 23:1298-1303). Taken together these findings suggest that shifts in *F. prausnitzii* numbers occur under several pathological disorders.

Relatively few studies have paid attention to the diversity within the genus *Faecalibacterium*. Recent phylogenetic analysis showed that mainly two different *F. prausnitzii* phylogroups were found in fecal samples of healthy subjects (Lopez-Siles et al. Appl Environ Microbiol. 2012; 78:420-428). More specifically, Lopez-Siles et al. 2012 analyzed the phylogenetic relationship of *F. prausnitzii* isolates to other members of *Clostridium* cluster IV based on 16S rRNA gene sequences and defined for the first time two phylogroups within *F. prausnitzii* species (FIG. 1), These *F. prausnitzii* phylogroups included five sequences reported previously for the cultured isolates M21/2, ATCC 27766, and ATCC 27768 (belonging to PHGI) and A2-165 and L2-6 (belonging to PHGII).

Besides, Jia et al. FEMS Microbiol Lett. 2010; 310:138-144 describe a method for the amplification in a single end point PCR of bacterial DNA sequences belonging to *F. prausnitzii* species. The primers used for the amplification (Fp.ID.F2 and Fp.ID.R2) were designed against the nucleotidyl transferase gene and the butyryl-CoA transferase gene sequences, respectively, of *F. prausnitzii* A2-165 and M21/2 strains and, yields of PCR products were classified as belonging to two different subgroups, namely the A2-165 subgroup and the M21/2 subgroup (see Table 1). Accordingly, the primers used for amplification of *F. prausnitzii* members were not targeting the *F. prausnitzii* 16S rRNA gene and were based on the sequence of two strains only. Furthermore, the members belonging to each subgroup were distinguished by the size of the PCR product and, no primer or probe was disclosed in Jia et al. 2010 specific for each of the A2-165 and M21/2 subgroups.

Nowadays, the diagnosis of IBD requires a comprehensive physical examination and a review of the patient's history. Various tests, including blood tests, stool examination, endoscopy, biopsies, and imaging studies help exclude other causes and confirm the diagnosis (World Gastroenterology Organisation Global Guidelines, Inflammatory bowel disease: a global perspective, June 2009).

Accurate IBD diagnosis is crucial for providing correct, evidence-based treatment, since treatment response and complications differ significantly among UC and CD patients (Farmer et al. Am J Gastroenterol 2000; 95: 3184-3188). From the clinician's perspective, accurate diagnosis and classification of these diseases would have potential benefits with respect to patient counselling, assessing disease prognosis, monitoring disease progression and relapses, and particularly with choosing the most appropriate treatment for each disease subtype. Besides, the issue of disease progression for both CD and UC is critical in studies relating genotype to phenotype, as disease behavior and severity will undoubtedly change over time (Satsangi et al., Gut 2006; 55, 749-753).

Despite significant advances having been made in the last twenty years in the discovery of molecular and serological markers related to IBD, there is an on-going need for improved methods for the accurate diagnosis, classification, study of the progression and/or prognosis of IBD and IBD phenotypes.

BRIEF SUMMARY

The inventors developed a novel method for an accurate quantification in intestinal samples of phylogroup I members (PHGI) and/or phylogroup II members (PHGII) of *F. prausnitzii* species. In particular, in order to simultaneously quantify both *F. prausnitzii* phylogroups, a multiplex quantitative polymerase chain reaction (qPCR) was developed comprising the use of a unique pair of species-specific primers for the 16S rRNA gene of *F. prausnitzii* and two hydrolysis probes targeting each of *F. prausnitzii* phylogroup members which were designed and optimized by the inventors to have broad coverage while preserving specificity. There is interindividual variability in the intestinal microbiota composition of patients suffering from an intestinal disease (e.g, suffering from IBD, Crohn's disease or ulcerative colitis), and some of the *F. prausnitzii* strains may not be represented in the intestinal bacterial population of a given individual. Therefore, the broad coverage of the primers and probes of the invention provides for a more accurate quantification of *F. prausnitzii* phylogroups.

For the design of the species-specific primers and phylogroup specific probes, 33 sequences of the 16S rRNA gene from *F. prausnitzii* were recovered from GenBank and aligned (see Table 14, where these sequences (in bold) were marked *, 1 and 2, respectively). From the generated consensus sequences for the *F. prausnitzii* 16S rRNA gene and for each phylogroup, both primers and hydrolysis probes were manually designed and optimized. Accordingly, in contrast with Jia et al. 2010 where the primers were designed based on the nucleotidyl transferase gene and the butyryl-CoA transferase gene sequence of *F. prausnitzii* A2-165 and M21/2 strains only, the design of the species-specific primers for *F. prausnitzii* 16S rRNA gene of the invention was based on the alignment of 33 known *F. prausnitzii* 16S rRNA gene sequences.

Moreover, for the first time probes specific of the *F. prausnitzii* phylogroup I members (PHGI) and phylogroup II members (PHGII) were described. For the design of the PHGI probe, 5 known *F. prausnitzii* 16S rRNA gene sequences were used as starting point and for PHGII probe 13 known *F. prausnitzii* 16S rRNA gene sequences (see Tables 3 and 5 below, respectively). Phylogroup classification of the known sequences was carried out according to Lopez-Siles et al. 2012.

The generated species-specific primers and phylogroup specific probes were submitted to in silico and in vivo testing to ensure broad coverage and specificity for the 16S rRNA gene of *F. prausnitzii* (inclusivity/exclusivity tests). PHGI probe (SEQ ID NO:3) was shown by the inventors to specifically hybridize with more than 1000 16S rRNA gene sequences, namely the 1196 sequences recited in Tables 3 and 4. Therefore, the term *Faecalibacterium prausnitzii* phylogroup I (PHGI) members as used herein includes those bacterial strains which 16S rRNA gene specifically hybridizes with PHGI probe (SEQ ID NO:3). Similarly, PHGII probe (SEQ ID NO:4), was shown by the inventors to specifically hybridize with more than 2000 16S rRNA gene sequences, namely the 2244 sequences recited in Tables 5 and 6. Accordingly, the term *Faecalibacterium prausnitzii* phylogroup II (PHGII) members as used herein includes those bacterial strains which 16S rRNA gene specifically hybridizes with PHGII probe (SEQ ID NO:4).

Using the newly developed method for the quantification of PHGI and PHGII members, the inventors determined the variation of mucosa-associated and feces-associated *F. prausnitzii* phylogroups between healthy subjects and patients suffering several intestinal disorders in order to establish whether the imbalance in *F. prausnitzii* includes the overall population or specifically affects a particular phylogroup.

Moreover, it was determined the usefulness of the quantification of *F. prausnitzii* phylogroups alone, in combination or in combination with other biomarkers (e.g., *F. prausnitzii* and *E. coli*) as biomarkers for detecting intestinal diseases, including the screening diagnosis, differential diagnosis (e.g., differential diagnosis of IBD phenotypes), determining disease activity and monitoring of disease activity or progression. Furthermore, its usefulness as biomarkers for the prediction of a therapeutic treatment effect in intestinal diseases, particularly in Crohn's disease and ulcerative colitis, Accordingly, the present invention provides a novel method for the quantification of PHGI and/or of PHGII members and its use as new biomarkers of intestinal disease, particularly of Crohn's disease and/or ulcerative colitis.

Thus, in accordance with the particular findings of the present invention, there is provided:

A first aspect of the invention relates to an in vitro method for determining the abundance of *Faecalibacterium prausnitzii* phylogroup I members (PHGI) and/or of *Faecalibacterium prausnitzii* phylogroup II members (PHGII) in an intestinal sample from a subject; wherein PHGI abundance determination comprises the use of a primer and/or probe with sequence SEQ ID NO: 3 or a sequence with at least 75% identity thereof; and wherein PHGII abundance determination comprises the use of a primer and/or a probe with sequence SEQ ID NO: 4 or a sequence with at least 75% identity thereof.

In a second aspect the invention relates to a method for the obtaining of useful information for the detection of an intestinal disease in a human subject and/or for the prediction of the efficacy of a drug in the therapeutic treatment of an intestinal disease in a human subject, comprising for determination of the abundance of PHGI and/or of PHGII according to the method of the invention.

In a third aspect, the invention relates to a method for detecting an intestinal disease in a human subject comprising the following steps:
  a. determining the abundance of *Faecalibacterium prausnitzii* phylogroup I members (PHGI) and/or *Faecalibacterium prausnitzii* phylogroup II members (PHGII) in an intestinal sample from said subject according to a method as described under the first aspect; and
  b. comparing the PHGI and/or PHGII abundance, and/or a mathematical combination thereof, and/or optionally a mathematical combination of any of these with Total *F. Prausnitzii* (FT) abundance and/or *E. coli* (EC) abundance, in the subject sample with the corresponding values in a reference sample, wherein a significant deviation in the subject sample values with regard to said reference sample is indicative of intestinal disease.

In a further aspect, the invention relates to the use of *Faecalibacterium prausnitzii* phylogroup I members (PHGI) and/or *Faecalibacterium prausnitzii* phylogroup II members (PHGII) abundance, and/or a mathematical combination thereof, and/or optionally a mathematical combination of any of these with Total *F. Prausnitzii* (FT) abundance and/or *E. coli* (EC) abundance, in an intestinal sample of a human subject as biomarker for the detection of an intestinal disease, and/or for predicting the efficacy of a drug in the treatment of an intestinal disease.

The invention further provides a kit comprising:
  a. a reagent for determining the abundance of *Faecalibacterium prausnitzii* phylogroup I members (PHGI) consisting of a primer and/or probe with sequence SEQ ID NO: 3 or a sequence with at least 75% identity thereof; and/or
  b. a reagent for determining the abundance of *Faecalibacterium prausnitzii* phylogroup II members (PHGII) consisting of a primer and/or a probe with sequence SEQ ID NO: 4 or a sequence with at least 75% identity thereof; and
  c. optionally, instructions for use of said reagent(s) to determine the abundance of PHGI, and/or PHGII, from a human intestinal sample.

A further aspect of the invention relates to a nucleic acid sequence selected from the group consisting of SEQ ID NO: 1, SEQ ID NO: 2, SEQ ID NO: 3, and SEQ ID NO: 4 or an oligonucleotide sequence with at least 75% identity thereof.

Still a further aspect of the invention relates to a method for the differential diagnosis of inflammatory bowel disease (IBD) phenotypes in a human subject comprising the following steps:
  i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and
  ii. comparing the subject sample abundance of one or more of said target microorganisms and/or a mathematical combination thereof, with the corresponding values in a reference sample of the IBD phenotypes to be distinguished from to determine the IBD phenotype the subject is suffering from; wherein the subject sample presenting values significantly similar to one of said IBD phenotypes will be indicative that the subject is suffering from said IBD phenotype; and
wherein said IBD phenotypes are defined by at least the combination of two, preferably three, of the following parameters:
  disease location;
  IBD type; and
  age at diagnosis,
optionally, comprising the use of additional biomarkers for the definition of said IBD phenotypes.

Another aspect of the invention relates to a method for diagnosing C-CD in a human subject suffering from IBD with colonic involvement comprising the following steps:
  i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and ii. comparing the subject sample abundance of one or more of said target microorganisms and/or a mathematical combination thereof, with the corresponding values in a reference sample, wherein a significant deviation in the subject sample values with regard to said reference sample is indicative of C-CD.

Also, another aspect of the invention relates to a method for diagnosing IC-CD in a human subject suffering from I-CD or C-CD comprising the following steps:

i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and ii. comparing the subject sample abundance of one or more of said target microorganisms and/or a mathematical combination thereof, with the corresponding values in a reference sample from said subject at around diagnose of I-CD or C-CD, wherein a significant deviation in the subject sample values with regard to said reference sample is indicative of IC-CD.

A further aspect of the invention relates to a method for the prognosis of inflammatory bowel disease (IBD) which comprises the determination of an IBD phenotype according to a method for the differential diagnosis of any of the above aspects of the invention and establishing prognosis according to the determined IBD phenotype.

Another additional aspect of the invention relates to the use of *Faecalibacterium prausnitzii* members (total FP) abundance, *Faecalibacterium prausnitzii* phylogroup I members (PHGI) abundance and/or *Faecalibacterium prausnitzii* phylogroup II members (PHGII) abundance determined in an intestinal sample of a human subject; and/or a mathematical combination thereof as biomarker for the differential diagnosis of inflammatory bowel disease (IBD) phenotypes.

Still another additional aspect of the invention relates to a kit for the differential diagnosis of inflammatory bowel disease (IBD) phenotypes according to a method of any of above aspects, comprising:

a reagent for determining the abundance of a target microorganism selected from the group consisting of *Faecalibacterium prausnitzii* members (total FP), *Faecalibacterium prausnitzii* phylogroup I members (PHGI), and *Faecalibacterium prausnitzii* phylogroup II members (PHGII); and instructions for use of said reagent(s) to determine the abundance levels of said target microorganism from a human intestinal sample.

DETAILED DESCRIPTION

Definitions

Figure 1:
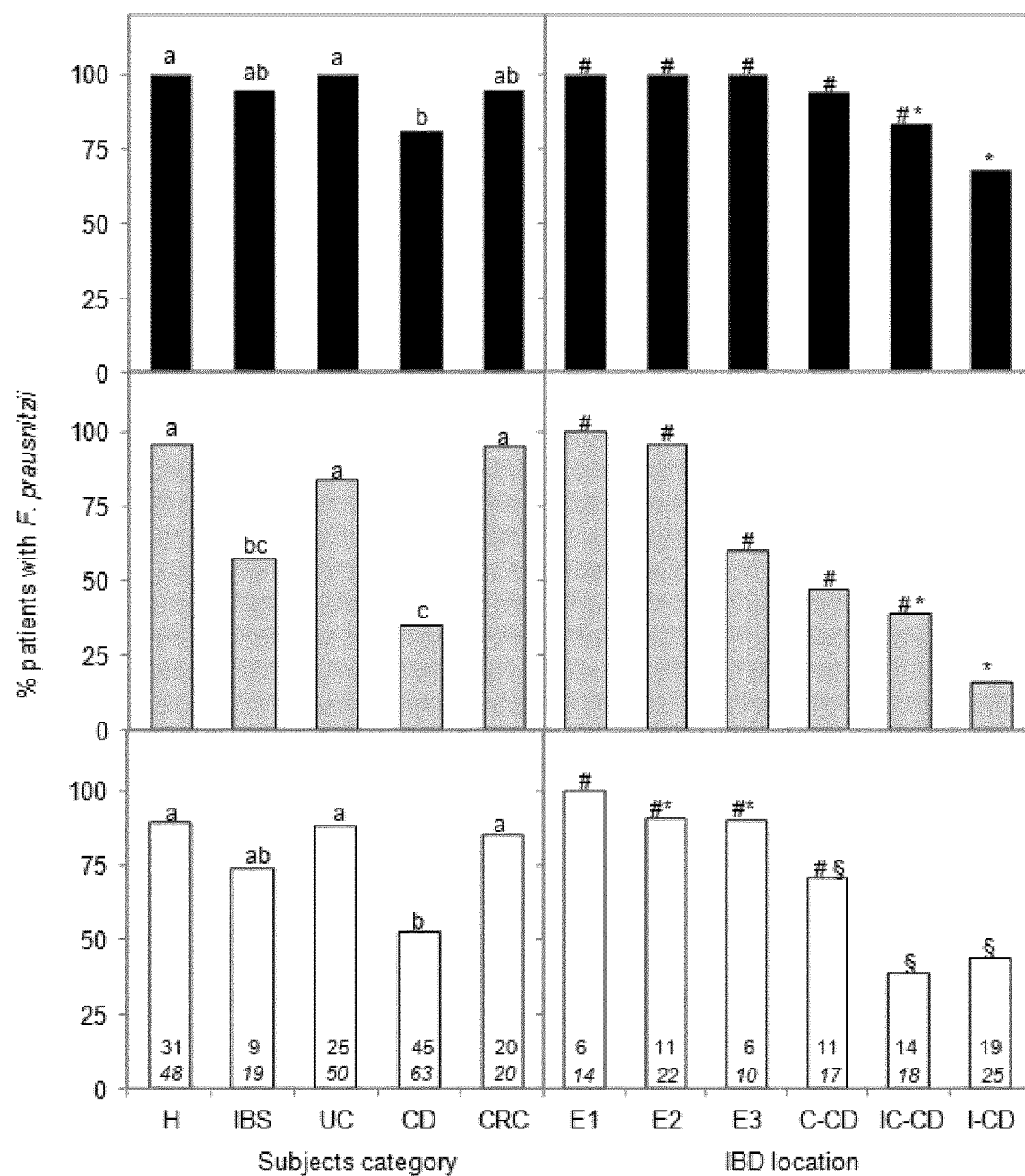
FIG. 1. Graphical representation of the prevalence of *F. prausnitzii* (black), *F. prausnitzii* phylogroup I (grey) and *F. prausnitzii* phylogroup II (white). Subjects were categorized by disease (left) and IBD location (right). The following abbreviations have been used: H, control subjects; CRC, colorectal cancer; IBS, irritable bowel syndrome; UC, ulcerative colitis; CD, Crohn's disease; E1, proctitis; E2, left-sided colitis; E3, pancolitis; C-CD, colonic CD; IC-CD, ileocolonic CD; I-CD, ileal CD; and IBD, inflammatory bowel disease. Numbers in the bars indicate the number of patients (biopsies) analyzed to calculate the prevalence. Statistics was calculated separately for each panel. Homogeneous subgroups (P>0.05) within each panel are indicated with the same symbols above the bars, whereas groups of patients with statistically different prevalence (P<0.05) do not share any superscript.

The term "prevalence" as used herein refers to a measure of the number of cases of disease occurring within the population under study, i.e., % of biological samples or individuals positive for a target microorganism from the total of biological samples or individuals analyzed. Prevalence is thus calculated from the qualitative determination (presence/absence) of said target microorganism within each of the samples or individuals under study.

The term "abundance" as used herein refers to a measure of the quantity of a target microorganism within a biological sample. It is also referred as "load". Bacterial quantification is generally carried out by molecular methods, typically by determining the number of 16S rRNA gene copies of said target microorganism, for instance by fluorescence in situ hybridization (FISH), quantitative polymerase chain reaction (qPCR) or PCR/pyrosequencing. Quantification of the abundance of a target nucleic acid sequence within a biological sample might be absolute or relative. "Relative quantification" is generally based on one or more internal reference genes, i.e., 16S rRNA genes from reference strains, such as determination of total bacteria using universal primers and expressing the abundance of the target nucleic acid sequence as a percentage of total bacterial 16S rRNA gene copies or normalized by *E. coli* 16S rRNA gene copies. "Absolute quantification" gives the exact number of target molecules by comparison with DNA standards or normalizing by DNA concentration.

The term "quantification levels" might be the concentration (DNA amount per unit of volume), the DNA amount or number of gene copies per number of cells, the cycle threshold value (Ct value) or any mathematical transformation thereof, such as the log 10 of the number of gene copies.

The expression "usefulness as biomarker" as used herein refers to how well the molecular marker identifies the target condition of interest, in other words, how well said parameter enables to discriminate between subjects belonging to different population groups, for instance between disease and non-disease group or between different disease phenotypes. This is referred as the "validity" or "performance" of the test.

Validity studies address the agreement between a proposed (index) test and a reference standard for the ability to identify a target condition (see Florkowski M. C., Clin Biochem Rev. 2008, 29 (Suppl 1): S83-S87). Sensitivity, specificity, accuracy, positive likelihood ratio, negative likelihood ratio, positive predictive value and negative predictive value are statistic values which can be defined to evaluate the test performance. Acronyms' definition and further details are provided in Table 1 below.

TABLE 1

Formulas and acronym's definition of parameters useful
for defining the validity of a test, Florkowski M. C.,
Clin Biochem Rev. 2008, 29 (Suppl 1): S83-S87.

| | Reference Standard | | |
|---|---|---|---|
| | Disease present | Disease absent | Total |
| Index Test positive | True positive (TP) | False positive (FP) | TP + FP |
| Index Test negative | False negative (FN) | True negative (TN) | TN + FN |
| Total | TP + FN | TN + FP | |

Sensitivity = TP/(TP + FN)
Specificity = TN/(TN + FP)
Positive predictive value (PPV) = TP/(TP + FP)
Negative predictive value (NPV) = TN/(TN + FN)
Positive likelihood ratio (LR+) = sensitivity/(1 − specificity)
Negative likelihood ratio (LR−) = (1 − sensitivity)/specificity The term "sensitivity" as used herein refers to the proportion of subjects who have the target condition (reference standard positive) and give positive test results (TP/(TP+FN)). It shows how good the test is at detecting a disease. Sensitivity ("sens") may be within the range of 0 (0%) <sens<1 (100%) and ideally, the number of false negatives equaling zero or close to equaling zero and sensitivity equaling one (100%) or close to equaling one (100%).

The term "specificity" as used herein refers to the proportion of subjects without the target condition (reference standard negative) and give negative test results (TN/(TN+FP)). It shows how good the test is at identifying normal (negative) condition. Specificity ("spec") may be within the range of 0 (0%)<spec<1 (100%) and ideally, the number of false positives equaling zero or close to equaling zero and specificity equaling one (100%) or close to equaling one (100%).

The term "accuracy" as used herein refers to the proportion of true results, either true positive or true negative, in a population. It measures the degree of veracity of a screening test on a condition, i.e., how correct is the determination and exclusion of a given condition (TN+TP)/(TN+TP+FN+FP). Accuracy ("acc") may be within the range of 0 (0%)<acc<1 (100%) and ideally, the number of false positives equaling zero or close to equaling zero and accuracy equaling one (100%) or close to equaling one (100%).

The term "Receiver Operating Characteristic (ROC) curves" as used herein refers to a graphical plot that illustrates the performance of a binary classifier system as its discrimination threshold is varied. The curve is created by plotting the true positive rate against the false positive rate at various threshold settings. The true positive rate is also known as sensitivity. The false positive rate is calculated as 1−specificity. The ROC curve is thus a way of graphically displaying the true positive rate versus the false positive rate (sensitivity vs (1−specificity)) across a range of cut-offs and of selecting the optimal cut-off for clinical use. Accuracy expressed as the area under the ROC curve (AUC) provides a useful parameter for comparing test performance. An AUC approaching 1 indicates that the test is highly sensitive as well as highly specific whereas an AUC approaching 0.5 indicates that the test is neither sensitive nor specific. In general, a test is considered to be a suitable discriminator if the AUC is from 0.6 to 0.75, to have high discrimination capacity if the AUC is from 0.75 to 0.9 and to be an excellent discriminator if the AUC is from 0.9 to 1. For further details see for instance, Zweig M R and Campbell G, Clinical Chemistry 1993; 39:561-577 or Greiner et al. Preventive Veterinary Medicine 2000; 45:23-41.

The term "significant" or "statistically significant" when referring to differences between the test sample and the control or reference sample, relates to the condition when using the appropriate statistical analysis the probability of the groups being the same is less than 5%, e.g. p<0.05. In other words, the probability of obtaining the same results on a completely random basis is less than 5 out of 100 attempts. A person skilled in the art will know how to choose the appropriate statistical analysis. Typically, the appropriate statistical analysis is determined based on whether the variable under study has a normal distribution, for instance by using the test of Kolmogorov-Smirnov and on whether there is homoscedasticity, which is determined for instance with the Levene test. Preferably, in those cases where there is a normal distribution and homoscedasticity, a parametric model such as t-test or ANOVA test is used; and where at least one of these two requirements is not accomplished then a non-parametric model such as Mann-Whitney U test or Kruskal-Wallis test is generally used.

The term "Inflammatory bowel disease (IBD)" as used herein refers to a group of idiopathic chronic inflammatory intestinal conditions. The two main disease categories the term covers are Crohn's disease (CD) and ulcerative colitis (UC), with both overlapping and distinct clinical and pathological features. The diagnosis of IBD requires a comprehensive physical examination and a review of the patient's history. Various tests, including blood tests, stool examination, endoscopy, biopsies, and imaging studies help exclude other causes and confirm the diagnosis. (World Gastroenterology Organisation Global Guidelines, Inflammatory bowel disease: a global perspective, June 2009; and Silverberg et al., Can J Gastroenterol. 2005, 19 Suppl A:5-36). With an increasing understanding of epidemiology and genetics of IBD, it has become evident to clinicians that UC and CD may actually represent several forms of IBD. Thus, the term "IBD" as used herein includes phenotypes thereof.

The term "IBD phenotypes" as used herein includes diseases or disorders such as CD, UC, indeterminate colitis, inflammatory bowel disease type unclassified (IBDU), pouchitis, microscopic colitis, diverticulitis (Mowat et al., Gut 2011, 1-37; Geboes et al., J Clin Pathol 2005; 58:1133-1134; Cheifetz A, and Itzkowitz S., J Clin Gastroenterol. 2004 May-June; 38(5 Suppl 1):S44-50). It further includes subtypes within an IBD disease or disorder. CD subtypes are for instance those defined by the Montreal classification, wherein CD is classified according to age at diagnosis, location and/or behavior. UC subtypes can be also those defined by the Montreal classification, wherein UC is classified according to disease extend and/or disease severity (World Gastroenterology Organisation Global Guidelines, Inflammatory bowel disease: a global perspective, June 2009; and Silverberg et al., Can J Gastroenterol. 2005, 19 Suppl A:5-36).

The term "indeterminate colitis (IC)" as used herein refers to those cases of chronic IBD without characteristic features of either UC or CD in a colectomy specimen (Silverberg et al., Can J Gastroenterol. 2005, 19 Suppl A:5-36; Satsangi et al., Gut 2006; 55, 749-753).

The term "inflammatory bowel disease type unclassified (IBDU)" as used herein refers to those cases wherein there is evidence on clinical and endoscopic grounds for chronic inflammatory bowel disease affecting the colon, without small bowel involvement and there is no histological or other evidence to establish either CD or UC, wherein infection has been ruled out (Satsangi et al., Gut 2006; 55, 749-753).

The term "diagnostic test" as used herein refers to a test which determines the presence or absence of a disease when a subject shows signs or symptoms of the disease. The test could be used to suggest or ruled out the disease or phenotype. The term diagnosis may include the differential diagnosis.

The term "screening test" as used herein refers to a test which identifies asymptomatic individuals who may have the disease and it is used for early detection of the disease. The test could be used to suspect the presence of the disease or phenotype.

The term "test for monitoring progression" as used herein for IBD refers to a test which determines whether the disease has been extended to other areas of the intestine, for instance monitoring whether the disease has progressed in a patient from I-CD (CD with ileal location) to IC-CD wherein the disease has been extended also to the colon.

The term "efficacy of a treatment" as used herein refers to the degree to which a treatment accomplishes the desired or projected outcomes, for instance the ability of a drug to achieve the desired effect.

The term "treatment" encompasses both a prophylactic or therapeutic treatment. The term "therapeutic treatment" or "therapy" as used herein refers to bringing a body from a pathological state or disease back to its normal, healthy state. The term "prophylactic treatment" as used herein refers to preventing a pathological state.

The term "probe" as used herein refers to synthetic or biologically produced nucleic acids, between 10 and 285 base pairs in length which contain specific nucleotide sequences that allow specific and preferential hybridization under predetermined conditions to target nucleic acid sequences, and optionally contain a moiety for detection or for enhancing assay performance. A minimum of ten nucleotides is generally necessary in order to statistically obtain specificity and to form stable hybridization products, and a maximum of 285 nucleotides generally represents an upper limit for length in which reaction parameters can be easily adjusted to determine mismatched sequences and preferential hybridization. Probes may optionally contain certain constituents that contribute to their proper or optimal functioning under certain assay conditions. For example, probes may be modified to improve their resistance to nuclease degradation (e.g., by end capping), to carry detection ligands (e.g., fluorescein) or to facilitate their capture onto a solid support (e.g., poly-deoxyadenosine "tails").

The term "primers" as used herein refers to oligonucleotides that can be used in an amplification method, such as a polymerase chain reaction ("PCR"), to amplify a nucleotide sequence. Primers are designed based on the polynucleotide sequence of a particular target sequence, e.g., one specific 16S rDNA sequence. Design and validation of primers and probes is well known in the art. For quantitative real-time PCR methods, see for instance Rodriguez A et al. (Methods Mol Biol., 2015, 1275:31-56).

The term "specific" as used herein means that a nucleotide sequence will hybridize to/amplify a predetermined target sequence and will not substantially hybridize to/amplify a non-target sequence under the assay conditions, generally stringent conditions are used.

The term "hybridization" as used herein refers to a process by which, under predetermined reaction conditions, two partially or completely complementary strands of nucleic acid are allowed to come together in an antiparallel fashion to form a double-stranded nucleic acid with specific and stable hydrogen bonds, following explicit rules pertaining to which nucleic acid bases may pair with one another.

The term "substantial hybridization" means that the amount of hybridization observed will be such that one observing the results would consider the result positive with respect to hybridization data in positive and negative controls. Data which is considered "background noise" is not substantial hybridization.

The term "stringent hybridization conditions" means approximately 35° C. to 65° C. in a salt solution of approximately 0.9 molar NaCl. Stringency may also be governed by such reaction parameters as the concentration and type of ionic species present in the hybridization solution, the types and concentrations of denaturing agents present, and the temperature of hybridization. Generally as hybridization conditions become more stringent, longer probes are preferred if stable hybrids are to be formed. As a rule, the stringency of the conditions under which hybridization is to take place will dictate certain characteristics of the preferred probes to be employed.

The term "identity" as used herein refers to an exact nucleotide-to-nucleotide or amino acid to amino acid correspondence of two polynucleotides or polypeptide sequences, respectively. Two or more sequences (polynucleotide or amino acid) can be compared by determining their "percent identity". The "percent identity" of two sequences, whether nucleic acid or amino acid sequences, is the number of exact matches between two aligned sequences divided by the length of the shorter sequence and multiplied by 100. Suitable programs for calculating the percent identity or similarity between sequences are well known in the art, such as the NCBI BLAST program, used for example with default parameters (http://www.ncbi.nlm.gov/cgi-bin/BLAST).

The term "kit" or "testing kit" denotes combinations of reagents and adjuvants required for an analysis. Although a test kit consists in most cases of several units, one-piece analysis elements are also available, which must likewise be regarded as testing kits.

A Method for Determining the Abundance of *Faecalibacterium Prausnitzii* PHGI and/or PHGII Members In a first aspect, the invention relates to an in vitro method for determining the abundance of *Faecalibacterium prausnitzii* phylogroup I members (PHGI) and/or of *Faecalibacterium prausnitzii* phylogroup II members (PHGII) in an intestinal sample from a subject; wherein PHGI abundance determination comprises the use of a primer and/or probe with sequence SEQ ID NO: 3 or a sequence with at least 75% identity thereof; and wherein PHGII abundance determination comprises the use of a primer and/or a probe with sequence SEQ ID NO: 4 or a sequence with at least 75% identity thereof.

*Faecalibacterium* is a new genus created by Duncan et al. (Duncan et al., Int J Syst Evol Microbiol. 2002; 52, 2141-2146) with the following description: *Faecalibacterium* (Fae.ca.li.bac.te«ri.um. L. adj. *faecalis* pertaining to feces; Gr. dim. n. bakterion a small rod; N.L. neut. n. *Faecalibacterium* rod from feces, as this bacterium is present in high numbers in feces in the colon, its presumed habitat). Gram-negative, non-spore-forming and strictly anaerobic. The non-motile organism produces butyrate,d-lactate and formate, and utilizes acetate. Genomic DNA G-C content is 47±57 mol (as determined by thermal denaturation). The type strain, whose characteristics were reported by Cato et al. (1974), is *Faecalibacterium prausnitzii* ATCC 27768T (NCIMB 13872T). However, most of the recent studies performed on this species in the last ten years are based on strain A2-165 (DSM 17677) also described by Duncan et al. (Duncan et al., Int J Syst Evol Microbiol. 2002; 52, 2141-2146).

Two phylogroups of *F. prausnitzii* have been previously described (Lopez-Siles et al. (Appl Environ Microbiol. 2012; 78:420-428). This study analyses the phylogenetic relationship of *F. prausnitzii* isolates to other members of *Clostridium* cluster IV based on 16S rRNA gene sequences and defines for the first time two phylogroups within *F. prausnitzii* species (FIG. 1), specifically it defines two branches within the Ruminococcaceae family with >97% sequence identity. These include five sequences reported previously for the isolates M21/2, ATCC 27766, and ATCC 27768 (belonging to PHGI) and A2-165 and L2-6 (belonging to PHGII).

In order to simultaneously quantify both *F. prausnitzii* phylogroups, it was developed a qPCR assay comprising the use of a unique pair of species-specific primers for 16S rRNA gene of *F. prausnitzii* and two hydrolysis probes targeting each *F. prausnitzii* phylogroup which were designed and optimized by the inventors. The oligonucleotides used in this study are shown in Table 15, see the Examples. The primers and probes used for the quantification of *F. prausnitzii* phylogroups have been newly designed whereas those for total *F. prausnitzii* were previously disclosed in Lopez-Siles et al., International Journal of Medical Microbiology 2014, 304:464-475.

The oligonucleotides recited in Table 15 are referred throughout the specification as SEQ ID NO: 1 to SEQ ID NO: 16 as shown in Table 2 below:

Design

Sequences of the 16S rRNA gene from *F. prausnitzii* and from closely related Ruminococcaceae were recovered from GenBank (Table 14, see the Examples) and aligned using Clustal W software to obtain the *F. prausnitzii* 16S rRNA gene, PHGI 16S rRNA gene and PHGII 16S rRNA gene, respective consensus sequences. Both primers and hydrolysis probes were manually designed from these consensus sequences and optimized.

In Silico Validation

Coverage was determined in silico using TestPrime™ against sequences in the SILVA database (the SILVA Probe Match and Evaluation Tool—TestProbe 3.0, http://www.arb-silva.de/search/testprobe/). TestPrime™ allows evaluating the performance of primer pairs by running an in silico PCR on the SILVA databases. From the results of the PCR, TestPrime computes coverages for each taxonomic group in all of the taxonomies offered by SILVA.

SILVA is a database which includes sequences of the 16S rRNA gene of all the *Faecalibacterium* sp. recovered through molecular methods by different studies. The designed primers were tested and targeted 74.85% of the of the 16S rRNA gene of *Faecalibacterium* sp. sequences in this dataset.

Accordingly, in a particular embodiment of the in vitro method for determining the abundance of *Faecalibacterium prausnitzii* phylogroup I members (PHGI) and/or of *Faecalibacterium prausnitzii* phylogroup II members (PHGII) of the invention, said primers enable the amplification of at least 60%, at least 65%, at least 70%, preferably around 75%

TABLE 2

Oligonucleotides for *F. prausnitzii* and the phylogroups thereof, total bacteria, *E. coli* and internal amplification control (IAC).

| | |
|---|---|
| SEQ ID NO: 1 (Fpra 136F) | CTCAAAGAGGGGGACAACAGTT |
| SEQ ID NO: 2 (Fpra 232R) | GCCATCTCAAAGCGGATTG |
| SEQ ID NO: 3 (PHG1 180PR oligont) | TAAGCCCACGACCCGGCATCG |
| SEQ ID NO: 4 (PHG2 180PR oligont) | TAAGCCCACRGCTCGGCATC |
| SEQ ID NO: 5 (Fpra 428 F) | TGTAAACTCCTGTTGTTGAGGAAGATAA |
| SEQ ID NO: 6 (Fpra 583 R) | GCGCTCCCTTTACACCCA |
| SEQ ID NO: 7 (Fpra 493 PR oligont) | CAAGGAAGTGACGGCTAACTACGTGCCAG |
| SEQ ID NO: 8 (F_Bact 1369) | CGGTGAATACGTTCCCGG |
| SEQ ID NO: 9 (R_Prok_1492) | TACGGCTACCTTGTTACGACTT |
| SEQ ID NO: 10 (P_TM_1389F oligont) | CTTGTACACACCGCCCGTC |
| SEQ ID NO: 11 (IAC F) | TACGGATGAGGAGGACAAAGGA |
| SEQ ID NO: 12 (IAC R) | CACTTCGCTCTGATCCATTGG |
| SEQ ID NO: 13 (IAC PR oligont) | CGCCGCTATGGGCATCGCA |
| SEQ ID NO: 14 (*e. coli* 395 F) | CATGCCGCGTGTATGAAGAA |
| SEQ ID NO: 15 (*e. coli* 490 R) | CGGGTAACGTCAATGAGCAAA |
| SEQ ID NO: 16 (*e. coli* 437 PR) | TATTAACTTTACTCCCTTCCTCCCCGCTGAA | of the known 16S rRNA gene of *Faecalibacterium* sp. In a particular embodiment the known 16S rRNA gene of *Faecalibacterium* sp are those included in the SILVA database at the time of filing the application.

Since SILVA database includes only sequences from 16S rRNA gene but there may be other parts of the genomes of bacterial species which can match with the primers and cause false positive results, the primers specificity was further tested by using Nucleotide BLAST (http://blast.ncbi.nlm.nih.gov/Blast.cgi?PROGRAM=blastn&PAGE_TYPE=BlastSearch&LINK_LOC=blasthome, NCBI BLAST: a better web interface. Johnson M et al. Nucleic Acids Res. 2008, 1; 36(Web Server issue): W5-9), limiting the search to "bacteria NOT uncultured". The results obtained confirmed specificity for *Faecalibacterium* sp.

In Vitro Validation

Furthermore, inclusivity/exclusivity tests in vitro were carried out. The primers showed to be able to specifically amplify the 16S rRNA gene of the 9 isolates available for *F. prausnitzii* and the probes were specific for each of the phylogroups. In addition, the same test was performed with no target species DNA (exclusivity test) and specificity confirmed (Table 16, see the Examples).

*Faecalibacterium prausnitzii* phylogroup I members are those bacterial sequences which 16S rRNA gene matched with the Phylogroup I probe (SEQ ID NO:3), this includes the 5 sequences used for probe design shown in Table 3 and the 1191 sequences matched in the SILVA database, which accession numbers are provided in Table 4 (it is understood that the sequences listed in Table 3 also matched in the SILVA database but have not been repeated herein). Thus, Phylogroup I probe (SEQ ID NO:3) was shown to hybridize specifically with a total of 1196 16S rRNA gene sequences.

TABLE 3

Accession number, phylogeny, organism name and length (bp) of the 16S rRNA gene bacterial sequences used as basis for the design of with the PHGI specific probe.

| Accession number | Phylogeny | Organism Name | length (bp) |
|---|---|---|---|
| AJ413954 | Bacteria; Firmicutes; Clostridia; Clostridiales; Ruminococcaceae; *Faecalibacterium*; | *Faecalibacterium prausnitzii* 16S rRNA gene, strain ATCC 27768 | 1462 |
| X85022 | Bacteria; Firmicutes; Clostridia; Clostridiales; Ruminococcaceae; *Faecalibacterium*; | *F. prausnitzii* DNA for 16S ribosomal RNA, strain ATCC 27766 | 1499 |
| AY305307 | Bacteria; Firmicutes; Clostridia; Clostridiales; Ruminococcaceae; *Faecalibacterium*; | Butyrate-producing bacterium M21/2 16S ribosomal RNA gene | 1433 |
| HQ457025 | Bacteria; Firmicutes; Clostridia; Clostridiales; Ruminococcaceae; *Faecalibacterium*; | *F. prausnitzii* strain S4L/4 16S ribosomal RNA gene | 1483 |
| HQ457024 | Bacteria; Firmicutes; Clostridia; Clostridiales; Ruminococcaceae; *Faecalibacterium*; | *F. prausnitzii* strain S3L/3 16S ribosomal RNA gene | 1469 |

TABLE 4

Accession numbers of the 1191 sequences hybridizing specifically with the PHGI specific probe in the SILVA database under default conditions.

| | | | | | | |
|---|---|---|---|---|---|---|
| AF132246 | AY977820 | AY979936 | AY984249 | DQ796476 | DQ797641 | DQ798487 |
| AJ408973 | AY977841 | AY980001 | AY984354 | DQ796525 | DQ797649 | DQ798541 |
| | AY978015 | AY980058 | AY984361 | DQ796571 | DQ797651 | DQ798562 |
| AM697227 | AY978111 | AY980091 | AY984496 | DQ796592 | DQ797657 | DQ798615 |
| AY850440 | AY978217 | AY980107 | AY984560 | DQ796696 | DQ797659 | DQ798647 |
| AY916168 | AY978256 | AY980109 | AY984598 | DQ796726 | DQ797661 | DQ798679 |
| AY916280 | AY978301 | AY980155 | AY984640 | DQ796734 | DQ797696 | DQ799921 |
| AY916290 | AY978311 | AY980177 | AY984652 | DQ796787 | DQ797712 | DQ799935 |
| AY974822 | AY978335 | AY980714 | AY984722 | DQ796854 | DQ797715 | DQ799950 |
| AY974935 | AY978411 | AY981125 | AY984772 | DQ796890 | DQ797719 | DQ799967 |
| AY975090 | AY978468 | AY981136 | AY984773 | DQ796971 | DQ797730 | DQ800008 |
| AY975146 | AY978536 | AY981192 | AY984841 | DQ796987 | DQ797737 | DQ800043 |
| AY975182 | AY978548 | AY981226 | AY984871 | DQ796999 | DQ797747 | DQ800115 |
| AY975217 | AY978554 | AY981236 | AY984874 | DQ797013 | DQ797750 | DQ800745 |
| AY975290 | AY978582 | AY981421 | AY984965 | DQ797018 | DQ797754 | DQ800932 |
| AY975353 | AY978660 | AY981477 | AY984996 | DQ797073 | DQ797757 | DQ801041 |
| AY975391 | AY978691 | AY981479 | AY985061 | DQ797107 | DQ797764 | DQ801054 |
| AY975464 | AY978708 | AY981631 | AY985082 | DQ797128 | DQ797776 | DQ801057 |
| AY975498 | AY978711 | AY981706 | AY985087 | DQ797136 | DQ797784 | DQ801077 |
| AY975558 | AY978734 | AY981710 | AY985131 | DQ797226 | DQ797785 | DQ801105 |
| AY975568 | AY978761 | AY981719 | AY985159 | DQ797231 | DQ797787 | DQ801112 |
| AY975691 | AY978779 | AY981750 | AY986127 | DQ797271 | DQ797803 | DQ801271 |
| AY975720 | AY978813 | AY981882 | BAAX01000032 | DQ797285 | DQ797806 | DQ801294 |
| AY975737 | AY978857 | AY981951 | BAAX01000131 | DQ797286 | DQ797810 | DQ801297 |
| AY975989 | AY978859 | AY982516 | DQ326015 | DQ797302 | DQ797835 | DQ801314 |
| AY976012 | AY978873 | AY982567 | DQ326327 | DQ797304 | DQ797836 | DQ801384 |
| AY976301 | AY978881 | AY982581 | DQ441336 | DQ797310 | DQ797846 | DQ801428 |
| AY976471 | AY978892 | AY982583 | DQ795780 | DQ797365 | DQ797847 | DQ801446 |
| AY976476 | AY978922 | AY982651 | DQ795835 | DQ797376 | DQ797871 | DQ801490 |
| AY976559 | AY978977 | AY982665 | DQ795862 | DQ797385 | DQ797908 | DQ801519 |
| AY976602 | AY979070 | AY982709 | DQ795878 | DQ797421 | DQ797931 | DQ801541 |
| AY976609 | AY979084 | AY982784 | DQ795925 | DQ797444 | DQ797964 | DQ801571 |
| AY976627 | AY979116 | AY983029 | DQ795954 | DQ797452 | DQ798075 | DQ801628 |

TABLE 4-continued

Accession numbers of the 1191 sequences hybridizing specifically with the PHGI specific probe in the SILVA database under default conditions.

| | | | | | | |
|---|---|---|---|---|---|---|
| AY976645 | AY979169 | AY983068 | DQ796034 | DQ797455 | DQ798141 | DQ801695 |
| AY976672 | AY979176 | AY983243 | DQ796041 | DQ797457 | DQ798149 | DQ801714 |
| AY976683 | AY979191 | AY983314 | DQ796042 | DQ797467 | DQ798184 | DQ801762 |
| AY976928 | AY979237 | AY983329 | DQ796058 | DQ797475 | DQ798223 | DQ801846 |
| AY977016 | AY979240 | AY983449 | DQ796134 | DQ797532 | DQ798226 | DQ801880 |
| AY977109 | AY979246 | AY983558 | DQ796201 | DQ797534 | DQ798239 | DQ801891 |
| AY977231 | AY979261 | AY983608 | DQ796294 | DQ797590 | DQ798258 | DQ802184 |
| AY977301 | AY979342 | AY983619 | DQ796359 | DQ797594 | DQ798278 | DQ802252 |
| AY977388 | AY979460 | AY983735 | DQ796372 | DQ797602 | DQ798316 | DQ802262 |
| AY977511 | AY979747 | AY983849 | DQ796384 | DQ797617 | DQ798337 | DQ802304 |
| AY977557 | AY979905 | AY984204 | DQ796459 | DQ797630 | DQ798404 | DQ802307 |
| DQ802315 | DQ805664 | DQ808693 | DQ824246 | DQ825077 | EF401116 | EF402793 |
| DQ802317 | DQ805679 | DQ808727 | DQ824247 | DQ825081 | EF401175 | EF402812 |
| DQ802330 | DQ805730 | DQ808739 | DQ824255 | DQ825084 | EF401184 | EF402860 |
| DQ802345 | DQ805736 | DQ808845 | DQ824261 | DQ825089 | EF401200 | EF402930 |
| DQ802349 | DQ805738 | DQ808853 | DQ824266 | DQ825095 | EF401203 | EF402973 |
| DQ802351 | DQ805771 | DQ808900 | DQ824302 | DQ825099 | EF401227 | EF402982 |
| DQ802376 | DQ805802 | DQ808935 | DQ824320 | DQ825109 | EF401283 | EF403019 |
| DQ802388 | DQ805849 | DQ808995 | DQ824327 | DQ825111 | EF401312 | EF403035 |
| DQ802390 | DQ805961 | DQ809023 | DQ824365 | DQ825119 | EF401374 | EF403087 |
| DQ802416 | DQ806097 | DQ809024 | DQ824379 | DQ825132 | EF401433 | EF403090 |
| DQ802430 | DQ806428 | DQ809064 | DQ824403 | DQ825136 | EF401490 | EF403170 |
| DQ802477 | DQ806552 | DQ809074 | DQ824439 | DQ825147 | EF401498 | EF403202 |
| DQ802537 | DQ806559 | DQ809087 | DQ824456 | DQ825203 | EF401537 | EF403224 |
| DQ802546 | DQ806634 | DQ809136 | DQ824459 | DQ825233 | EF401593 | EF403240 |
| DQ802574 | DQ806635 | DQ809289 | DQ824481 | DQ825244 | EF401601 | EF403246 |
| DQ802578 | DQ806659 | DQ809290 | DQ824509 | DQ825245 | EF401643 | EF403251 |
| DQ802590 | DQ806688 | DQ809292 | DQ824772 | DQ825246 | EF401659 | EF403293 |
| DQ802658 | DQ806704 | DQ809295 | DQ824800 | DQ825251 | EF401719 | EF403314 |
| DQ802743 | DQ806714 | DQ809805 | DQ824810 | DQ825252 | EF401740 | EF403326 |
| DQ802764 | DQ806745 | DQ809860 | DQ824817 | DQ825253 | EF401748 | EF403370 |
| DQ802816 | DQ806778 | DQ809892 | DQ824822 | DQ825261 | EF401771 | EF403380 |
| DQ803339 | DQ806864 | DQ810047 | DQ824824 | DQ825280 | EF401840 | EF403455 |
| DQ804511 | DQ806868 | DQ810166 | DQ824825 | DQ825281 | EF401888 | EF403457 |
| DQ804536 | DQ806951 | DQ823651 | DQ824829 | DQ825294 | EF401979 | EF403464 |
| DQ804556 | DQ807292 | DQ823661 | DQ824850 | DQ825301 | EF401998 | EF403469 |
| DQ804564 | DQ807305 | DQ823664 | DQ824858 | DQ825309 | EF402038 | EF403552 |
| DQ804568 | DQ807378 | DQ823694 | DQ824865 | DQ825311 | EF402117 | EF403588 |
| DQ804597 | DQ807383 | DQ823731 | DQ824877 | DQ825322 | EF402124 | EF403703 |
| DQ804616 | DQ807392 | DQ823803 | DQ824893 | DQ825328 | EF402129 | EF403716 |
| DQ804632 | DQ807458 | DQ823824 | DQ824895 | DQ825336 | EF402161 | EF403721 |
| DQ804660 | DQ808476 | DQ823827 | DQ824921 | DQ825339 | EF402189 | EF403761 |
| DQ804733 | DQ808489 | DQ823860 | DQ824938 | DQ904651 | EF402250 | EF403762 |
| DQ804758 | DQ808519 | DQ823915 | DQ824947 | DQ904678 | EF402359 | EF403845 |
| DQ804764 | DQ808522 | DQ823917 | DQ824962 | DQ904701 | EF402414 | EF403882 |
| DQ804767 | DQ808530 | DQ823929 | DQ824972 | DQ904876 | EF402460 | EF403887 |
| DQ804799 | DQ808555 | DQ823958 | DQ824977 | EF400765 | EF402461 | EF404000 |
| DQ804807 | DQ808580 | DQ823982 | DQ824979 | EF400784 | EF402470 | EF404029 |
| DQ805089 | DQ808593 | DQ824007 | DQ824994 | EF400802 | EF402473 | EF404036 |
| DQ805139 | DQ808630 | DQ824020 | DQ825019 | EF400835 | EF402530 | EF404121 |
| DQ805142 | DQ808646 | DQ824084 | DQ825025 | EF400958 | EF402548 | EF404156 |
| DQ805143 | DQ808649 | DQ824087 | DQ825028 | EF400974 | EF402552 | EF404228 |
| DQ805180 | DQ808664 | DQ824173 | DQ825053 | EF401005 | EF402620 | EF404234 |
| DQ805268 | DQ808673 | DQ824217 | DQ825062 | EF401023 | EF402758 | EF404284 |
| DQ805429 | DQ808680 | DQ824229 | DQ825068 | EF401093 | EF402771 | EF404288 |
| EF404298 | EU762904 | FJ363528 | FJ369154 | FJ504501 | FJ509240 | FJ512284 |
| EF404352 | EU762928 | FJ363552 | FJ370804 | FJ504518 | FJ509248 | FJ512285 |
| EF404375 | EU763004 | FJ363717 | FJ371152 | FJ504586 | FJ509495 | FJ512286 |
| EF404442 | EU763044 | FJ363882 | FJ371164 | FJ504593 | FJ509496 | FJ512287 |
| EF404447 | EU763072 | FJ363897 | FJ371170 | FJ504619 | FJ509506 | FJ512288 |
| EF404456 | EU763100 | FJ364270 | FJ371179 | FJ504629 | FJ509507 | FJ512289 |
| EF404497 | EU763157 | FJ364354 | FJ371203 | FJ504633 | FJ509850 | FJ512290 |
| EF404505 | EU764022 | FJ364498 | FJ371234 | FJ504698 | FJ510190 | FJ512291 |
| EF404521 | EU765786 | FJ364535 | FJ371245 | FJ504713 | FJ510191 | FJ512292 |
| EF404538 | EU766096 | FJ364947 | FJ371389 | FJ504723 | FJ510192 | FJ512293 |
| EF404576 | EU767077 | FJ364952 | FJ371429 | FJ504729 | FJ510193 | FJ512294 |
| EF404583 | EU767203 | FJ364960 | FJ371718 | FJ504796 | FJ510514 | FJ512295 |
| EF404591 | EU767429 | FJ365109 | FJ371731 | FJ504816 | FJ510518 | FJ512296 |
| EF404617 | EU768089 | FJ365124 | FJ371732 | FJ506821 | FJ510519 | FJ512297 |
| EF404622 | EU768103 | FJ365130 | FJ371746 | FJ506893 | FJ510525 | FJ512298 |
| EF404629 | EU768453 | FJ365144 | FJ371786 | FJ506907 | FJ510526 | FJ512299 |
| EF404652 | EU768534 | FJ365238 | FJ371790 | FJ506974 | FJ510528 | FJ512300 |
| EF404689 | EU774102 | FJ366075 | FJ371792 | FJ507033 | FJ510529 | FJ512301 |
| EF404698 | EU774128 | FJ366221 | FJ371813 | FJ507085 | FJ510530 | FJ512302 |
| EF404759 | EU774255 | FJ366894 | FJ371860 | FJ507130 | FJ510531 | FJ512303 |
| EF404787 | EU775393 | FJ366936 | FJ371873 | FJ507672 | FJ510532 | FJ512304 |
| EF404868 | EU777345 | FJ366953 | FJ371913 | FJ507673 | FJ510533 | FJ512305 |

TABLE 4-continued

Accession numbers of the 1191 sequences hybridizing specifically with the PHGI specific probe in the SILVA database under default conditions.

| | | | | | | |
|---|---|---|---|---|---|---|
| EF404872 | EU778127 | FJ366977 | FJ371915 | FJ507675 | FJ510546 | FJ512343 |
| EF404886 | EU778130 | FJ367026 | FJ371948 | FJ507676 | FJ510547 | FJ512344 |
| EF404958 | EU778240 | FJ367036 | FJ372236 | FJ507887 | FJ510548 | FJ512888 |
| EF404962 | EU778287 | FJ367066 | FJ372239 | FJ507888 | FJ510860 | FJ512889 |
| EF404970 | EU778343 | FJ367076 | FJ372286 | FJ507889 | FJ510863 | FJ512891 |
| EF404992 | FJ362670 | FJ367117 | FJ503869 | FJ507890 | FJ510864 | FJ512892 |
| EF405005 | FJ362673 | FJ367178 | FJ504079 | FJ507898 | FJ510865 | FJ512893 |
| EF405017 | FJ362734 | FJ367407 | FJ504238 | FJ507899 | FJ510866 | FJ512894 |
| EF405058 | FJ362750 | FJ367413 | FJ504239 | FJ507900 | FJ510867 | FJ512895 |
| EF405176 | FJ362806 | FJ367496 | FJ504269 | FJ508226 | FJ510868 | FJ512896 |
| EF405256 | FJ362812 | FJ367506 | FJ504294 | FJ508617 | FJ510872 | FJ512897 |
| EF405259 | FJ362819 | FJ368253 | FJ504338 | FJ508618 | FJ510873 | FJ512898 |
| EF405285 | FJ362867 | FJ368294 | FJ504351 | FJ508619 | FJ510874 | FJ512900 |
| EF405286 | FJ362934 | FJ368328 | FJ504352 | FJ508620 | FJ510875 | FJ512901 |
| EF405292 | FJ362977 | FJ368355 | FJ504358 | FJ508621 | FJ511314 | FJ512903 |
| EF405327 | FJ363063 | FJ368365 | FJ504360 | FJ508622 | FJ511315 | FJ512904 |
| EF405374 | FJ363216 | FJ368366 | FJ504362 | FJ508623 | FJ511316 | FJ512905 |
| EF405465 | FJ363272 | FJ368368 | FJ504378 | FJ508929 | FJ511318 | FJ673014 |
| EF405490 | FJ363301 | FJ368390 | FJ504379 | FJ508930 | FJ511823 | FJ673121 |
| EU462466 | FJ363322 | FJ368396 | FJ504383 | FJ508931 | FJ511824 | FJ673295 |
| EU761801 | FJ363461 | FJ368404 | FJ504387 | FJ508932 | FJ512282 | FJ673582 |
| EU762168 | FJ363490 | FJ368453 | FJ504467 | FJ508954 | FJ512283 | FJ673757 |
| FJ673815 | GQ448269 | HQ773650 | HQ778925 | HQ790769 | HQ810774 | JQ183352 |
| FJ675804 | GQ448311 | HQ773659 | HQ780359 | HQ790907 | HQ810792 | JQ183361 |
| FJ677025 | GQ448314 | HQ773793 | HQ780655 | HQ791073 | HQ810990 | JQ185070 |
| FJ677540 | GQ448356 | HQ774044 | HQ780752 | HQ791510 | HQ812306 | JQ185237 |
| FJ677745 | GQ448360 | HQ774190 | HQ780833 | HQ791809 | HQ812417 | JQ186576 |
| FJ678131 | GQ448933 | HQ774867 | HQ780901 | HQ792145 | HQ812781 | JQ186663 |
| FJ678272 | GQ448935 | HQ774908 | HQ781001 | HQ792597 | HQ812874 | JQ186829 |
| FJ678292 | GQ492289 | HQ775044 | HQ781061 | HQ792702 | HQ812904 | JQ186959 |
| FJ678301 | GQ896631 | HQ775050 | HQ781201 | HQ792748 | HQ813593 | JQ186967 |
| FJ678584 | GQ896641 | HQ775094 | HQ781254 | HQ792749 | HQ813618 | JQ186970 |
| FJ678825 | GQ896844 | HQ775197 | HQ781305 | HQ792781 | HQ813736 | JQ189296 |
| FJ679029 | GQ896855 | HQ775678 | HQ781340 | HQ792877 | HQ813981 | JQ190076 |
| FJ679163 | GQ896912 | HQ775978 | HQ781412 | HQ792891 | HQ815495 | JQ190310 |
| FJ679406 | GQ897054 | HQ776013 | HQ781432 | HQ792898 | HQ816070 | JQ190464 |
| FJ679719 | GQ897060 | HQ776300 | HQ781543 | HQ792944 | HQ816084 | JQ190600 |
| FJ679826 | GQ897108 | HQ776346 | HQ782498 | HQ792951 | HQ816102 | JQ941034 |
| FJ679975 | GQ897135 | HQ776618 | HQ783938 | HQ792995 | HQ816209 | KF079369 |
| FJ680543 | GQ897267 | HQ777044 | HQ784200 | HQ793834 | HQ816240 | KF080223 |
| FJ682837 | GQ897282 | HQ777084 | HQ784870 | HQ793984 | HQ819688 | KF083506 |
| FJ682920 | GQ898058 | HQ777252 | HQ784924 | HQ794481 | HQ819689 | KF088388 |
| FJ683068 | GQ898130 | HQ777343 | HQ785169 | HQ794501 | HQ819924 | KF098066 |
| FJ683129 | GQ898135 | HQ777348 | HQ785309 | HQ794558 | JF030154 | KF101388 |
| FJ683190 | GQ898417 | HQ777372 | HQ785926 | HQ794613 | JF030218 | KF841632 |
| FJ683291 | GQ898476 | HQ777421 | HQ786337 | HQ794617 | JF118323 | KF841685 |
| FJ683292 | GQ898574 | HQ777422 | HQ786925 | HQ798175 | JF124766 | KF841718 |
| FJ683324 | GQ898622 | HQ777471 | HQ787097 | HQ798180 | JF135842 | KF841733 |
| FJ683435 | HM262976 | HQ777476 | HQ787112 | HQ798362 | JF159724 | KF841834 |
| FJ683771 | HM272035 | HQ777484 | HQ787194 | HQ805740 | JF160987 | KF841916 |
| FJ683934 | HM343866 | HQ777544 | HQ787204 | HQ805865 | JF161120 | KF841925 |
| FJ685187 | | HQ777554 | HQ787293 | HQ806134 | JF161374 | KF841935 |
| FM873803 | HQ751556 | HQ777570 | HQ787414 | HQ806142 | JF161478 | KF841994 |
| FM873958 | HQ759466 | HQ777587 | HQ788628 | HQ807875 | JF161700 | KF842592 |
| GQ158585 | HQ759508 | HQ777629 | HQ788644 | HQ807965 | JF162159 | KF843045 |
| GQ159565 | HQ759528 | HQ777647 | HQ788709 | HQ808038 | JF163182 | KF843344 |
| GQ159566 | HQ759703 | HQ777860 | HQ788757 | HQ808188 | JF163209 | KF843510 |
| GQ159567 | HQ765918 | HQ777870 | HQ788806 | HQ808300 | JF177473 | |
| GQ448252 | HQ766177 | HQ778076 | HQ788855 | HQ809864 | JF180334 | |
| GQ448253 | HQ766193 | HQ778126 | HQ788864 | HQ810227 | JF220917 | |
| GQ448258 | HQ773645 | HQ778920 | HQ790114 | HQ810729 | JN413782 | |

*Faecalibacterium prausnitzii* phylogroup II members are those bacterial sequences which 16S rRNA gene matched with the Phylogroup II probe (SEQ ID NO:4), this includes the 13 sequences used for probe design shown in Table 5 and the 2231 sequences matched in the SILVA database, which accession numbers are provided in Table 6 (it is understood that the sequences listed in Table 5 also matched in the SILVA database but have not been repeated herein). Thus, Phylogroup II probe (SEQ ID NO:4) was shown to hybridize specifically with a total of 2244 16S rRNA gene sequences.

TABLE 5

Accession number, phylogeny, organism name and length (bp) of the 16S rRNA gene bacterial sequences used as basis for the design of the PHGII specific probe.

| Accession number | Phylogeny | Organism Name | length (bp) |
| --- | --- | --- | --- |
| AJ270469 | Bacteria; Firmicutes; Clostridia; Clostridiales; Ruminococcaceae; *Faecalibacterium*; | Butyrate-producing bacterium A2-165 16S rRNA gene | 1466 |
| AJ270470 | Bacteria; Firmicutes; Clostridia; Clostridiales; Ruminococcaceae; *Faecalibacterium*; | Butyrate-producing bacterium L2-6 16S rRNA gene | 1464 |
| JN037415 | Bacteria; Firmicutes; Clostridia; Clostridiales; Ruminococcaceae; *Faecalibacterium*; | *F. prausnitzii* strain L2-15 16S ribosomal RNA gene | 1258 |
| JN037416 | Bacteria; Firmicutes; Clostridia; Clostridiales; Ruminococcaceae; *Faecalibacterium*; | *F. prausnitzii* strain L2-39 16S ribosomal RNA gene | 1279 |
| JN037417 | Bacteria; Firmicutes; Clostridia; Clostridiales; Ruminococcaceae; *Faecalibacterium*; | *F. prausnitzii* strain L2-61 16S ribosomal RNA gene | 1238 |
| HQ457026 | Bacteria; Firmicutes; Clostridia; Clostridiales; Ruminococcaceae; *Faecalibacterium*; | *F. prausnitzii* strain HTF-A 16S ribosomal RNA gene | 1378 |
| HQ457027 | Bacteria; Firmicutes; Clostridia; Clostridiales; Ruminococcaceae; *Faecalibacterium*; | *F. prausnitzii* strain HTF-B 16S ribosomal RNA gene | 1402 |
| HQ457028 | Bacteria; Firmicutes; Clostridia; Clostridiales; Ruminococcaceae; *Faecalibacterium*; | *F. prausnitzii* strain HTF-C 16S ribosomal RNA gene | 1424 |
| HQ457029 | Bacteria; Firmicutes; Clostridia; Clostridiales; Ruminococcaceae; *Faecalibacterium*; | *F. prausnitzii* strain HTF-E 16S ribosomal RNA gene | 1406 |
| HQ457030 | Bacteria; Firmicutes; Clostridia; Clostridiales; Ruminococcaceae; *Faecalibacterium*; | *F. prausnitzii* strain HTF-F 16S ribosomal RNA gene | 1394 |
| HQ457031 | Bacteria; Firmicutes; Clostridia; Clostridiales; Ruminococcaceae; *Faecalibacterium*; | *F. prausnitzii* strain HTF-I 16S ribosomal RNA gene | 1308 |
| HQ457032 | Bacteria; Firmicutes; Clostridia; Clostridiales; Ruminococcaceae; *Faecalibacterium*; | *F. prausnitzii* strain HTF-60C 16S ribosomal RNA gene | 1405 |
| HQ457033 | Bacteria; Firmicutes; Clostridia; Clostridiales; Ruminococcaceae; *Faecalibacterium*; | *F. prausnitzii* strain HTF-75H 16S ribosomal RNA gene | 1351 |

TABLE 6

Accession numbers of the 2231 sequences hybridizing specifically with the PHGII specific probe in the SILVA database under default conditions.

| | | | | | | |
| --- | --- | --- | --- | --- | --- | --- |
| AB506178 | AY976695 | AY978972 | AY981592 | AY984645 | DQ793377 | DQ796243 |
| AJ409008 | AY976779 | AY979066 | AY981727 | AY984702 | DQ793398 | DQ796295 |
| AM277069 | AY976925 | AY979072 | AY981781 | AY984716 | DQ793502 | DQ796342 |
| AY850522 | AY977090 | AY979089 | AY981943 | AY984864 | DQ793517 | DQ796425 |
| AY916181 | AY977105 | AY979094 | AY981990 | AY984873 | DQ793523 | DQ796434 |
| AY916214 | AY977110 | AY979105 | AY981996 | AY984975 | DQ793661 | DQ796461 |
| AY916305 | AY977165 | AY979117 | AY982015 | AY985063 | DQ793829 | DQ796604 |
| AY974954 | AY977188 | AY979138 | AY982115 | AY985128 | DQ793946 | DQ796609 |
| AY974998 | AY977264 | AY979152 | AY982232 | AY985138 | DQ794011 | DQ796660 |
| AY975016 | AY977370 | AY979205 | AY982278 | AY985161 | DQ794016 | DQ796668 |
| AY975134 | AY977419 | AY979247 | AY982342 | AY985204 | DQ794040 | DQ796704 |
| AY975187 | AY977435 | AY979345 | AY982343 | AY985588 | DQ794060 | DQ796705 |
| AY975227 | AY977468 | AY979407 | AY982473 | AY985652 | DQ794084 | DQ796725 |
| AY975313 | AY977565 | AY979484 | AY982573 | AY986013 | DQ794102 | DQ796970 |
| AY975322 | AY977588 | AY979499 | AY982780 | AY986185 | DQ794128 | DQ796982 |
| AY975331 | AY977710 | AY979529 | AY982811 | AY986192 | DQ794134 | DQ797012 |
| AY975375 | AY977724 | AY979619 | AY982822 | AY986207 | DQ794141 | DQ797025 |
| AY975402 | AY977732 | AY979852 | AY982856 | AY986232 | DQ794142 | DQ797050 |
| AY975435 | AY977749 | AY979899 | AY982906 | BAAU01000008 | DQ794171 | DQ797059 |
| AY975537 | AY977789 | AY979902 | AY983023 | BAAU01000686 | DQ794183 | DQ797106 |
| AY975603 | AY977848 | AY979928 | AY983235 | BAAX01000042 | DQ794313 | DQ797119 |
| AY975644 | AY977860 | AY980032 | AY983274 | BAAX01000205 | DQ794322 | DQ797124 |
| AY975678 | AY977915 | AY980038 | AY983342 | BAAX01000694 | DQ794455 | DQ797142 |
| AY975687 | AY977925 | AY980040 | AY983445 | BAAY01002722 | DQ794479 | DQ797160 |
| AY975701 | AY978094 | AY980124 | AY983550 | BABA01001765 | DQ794542 | DQ797178 |
| AY975782 | AY978128 | AY980135 | AY983605 | BABD01001073 | DQ794767 | DQ797182 |
| AY975853 | AY978198 | AY980137 | AY983740 | BABG01000003 | DQ794834 | DQ797191 |
| AY975872 | AY978251 | AY980139 | AY983820 | BABG01000051 | DQ794898 | DQ797216 |
| AY975906 | AY978265 | AY980164 | AY983923 | DQ325670 | DQ795019 | DQ797224 |
| AY975935 | AY978309 | AY980211 | AY984008 | DQ325799 | DQ795021 | DQ797230 |
| AY976066 | AY978313 | AY980222 | AY984038 | DQ325893 | DQ795034 | DQ797233 |
| AY976079 | AY978325 | AY980271 | AY984170 | DQ326036 | DQ795038 | DQ797289 |
| AY976086 | AY978340 | AY980273 | AY984209 | DQ326038 | DQ795063 | DQ797312 |
| AY976111 | AY978358 | AY980419 | AY984280 | DQ326054 | DQ795078 | DQ797344 |
| AY976115 | AY978424 | AY980466 | AY984282 | DQ326121 | DQ795124 | DQ797347 |

TABLE 6-continued

Accession numbers of the 2231 sequences hybridizing specifically with the PHGII specific probe in the SILVA database under default conditions.

| | | | | | | |
|---|---|---|---|---|---|---|
| AY976189 | AY978428 | AY980489 | AY984300 | DQ326221 | DQ795130 | DQ797405 |
| AY976214 | AY978438 | AY980494 | AY984306 | DQ326396 | DQ795158 | DQ797406 |
| AY976309 | AY978505 | AY980637 | AY984407 | DQ326490 | DQ795781 | DQ797409 |
| AY976318 | AY978678 | AY980716 | AY984537 | DQ469229 | DQ795787 | DQ797443 |
| AY976409 | AY978773 | AY980819 | AY984582 | DQ469240 | DQ795802 | DQ797465 |
| AY976506 | AY978829 | AY981036 | AY984597 | DQ793254 | DQ795919 | DQ797471 |
| AY976534 | AY978874 | AY981072 | AY984599 | DQ793280 | DQ795927 | DQ797485 |
| AY976564 | AY978905 | AY981164 | AY984612 | DQ793299 | DQ795984 | DQ797501 |
| AY976679 | AY978957 | AY981461 | AY984627 | DQ793306 | DQ796105 | DQ797514 |
| DQ797519 | DQ798579 | DQ800223 | DQ801698 | DQ805666 | DQ808483 | DQ823721 |
| DQ797562 | DQ798596 | DQ800234 | DQ801703 | DQ805696 | DQ808533 | DQ823885 |
| DQ797565 | DQ798617 | DQ800251 | DQ801825 | DQ805705 | DQ808548 | DQ823889 |
| DQ797593 | DQ798653 | DQ800255 | DQ801929 | DQ805707 | DQ808550 | DQ824033 |
| DQ797647 | DQ798665 | DQ800275 | DQ801940 | DQ805720 | DQ808569 | DQ824161 |
| DQ797650 | DQ798678 | DQ800345 | DQ801946 | DQ805816 | DQ808570 | DQ824923 |
| DQ797686 | DQ798699 | DQ800359 | DQ801984 | DQ805822 | DQ808585 | DQ825046 |
| DQ797720 | DQ798709 | DQ800367 | DQ801990 | DQ805837 | DQ808609 | DQ825130 |
| DQ797723 | DQ798715 | DQ800384 | DQ802009 | DQ805847 | DQ808654 | DQ825149 |
| DQ797761 | DQ798784 | DQ800387 | DQ802010 | DQ805870 | DQ808662 | DQ825174 |
| DQ797766 | DQ798785 | DQ800398 | DQ802088 | DQ805871 | DQ808677 | DQ904703 |
| DQ797832 | DQ798823 | DQ800622 | DQ802096 | DQ805908 | DQ808722 | DQ904941 |
| DQ797833 | DQ798824 | DQ800929 | DQ802109 | DQ805928 | DQ808728 | DQ904977 |
| DQ797865 | DQ798910 | DQ800956 | DQ802129 | DQ806084 | DQ808732 | DQ905073 |
| DQ797878 | DQ798997 | DQ800973 | DQ802139 | DQ806234 | DQ808762 | DQ905116 |
| DQ797892 | DQ799005 | DQ801033 | DQ802159 | DQ806272 | DQ808797 | DQ905134 |
| DQ797928 | DQ799101 | DQ801044 | DQ802161 | DQ806329 | DQ808833 | DQ905156 |
| DQ797963 | DQ799149 | DQ801056 | DQ802202 | DQ806334 | DQ808834 | DQ905174 |
| DQ797997 | DQ799182 | DQ801100 | DQ802259 | DQ806367 | DQ808850 | DQ905305 |
| DQ798009 | DQ799247 | DQ801139 | DQ802431 | DQ806371 | DQ808851 | DQ905685 |
| DQ798044 | DQ799252 | DQ801167 | DQ802488 | DQ806390 | DQ808865 | DQ905722 |
| DQ798050 | DQ799361 | DQ801193 | DQ802576 | DQ806427 | DQ808898 | DQ905741 |
| DQ798053 | DQ799388 | DQ801201 | DQ802632 | DQ806431 | DQ808907 | DQ905743 |
| DQ798064 | DQ799443 | DQ801227 | DQ802689 | DQ806512 | DQ808926 | DQ905762 |
| DQ798119 | DQ799461 | DQ801239 | DQ802768 | DQ806522 | DQ808984 | DQ905805 |
| DQ798135 | DQ799493 | DQ801254 | DQ804576 | DQ806536 | DQ809045 | DQ905818 |
| DQ798140 | DQ799498 | DQ801256 | DQ804662 | DQ806563 | DQ809049 | DQ905899 |
| DQ798214 | DQ799510 | DQ801263 | DQ804785 | DQ806570 | DQ809066 | DQ905919 |
| DQ798241 | DQ799520 | DQ801269 | DQ805106 | DQ806750 | DQ809080 | EF399784 |
| DQ798245 | DQ799559 | DQ801272 | DQ805109 | DQ806763 | DQ809088 | EF399839 |
| DQ798290 | DQ799564 | DQ801295 | DQ805122 | DQ806773 | DQ809109 | EF399899 |
| DQ798294 | DQ799631 | DQ801304 | DQ805125 | DQ806783 | DQ809197 | EF399905 |
| DQ798311 | DQ799632 | DQ801315 | DQ805132 | DQ806857 | DQ809307 | EF399941 |
| DQ798326 | DQ799671 | DQ801355 | DQ805164 | DQ806902 | DQ809483 | EF399994 |
| DQ798372 | DQ799672 | DQ801372 | DQ805170 | DQ807022 | DQ809610 | EF400079 |
| DQ798395 | DQ799695 | DQ801449 | DQ805186 | DQ807193 | DQ809649 | EF400085 |
| DQ798409 | DQ799747 | DQ801451 | DQ805240 | DQ807266 | DQ809651 | EF400221 |
| DQ798412 | DQ799824 | DQ801459 | DQ805282 | DQ807344 | DQ809715 | EF400285 |
| DQ798421 | DQ799978 | DQ801491 | DQ805298 | DQ807398 | DQ809746 | EF400292 |
| DQ798428 | DQ800105 | DQ801540 | DQ805302 | DQ807434 | DQ809844 | EF400306 |
| DQ798510 | DQ800128 | DQ801576 | DQ805620 | DQ807527 | DQ809906 | EF400361 |
| DQ798520 | DQ800190 | DQ801636 | DQ805642 | DQ807540 | DQ810021 | EF400533 |
| DQ798521 | DQ800201 | DQ801678 | DQ805651 | DQ807611 | DQ810074 | EF400658 |
| DQ798555 | DQ800205 | DQ801687 | DQ805658 | DQ808238 | DQ810178 | EF400678 |
| EF400716 | EF402443 | EF403107 | EF404511 | EU762211 | EU766034 | EU768395 |
| EF400777 | EF402449 | EF403134 | EF404601 | EU762301 | EU766632 | EU768423 |
| EF400840 | EF402465 | EF403166 | EF404676 | EU762325 | EU766644 | EU768448 |
| EF400977 | EF402489 | EF403207 | EF404719 | EU762396 | EU766645 | EU768660 |
| EF400999 | EF402495 | EF403241 | EF404739 | EU762527 | EU766649 | EU768686 |
| EF401031 | EF402512 | EF403262 | EF404843 | EU762608 | EU766701 | EU768728 |
| EF401085 | EF402524 | EF403312 | EF404888 | EU762674 | EU766703 | EU768737 |
| EF401216 | EF402535 | EF403334 | EF404910 | EU762758 | EU766722 | EU768756 |
| EF401235 | EF402551 | EF403369 | EF404926 | EU762767 | EU766725 | EU768771 |
| EF401244 | EF402572 | EF403400 | EF405006 | EU762798 | EU766758 | EU773399 |
| EF401246 | EF402586 | EF403448 | EF405070 | EU762839 | EU766846 | EU773475 |
| EF401329 | EF402591 | EF403461 | EF405076 | EU762845 | EU766848 | EU774095 |
| EF401446 | EF402598 | EF403468 | EF405180 | EU762846 | EU766860 | EU774207 |
| EF401526 | EF402614 | EF403472 | EF405183 | EU762902 | EU766916 | EU775408 |
| EF401595 | EF402624 | EF403493 | EF405188 | EU762912 | EU766990 | EU778073 |
| EF401693 | EF402632 | EF403511 | EF405200 | EU763011 | EU766995 | EU778081 |
| EF401729 | EF402644 | EF403519 | EF405203 | EU763234 | EU767009 | EU778088 |
| EF401734 | EF402650 | EF403608 | EF405227 | EU763276 | EU767016 | EU778090 |
| EF401777 | EF402657 | EF403613 | EF405375 | EU763302 | EU767049 | EU778110 |
| EF401933 | EF402685 | EF403642 | EF405376 | EU763391 | EU767071 | EU778135 |
| EF401942 | EF402689 | EF403646 | EF405391 | EU763433 | EU767085 | EU778170 |
| EF401970 | EF402737 | EF403655 | EF405429 | EU763531 | EU767110 | EU778187 |
| EF401971 | EF402763 | EF403675 | EF405462 | EU763562 | EU767114 | EU778193 |
| EF401988 | EF402766 | EF403681 | EF405494 | EU763607 | EU767123 | EU778227 |

TABLE 6-continued

Accession numbers of the 2231 sequences hybridizing specifically with the PHGII specific probe in the SILVA database under default conditions.

| | | | | | | |
|---|---|---|---|---|---|---|
| EF402005 | EF402777 | EF403775 | EF405524 | EU763792 | EU767130 | EU778236 |
| EF402014 | EF402790 | EF403778 | EU462258 | EU763820 | EU767143 | EU778253 |
| EF402028 | EF402791 | EF403830 | EU466841 | EU763909 | EU767149 | EU778265 |
| EF402041 | EF402799 | EF403853 | EU467322 | EU763945 | EU767181 | EU778272 |
| EF402060 | EF402839 | EF403911 | EU530262 | EU763991 | EU767239 | EU778278 |
| EF402108 | EF402872 | EF403932 | EU530453 | EU763992 | EU767259 | EU778292 |
| EF402167 | EF402896 | EF403939 | EU530480 | EU764005 | EU767420 | EU778299 |
| EF402182 | EF402970 | EF403960 | EU531954 | EU764009 | EU767488 | EU778300 |
| EF402195 | EF402971 | EF404019 | EU728783 | EU764019 | EU767489 | EU778310 |
| EF402238 | EF402972 | EF404051 | EU761610 | EU764026 | EU767497 | EU778317 |
| EF402263 | EF402980 | EF404063 | EU761613 | EU764071 | EU767527 | EU778336 |
| EF402267 | EF402987 | EF404101 | EU761638 | EU764127 | EU767943 | EU778349 |
| EF402315 | EF403020 | EF404138 | EU761684 | EU764558 | EU767999 | EU778361 |
| EF402319 | EF403024 | EF404157 | EU761731 | EU764825 | EU768031 | EU778364 |
| EF402368 | EF403043 | EF404239 | EU761829 | EU764935 | EU768147 | FJ362628 |
| EF402389 | EF403045 | EF404243 | EU761839 | EU764987 | EU768184 | FJ362669 |
| EF402415 | EF403066 | EF404268 | EU761869 | EU765118 | EU768193 | FJ362727 |
| EF402423 | EF403069 | EF404348 | EU761965 | EU765489 | EU768200 | FJ362730 |
| EF402435 | EF403076 | EF404462 | EU762028 | EU765828 | EU768295 | FJ362735 |
| EF402438 | EF403101 | EF404490 | EU762144 | EU765973 | EU768326 | FJ362744 |
| FJ362745 | FJ364312 | FJ365874 | FJ370192 | FJ372377 | FJ504469 | FJ504982 |
| FJ362767 | FJ364337 | FJ365882 | FJ370204 | FJ503669 | FJ504472 | FJ504983 |
| FJ362776 | FJ364373 | FJ365891 | FJ370206 | FJ503676 | FJ504504 | FJ504987 |
| FJ362780 | FJ364378 | FJ365927 | FJ370239 | FJ503681 | FJ504505 | FJ504988 |
| FJ362808 | FJ364417 | FJ366006 | FJ370296 | FJ503753 | FJ504529 | FJ504990 |
| FJ362905 | FJ364428 | FJ366039 | FJ370322 | FJ503758 | FJ504535 | FJ504992 |
| FJ362917 | FJ364451 | FJ366101 | FJ370369 | FJ503780 | FJ504543 | FJ504994 |
| FJ362929 | FJ364478 | FJ366119 | FJ370385 | FJ503974 | FJ504545 | FJ504995 |
| FJ362949 | FJ364484 | FJ366387 | FJ370407 | FJ503982 | FJ504548 | FJ504996 |
| FJ362973 | FJ364511 | FJ366399 | FJ370413 | FJ504090 | FJ504558 | FJ504998 |
| FJ363037 | FJ364590 | FJ366455 | FJ370948 | FJ504097 | FJ504561 | FJ505001 |
| FJ363121 | FJ364601 | FJ366724 | FJ370960 | FJ504122 | FJ504563 | FJ505002 |
| FJ363122 | FJ364880 | FJ366865 | FJ371106 | FJ504137 | FJ504565 | FJ505003 |
| FJ363128 | FJ365031 | FJ367435 | FJ371133 | FJ504144 | FJ504589 | FJ505187 |
| FJ363149 | FJ365059 | FJ367852 | FJ371147 | FJ504147 | FJ504594 | FJ505198 |
| FJ363256 | FJ365097 | FJ367860 | FJ371182 | FJ504150 | FJ504595 | FJ505221 |
| FJ363265 | FJ365205 | FJ367888 | FJ371239 | FJ504164 | FJ504596 | FJ505227 |
| FJ363269 | FJ365271 | FJ368000 | FJ371246 | FJ504188 | FJ504603 | FJ505239 |
| FJ363310 | FJ365290 | FJ368033 | FJ371249 | FJ504190 | FJ504608 | FJ505259 |
| FJ363311 | FJ365339 | FJ368052 | FJ371264 | FJ504203 | FJ504627 | FJ505262 |
| FJ363312 | FJ365343 | FJ368096 | FJ371302 | FJ504253 | FJ504630 | FJ505263 |
| FJ363392 | FJ365364 | FJ368195 | FJ371336 | FJ504276 | FJ504687 | FJ505266 |
| FJ363395 | FJ365370 | FJ368202 | FJ371350 | FJ504278 | FJ504692 | FJ505268 |
| FJ363429 | FJ365444 | FJ368256 | FJ371394 | FJ504286 | FJ504699 | FJ505281 |
| FJ363435 | FJ365445 | FJ368265 | FJ371672 | FJ504290 | FJ504704 | FJ505300 |
| FJ363446 | FJ365450 | FJ368275 | FJ371736 | FJ504292 | FJ504709 | FJ505322 |
| FJ363484 | FJ365467 | FJ368369 | FJ371741 | FJ504302 | FJ504716 | FJ505354 |
| FJ363485 | FJ365469 | FJ368385 | FJ371751 | FJ504308 | FJ504717 | FJ505355 |
| FJ363486 | FJ365498 | FJ368388 | FJ371801 | FJ504311 | FJ504721 | FJ505362 |
| FJ363488 | FJ365502 | FJ368415 | FJ371852 | FJ504315 | FJ504727 | FJ505388 |
| FJ363513 | FJ365506 | FJ368421 | FJ371993 | FJ504320 | FJ504728 | FJ505412 |
| FJ363555 | FJ365513 | FJ368436 | FJ372036 | FJ504324 | FJ504742 | FJ505422 |
| FJ363566 | FJ365543 | FJ368697 | FJ372056 | FJ504335 | FJ504761 | FJ505430 |
| FJ363574 | FJ365551 | FJ369071 | FJ372080 | FJ504339 | FJ504765 | FJ505441 |
| FJ363642 | FJ365569 | FJ369823 | FJ372098 | FJ504350 | FJ504770 | FJ505448 |
| FJ363646 | FJ365576 | FJ369848 | FJ372125 | FJ504369 | FJ504807 | FJ505452 |
| FJ363715 | FJ365666 | FJ369910 | FJ372178 | FJ504374 | FJ504828 | FJ505455 |
| FJ363799 | FJ365677 | FJ369985 | FJ372190 | FJ504382 | FJ504839 | FJ505456 |
| FJ363861 | FJ365712 | FJ370091 | FJ372209 | FJ504388 | FJ504969 | FJ505461 |
| FJ363893 | FJ365734 | FJ370097 | FJ372241 | FJ504400 | FJ504970 | FJ505463 |
| FJ363906 | FJ365752 | FJ370104 | FJ372247 | FJ504433 | FJ504971 | FJ506841 |
| FJ363908 | FJ365840 | FJ370159 | FJ372288 | FJ504435 | FJ504973 | FJ506853 |
| FJ363917 | FJ365847 | FJ370180 | FJ372328 | FJ504436 | FJ504977 | FJ506937 |
| FJ364280 | FJ365873 | FJ370184 | FJ372330 | FJ504458 | FJ504979 | FJ507023 |
| FJ507029 | FJ510167 | FJ512860 | FJ673425 | FJ675669 | FJ676696 | FJ677462 |
| FJ507051 | FJ510168 | FJ512861 | FJ673427 | FJ675701 | FJ676704 | FJ677575 |
| FJ507084 | FJ510169 | FJ512863 | FJ673481 | FJ675708 | FJ676705 | FJ677611 |
| FJ507346 | FJ510170 | FJ512864 | FJ673534 | FJ675744 | FJ676729 | FJ677631 |
| FJ507347 | FJ510172 | FJ512865 | FJ673554 | FJ675765 | FJ676737 | FJ677694 |
| FJ507352 | FJ510173 | FJ512866 | FJ673597 | FJ675796 | FJ676831 | FJ677730 |
| FJ507649 | FJ510175 | FJ512867 | FJ673618 | FJ675864 | FJ676846 | FJ677737 |
| FJ507650 | FJ510176 | FJ512868 | FJ673658 | FJ675865 | FJ676871 | FJ677780 |
| FJ507651 | FJ510178 | FJ512869 | FJ673688 | FJ675866 | FJ676940 | FJ677782 |
| FJ507652 | FJ510183 | FJ512870 | FJ673706 | FJ675872 | FJ676962 | FJ677797 |
| FJ507653 | FJ510185 | FJ512871 | FJ673728 | FJ675906 | FJ676965 | FJ677857 |
| FJ507655 | FJ510520 | FJ512874 | FJ673732 | FJ675939 | FJ677004 | FJ677865 |
| FJ507656 | FJ510521 | FJ512875 | FJ673737 | FJ675969 | FJ677020 | FJ677882 |

TABLE 6-continued

Accession numbers of the 2231 sequences hybridizing specifically with the PHGII specific probe in the SILVA database under default conditions.

| | | | | | | |
|---|---|---|---|---|---|---|
| FJ507657 | FJ510534 | FJ512885 | FJ673761 | FJ675980 | FJ677040 | FJ677909 |
| FJ507658 | FJ510535 | FJ512886 | FJ673763 | FJ675993 | FJ677043 | FJ677912 |
| FJ507660 | FJ510537 | FJ512887 | FJ673765 | FJ676008 | FJ677070 | FJ677915 |
| FJ507661 | FJ510538 | FJ672951 | FJ673785 | FJ676037 | FJ677073 | FJ677929 |
| FJ507667 | FJ510540 | FJ672975 | FJ673804 | FJ676047 | FJ677086 | FJ677932 |
| FJ507670 | FJ510543 | FJ672979 | FJ673805 | FJ676061 | FJ677098 | FJ677967 |
| FJ507671 | FJ510544 | FJ672996 | FJ673821 | FJ676063 | FJ677126 | FJ677986 |
| FJ507894 | FJ510545 | FJ673009 | FJ673825 | FJ676064 | FJ677143 | FJ678047 |
| FJ507906 | FJ510844 | FJ673029 | FJ673842 | FJ676070 | FJ677148 | FJ678060 |
| FJ508214 | FJ510845 | FJ673049 | FJ673868 | FJ676113 | FJ677155 | FJ678151 |
| FJ508224 | FJ510846 | FJ673068 | FJ673880 | FJ676193 | FJ677162 | FJ678172 |
| FJ508636 | FJ510847 | FJ673082 | FJ673884 | FJ676205 | FJ677164 | FJ678240 |
| FJ508913 | FJ510850 | FJ673085 | FJ673886 | FJ676208 | FJ677176 | FJ678348 |
| FJ508914 | FJ510853 | FJ673090 | FJ673914 | FJ676223 | FJ677213 | FJ678349 |
| FJ508933 | FJ510855 | FJ673097 | FJ673930 | FJ676226 | FJ677225 | FJ678365 |
| FJ508934 | FJ510858 | FJ673099 | FJ673952 | FJ676247 | FJ677262 | FJ678373 |
| FJ509234 | FJ510876 | FJ673101 | FJ673984 | FJ676365 | FJ677264 | FJ678388 |
| FJ509235 | FJ512306 | FJ673113 | FJ674055 | FJ676367 | FJ677273 | FJ678390 |
| FJ509246 | FJ512308 | FJ673158 | FJ674061 | FJ676378 | FJ677280 | FJ678422 |
| FJ509247 | FJ512309 | FJ673187 | FJ674063 | FJ676393 | FJ677300 | FJ678426 |
| FJ509494 | FJ512310 | FJ673191 | FJ674077 | FJ676410 | FJ677326 | FJ678466 |
| FJ509498 | FJ512311 | FJ673257 | FJ674086 | FJ676411 | FJ677335 | FJ678508 |
| FJ509514 | FJ512312 | FJ673284 | FJ674104 | FJ676412 | FJ677368 | FJ678517 |
| FJ509842 | FJ512332 | FJ673301 | FJ674111 | FJ676416 | FJ677381 | FJ678533 |
| FJ509843 | FJ512333 | FJ673310 | FJ674114 | FJ676446 | FJ677390 | FJ678558 |
| FJ509844 | FJ512334 | FJ673321 | FJ674128 | FJ676481 | FJ677397 | FJ678576 |
| FJ509846 | FJ512336 | FJ673324 | FJ674151 | FJ676536 | FJ677399 | FJ678599 |
| FJ509847 | FJ512339 | FJ673343 | FJ674170 | FJ676590 | FJ677408 | FJ678639 |
| FJ509849 | FJ512340 | FJ673351 | FJ674188 | FJ676591 | FJ677419 | FJ678640 |
| FJ509852 | FJ512341 | FJ673383 | FJ674262 | FJ676620 | FJ677420 | FJ678642 |
| FJ509854 | FJ512859 | FJ673415 | FJ674266 | FJ676646 | FJ677448 | FJ678678 |
| FJ678704 | FJ679772 | FJ681202 | FJ682839 | FJ683727 | GQ079161 | GQ898110 |
| FJ678718 | FJ679782 | FJ681394 | FJ682856 | FJ683739 | GQ079284 | GQ898111 |
| FJ678720 | FJ679793 | FJ681399 | FJ682907 | FJ683764 | GQ079599 | GQ898115 |
| FJ678732 | FJ679834 | FJ681478 | FJ682937 | FJ683832 | GQ079614 | GQ898119 |
| FJ678740 | FJ679857 | FJ681568 | FJ682975 | FJ683833 | GQ106380 | GQ898138 |
| FJ678769 | FJ679858 | FJ681572 | FJ683009 | FJ683865 | GQ156701 | GQ898174 |
| FJ678782 | FJ679875 | FJ681597 | FJ683033 | FJ683870 | GQ156702 | GQ898186 |
| FJ678798 | FJ679900 | FJ681616 | FJ683091 | FJ683915 | GQ157298 | GQ898283 |
| FJ678815 | FJ679967 | FJ681716 | FJ683114 | FJ683916 | GQ157299 | GQ898285 |
| FJ678820 | FJ679977 | FJ681947 | FJ683130 | FJ683918 | GQ158092 | GQ898309 |
| FJ678822 | FJ679979 | FJ681951 | FJ683137 | FJ683940 | GQ158184 | GQ898312 |
| FJ678847 | FJ680015 | FJ681996 | FJ683181 | FJ683963 | GQ158583 | GQ898333 |
| FJ678849 | FJ680023 | FJ682002 | FJ683211 | FJ684002 | GQ158831 | GQ898350 |
| FJ678852 | FJ680033 | FJ682049 | FJ683213 | FJ684008 | GQ159043 | GQ898408 |
| FJ678861 | FJ680041 | FJ682074 | FJ683231 | FJ684079 | GQ159217 | GQ898441 |
| FJ678948 | FJ680048 | FJ682075 | FJ683259 | FJ684122 | GQ159572 | GQ898501 |
| FJ678955 | FJ680054 | FJ682091 | FJ683272 | FJ684131 | GQ448015 | GQ898624 |
| FJ678964 | FJ680071 | FJ682107 | FJ683320 | FJ684184 | GQ448026 | GQ898681 |
| FJ678999 | FJ680077 | FJ682112 | FJ683322 | FJ684234 | GQ448468 | GQ898737 |
| FJ679008 | FJ680081 | FJ682123 | FJ683355 | FJ684295 | GQ448799 | GQ898777 |
| FJ679074 | FJ680083 | FJ682135 | FJ683359 | FJ684331 | GQ448805 | GQ898790 |
| FJ679091 | FJ680125 | FJ682161 | FJ683367 | FJ684341 | GQ491965 | GQ898862 |
| FJ679099 | FJ680153 | FJ682306 | FJ683387 | FJ684396 | GQ492999 | HM282132 |
| FJ679157 | FJ680161 | FJ682308 | FJ683410 | FJ684413 | GQ493175 | HM284779 |
| FJ679193 | FJ680188 | FJ682340 | FJ683417 | FJ684553 | GQ896577 | HM285702 |
| FJ679254 | FJ680206 | FJ682349 | FJ683423 | FJ684556 | GQ896588 | HM285980 |
| FJ679261 | FJ680211 | FJ682383 | FJ683439 | FJ684619 | GQ896639 | HM286500 |
| FJ679304 | FJ680223 | FJ682388 | FJ683442 | FJ684635 | GQ896681 | HM286526 |
| FJ679320 | FJ680224 | FJ682430 | FJ683444 | FJ684695 | GQ896705 | HM286682 |
| FJ679366 | FJ680285 | FJ682443 | FJ683493 | FJ684742 | GQ896750 | HM286702 |
| FJ679369 | FJ680292 | FJ682454 | FJ683496 | FJ684971 | GQ896769 | HM286714 |
| FJ679376 | FJ680530 | FJ682461 | FJ683515 | FJ685011 | GQ896871 | HM286731 |
| FJ679411 | FJ680557 | FJ682484 | FJ683526 | FJ685265 | GQ896961 | HM286935 |
| FJ679434 | FJ680563 | FJ682489 | FJ683533 | FJ685342 | GQ897005 | HM300409 |
| FJ679538 | FJ680601 | FJ682509 | FJ683537 | FJ685392 | GQ897144 | HM304758 |
| FJ679571 | FJ680690 | FJ682513 | FJ683572 | FJ685400 | GQ897176 | HM335106 |
| FJ679591 | FJ680784 | FJ682623 | FJ683595 | FM872976 | GQ897244 | HQ743862 |
| FJ679646 | FJ680786 | FJ682640 | FJ683638 | FM873424 | GQ897285 | HQ744069 |
| FJ679695 | FJ680807 | FJ682660 | FJ683641 | FM873865 | GQ897292 | HQ744243 |
| FJ679698 | FJ680864 | FJ682702 | FJ683649 | GQ016078 | GQ897310 | HQ751613 |
| FJ679709 | FJ680954 | FJ682740 | FJ683668 | GQ016178 | GQ897318 | HQ751663 |
| FJ679711 | FJ681114 | FJ682763 | FJ683692 | GQ016589 | GQ897884 | HQ751700 |
| FJ679735 | FJ681165 | FJ682765 | FJ683693 | GQ016610 | GQ897933 | HQ751875 |
| FJ679746 | FJ681199 | FJ682808 | FJ683700 | GQ042959 | GQ897941 | HQ751953 |
| HQ759329 | HQ780099 | HQ784959 | HQ793040 | HQ800953 | HQ804342 | HQ810967 |
| HQ759343 | HQ780124 | HQ784980 | HQ793057 | HQ801021 | HQ804343 | HQ810974 |

TABLE 6-continued

Accession numbers of the 2231 sequences hybridizing specifically with the
PHGII specific probe in the SILVA database under default conditions.

| | | | | | | |
|---|---|---|---|---|---|---|
| HQ759481 | HQ780138 | HQ785068 | HQ793193 | HQ801073 | HQ805890 | HQ810977 |
| HQ759542 | HQ780326 | HQ785524 | HQ793266 | HQ801078 | HQ805909 | HQ810981 |
| HQ759543 | HQ780371 | HQ785553 | HQ793714 | HQ801088 | HQ805946 | HQ810998 |
| HQ759648 | HQ780404 | HQ786386 | HQ793823 | HQ801094 | HQ805972 | HQ811001 |
| HQ759677 | HQ780501 | HQ786387 | HQ793996 | HQ801108 | HQ805994 | HQ811006 |
| HQ759694 | HQ780562 | HQ786448 | HQ794414 | HQ801131 | HQ806000 | HQ811009 |
| HQ763046 | HQ780574 | HQ786580 | HQ794417 | HQ801152 | HQ806003 | HQ811119 |
| HQ763235 | HQ780635 | HQ786805 | HQ794432 | HQ802076 | HQ806138 | HQ811422 |
| HQ766415 | HQ780821 | HQ786813 | HQ794439 | HQ802969 | HQ806805 | HQ811934 |
| HQ766742 | HQ780975 | HQ786854 | HQ794473 | HQ802982 | HQ806884 | HQ812242 |
| HQ774887 | HQ780989 | HQ786986 | HQ794477 | HQ803800 | HQ806987 | HQ813677 |
| HQ775180 | HQ780999 | HQ786993 | HQ794572 | HQ803802 | HQ807243 | HQ813752 |
| HQ775251 | HQ781058 | HQ787025 | HQ794586 | HQ803815 | HQ810078 | HQ814198 |
| HQ775806 | HQ781122 | HQ787211 | HQ794622 | HQ803839 | HQ810609 | HQ814234 |
| HQ775813 | HQ781128 | HQ787247 | HQ794624 | HQ803870 | HQ810666 | HQ814355 |
| HQ775906 | HQ781154 | HQ787334 | HQ794642 | HQ803885 | HQ810689 | HQ814359 |
| HQ775981 | HQ781184 | HQ787347 | HQ795103 | HQ803886 | HQ810713 | HQ814379 |
| HQ776261 | HQ781187 | HQ787408 | HQ795113 | HQ803936 | HQ810731 | HQ814451 |
| HQ776430 | HQ781221 | HQ787431 | HQ795421 | HQ803961 | HQ810732 | HQ814510 |
| HQ776566 | HQ781232 | HQ788630 | HQ795518 | HQ803972 | HQ810737 | HQ814529 |
| HQ776759 | HQ781248 | HQ788656 | HQ797391 | HQ804005 | HQ810739 | HQ814565 |
| HQ777121 | HQ781284 | HQ788686 | HQ797519 | HQ804009 | HQ810769 | HQ814814 |
| HQ777241 | HQ781285 | HQ788690 | HQ797605 | HQ804011 | HQ810775 | HQ814861 |
| HQ777291 | HQ781328 | HQ788713 | HQ797621 | HQ804027 | HQ810787 | HQ815161 |
| HQ777328 | HQ781343 | HQ788721 | HQ797700 | HQ804052 | HQ810796 | HQ815406 |
| HQ777447 | HQ781381 | HQ788734 | HQ797770 | HQ804058 | HQ810808 | HQ815431 |
| HQ777449 | HQ781431 | HQ788882 | HQ797860 | HQ804060 | HQ810821 | HQ815458 |
| HQ777517 | HQ781558 | HQ790288 | HQ797871 | HQ804062 | HQ810853 | HQ815650 |
| HQ777969 | HQ781581 | HQ790332 | HQ797898 | HQ804065 | HQ810863 | HQ815963 |
| HQ779055 | HQ781723 | HQ790735 | HQ797979 | HQ804135 | HQ810867 | HQ816034 |
| HQ779520 | HQ781758 | HQ790865 | HQ800194 | HQ804154 | HQ810875 | HQ816295 |
| HQ779702 | HQ783571 | HQ791058 | HQ800627 | HQ804181 | HQ810877 | HQ816959 |
| HQ779714 | HQ783636 | HQ791071 | HQ800687 | HQ804218 | HQ810878 | HQ817913 |
| HQ779798 | HQ783824 | HQ791104 | HQ800705 | HQ804245 | HQ810904 | HQ818200 |
| HQ779804 | HQ783906 | HQ791126 | HQ800721 | HQ804267 | HQ810920 | HQ821275 |
| HQ779820 | HQ783929 | HQ791177 | HQ800749 | HQ804287 | HQ810924 | JF117521 |
| HQ779841 | HQ784028 | HQ791185 | HQ800757 | HQ804288 | HQ810925 | JF128397 |
| HQ780016 | HQ784038 | HQ792630 | HQ800760 | HQ804291 | HQ810928 | JF128446 |
| HQ780047 | HQ784040 | HQ792645 | HQ800808 | HQ804305 | HQ810930 | JF133787 |
| HQ780061 | HQ784398 | HQ792682 | HQ800875 | HQ804313 | HQ810940 | JF133856 |
| HQ780078 | HQ784403 | HQ792883 | HQ800879 | HQ804322 | HQ810951 | JF135768 |
| HQ780086 | HQ784883 | HQ792973 | HQ800917 | HQ804327 | HQ810964 | JF145440 |
| JF152180 | JF168288 | JQ183885 | JQ188414 | JQ189840 | KF841715 | KF842659 |
| JF159588 | JF168414 | JQ184737 | JQ188516 | JQ189871 | KF841774 | KF842663 |
| JF160220 | JF168451 | JQ185267 | JQ188602 | JQ190412 | KF841799 | KF842748 |
| JF161316 | JF188128 | JQ186559 | JQ188618 | JQ190807 | KF841981 | KF842843 |
| JF161642 | JF234854 | JQ186613 | JQ188625 | JQ190977 | KF842167 | KF842928 |
| JF161844 | JF237768 | JQ186648 | JQ188631 | JQ940410 | KF842183 | KF843160 |
| JF162799 | JF239714 | JQ186700 | JQ188868 | JQ940685 | KF842294 | KF843215 |
| JF163115 | | JQ186758 | JQ189425 | KF097757 | KF842468 | KF843241 |
| JF163215 | JN157660 | JQ186808 | JQ189454 | KF101719 | KF842504 | KF843624 |
| JF163805 | JN187070 | JQ186977 | JQ189471 | KF841668 | KF842632 | LN612658 |
| JF163913 | JQ183445 | JQ187055 | JQ189754 | KF841714 | KF842638 | |

A Method for the Obtaining of Useful Information

In a second aspect, the invention relates to a method for the obtaining of useful information for the detection of an intestinal disease in a human subject and/or for the prediction of the efficacy of a drug in the therapeutic treatment of an intestinal disease in a human subject, comprising the determination of the abundance of PHGI and/or of PHGII according to a method of the first aspect; wherein preferably said intestinal disease is selected from the group consisting of inflammatory bowel disease (IBD), irritable bowel syndrome (IBS) and colorectal cancer (CRC).

In a particular embodiment the invention pertains to a method for obtaining useful information from an intestinal sample of a human subject comprising the following steps:

a. determining the abundance of *Faecalibacterium prausnitzii* phylogroup I members (PHGI) in an intestinal sample from said subject; and b. optionally, determining the abundance of *Faecalibacterium prausnitzii* phylogroup II members (PHGII) in an intestinal sample from said subject.

Another embodiment pertains to a method for obtaining useful information from an intestinal sample of a human subject comprising determining the abundance of *Faecalibacterium prausnitzii* phylogroup I members (PHGI) in an intestinal sample from said subject. A further embodiment relates to a method for obtaining useful information from an intestinal sample of a human subject comprising determining the abundance of PHGI and of PHGII in an intestinal sample from said subject.

Said information could be useful for detecting an intestinal disease in said human subject when comparing the PHGI abundance, and/or the PHGII abundance and/or a mathematical combination thereof, and/or optionally a mathematical combination of any of these with Total *F. Prausnitzii* (FT) abundance and/or *E. coli* (EC) abundance, in the subject sample with the corresponding values in a reference sample, wherein a significant deviation in the subject sample values with regard to said reference sample is indicative of intestinal disease. This and other uses of the quantification of PHGI and/or PHGII abundance are as described herein.

A Method for Detecting Intestinal Disease

In a third aspect, the invention relates to a method for detecting an intestinal disease in a human subject comprising the following steps:
  a. determining the abundance of *Faecalibacterium prausnitzii* phylogroup I members (PHGI) and/or *Faecalibacterium prausnitzii* phylogroup II members (PHGII) in an intestinal sample from said subject according to a method as described under the first aspect; and
  b. comparing the PHGI and/or PHGII abundance, and/or a mathematical combination thereof, and/or optionally a mathematical combination of any of these with Total *F. Prausnitzii* (FT) abundance and/or *E. coli* (EC) abundance, in the subject sample with the corresponding values in a reference sample,
  wherein a significant deviation in the subject sample values with regard to said reference sample is indicative of intestinal disease;
  wherein preferably said intestinal disease is selected from the group consisting of inflammatory bowel disease (IBD), irritable bowel syndrome (IBS) and colorectal cancer (CRC); and wherein said reference sample is preferably a healthy subject sample and/or the sample of a patient with intestinal disease in remission.

Preferably, it relates to a method for detecting an intestinal disease in a human subject comprising the following steps:
  a. determining the abundance of *Faecalibacterium prausnitzii* phylogroup I members (PHGI) in an intestinal sample from said subject;
  b. optionally, determining the abundance of *Faecalibacterium prausnitzii* phylogroup II members (PHGII) in an intestinal sample from said subject; and
  c. comparing the PHGI abundance, optionally the PHGII abundance and/or a mathematical combination thereof, and/or optionally a mathematical combination of any of these with Total *F. Prausnitzii* (FT) abundance and/or *E. coli* (EC) abundance, in the subject sample with the corresponding values in a reference sample,
  wherein a significant deviation in the subject sample values with regard to said reference sample is indicative of intestinal disease.

The term detecting an intestinal disease as used herein includes the screening, diagnosis, differential diagnosis, and/or monitoring of disease activity and/or progression.

In a particular embodiment, it relates to a method for detecting intestinal disease in a human subject comprising the following steps:
  a. determining the abundance of *Faecalibacterium prausnitzii* phylogroup I members (PHGI) in an intestinal sample from said subject; and
  b. comparing the subject sample abundance levels with the abundance levels in a reference sample,
  wherein a significant reduction of abundance levels in the subject sample with regard to said reference sample is indicative of intestinal disease.

In another particular embodiment it relates to a method for detecting intestinal disease in a human subject comprising the following steps:
  a. determining the abundance of PHGI in an intestinal sample from said subject;
  b. determining the abundance of PHGII in an intestinal sample from said subject; and
  c. comparing the PHGI abundance, the PHGII abundance and/or a mathematical combination thereof in the subject sample, with the corresponding values in a reference sample,
  wherein a significant deviation in the subject sample values with regard to said reference sample is indicative of intestinal disease.

In one particular embodiment of the invention the PHGI abundance and PHGII abundance are determined. In another particular embodiment, the PHGI abundance and PHGII abundance, as well as the mathematical combination or relationship between said sequences (e.g. ratio, multivariant analysis, etc.) is determined. In a further embodiment, the PHGI abundance and/or PHGII abundance is determined, as well as the mathematical combination or relationship between any of these (e.g. ratio, multivariant analysis, etc.) with the Total *F. Prausnitzii* (FT) abundance and/or *E. coli* (EC) abundance. The ratio between PHGI, PHGII, FT and/or EC abundance may be obtained by dividing the quantification levels of a first sequence by the quantification levels of a second sequence. For instance, the ratio of PHGII abundance/PHGI abundance is obtained by dividing the PHGII 16S rRNA gene sequence quantification levels by the PHGI 16S rRNA gene sequence quantification levels.

The ratio between PHGI, PHGII, FT and/or EC abundance may also be obtained by subtracting from the quantification levels of a first sequence the quantification levels of a second sequence. For instance, the ratio of PHGII abundance/PHGI abundance is obtained by subtracting from the PHGII 16S rRNA gene sequence quantification levels the PHGI 16S rRNA gene sequence quantification levels.

Preferred ratios of the invention are PHGI abundance/PHGII abundance (PHGI/PHGII), PHGI abundance/EC abundance (PHGI/EC), PHGII abundance/EC abundance (PHGII/EC), FT abundance/PHGI abundance (FT/PHGI), and FT abundance/PHGII abundance (FT/PHGII) and vice versa. Particularly preferred ratios are PHGI/EC and PHGII/EC.

Preferably, quantification has been performed by qPCR (described below) and quantification levels are expressed as the cycle threshold value (Ct value). More preferably, the ratios are calculated by subtraction.

In a particular embodiment, the ratio between the PHGII abundance and the PHGI abundance (PHGII/PHGI ratio) is determined and the PHGII/PHGI ratio in said subject sample compared with the PHGII/PHGI ratio in a reference sample, wherein a significant deviation in the subject sample values with regard to said reference sample is indicative of intestinal disease.

One of ordinary skill in the art knows several methods and devices for the determination of the abundance of *Faecalibacterium prausnitzii* PHGI and/or PHGII. It is typically performed by bacterial gene quantification. The term "quantifying" refers to the ability to determine the amount of a specific nucleic acid sequence in a sample.

Molecular biology methods for measuring quantities of target nucleic acid sequences are well known in the art. These methods include but are not limited to end pointPCR, competitive PCR, reverse transcriptase-PCR (RT-PCR), quantitative PCR (qPCR), reverse transcriptase qPCR (RT-qPCR), PCR-pyrosequencing, PCR-ELISA, DNA microarrays, in situ hybridization assays such as dot-blot or Fluorescence In Situ Hybridization assay (FISH), branched DNA (Nolte, Adv. Clin. Chem. 1998, 33:201-235) and to multiplex versions of said methods (see for instance, Andoh et al., Current Pharmaceutical Design, 2009; 15, 2066-2073). For a review on molecular approaches to study gut microbiota see also Manichanh et al., (Nat. Rev. Gastroenterol. Hepatol. 2012; 9, 599-608) and Weinstock B. M (Nature 2012, 489, 250-256). A multiplex assay is an assay that simultaneously measures multiple analytes, typically dozens or more, in a single run/cycle of the assay.

Preferred primers and/or probes react in a predictable manner, typically by offering a direct and linear response to increasing amounts of bacterial nucleic acid sequences. By preparation of and by comparison to appropriate standards, one can readily quantify the amount of a given nucleic acid sequence in a sample. Preferably, said molecular method for gene quantification is selected from the group consisting of quantitative Polymerase Chain Reaction (qPCR), PCR-pyrosequencing, fluorescence in-situ hybridization (FISH), DNA microarrays, and PCR-ELISA.

One particularly preferred quantification method is FISH, which combines probe hybridization with fluorescent light microscopy, confocal laser microscopy or flow cytometry for direct quantification of individual bacterial sequences. For reviews of FISH methodology, see, e.g., Harmsen et al., Appl Environ Microbiol, 2002; 68 2982-2990, Kalliomaki et al., J AllergClinImmunol, 2001; 107 129-134; Tkachuk et al., Genet. Anal. Tech. Appl., 1991; 8: 67-74; Trask et al., Trends Genet., 1991; 7 (5): 149-154; and Weier et al., Expert Rev. Mol. Diagn., 2002, 2(2):109-119; and U.S. Pat. No. 6,174,681.

Another particularly preferred quantification method is quantitative PCR (qPCR), also known as real-time PCR. Different instruments are available, such as ABI Prism 7700 SDS, GeneAmp 5700 SDS, ABI Prism 7900 HT SDS from Applied Biosystems; iCycler iQ from Bio-Rad; Smart Cycler from Cepheid; Rotor-Gene from Corbett Research; LightCycler from Roche Molecular Biochemicals and Mx4000 Multiplex from Stratagene. The qPCR process enables accurate quantification of the PCR product in real-time by measuring PCR product accumulation very early in the exponential phase of the reaction, thus reducing bias in the quantification linked to the PCR amplification efficiency occurring in end-point PCR. Real-time PCR is well known in the art and is thus not described in detail herein. Technology overview and protocols for qPCR are available for instance from the above-mentioned vendors, e.g., http://www.sigmaaldrich.com/technical-documents/protocols/biology/sybr-green-qper.html or http://www.sigmaaldrich.com/life-science/molecular-biology/per/quantitative-per/qper-technical-guide.html. For a review of qPCR methods see Smith C J and Osborn A M., FEMS Microbiol Ecol., 2009; 67(1):6-20 and Giulietti et al., Methods 2001; 25, 386-401. In a preferred embodiment, the quantification method is a multiplex qPCR.

Several genes can be used for bacterial quantification purposes. Typically, a specific target bacteria is quantified by PCR amplification of the 16S rRNA gene. 16S rRNA differs for each bacterial species. A bacterial species is hard to define, but is often taken as organisms with 16S rRNA gene sequences having at least 97% identity, defined as an operational taxonomic unit (OTU). A 16S rRNA gene sequence of about 1.5 kilobases has nine short hypervariable regions that distinguish bacterial taxa; the sequences of one or more of these regions are targeted in a community census (Weinstock B. M, Nature 2012, 489, 250-256).

Protein coding genes, for instance housekeeping genes may also be used. Roux et al. (FEMS Microbiol Ecol 78 (2011) 617-628), describes the use of five protein marker genes (rplB, pyrG, fusA, leuS and rpoB), for which primer sets were available, as taxonomic markers for ecological studies. The use of nucleotidyl transferase gene and the butyryl-CoA transferase gene for specific target bacteria quantification purposes has also been described (Jia et al. FEMS Microbiol Lett. 2010; 310:138-144).

Different detecting chemistries are available for qPCR. All of them can be used with the above-mentioned qPCR instruments. The term "detection chemistry" refers to a method to report amplification of specific PCR product in real-time PCR and may include hydrolysis or TaqMan® probes; molecular beacons; scorpions; hybridization probes and DNA-binding dyes such as SYBR® Green I. These are described in detail for instance in Giulietti et al., Methods 2001; 25, 386-401.

In a preferred embodiment said probes are dual-labelled oligonucleotides, such as hydrolysis probes or molecular beacons. The 5' end of the oligonucleotide is typically labelled with a fluorescent reporter molecule while the 3' end is labelled with a quencher molecule. The sequence of the probe is specific for a region of interest in the amplified target molecule. In a more preferred embodiment, said probe is a hydrolysis probe which is designed so that the length of the sequence places the 5' fluorophore and the 3' quencher in close enough proximity so as to suppress fluorescence.

Several reporter molecules and quenchers for use in qPCR probes are well known in the art. These being available for instance from https://www.eurofinsgenomics.eu/en/dna-rna-oligonucleotides/optimised-application-oligos/qper-probes.aspx:. For illustration purposes, Table 7 below provides a non-exhaustive list of dual labeled probes for qPCR analysis.

TABLE 7

Dual labeled probes for qPCR analysis with different reporter dye-quencher combinations and the corresponding absorption and emission wavelengths.

| 5' Reporter | Abs [nm] | Em [nm] | 3' Quencher |
|---|---|---|---|
| FAM | 495 | 520 | TAM, BHQ1, DAB, Eclip |
| TET | 521 | 536 | TAM, BHQ1 |
| JOE | 520 | 548 | TAM, BHQ1, BHQ2 |
| Yakima Yellow | 530 | 549 | BHQ1, Eclip |
| HEX | 535 | 556 | TAM, BHQ1, BHQ2, Eclip, BBQ650 |
| Cyanine3 | 552 | 570 | BHQ1, BHQ2, BBQ650 |
| ATTO 550 | 554 | 576 | TAM, BHQ2 |
| TAMRA | 544 | 576 | BHQ2 |
| ROX | 575 | 602 | TAM, BHQ2, BBQ650 |
| Texas Red | 583 | 603 | BHQ2, BBQ650 |
| Cyanine3.5 | 588 | 604 | BHQ2 |
| LC 610 | 590 | 610 | BHQ2 |
| LC 640 | 625 | 640 | BHQ2, BBQ650 |
| ATTO 647N | 644 | 669 | BHQ2, BHQ3, BBQ650 |
| Cyanine5 | 649 | 670 | BHQ2, BHQ3, BBQ650 |
| Cyanine5.5 | 675 | 694 | BHQ2, BHQ3, BBQ650 |
| ATTO 680 | 680 | 700 | BHQ3, BBQ650 |

Preferably, PHGI and/or PHGII abundance determination is carried out by 16S rRNA gene quantification.

In a particular embodiment, PHGI abundance determination is carried out by quantifying *Faecalibacterium prausnitzii* 16S rRNA gene sequences hybridizing specifically with SEQ ID NO: 3 or a sequence with at least 75% identity thereof. In an alternative embodiment, PHGI abundance determination is carried out by quantifying a *Faecalibacterium prausnitzii* 16S rRNA gene sequence comprising or consisting of SEQ ID NO: 3 or a sequence with at least 75% identity thereof.

In another embodiment, PHGII abundance determination is carried out by quantifying *Faecalibacterium prausnitzii* 16S rRNA gene sequences hybridizing specifically with SEQ ID NO: 4 or a sequence with at least 75% identity thereof. In an alternative embodiment, PHGII abundance is determined by quantifying a *Faecalibacterium prausnitzii* 16S rRNA gene sequence comprising or consisting of SEQ ID NO: 4 or a sequence with at least 75% identity thereof. In a preferred embodiment, PHGI abundance determination is carried out by quantifying a *Faecalibacterium* prausnitzii 16S rRNA gene sequence comprising or consisting of SEQ ID NO: 3 and PHGII abundance by quantifying a *Faecalibacterium prausnitzii* 16S rRNA gene sequence comprising or consisting of SEQ ID NO: 4.

In preferred embodiments, PHGI 16S rRNA gene quantification is performed with at least one oligonucleotide molecule of sequence SEQ ID NO: 1 or SEQ ID NO: 2, or a sequence with at least 75% identity thereof; and/or an oligonucleotide molecule of sequence SEQ ID NO: 3 or a sequence with at least 75% identity thereof. Preferably, oligonucleotide molecules of sequence SEQ ID NO: 1 and SEQ ID NO: 2 are used.

In a further preferred embodiment, PHGI 16S rRNA gene quantification is performed with primers consisting of oligonucleotide sequences SEQ ID NO: 1 and SEQ ID NO: 2, or a sequence with at least 75% identity thereof; and/or a probe consisting of oligonucleotide sequence SEQ ID NO: 3 or a sequence with at least 75% identity thereof.

It is preferred that PHGII 16S rRNA gene quantification is performed with at least one, oligonucleotide molecule of sequence SEQ ID NO: 1 or SEQ ID NO: 2, or a sequence with at least 75% identity thereof; and/or an oligonucleotide molecule of sequence SEQ ID NO: 4, or a sequence with at least 75% identity thereof. Preferably, oligonucleotide molecules of sequence SEQ ID NO: 1 and SEQ ID NO: 2 are used.

In another preferred embodiment, PHGII 16S rRNA gene quantification is performed with primers consisting of oligonucleotide sequences SEQ ID NO: 1 and SEQ ID NO: 2, or a sequence with at least 75% identity thereof; and/or a probe consisting of oligonucleotide sequence SEQ ID NO: 4, or a sequence with at least 75% identity thereof.

Preferably, said oligonucleotide sequences with at least 75% identity described herein have at least 80%, at least 85%, at least 90%, at least 95%, more preferably 96%, 97%, 98%, 99% or 100% identity with the respective sequence (e.g., SEQ ID NO: 1, SEQ ID NO: 2, SEQ ID NO: 3 and/or SEQ ID NO: 4 respectively); a nucleotide molecule with a sequence identity of 100% being particularly preferred. Furthermore, these oligonucleotide sequences with at least 75% identity may have the same nucleotide number, may be longer or shorter than SEQ ID NO: 1, SEQ ID NO: 2, SEQ ID NO: 3 and/or SEQ ID NO: 4.

In particularly preferred embodiments, PHGI 16S rRNA gene quantification is performed, preferably by qPCR, with primers consisting of oligonucleotide sequences SEQ ID NO: 1 and SEQ ID NO: 2, and a probe consisting of oligonucleotide sequence SEQ ID NO: 3. In further preferred embodiments, PHGII 16S rRNA gene quantification is performed, preferably by qPCR, with primers consisting of oligonucleotide sequences SEQ ID NO: 1 and SEQ ID NO: 2, and a probe consisting of oligonucleotide sequence SEQ ID NO: 4.

Said oligonucleotide sequences may be modified. For example, probes may be modified to improve their resistance to nuclease degradation (e.g., by end capping), to carry detection ligands (e.g., fluorescein) or to facilitate their capture onto a solid support (e.g., poly-deoxyadenosine "tails").

In a preferred embodiment, said PHGI specific probe consists of SEQ ID NO: 3 or a sequence with at least 75% identity thereof which has been modified. Preferably, it is a dual labelled probe as described above, more preferably a hydrolysis probe. In a more preferred embodiment, SEQ ID NO: 3 is modified with 6FAM (6-carboxyfluorescein) in its 5' end and with BHQ1 (Black Hole Quencher1) in its 3' end and it is represented as 6FAM-TAAGCCCACGACCCGG-CATCG-BHQ1.

In another preferred embodiment, said PHGII specific probe consists of SEQ ID NO: 4 or a sequence with at least 75% identity thereof, which has been modified. Preferably, it is a dual labelled probe, more preferably a hydrolysis probe. In a more preferred embodiment, SEQ ID NO: 4 is modified with JOE (4',5'-dichloro-2',7'-dimethoxy-5(6)-carboxyfluorescein) in its 5' end and with BHQ1 (Black Hole Quencher1) in its 3' end and it is represented as JOE-TAAGCCCACRGCTCGGCATC-BHQ1.

The determination of the PGHI and/or PGHII abundance in an intestinal sample by the method of the invention is performed in vitro. Said intestinal sample may be an intestinal biopsy. Several methods are well known in the art for the obtaining of intestinal biopsies, e.g. by endoscopy. In a preferred embodiment said intestinal sample is a non-invasive intestinal sample. A non-invasive intestinal sample may be for instance, an intestinal biopsy obtained by a non-invasive method, such as a rectal sigmoidoscopy, and also a feces sample. In a more preferred embodiment, said intestinal sample is a feces sample.

It is preferred in the method of the invention that DNA is extracted from the intestinal sample prior to gene quantification. After sample collection, fresh samples can be processed and DNA extracted immediately. Alternatively, several treatments are commonly known in order to preserve the quality of DNA before extraction, such as freezing or mixing with a buffer or DNA stabilization solution. Prior to DNA extraction, the sample may also be subject to additional processing, such as to one or more washing cycles.

In a particular embodiment, said intestinal sample is a biopsy sample and DNA is extracted from said sample prior to the quantification of said bacterial sequences. In a preferred embodiment, said intestinal sample is a feces sample and DNA is extracted from the feces sample prior to the quantification of said bacterial sequences.

Several DNA extraction methods from biological samples are well known in the art, all these methods relying on chemical or mechanical disruption of the cells, lysis using detergents, or a combination of these approaches (Kennedy A. et al., PLoS One, 2014; 9(2):e88982). DNA from a biopsy sample may be extracted for instance using the Nucleo-Spin® Tissue Kit (Macherey-Nagel Gmbh& Co. KG).

Methods for extraction of bacterial DNA in fecal samples are known from instance from M Corist et al., Journal of Microbiological Methods, 2002; 50(2):131-139, Whitney D et al., Journal of Molecular Diagnostics, American Society for Investigative Pathology, 2004; 6(4):386-395 and WO2003/068788. Preferred, methods use a combination of mechanical disruption, such as high speed bead beating extraction, chemical lysis and a final purification step, preferably using silica membrane column such as those included in the commercially available DNA extraction kits "MobioPowerSoil® DNA extraction procedure" (Mo-Bio Laboratories Inc.,), FastDNA® SPIN Kit for soil procedure (MP biomedicals) and NucleoSpin® Soil (Macherey-Nagel Gmbh& Co. KG). The presence of PCR inhibitors in the DNA extracts from fecal samples such as bilirubins, bile salts and complex carbohydrates is one of the difficulties faced for the determination of DNA biomarkers in DNA extracts from feces (Fleckna et al., Mol Cell Probes, 2007; 21(4):282-7). Preferred DNA extraction methods are those that provide fecal extracts with a low amount of PCR inhibitors, such as less than 5%, preferably less than 2%, more preferably less than 1%, even more preferably less than 0.5%, such as less than 0.25%, 0.1%, 0.05% or 0.01%.

Quantification levels can be absolute or relative. It is generally preferred that the abundance levels are normalized. Normalization can be performed with respect to different measurements in the sample, such as by sample weight, human cells quantification, total DNA quantification, total bacteria quantification, total *F. prausnitzii* quantification or the other *F. prausnitzii* phylogroup quantification. These methods are well known to a person skilled in the art.

In a particular embodiment, the quantification of PHGI and/or PHGII abundance levels is performed by qPCR and the quantification levels are normalized. In a preferred embodiment, normalization is carried out with respect to total bacteria 16S rRNA gene quantification, for example as the median log 10 16S rRNA gene copies/million bacterial rRNA gene copies. Several primers and probes have been described for the quantification of total bacteria, reference is made for instance to those described in Furet J-P, et al. FEMS Microbiology Ecology 2009, 68:351-362, Corless et al., J Clin Microbiol. 2000, 38(5):1747-52, Suzuki et al., Appl Environ Microbiol. 2000, 66(11):4605-14, Bach et al., J Microbiol Methods. 2002, 49(3):235-45, Nadkarni et al., Microbiology. 2002, 148(Pt 1):257-66. Preferred primers and probe for total bacteria quantification are those described in Furet J-P, et al. FEMS Microbiology Ecology. 2009; 68:351-362 and specified in Table 15, see the Examples.

The method of the invention may further comprise detecting and/or quantifying one or more biomarkers of intestinal disease, preferably these markers are specific of IBD or a particular IBD phenotype, more preferably these markers are specific of UC or CD, even more preferably these markers are specific of CD. IBD biomarkers and its implications for classification and diagnosis are described for instance in Silverberg et al., Can J Gastroenterol. 2005, 19 Suppl A:5-36, and Satsangi et al., Gut 2006; 55, 749-753.

The term "biomarker" as used herein refers to markers of disease which are typically substances found in a bodily sample that can be easily measured. Said bodily sample can be for instance a blood, plasma or feces sample. Typically, the measured amount correlates to an underlying disease pathophysiology, such as presence or absence of a particular IBD disease or phenotype, making it useful for diagnosing and measuring the progress of a disease or the effects of a treatment. The term biomarker encompasses biophysical and biochemical determinations, including genetic and serological markers.

Serological biomarkers may be used, such as for instance anti-*Saccharomyces cerevisiae* antibodies (ASCA), antineutrophil cytoplasmic autoantibodies (ANCA), anti-OMPC and anti-I2, and anti-CBir1 flagellin antibodies. Other authors have reported that the combination of ASCA, ANCA, anti-OmpC, and anti-I2 may help in the subclassification of CD, in particular that these serological markers are associated with particularly complicated and severe diseasebehaviour, including need for surgery. Genetic markers might also be used, such as NOD2/CARD15, HLA, MDR1, DLGS or TLR4 genes.

Microbiota biomarkers may also be used. In a particular embodiment, PHGI and/or PHGII abundance is used in combination with leucocyte counts. It has been previously reported that CD and UC could be differentiated through monitoring *F. prausnitzii* abundance in conjunction with fecal leucocyte counts (Swidsinski et al., Inflamm Bowel Dis. 2008; 14:147-161). In a particularly preferred embodiment, PHGI and/or PHGII abundance is used in combination with *Escherichia coli* abundance. Lopez-Siles et al. (International Journal of Medical Microbiology. 2014; 304:464-475) described the use of *F. prausnitzii* abundance in combination with *Escherichia coli* abundance as a complementary contrasting indicator.

In a particular embodiment, the method of the invention further comprises the quantification of total *F. prausnitzii* (FT) and/or *E. coli* (EC). FT abundance determination may be performed with primers with sequence SEQ ID NO: 5 and SEQ ID NO: 6, or a sequence with at least 75% identity thereof; and a probe with sequence SEQ ID NO: 7 or a sequence with at least 75% identity thereof. Similarly, EC abundance determination may be performed with primers with sequence SEQ ID NO: 14 and SEQ ID NO: 15, or a sequence with at least 75% identity thereof; and a probe with sequence SEQ ID NO: 16 or a sequence with at least 75% identity thereof.

Preferably, said oligonucleotide sequences with at least 75% identity described herein have at least 80%, at least 85%, at least 90%, at least 95%, more preferably 96%, 97%, 98%, 99% or 100% identity with the respective sequence (e.g., SEQ ID NO: 5, SEQ ID NO: 6, SEQ ID NO: 7, SEQ ID NO: 14, SEQ ID NO: 15, and/or SEQ ID NO: 16, respectively); a nucleotide molecule with a sequence identity of 100% being particularly preferred.

In the method of the invention, said reference sample can be an individual sample or a collection of samples of the population of reference. The population of reference is generally selected according to the use given to the method of the invention, for example, for diagnosis said population of reference would typically be a healthy subject or a patient in remission, whereas for determining the activity or progression of the disease the population of reference would generally be the same patient at a previous point in time, e.g. at diagnosis or in remission.

The term intestinal disease refers to those diseases affecting the small intestine, the colon and/or rectum. Preferably, said intestinal disease is selected from the group consisting of CRC, IBS and IBD. In a particular embodiment, said intestinal disease is CRC. In another particular embodiment, said intestinal disease is IBS. In a preferred embodiment, said intestinal disease is IBD.

The method of the invention may be used for the screening or early detection of intestinal disease, for the diagnosis of intestinal disease, for the determination of disease activity, for monitoring of progression and/or activity of intestinal disease, for monitoring relapses of intestinal disease, and/or for monitoring postsurgical recurrence of intestinal disease, and/or for determining efficacy of a treatment on an intestinal disease.

In preferred embodiments, the method of the invention is used for the screening or early detection of IBD, for the diagnosis of IBD, for monitoring progression of IBD, for monitoring relapses of IBD, and/or for monitoring postsurgical recurrence of IBD, and/or for determining efficacy of a treatment on IBD.

IBD alternates periods where the patients have symptoms of the disease (flare ups) and other periods where they do not have the symptoms and they are in remission. When a patient is in a remission period and then switches to present them they have a relapse. A test for detecting presence of the disease may also enable to detect relapses.

One of the available treatments that can be applied to IBD patients is the surgical resection of the affected zone in the gut. The expression post-surgical recurrence refers to those situations where the treatment is unsuccessful and after a certain period of time the patient suffers from IBD again. A test for detecting presence of the disease may also enable to detect postsurgical recurrence.

In a more preferred embodiment; the method of the invention is used for the screening and/or diagnosis of an intestinal disease, preferably of IBD. Preferably, said reference sample is a healthy subject sample and/or the sample of a subject with intestinal disease in remission. A healthy subject is defined as a subject not suffering from intestinal disease, preferably not suffering from IBD, more preferably not suffering of CD or UC. Said sample from a healthy patient, can be obtained for instance from patients who underwent colonoscopy for different reasons, such as rectorrhagia, CRC familial history or abdominal pain. In a preferred embodiment, said reference sample is the sample of the same subject in remission.

Biomarkers for the determination of healthy digestive status according to the present invention are shown in Examples 14 and 15. Particularly preferred biomarkers for the determination of healthy digestive status are PHGI/EC, PHGII/EC, FT/PHGI and FT/PHGII. The PHGI/EC, PHGII/EC ratios were shown to decrease in samples from healthy patients in Example 14, whereas FT/PHGI and FT/PHGII were shown to be good discriminators by ROC curve analysis in Example 15

A person skilled in the art will know that establishing the right diagnostic will enable to provide a more accurate prognostic, to choose the most appropriate prophylactic or therapeutic treatment for each disease or disease subtype, and even to predict the efficacy of a particular treatment. In a particular embodiment, the method of the invention is used for prognosis purposes. In another embodiment, the method of the invention is used for selecting the most appropriate prophylactic or therapeutic treatment. In a further embodiment, the method of the invention is used for predicting the efficacy or usefulness of a given prophylactic or therapeutic treatment. Preferably, said treatment is a therapeutic treatment.

Biomarkers for the screening and/or diagnosis of IBD, CD and/or UC according to the present invention are shown in Examples 14 and 15. Particularly preferred biomarkers for the screening and/or diagnosis of IBD are PHGI, PHGII, PHGI/EC and PHGII/EC. PHGI and PHGII whose abundance decreases in IBD, and PHGI/EC and PHGII/EC ratios that increase in IBD. IBD may be UC or CD. In a particular embodiment, said IBD is UC. Particularly preferred biomarkers for the screening and/or diagnosis of UC are PHGI, PHGII PHGI/EC and PHGII/EC. PHGI, PHGII whose abundance decreases in UC, and PHGI/EC and PHGII/EC ratios that increase in UC, preferably PHGI/EC and PHGII/EC. In a preferred embodiment said IBD is CD. Particularly preferred biomarkers for the screening and/or diagnosis of CD are PHGI, PHGII, PHGI/EC and PHGII/EC. PHGI, PHGII, whose abundance decrease in CD, and PHGI/EC and PHGII/EC that increase in CD preferably PHGI/EC and PHGII/EC.

Typically, CD is distinguished from UC by disease proximal to the colon, perineal disease, fistulas, histologic granulomas, and full-thickness as opposed to mucosa-limited disease. Generally, in CD, granulomas are evident in up to 50% of patients and fistulas in 25%. Table 7 below from the World Gastroenterology Organisation Global Guidelines (Inflammatory bowel disease: a global perspective, June 2009) provides an overview on the current diagnostic criteria for UC and CD:

TABLE 8

Diagnosis of Ulcerative colitis (UC) and Crohn's disease (CD).

| Diagnosis | UC | CD |
|---|---|---|
| Suspected | Presence of typical clinical manifestations-further investigation required | |
| Suggested | Presence of clinical features + either positive image or endoscopic findings | |
| Rule out: | Chronic schistosomiasis | Chronic intestinal infections (small-intestinal TB, amebiasis, *Yersinia*) |
| | Amebiasis | Lymphogranuloma venereum |
| | Intestinal tuberculosis (TB) | Actinomycosis |
| | | Intestinal lymphoma |
| | Ischemic colitis | Chronic diverticulitis |
| | Radiation colitis | Ischemic colitis |
| | CD in the colon | Behçet's disease |
| | | UC |
| | | NSAID enteropathy |
| Define | Suggested diagnosis + other causes ruled out + typical hystopathy of resected specimen. In areas of high TB prevalence: a negative TB culture (biopsy or resected bowel) | |

Furthermore, features for differentiating between UC and CD are provided in Table 9 below from the World Gastroenterology Organisation Global Guidelines (Inflammatory bowel disease: a global perspective, June 2009):

TABLE 9

Main differential diagnoses for Ulcerative colitis (UC) and Crohn's disease (CD).

| | Typical UC features | Typical CD features |
|---|---|---|
| Clinical | Frequent small-volume diarrhea with urgency Predominantly bloody diarrhea | Diarrhea accompanied by abdominal pain and malnutrition Stomatitis Abdominal mass Perianal lesions |
| Endoscopic and radiological | Diffuse superficial colonic inflammation Involvement of rectum, but this can be patchy Shallow erosions and ulcers Spontaneous bleeding | Discontinuous transmural asymmetric lesions Mainly involving ileum and right-sided colon Cobblestone appearance Longitudinal ulcer Deep fissures |
| Histopathological | Diffuse inflammation in mucosa or submucosa Crypt architecture distortion | Granulomatous inflammation Fissures or aphthous ulcers can be seen; often transmural inflammation |
| Serological markers | Antineutrophil cytoplasmic antibodies | Anti-*Saccharomyces cerevisiae* antibodies |

In a further embodiment, the method of the invention for the detection of an intestinal disease is a method for the differential diagnosis between CD and UC. Biomarkers for the differential diagnosis between CD and UC according to the present invention are shown in Examples 14 and 15. Particularly preferred biomarkers for the differential diagnosis between CD and UC are PHGI, PHGII as identified by ROC curve analysis and, PHGI/EC and PHGII/EC ratios that increase in CD.

Subtypes classification is typically performed using international classifications, such as those issued by the international working group on its report of Rome 1991, Vienna 1998 or Montreal 2005. Preferably, IBD subtypes are determined according to the Montreal classification (further details on the Montreal classification are provided below).

In a preferred embodiment UC patients are classified by the extent of colorectal inflammation in the following subtypes:
- E1: ulcerative proctitis: involvement limited to the rectum,
- E2: distal colitis: involvement limited to the portion of the colorectum distal to the splenic flexure, and
- E3: extensive UC or pancolitis: involvement extends proximal to the splenic flexure.

In another preferred embodiment, CD patients are classified according to the location of the disease in the following sub-types: ileal CD (I-CD), ileocolonic CD (IC-CD), and colonic CD (C-CD).

Biomarkers for the detection of I-CD, IC-CD and C-CD according to the present invention are shown in Example 16. Particularly preferred biomarkers for the detection of I-CD are PHGI/PHGII, and FT/PHGII which were shown to be good discriminators by ROC curve analysis. A preferred biomarker for the detection of IC-CD is FT/PHGI which was shown to be a good discriminator by ROC curve analysis. Preferably, said ratios have been calculated by subtraction as described above and in the Examples. In a particular embodiment, PHGI abundance is determined and a significant reduction of PHGI abundance levels in the subject sample with regard to said reference sample is indicative of CD, preferably of CD with ileal involvement (IC-CD or I-CD).

Particularly preferred biomarkers for the detection of C-CD are PHGI, PHGII, PHGI/PHGII, PHGI/EC and PHGII/EC, preferably PHGI and PHGI/EC which were shown to be good discriminators by ROC curve analysis. Preferably, said ratios have been calculated by subtraction as described above and in the Examples.

In another particular embodiment, the PHGII/PHGI ratio is determined and a significant deviation in the subject sample values with regard to said reference sample is indicative of CD, preferably of CD with colonic involvement (C-CD or IC-CD).

In a further particular embodiment, PHGI abundance and PHGII abundance is determined and a significant reduction of PHGII with no significant reduction of PHGI is indicative of I-CD.

The method of the invention may also comprise combining the results of PHGI abundance, PHGII abundance and/or further biomarkers detection and/or quantification as described herein with other indicators of intestinal disease, preferably of IBD.

The diagnosis of IBD is generally confirmed by clinical evaluation and a combination of laboratory, endoscopic, histological, or imaging-based investigations. The result of these clinical, laboratory, endoscopic, histological, and imaging-based investigations alone or in combination can be indicators of IBD. Clinical investigations are typically endoscopy, histopathology, and imaging tests, including ultrasound, magnetic resonance imaging, computed tomography scanning, barium fluoroscopy and/or isotope-labelled scans (Mowat et al., Gut 2011, 1-37).

Laboratory investigations may include full blood count, urea and electrolytes, liver function tests, erythrocyte sedimentation rate, C reactive protein, ferritin, transferrin saturation, vitamin B12, and folate.

Preferably, said laboratory tests include fecal tests. Fecal tests commonly used for IBD diagnosis are routine fecal examinations and cultures to eliminate bacterial, viral or parasitic causes of diarrhea, to exclude inter alia *Clostridium difficile* or cytomegalovirus infections, checking for occult blood or fecal leukocytes, calprotectin, lactoferrin and α1-antitripsin.

In a particular embodiment, the method of the invention is used in combination with the fecal calprotectin test. Calprotectin is an abundant neutrophil protein found in both plasma and stool that is markedly elevated in infectious and inflammatory conditions, including IBD. The role of fecal calprotectin as a biomarker of intestinal inflammation in IBD has previously been described, see for instance, Konikoff and Denson, Inflamm Bowel Dis. 2006; 12(6):524-34; or Van Rheenen et al. BMJ 2010; 341:c3369.

There are several indexes used to assess disease activity, these can be for instance validated clinical indices: Crohn's Disease Activity Index (CDAI) (Best, W. R., et al. Gastroenterology, 1976. 70(3): p. 439-44.), Harvey-Bradshaw (*Lancet*. 1980; 315 (8167):514), Mayo (Pineton de Chambrun, G., L. et al. Nat Rev Gastroenterol Hepatol, 2010. 7(1): p. 15-29), Perianal Disease Activity Index (PDAI), fistula drainage assessment, quality of life scores: Inflammatory Bowel Disease Questionnaire (IBDQ), and endoscopic indices: Crohn's Disease Endoscopic Index of Severity (CDEIS)/Simple Endoscopic Score for Crohn's Disease (SES-CD), Rutgeeerts' score for postsurgical recurrence), see Sostegni et al., Aliment Pharmacol Ther. 2003; 17 Suppl 2:11-7. In particular, for UC see for instance, True Love and Witts (Journal of Crohn's and colitis 2008; 2:1-23) or the Sutherland Disease Activity Index (Sutherland et al. *Gastroenterology* 1987; 92:1894-8; and for CD, see for instance the Harvey-Bradshaw simplified Crohn's disease activity index (*Lancet*. 1980; 315 (8167):514).

In a further aspect, the invention relates to a method for determining disease activity (i.e., calprotectin levels over 250 μg/g) wherein said method comprises steps a) and b) as defined in the above aspect, wherein a significant deviation in the subject sample values with regard to said reference sample is indicative of active intestinal disease.

Biomarkers for detecting disease activity in IBD, UC or CD according to the present invention are shown in Example 18. Particularly preferred biomarkers for detecting disease activity in CD are PHGI, PHGII, PHGII/EC. PHGI which was shown to be a good discriminator by ROC curve, PHGII, whose abundance decreases in active CD, and PHGII/EC ratio that increases. On the other hand, particularly preferred biomarkers for detecting disease activity in UC are PHGI, PHGII, FT/PHGI, and PHGI/PHGII. PHGI, whose abundance decreases in active UC, PHGII which was shown to be a good discriminator by ROC curve, FT/PHGI ratio that decreases, PHGI/PHGII ratio that decreases, and PHGI/EC ratio that increases. PHII for CD and PHI for UC disease appear to be the perfect discriminators for disease activity (i.e., calprotectin levels over 250 μg/g).

In a related aspect, the invention refers to a method for the monitoring of the activity of an intestinal disease in a human subject comprising steps a) and b) as defined in the above aspect, wherein a significant deviation in the subject sample values with regard to said reference sample is indicative of active intestinal disease and wherein said reference sample is preferably a previous sample of the same subject (e.g., at diagnosis or in remission).

For any of these aspects, said intestinal disease is preferably selected from the group consisting of inflammatory bowel disease (IBD), irritable bowel syndrome (IBS) and colorectal cancer (CRC), and more preferably is IBD. In a particular embodiment, said mathematical combination with FT abundance and/or EC abundance is a ratio selected from the group consisting of: PHGI abundance/EC abundance, PHGII abundance/EC abundance, FT abundance/PHGI abundance, and FT abundance/PHGII abundance. Preferably, abundance determination is performed by qPCR and is expressed as threshold cycle (Ct) value and said ratio is obtained by subtracting from the first Ct value the second Ct value.

Biomarkers for the monitoring of disease activity according to the present invention are shown in Example 19. Particularly preferred biomarkers for the monitoring of disease activity (i.e., determination of increased inflammatory activity between two time points) in UC are PHGI, and, FT/PHGI ratio, that decrease.

Several treatments are currently available for IBD management. The most appropriate treatment will generally be selected according to the disease location, severity and activity. Common pharmacotherapies currently used are anti-inflammatory chemicals derived from sialicylic acid (i.e. mesalazine, and sulfasalazine), corticosteroids (i.e. prednisone, methyl-prednisone and budesonide), antibiotics (i.e. metronidazole and ciprofloxacin), immunosuppressors (i.e. azathioprine and mercaptopurine), antimetabolite and antifolate methotrexate, and the so called "biological" drugs consisting of antibodies against tumour necrosis factor α (TNFα), such as infliximab, adalimumab, cetolizumab pegol, etanercept, and golimumab. Intestinal resection is also indicated in those patients with fulminant or fistulising CD and for those patients unresponsive to any of the previously mentioned medication (refractory cases). More recently, persistence of unmet therapeutic needs in CD patients with refractory disease has raised interest in innovative cellular immunoregulatory and regenerative medicines including autologous hematopoietic stem cell transplant. Also a growing body of literature supports the emerging concept that suggests that probiotics or prebiotics may have therapeutic effects in IBD through balancing the disbiosis. For instance, studies in animal models have pointed out that some species of the gut microbiota such as *Bacteroides fragilis* and *F. prausnitzii* are able to produce molecules that prevent colitis or with anti-inflammatory effects respectively, which shed new light on the future use of gut microbiota as therapeutics in this intestinal disorders. Preferred treatments are mesalazine, moderate immunosuppressants, such as azathioprine, or methotrexate, and anti-TNF a agents, such as infliximab, adalimumab, cetolizumab pegol, etanercept, and golimumab.

The invention further provides a method for predicting the efficacy of a treatment. A particular embodiment relates to a method for predicting the efficacy of a treatment in a human subject suffering from IBD, wherein said method comprises:
 a. determining the abundance of *Faecalibacterium prausnitzii* phylogroup I members (PHGI) and/or *Faecalibacterium prausnitzii* phylogroup II members (PHGII) in an intestinal sample from said subject according to a method of the first aspect; and
 b. comparing the PHGI and/or PHGII abundance, and/or a mathematical combination thereof, and/or optionally a mathematical combination of any of these with Total *F. Prausnitzii* (FT) abundance and/or *E. coli* (EC) abundance, in the subject sample with the corresponding values in a reference sample,
wherein a significant deviation in the subject sample values with regard to said reference sample is indicative of increased possibilities of response to the treatment.

In a related aspect, the invention refers to an in vitro method for the classification of a subject suffering from IBD as responder to a treatment, said method comprising steps a) and b) of the above aspect of the invention, wherein a significant deviation in the subject sample values with regard to said reference sample is indicative of increased possibilities of response to the treatment and wherein a subject with increased possibilities of response is classified as responder. In a further related aspect, the invention refers to a method for selecting a treatment for a subject suffering from IBD, said method comprising the classification of the subjects as responders or non-responders to a treatment as described in the above aspect, and the selection of said treatment for responders.

Said treatment may be any of the recited above. In a particular embodiment, said treatment is with an anti-TNFalpha agent. Preferably, said reference sample is a healthy subject sample or a sample of a patient with intestinal disease in remission. Other preferred features and embodiments are as defined above for other aspects of the invention.

Biomarkers for the determination of response to TNF-alpha treatment according to the present invention are shown in Example 20. Particularly preferred biomarkers for the classification of subjects as responders or non-responders of TNF-alpha treatment are PHGI and PHGII. In Example 20, it was observed that PHGI Ct were increased in non-responders of UC and CD (26.80% and 53.94%, respectively) and PHGII Ct were 66.82% increased in non-responders of UC.

The term "responder" as used herein refers to those subjects suffering from IBD (e.g., CD or UC) which show a decrease in inflammation, i.e., a decrease of calprotectin levels below 250 µg/G after biological treatment induction. The term "induction" as used herein refers to the time period where different treatment dosage is given to achieve the therapeutic dose.

On the other hand, treatment may be based on surgery. Preferably, the treatment is a combination of pharmacotherapy and surgery. UC is typically surgically curable. However, surgical resection is often not curative in CD, with recurrence being the norm. Surgical intervention in IBD includes inter alia the following:
 UC: Proctocolectomy with ileostomy, total proctocolectomy with ileoanal anastomosis;
 Fulminant colitis: Surgical procedure of choice is subtotal colectomy with end ileostomy and creation of a Hartmann pouch;
 CD: Surgery most commonly performed in cases of disease complications of the disease; generally consists of conservative resection (eg, potential stricturoplasty vs resective surgery) to preserve bowel length in case future additional surgery needed;
 Selected patients with distal ileal or proximal colonic disease: Option for ileorectal or ileocolonic anastomosis;
 Severe perianal fistulas: Option for diverting ileostomy; generally, resection for symptomatic enteroenteric fistulas.

The invention further provides a method for treating a subject which has an intestinal disease, wherein said method comprises the steps of the method of the invention for the detection of an intestinal disease as described herein and further comprises c) administering a treatment to this subject. Preferably, wherein said treatment is an anti-TNF alpha agent.

The invention also provides a method for treating a subject which has an intestinal disease, wherein said method comprises the steps of the method of the invention for classifying a subject as a responder or non-responder and further comprises c) administering a treatment to a subject which is a responder. Preferably, wherein said treatment is an anti-TNF alpha agent.

Preferably, the method of the invention further comprises storing the results of the method in a data carrier. In one embodiment, said data carrier is a paper sheet. In a preferred embodiment, said data carrier is a computer readable medium. As used herein, "a computer readable medium" can be any apparatus that may include, store, communicate, propagate, or transport the results of the determination of the method of the invention. The medium can be an electronic, magnetic, optical, electromagnetic, infrared, or semiconductor system (or apparatus or device) or a propagation medium.

Sensitivity, specificity, and accuracy, or a combination thereof, are parameters typically used to describe the validity or performance of a test. In particular, they are used to quantify how good and reliable the method is.

Preferably, the method of the invention has a sensitivity of 70% to 90%, 75% to 95%, 80% to 95%, 85% to 100%, or 90% to 100%. More preferably, the method of the invention has sensitivity values of at least 85%, such as about 86%, 87%, 88%, 89%, 90%, 91%, 92%, 93%, 94%, 95%, 96%, 97%, 97.5%, 98%, 99% or 100%.

Preferably, the method of the invention has a specificity of 70% to 90%, 75% to 95%, 80% to 95%, 85% to 100%, or 90% to 100%. More preferably, the method of the invention has specificity values of at least 85%, such as about 86%, 87%, 88%, 89%, 90%, 91%, 92%, 93%, 94%, 95%, 96%, 97%, 97.5%, 98%, 99% or 100%.

In a preferred embodiment, the method for detecting inflammatory bowel disease (IBD) of the present invention diagnoses, early detects, determines progression, determines relapses, determines recurrence and/or determines efficacy of a treatment in an statistically significant manner with a sensitivity and/or specificity of at least 60%, at least 65%, at least 70%, at least 75%, at least 80%, at least 85%, at least 90%, at least 95%, at least 97.5%, or preferably 100%.

Preferably, the accuracy of the method of the invention is of at least 60%, at least 65%, at least 70%, at least 75%, at least 80%, at least 85%, at least 90%, at least 95%, at least 97.5%, or preferably 100%. In a preferred embodiment, it has an accuracy of 70% to 90%, 75% to 95%, 80% to 95%, 85% to 100%, or 90% to 100%. Preferably, the method of the invention has accuracy values of at least 85%, such as about 86%, 87%, 88%, 89%, 90%, 91%, 92%, 93%, 94%, 95%, 96%, 97%, 97.5%, 98%, 99% or 100%.

Sensitivity, specificity and accuracy parameters are proportions, thus the according confidence intervals can be calculated by using standard methods for proportions well known in the art. Two types of 95% confidence intervals are generally defined around proportions. The exact confidence interval is defined by using binomial distribution to reach an exact estimate. Asymptotic confidence interval is calculated by assuming a normal approximation of the sample distribution. A person skilled in the art will know how to define the appropriate confidence interval. The choice of one or another type of confidence interval will typically depend on whether the sample proportion is a good approximation to a normal distribution.

Accuracy is preferably determined by the area under the ROC curve. The "ROC curve" is a graphic presentation of the relationship between both sensitivity and specificity and it helps to decide the optimal model through determining the best threshold (optimal cut-point) for the screening test. The area under ROC curve (AUC) provides a way to measure the accuracy of a test. Preferably, the AUC range values of the method of the invention are from 0.6 to 1, more preferably 0.7 to 1, more preferred values being in the range of 0.75 to 1, more preferably of 0.8 to 1 or of 0.9 to 1. In preferred embodiments, AUC is from 0.7 to 0.9, from 0.7 to 0.95, from 0.75 to 0.9, from 0.75 to 0.95, from 0.8 to 0.9, from 0.8 to 0.95, from 0.85 to 0.9, or from 0.85 to 0.95.

In a preferred embodiment, the method for detecting inflammatory bowel disease (IBD) of the present invention diagnoses, early detects, determines progression, determines relapses, determines recurrence and/or determines efficacy of a treatment in an statistically significant manner with an AUC value of at least 0.6, at least 0.65, at 0.7, at least 0.75, at least 0.8, at least 0.85, at least 0.9, at least 0.95 or higher.

Use of PHGI and/or PHGII Abundance as Biomarker for the Detection of Intestinal Diseases In a further aspect, the invention relates to the use of *Faecalibacterium prausnitzii* phylogroup I members (PHGI) and/or *Faecalibacterium prausnitzii* phylogroup II members (PHGII) abundance, and/or a mathematical combination thereof, and/or optionally a mathematical combination of any of these with Total *F. Prausnitzii* (FT) abundance and/or *E. coli* (EC) abundance, in an intestinal sample of a human subject as biomarker for the detection of an intestinal disease, and/or for predicting the efficacy of a drug in the treatment of an intestinal disease, In a particular embodiment, it relates to the use of *Faecalibacterium prausnitzii* phylogroup I members (PHGI) abundance, optionally with *Faecalibacterium prausnitzii* phylogroup II members (PHGII) abundance, including any mathematical combinations thereof, in an intestinal sample of a human subject as biomarker for the detection of intestinal disease. The determination of the PGHI and/or PGHII abundance in an intestinal sample is performed in vitro according to the method of the invention.

In preferred embodiments, PHGI abundance is used in combination with PHGII abundance, including any mathematical combinations thereof, in an intestinal sample of said human subject, preferably wherein the ratio between the PHGII abundance and the PHGI abundance (PHGII/PHGI ratio) is determined.

As above-mentioned, one of ordinary skill in the art knows several methods and devices for the determination of the abundance of *Faecalibacterium prausnitzii* PHGI and/or PHGII. Further details are provided above.

In preferred embodiments, PHGI and/or PHGII abundance determination is performed by gene quantification with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

Also, several genes can be used for bacterial quantification purposes as described above. Preferably, PHGI and/or PHGII abundance determination is carried out by 16S rRNA gene quantification. In a particular embodiment, PHGI abundance determination is carried out by quantifying a *Faecalibacterium prausnitzii* 16S rRNA gene sequence comprising or consisting of SEQ ID NO: 3. In another embodiment, PHGII abundance is determined by quantifying a *Faecalibacterium prausnitzii* 16S rRNA gene sequence comprising or consisting of SEQ ID NO: 4. In a preferred embodiment, PHGI abundance determination is carried out by quantifying a *Faecalibacterium prausnitzii* 16S rRNA gene sequence comprising or consisting of SEQ ID NO: 3 and PHGII abundance by quantifying a *Faecalibacterium prausnitzii*

16S rRNA gene sequence comprising or consisting of SEQ ID NO: 4. Preferred oligonucleotides for PHGI and/or PHGII abundance determination, detection chemistries and preferred embodiments of the quantification method are provided above.

Said intestinal sample may be an intestinal biopsy. In a preferred embodiment said intestinal sample is an intestinal biopsy obtained by a non-invasive method, such as a rectal sigmoidoscopy. In another preferred embodiment, said intestinal sample is a feces sample. Preferred embodiments on the processing of the sample are provided above.

Preferably, said intestinal disease is selected from the group consisting of CRC, IBS and IBD. In preferred embodiments, said intestinal disease is IBD, preferably said IBD is Ulcerative colitis (UC) or Crohn's disease (CD), more preferably said IBD is CD. Further details on the diagnosis, classification, and treatment of said intestinal diseases are provided above.

In preferred embodiments, PHGI and/or PHGII abundance in an intestinal sample is used as biomarker for the screening, for the diagnosis, for monitoring progression, for monitoring relapses, and/or for monitoring postsurgical recurrence of an intestinal disease, and/or for determining efficacy of a treatment on an intestinal disease; preferably for the screening or diagnosis of an intestinal disease.

Additional details and other preferred embodiments on the use of PHGI and/or PHGII abundance in an intestinal sample of a human subject as biomarker for the detection of intestinal disease are as provided under the above aspects of the invention.

A Kit for Detecting Intestinal Disease

A further aspect of the invention relates to a kit for detecting intestinal disease according to a method as described under the third aspect of the invention, said kit comprising:
- a reagent for determining the abundance of *Faecalibacterium prausnitzii* phylogroup I members (PHGI);
- optionally, a reagent for determining the abundance of *Faecalibacterium prausnitzii* phylogroup II members (PHGII); and
- instructions for use of said reagent(s) to determine the abundance levels of PHGI, and optionally PHGII, from a human intestinal sample.

The invention further provides a kit comprising:
- a reagent for determining the abundance of *Faecalibacterium prausnitzii* phylogroup I members (PHGI) consisting of a primer and/or probe with sequence SEQ ID NO: 3 or a sequence with at least 75% identity thereof; and/or
- a reagent for determining the abundance of *Faecalibacterium prausnitzii* phylogroup II members (PHGII) consisting of a primer and/or a probe with sequence SEQ ID NO: 4 or a sequence with at least 75% identity thereof; and
- optionally, instructions for use of said reagent(s) to determine the abundance of PHGI, and/or PHGII, from a human intestinal sample.

Preferably, said intestinal sample is a feces sample.

Said kit may be used for the screening, for the diagnosis, for determining disease activity, for monitoring activity and/or progression, for monitoring relapses, and/or for monitoring postsurgical recurrence of intestinal disease, and/or for determining efficacy of a treatment on intestinal disease; preferably for the screening and/or diagnosis of intestinal disease. Accordingly, the invention further relates to the use of a kit as described herein for detecting an intestinal disease, for predicting the efficacy of a drug in the treatment of an intestinal disease, and/or for the differential diagnosis of IBD phenotypes.

Reagents for determining PHGI and/or PHGII abundance are as described above for the previous aspects of the invention.

In a particular embodiment, said reagent for determining PHGI abundance is selected from the group consisting of:
- a pair of nucleic acid primers consisting of oligonucleotide sequences SEQ ID NO: 1 and SEQ ID NO: 2 or an oligonucleotide sequence with at least 75% identity thereof, and/or
- a probe consisting of oligonucleotide sequence SEQ ID NO: 3 or an oligonucleotide sequence with at least 75% of identity thereof.

In another particular embodiment, said reagent for determining PHGII abundance is selected from the group consisting of:
- a pair of nucleic acid primers consisting of oligonucleotide sequences SEQ ID NO: 1 and SEQ ID NO: 2 or an oligonucleotide sequence with at least 75% identity thereof, and/or
- a probe consisting of oligonucleotide sequence SEQ ID NO: 4 or an oligonucleotide sequence with at least 75% identity thereof.

In a preferred embodiment, said reagent for determining PHGI abundance and said reagent for determining PHGII abundance are those in the particular embodiments defined above for the previous aspects of the invention.

In a preferred embodiment, the kit may further comprise DNA extraction means, means for carrying out the hybridization and/or amplification, detection means, and/or one or more containers for collecting and/or holding the biological sample.

The kit of the invention may further comprise a reference reagent for normalizing data, preferably wherein said reagent are primers and/or a probe for the quantification of total bacteria. Further details on quantification data normalization are provided above.

Preferably, said intestinal disease is selected from the group consisting of CRC, IBS and IBD. In preferred embodiments, said intestinal disease is IBD, preferably said IBD is Ulcerative colitis (UC) or Crohn's disease (CD), more preferably said IBD is CD. Further details on the diagnosis, classification, and treatment of said intestinal diseases are provided above.

Additional details and other preferred embodiments of the kit of the invention for the detection of intestinal disease are as provided for the previous aspects of the invention.

A Nucleic Acid Sequence of the Invention

An additional aspect of the invention relates to a nucleic acid molecule with a sequence selected from the group consisting of SEQ ID NO: 1, SEQ ID NO: 2, SEQ ID NO: 3, and SEQ ID NO: 4 or an oligonucleotide sequence with at least 75% identity thereof. Preferably, said oligonucleotide sequence with at least 75% identity have at least 80%, at least 85%, at least 90%, at least 95%, more preferably, 96%, 97%, 98%, 99% or 100% identity with SEQ ID NO: 1, SEQ ID NO: 2, SEQ ID NO: 3 and/or SEQ ID NO: 4. Furthermore, these oligonucleotide sequences with at least 75% identity may have the same nucleotide number, may be longer or shorter than SEQ ID NO: 1, SEQ ID NO: 2, SEQ ID NO: 3 and/or SEQ ID NO: 4.

In a particular embodiment, said nucleic acid molecule has a sequence selected from the group consisting of SEQ ID NO: 1 or a sequence with at least 80% identity thereof; SEQ ID NO: 2 or a sequence with at least 90% identity thereof;

SEQ ID NO: 3 or a sequence with at least 80% identity thereof; and SEQ ID NO: 4 or a sequence with at least 85% identity thereof.

Said nucleic acid molecules may be used as primers or probes in the method of the invention, and may be modified as described above. Additional details and other preferred embodiments are as provided for the previous aspects of the invention.

A Method for Determining the Abundance of PHGI and/or PHGII in an Intestinal Sample This section provides additional embodiments under the first aspect of the invention. In a particular embodiment relates to a method for determining the abundance of *Faecalibacterium prausnitzii* phylogroup I members (PHGI) and/or the abundance of *Faecalibacterium prausnitzii* phylogroup II members (PHGII) in an intestinal sample from a subject wherein said determination is carried out by 16S rRNA gene quantification, wherein PHGI abundance determination is carried out by quantifying a *Faecalibacterium* prausnitzii 16S rRNA gene sequence comprising or consisting of SEQ ID NO: 3, and wherein PHGII abundance determination is carried out by quantifying a *Faecalibacterium* prausnitzii 16S rRNA gene sequence comprising or consisting of SEQ ID NO: 4.

As above-mentioned, one of ordinary skill in the art knows several methods and devices for the determination of the abundance of *Faecalibacterium prausnitzii* PHGI and/or PHGII. Further details are provided above.

In preferred embodiments, 16S rRNA gene quantification is carried out with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

In preferred embodiments, PHGI 16S rRNA gene quantification is performed with at least one oligonucleotide molecule of sequence SEQ ID NO: 1 or SEQ ID NO: 2, or a sequence with at least 75% identity thereof and/or an oligonucleotide molecule of sequence SEQ ID NO: 3 or a sequence with at least 75% identity thereof. Preferably, oligonucleotide molecules of sequence SEQ ID NO: 1 and SEQ ID NO: 2 are used.

In a further preferred embodiment, PHGI 16S rRNA gene quantification is performed with primers consisting of oligonucleotide sequences SEQ ID NO: 1 and SEQ ID NO: 2, or a sequence with at least 75% identity thereof and/or a probe consisting of oligonucleotide sequence SEQ ID NO: 3 or a sequence with at least 75% identity thereof.

It is preferred that PHGII 16S rRNA gene quantification is performed with at least one, oligonucleotide molecule of sequence SEQ ID NO: 1 or SEQ ID NO: 2, or a sequence with at least 75% identity thereof; and/or an oligonucleotide molecule of sequence SEQ ID NO: 4, or a sequence with at least 75% identity thereof. Preferably, oligonucleotide molecules of sequence SEQ ID NO: 1 and SEQ ID NO: 2 are used.

In another preferred embodiment, PHGII 16S rRNA gene quantification is performed with primers consisting of oligonucleotide sequences SEQ ID NO: 1 and SEQ ID NO: 2, or a sequence with at least 75% identity thereof; and/or a probe consisting of oligonucleotide sequence SEQ ID NO: 4, or a sequence with at least 75% identity thereof.

Preferably, said oligonucleotide sequences with at least 75% identity have at least 80%, at least 85%, at least 90%, at least 95%, more preferably, 96%, 97%, 98%, 99% or 100% identity with SEQ ID NO: 1, SEQ ID NO: 2, SEQ ID NO: 3 and/or SEQ ID NO: 4. Furthermore, these oligonucleotide sequences with at least 75% identity may have the same nucleotide number, may be longer or shorter than SEQ ID NO: 1, SEQ ID NO: 2, SEQ ID NO: 3 and/or SEQ ID NO: 4.

More specifically, PHGI 16S rRNA gene quantification is preferably performed by qPCR with primers consisting of oligonucleotide sequences SEQ ID NO: 1 and SEQ ID NO: 2, and a probe consisting of oligonucleotide sequence SEQ ID NO: 3. Also, PHGII 16S rRNA gene quantification is preferably performed by qPCR with primers consisting of oligonucleotide sequences SEQ ID NO: 1 and SEQ ID NO: 2, and a probe consisting of oligonucleotide sequence SEQ ID NO: 4.

Said oligonucleotide sequences may be modified. In a preferred embodiment, said PHGI specific probe consists of SEQ ID NO: 3 or a sequence with at least 75% identity thereof which has been modified. Preferably, it is a dual labelled probe, more preferably a hydrolysis probe. In a more preferred embodiment, SEQ ID NO: 3 is modified with 6FAM (6-carboxyfluorescein) in its 5' end and with BHQ1 (Black Hole Quencher1) in its 3' end and it is represented as 6FAM-TAAGCCCACGACCCGGCATCG-BHQ1.

In another preferred embodiment, said PHGII specific probe consists of SEQ ID NO: 4 or a sequence with at least 75% identity thereof, which has been modified. Preferably, it is a dual labelled probe, more preferably a hydrolysis probe. In a more preferred embodiment, SEQ ID NO: 4 is modified with JOE (4',5'-dichloro-2',7'-dimethoxy-5(6)-carboxyfluorescein) in its 5' end and with BHQ1 (Black Hole Quencher1) in its 3' end and it is represented as JOE-TAAGCCCACRGCTCGGCATC-BHQ1.

In preferred embodiments, the PHGI and/or PHGII abundance levels are normalized as described above. Preferably, normalization is carried out with respect to total bacteria quantification.

Further details on the PHGI and/or PHGII abundance quantification methods, detection chemistries and other specifics are as provided above.

The determination of the PGHI and/or PGHII abundance in an intestinal sample by the method of the invention is performed in vitro. Said intestinal sample may be an intestinal biopsy. Several methods are well known in the art for the obtaining of intestinal biopsies, e.g. by endoscopy. In a preferred embodiment said intestinal sample is a non-invasive intestinal sample. A non-invasive intestinal sample may be an intestinal biopsy obtained by a non-invasive method, such as a rectal sigmoidoscopy, and also a feces sample. In a more preferred embodiment, said intestinal sample is a feces sample. Preferred embodiments on the processing of the sample are provided above. In a preferred embodiment, DNA is extracted from the intestinal sample prior to PHGI and PHGII gene quantification.

Additional details and other preferred embodiments on the method for determining the abundance of PHGI and/or PHGII in an intestinal sample are as provided under the previous aspects of the invention.

A Method for the Differential Diagnosis of Inflammatory Bowel Disease (IBD) Phenotypes in a Human Subject An additional aspect of the invention relates to a method for the differential diagnosis of inflammatory bowel disease (IBD) phenotypes in a human subject comprising the following steps:

i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and ii. comparing the subject sample abundance of one or more of said target microorganisms and/or a mathematical combination thereof, and/or optionally a mathematical combination of any of these with Total *F. Prausnitzii* (FT) abundance and/or *E. coli* (EC) abundance, with the corresponding values in a reference sample of the IBD phenotypes to be distinguished from to determine the IBD phenotype the subject is suffering from; wherein the subject sample presenting values significantly similar to one of said IBD phenotypes will be indicative that the subject is suffering from said IBD phenotype; and wherein said IBD phenotypes are defined by at least the combination of two, preferably three, of the following parameters:
disease location;
IBD type; and
age at diagnosis,
optionally, comprising the use of additional biomarkers for the definition of said IBD phenotypes.

IBD types, this term as used herein referring to IBD diseases or disorders have been recited above. Preferably, said IBD type is selected from the group consisting of Ulcerative Colitis (UC), Crohn's disease (CD), indeterminate colitis and inflammatory bowel disease unclassified (IBDU).

Subtypes may be defined within an IBD disease or disorder. Subtypes classification is typically performed using international classifications, such as those issued by the international working group on its report of Rome 1991, Vienna 1998 or Montreal 2005. Preferably, IBD subtypes are determined according to the Montreal classification.

In a preferred embodiment, said IBD phenotypes are selected from the group consisting of:

i. CD phenotypes defined by one or more, preferably all, of the following parameters:
   disease location;
   age at diagnosis; and
   behavior;

ii. UC phenotypes defined by one or more, preferably all, of the following parameters:
   disease location or extent; and
   severity.

Preferably, CD subtypes are for those defined by the Montreal classification, wherein CD is classified according to age at diagnosis, location and/or behavior. Similarly, preferred UC subtypes are those defined by the Montreal classification, wherein UC is classified according to disease extend and/or disease severity (World Gastroenterology Organisation Global Guidelines, Inflammatory bowel disease: a global perspective, June 2009; Satsangi et al., Gut 2006; 55, 749-753 and Silverberg et al., Can J Gastroenterol. 2005, 19 Suppl A:5-36). The specific subtypes defined according to these parameters are provided in the tables below from Satsangi et al (Satsangi et al., Gut 2006; 55, 749-753).

TABLE 10

Vienna and Montreal classification for CD.

| | Vienna | Montreal |
|---|---|---|
| Age at diagnosis | A1 below 40 y<br>A2 above 40 y | A1 below 16 y<br>A2 between 17 and 40 y<br>A3 above 40 y |

TABLE 10-continued

Vienna and Montreal classification for CD.

| | Vienna | Montreal |
|---|---|---|
| Location | L1 ileal<br>L2 colonic<br>L3 ileocolonic<br>L4 upper | L1 ileal<br>L2 colonic<br>L3 ileocolonic<br>L4 isolated upper disease* |
| Behaviour | B1 non-stricturing, non-penetrating<br>B2 stricturing<br>B3 penetrating | B1 non-stricturing, non-penetrating<br>B2 stricturing<br>B3 penetrating<br>p perianal disease modifier[†] |

*L4 is a modifier that can be added to L1-L3 when concomitant upper gastrointestinal disease is present.
[†]"p" is added to B1-B3 when concomitant perianal disease is present

TABLE 11

Montreal classification of extent of UC.

| Extent | | Anatomy |
|---|---|---|
| E1 | Ulcerative proctitis | Involvement limited to the rectum (that is, proximal extent of inflammation is distal to the rectosigmoid junction) |
| E2 | Left sided UC (distal UC) | Involvement limited to a proportion of the colorectum distal to the splenic flexure |
| E3 | Extensive UC (pancolitis) | Involvement extends proximal to the splenic flexure |

TABLE 12

Montreal classification of severity of UC.

| Severity | | Definition |
|---|---|---|
| S0 | Clinical remission | Asymptomatic |
| S1 | Mild UC | Passage of four or fewer stools/day (with or without blood), absence of any systemic illness, and normal inflammatory markers (ESR) |
| S2 | Moderate UC | Passage of more than four stools per day but with minimal signs of systemic toxicity |
| S3 | Severe UC | Passage of at least six bloody stools daily, pulse rate of at least 90 beats per minute, temperature of at least 37.5° C., haemoglobin of less than 10.5 g/100 ml, and ESR of at least 30 mm/h |

ESR, erythrocyte sedimentation rate.

In a further preferred embodiment said IBD phenotypes are defined by disease location, more preferably, these are selected from the group consisting of:

CD phenotypes consisting of ileal CD (I-CD), ileocolonic CD (IC-CD) and colonic CD (C-CD); and UC phenotypes consisting of ulcerative proctitis (UC-E1), distal colitis (UC-E2) and extensive UC or pancolitis (UC-E3).

The method of the invention may be useful for the differential diagnosis between one or more of the following IBD subtypes: UC vs C-CD, UC-E2 vs UC-E3, UC-E2 vs C-CD, UC-E2 vs IC-CD, UC-E2 vs I-CD, UC-E3 vs C-CD, UC-E3 vs IC-CD, UC-E3 vs I-CD, C-CD vs IC-CD, C-CD vs I-CD or I-CD vs IC-CD; preferably selected from the list consisting of UC vs C-CD, UC-E3 vs C-CD, I-CD vs IC-CD and C-CD vs IC-CD.

Said intestinal sample may be an intestinal biopsy. In a preferred embodiment said intestinal sample is an intestinal biopsy obtained by a non-invasive method, such as a rectal sigmoidoscopy. In another preferred embodiment, said intestinal sample is a feces sample. Preferred embodiments on the processing of the sample are provided above.

In a preferred embodiment, said IBD phenotypes are UC-E3 and C-CD and the subject sample values are compared with a UC-E3 positive reference sample and/or a C-CD positive reference sample, wherein the subject sample presenting values significantly similar to UC-E3 or C-CD will be indicative that the subject is suffering from said IBD phenotype. Preferably, said human subject has previously been diagnosed of IBD with colonic involvement. In a further preferred embodiment, optionally in combination of any of the above, said target microorganism is the PHGII.

In another further preferred embodiment, optionally in combination of any of the above, said mathematical combination with FT abundance and/or EC abundance is a ratio selected from the group consisting of: PHGI abundance/EC abundance, PHGII abundance/EC abundance, FT abundance/PHGI abundance, and FT abundance/PHGII abundance. Preferably, abundance determination is performed by qPCR and is expressed as threshold cycle (Ct) value and said ratio is obtained by subtracting from the first Ct value the second Ct value.

Biomarkers for differential diagnosis of UC from C-CD according to the present invention are shown in Example 17. Particularly preferred biomarkers for differential diagnosis of UC and C-CD are PHGI, PHGII, PHGI/EC and PHGII/EC ratios. PHGI and PHGII abundance increases in UC, and PHGI/EC and PHGII/EC ratios decrease in UC. Other particularly preferred biomarkers for differential diagnosis of UC from C-CD are FT/PHGI and FT/PHGII ratios which were shown to be good discriminators by ROC curve analysis. On the other hand, particularly preferred biomarkers for differential diagnosis of C-CD from UC are PHGI, PHGII, PHGI/PHGII, PHGI/EC, and PHGII/EC, preferably PHGI and PHGI/EC that were shown to be good discriminators by ROC curve analysis.

A Method for Diagnosing C-CD in a Human Subject Suffering from IBD with Colonic Involvement A further aspect of the invention relates to a method for diagnosing C-CD in a human subject suffering from IBD with colonic involvement comprising the following steps:
i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and
ii. comparing the subject sample abundance of one or more of said target microorganisms and/or a mathematical combination thereof, and/or optionally a mathematical combination of any of these with Total *F. Prausnitzii* (FT) abundance and/or *E. coli* (EC) abundance, with the corresponding values in a reference sample, wherein a significant deviation in the subject sample values with regard to said reference sample is indicative of C-CD.

In a particular embodiment, said target microorganism is PHGI and PHGII. In another particular embodiment said target microorganism is PHGI. In another particular embodiment, said target microorganism is PHGII.

As above-mentioned, particularly preferred biomarkers for the detection of C-CD are PHGI, PHGII, PHGI/PHGII, PHGI/EC and PHGII/EC, preferably PHGI and PHGI/EC. Preferably, said ratios have been calculated by subtraction as described above and in the Examples.

In a preferred embodiment, it relates to a method for diagnosing C-CD in a human subject suffering from IBD with colonic involvement comprising the following steps:
i. determining the abundance of *Faecalibacterium prausnitzii* phylogroup II members (PHGII) in an intestinal sample from said subject; and
ii. comparing the subject sample abundance levels with the levels in a reference sample, wherein a significant reduction of abundance levels in the subject sample with regard to said reference sample is indicative of C-CD.

Preferably, said reference sample is a sample of a healthy subject and/or a sample of a patient with IBD in remission, more preferably a sample of the same subject in remission.

In preferred embodiments, said IBD phenotypes are selected from the group consisting of I-CD, C-CD and IC-CD and the subject sample values are compared with an I-CD positive reference sample, a C-CD positive reference sample and/or a IC-CD positive reference sample, wherein the subject sample presenting values significantly similar to I-CD, C-CD or IC-CD will be indicative that the subject is suffering from said IBD phenotype.

In a preferred embodiment, the method of the invention is used for determining extension of the disease to the colonic area (IC-CD) in a human subject who has previously been diagnosed with I-CD. Preferably, said target microorganism is the PHGII.

In another preferred embodiment, the method of the invention is used for determining extension of the disease to the ileal area (IC-CD) in a human subject who has previously been diagnosed with C-CD. Preferably, said target microorganism is the PHGII.

A Method for Diagnosing IC-CD in a Human Subject Suffering from I-CD or C-CD

An additional aspect of the invention relates to a method for diagnosing IC-CD in a human subject suffering from I-CD or C-CD comprising the following steps:
i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and
ii. comparing the subject sample abundance of one or more of said target microorganisms and/or a mathematical combination thereof, and/or optionally a mathematical combination of any of these with Total *F. Prausnitzii* (FT) abundance and/or *E. coli* (EC) abundance, with the corresponding values in a reference sample from said subject at around diagnose of I-CD or C-CD, wherein a significant deviation in the subject sample values with regard to said reference sample is indicative of IC-CD.

In a particular embodiment, said target microorganism is PHGI and PHGII. In another particular embodiment said target microorganism is PHGI. In another particular embodiment, said target microorganism is PHGII. In a further embodiment, said target microorganism is FT and PHGI. As above-mentioned a preferred biomarker for the detection of IC-CD is FT/PHGI.

In a preferred embodiment, it relates to a method for diagnosing IC-CD in a human subject suffering from I-CD or C-CD comprising the following steps:
i. determining the abundance of *Faecalibacterium prausnitzii* phylogroup II members (PHGII) in an intestinal sample from said subject; and ii. comparing the subject sample PHGII abundance levels with the levels in a reference sample from said subject at around diagnose of I-CD or C-CD, wherein a significant reduction of abundance levels in the subject sample with regard to said reference sample is indicative of IC-CD.

As above-mentioned, one of ordinary skill in the art knows several methods and devices for the determination of the abundance of a target microorganism. Further details are provided above.

In preferred embodiments, said target microorganism abundance determination is performed by gene quantification with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

Also, several genes can be used for bacterial quantification purposes as described above. Preferably, said target microorganism abundance determination is carried out by 16S rRNA gene quantification.

Said target microorganism is preferably selected from the group consisting of PHGI and PHGII. In a preferred embodiment, PHGII abundance is used in combination with PHGII abundance, including any mathematical combinations thereof, in an intestinal sample of said human subject, preferably wherein the ratio between the PHGII abundance and the PHGI abundance (PHGII/PHGI ratio) is determined.

In a preferred embodiment, PHGI abundance determination is carried out by quantifying a *Faecalibacterium prausnitzii* 16S rRNA gene sequence comprising or consisting of SEQ ID NO: 3. In another embodiment, PHGII abundance is determined by quantifying a *Faecalibacterium prausnitzii* 16S rRNA gene sequence comprising or consisting of SEQ ID NO: 4. In a preferred embodiment, PHGI abundance determination is carried out by quantifying a *Faecalibacterium prausnitzii* 16S rRNA gene sequence comprising or consisting of SEQ ID NO: 3 and PHGII abundance by quantifying a *Faecalibacterium prausnitzii* 16S rRNA gene sequence comprising or consisting of SEQ ID NO: 4. Preferred oligonucleotides for PHGI and/or PHGII abundance determination, detection chemistries and preferred embodiments of the quantification method are provided under the above aspects of the invention.

With regard to total FP 16S rRNA gene quantification is performed by quantifying a *Faecalibacterium prausnitzii* 16S rRNA gene sequence comprising or consisting of SEQ ID NO: 7.

In preferred embodiments, total FP 16S rRNA gene quantification is performed with at least one oligonucleotide molecule of sequence SEQ ID NO: 5 or SEQ ID NO: 6, or a sequence with at least 75% identity thereof; and/or an oligonucleotide molecule of sequence SEQ ID NO: 7 or a sequence with at least 75% identity thereof. Preferably, oligonucleotide molecules of sequence SEQ ID NO: 5 and SEQ ID NO: 6 are used.

In a further preferred embodiment, PHGI 16S rRNA gene quantification is performed with primers consisting of oligonucleotide sequences SEQ ID NO: 5 and SEQ ID NO: 6 or a sequence with at least 75% identity thereof; and/or a probe consisting of oligonucleotide sequence SEQ ID NO: 7 or a sequence with at least 75% identity thereof. In a preferred embodiment, total FP 16S rRNA gene quantification is performed, preferably by qPCR, with primers consisting of oligonucleotide sequences SEQ ID NO: 5 and SEQ ID NO: 6, and a probe consisting of oligonucleotide sequence SEQ ID NO: 7.

Preferably, said oligonucleotide sequences with at least 75% identity have at least 80%, at least 85%, at least 90%, at least 95%, more preferably, 96%, 97%, 98%, 99% or 100% identity with SEQ ID NO: 5, SEQ ID NO: 6, and/or SEQ ID NO: 7. Furthermore, these oligonucleotide sequences with at least 75% identity may have the same nucleotide number, may be longer or shorter than SEQ ID NO: 5, SEQ ID NO: 6, and/or SEQ ID NO: 7.

In a preferred embodiment, said total FP probe consists of SEQ ID NO: 7 or a sequence with at least 75% identity thereof which has been modified. Preferably, it is a dual labelled probe, more preferably a hydrolysis probe. In a more preferred embodiment, SEQ ID NO: 7 is modified with 6FAM (6-carboxyfluorescein) in its 5' end and with TAMRA (tetramethylrhodamin) in its 3' end and it is represented as 6FAM-CAAGGAAGTGACGGCTAACTACGTGCCAG-TAMRA Further details and preferred embodiments of the quantification method are provided under the above aspects of the invention.

In a preferred embodiment, said method further comprises detecting and/or quantifying one or more biomarkers of intestinal disease, preferably of IBD.

In a further preferred embodiment, said method further comprises combining the results of the target microorganism quantification and/or said further biomarkers detection and/or quantification with clinical signs and/or symptoms which are independent predictors of IBD.

In another embodiment, said method further comprises storing the method results in a data carrier, preferably wherein said data carrier is a computer readable medium.

Additional details and other preferred embodiments on a method for the differential diagnosis of inflammatory bowel disease (IBD) phenotypes in a human subject according to any of the sixth to eight aspects of the invention are as provided for the previous aspects of the invention.

A Method for the Prognosis of Inflammatory Bowel Disease (IBD)

In still an additional aspect, the invention relates to a method for the prognosis of inflammatory bowel disease (IBD) which comprises the determination of an IBD phenotype according to a method for the differential diagnosis as described herein of the invention and establishing prognosis according to the determined IBD phenotype.

The Use of Total FP, PHGI and/or PHGII Abundance as Biomarker for the Differential Diagnosis of IBD Phenotypes.

In a further aspect, the invention relates to the use of *Faecalibacterium prausnitzii* phylogroup I members (PHGI) and/or *Faecalibacterium prausnitzii* phylogroup II members (PHGII) abundance, and/or mathematical combinations thereof, and/or optionally a mathematical combination of any of these with Total *F. Prausnitzii* (FT) abundance and/or (EC) *E. coli* abundance, in an intestinal sample of a human subject as biomarker for the differential diagnosis of IBD phenotypes, wherein the abundance of PHGI and/or PHGII in an intestinal sample from said subject is determined according to the method of the invention.

In a particular embodiment, relates to the use of *Faecalibacterium prausnitzii* members (total FP) abundance, *Faecalibacterium prausnitzii* phylogroup I members (PHGI) abundance and/or *Faecalibacterium prausnitzii* phylogroup II members (PHGII) abundance determined in an intestinal sample of a human subject; and/or a mathematical combination thereof as biomarker for the differential diagnosis of inflammatory bowel disease (IBD) phenotypes. The determination of total FP, PGHI and/or PGHII abundance in an intestinal sample is performed in vitro.

Further details and preferred embodiments on IBD phenotypes are provided above. In a preferred embodiment, said IBD phenotypes are selected from the group consisting of:
- Ulcerative Colitis (UC) phenotypes consisting of ulcerative proctitis (UC-E1), distal colitis (UC-E2) and extensive UC or pancolitis (UC-E3); and
- Crohn's disease (CD) phenotypes consisting of ileal CD (I-CD), ileocolonic CD (IC-CD) and colonic CD (C-CD).

In a preferred embodiment, the abundance of PHGI, the abundance of PHGII and/or a mathematical combination thereof is used as biomarker. In a further preferred embodiment, a mathematical combination of PHGI and PHGII abundance is used as biomarker, preferably wherein the ratio between the PHGII and the PHGI abundance (PHGII/PHGI ratio) is used as biomarker.

In another preferred embodiment, said target microorganism abundance determination is performed by gene quantification with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

In a further preferred embodiment, wherein said target microorganism abundance determination is carried out by 16S rRNA gene quantification.

In yet another preferred embodiment, said intestinal sample is a feces sample.

Additional details and other preferred embodiments on the use of total FP, PHGI and/or PHGII abundance in an intestinal sample of a human subject as biomarker for the differential diagnosis of inflammatory bowel disease (IBD) phenotypes are as provided for the previous aspects of the invention.

A Kit for the Differential Diagnosis of Inflammatory Bowel Disease (IBD) Phenotypes In one more aspect of the invention relates to a kit for the differential diagnosis of inflammatory bowel disease (IBD) phenotypes according to a method of any of the sixth to eight aspects, comprising:
- a reagent for determining the abundance of a target microorganism selected from the group consisting of *Faecalibacterium prausnitzii* members (total FP), *Faecalibacterium prausnitzii* phylogroup I members (PHGI), and *Faecalibacterium prausnitzii* phylogroup II members (PHGII); and
- instructions for use of said reagent(s) to determine the abundance levels of said target microorganism from a human intestinal sample.

In a preferred embodiment, said intestinal sample is a feces sample.

In another preferred embodiment, said reagent for determining PHGI abundance is selected from the group consisting of:
- a pair of nucleic acid primers consisting of oligonucleotide sequences SEQ ID NO: 1 and SEQ ID NO: 2 or an oligonucleotide sequence with at least 75% identity thereof, and/or
- a probe consisting of oligonucleotide sequence SEQ ID NO: 3 or an oligonucleotide sequence with at least 75% of identity thereof.

In a further preferred embodiment, said reagent for determining PHGII abundance is selected from the group consisting of:
- a pair of nucleic acid primers consisting of oligonucleotide sequences SEQ ID NO: 1 and SEQ ID NO: 2 or an oligonucleotide sequence with at least 75% identity thereof, and/or
- a probe consisting of oligonucleotide sequence SEQ ID NO: 4 or an oligonucleotide sequence with at least 75% identity thereof.

In yet another preferred embodiment, said reagent for determining total FP abundance is selected from the group consisting of:
- a pair of nucleic acid primers consisting of oligonucleotide sequences SEQ ID NO: 5 and SEQ ID NO: 6 or an oligonucleotide sequence with at least 75% identity thereof, and/or
- a probe consisting of oligonucleotide sequence SEQ ID NO: 7 or an oligonucleotide sequence with at least 75% identity thereof.

In an additionally preferred embodiment, said kit further comprises a reference reagent for normalizing data, preferably wherein said reagent are primers and/or a probe for the quantification of total bacteria.

Additional details and other preferred embodiments on a kit for the differential diagnosis of inflammatory bowel disease (IBD) phenotypes are as provided for the previous aspects of the invention.

Items Related to the Method for Detecting Intestinal Disease in a Human Subject

1. A method for detecting intestinal disease in a human subject comprising the following steps:
   a. determining the abundance of *Faecalibacterium prausnitzii* phylogroup I members (PHGI) in an intestinal sample from said subject;
   b. optionally, determining the abundance of *Faecalibacterium prausnitzii* phylogroup II members (PHGII) in an intestinal sample from said subject; and
   c. comparing the PHGI abundance, optionally the PHGII abundance and/or a mathematical combination thereof, in the subject sample with the corresponding values in a reference sample, wherein a significant deviation in the subject sample values with regard to said reference sample is indicative of intestinal disease.

2. The method according to item 1, comprising the following steps:
   a. determining the abundance of PHGI in an intestinal sample from said subject; and
   b. comparing the subject sample abundance levels with the levels in a reference sample, wherein a significant reduction of abundance levels in the subject sample with regard to said reference sample is indicative of intestinal disease.

3. The method according to item 1, comprising the following steps:
   a. determining the abundance of PHGI in an intestinal sample from said subject;
   b. determining the abundance of PHGII in an intestinal sample from said subject; and
   c. comparing the PHGI abundance, the PHGII abundance and/or a mathematical combination thereof, in the subject sample with the corresponding values in a reference sample, wherein a significant deviation in the subject sample values with regard to said reference sample is indicative of intestinal disease, wherein preferably the ratio between the PHGII abundance and the PHGI abundance (PHGII/PHGI ratio) is determined; and the PHGII/PHGI ratio in said subject sample is compared with the PHGII/PHGI ratio in a reference sample.

4. The method according to any of items 1 to 3, wherein said method is used for the screening, for the diagnosis, for monitoring progression, for monitoring relapses, and/or for monitoring postsurgical recurrence of intestinal disease, and/or for determining efficacy of a treatment on intestinal disease; preferably for the screening and/or diagnosis of intestinal disease.

5. The method according to any of items 1 to 4, wherein PHGI and/or PHGII abundance determination is performed by gene quantification with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

6. The method according to any of items 1 to 5, wherein PHGI and/or PHGII abundance determination is carried out by 16S rRNA gene quantification.

7. The method according to any of items 1 to 6, wherein PHGI abundance determination is carried out by quantifying a *Faecalibacterium prausnitzii* 16S rRNA gene sequence comprising or consisting of SEQ ID NO: 3.

8. The method according to any of items 1 to 7, wherein PHGI 16S rRNA gene quantification is performed with primers consisting of oligonucleotide sequences SEQ ID NO: 1 and SEQ ID NO: 2 or a sequence with at least 75% identity thereof; and/or a probe consisting of oligonucleotide sequence SEQ ID NO: 3 or a sequence with at least 75% identity thereof.

9. The method according to any of items 1 to 8, wherein PHGI 16S rRNA gene quantification is performed with primers consisting of oligonucleotide sequences SEQ ID NO: 1 and SEQ ID NO: 2, and a probe consisting of oligonucleotide sequence SEQ ID NO: 3.

10. The method according to any of items 1 to 9, wherein PHGII abundance determination is carried out by quantifying a *Faecalibacterium prausnitzii* 16S rRNA gene sequence comprising or consisting of SEQ ID NO: 4.

11. The method according to any of items 3 to 10, wherein PHGII 16S rRNA gene quantification is performed with primers consisting of oligonucleotide sequences SEQ ID NO: 1 and SEQ ID NO: 2 or a sequence with at least 75% identity thereof; and/or a probe consisting of oligonucleotide sequence SEQ ID NO: 4 or a sequence with at least 75% identity thereof.

12. The method according to any of items 3 to 11, wherein PHGII 16S rRNA gene quantification is performed with primers consisting of oligonucleotide sequences SEQ ID NO: 1 and SEQ ID NO: 2, and a probe consisting of oligonucleotide sequence SEQ ID NO: 4.

13. The method according to any of items 5 to 12, wherein DNA is extracted from the intestinal sample prior to PHGI and/or PHGII gene quantification.

14. The method according to any of items 1 to 13, wherein the PHGI and/or PHGII abundance levels are normalized, preferably wherein normalization is carried out with respect to total bacteria quantification.

15. The method according to any of items 1 to 14, wherein said intestinal sample is a feces sample.

16. The method according to any of items 1 to 15, wherein said reference sample is a healthy subject sample and/or the sample of a patient with intestinal disease in remission, preferably a sample of the same subject in remission.

17. The method according to any of items 1 to 16, wherein said an intestinal disease is IBD, preferably wherein said IBD is Ulcerative colitis (UC) or Crohn's disease (CD), more preferably wherein said IBD is CD.

18. The method according to any of items 1 to 17, wherein PHGI abundance is determined and a significant reduction of PHGI abundance levels in the subject sample with regard to said reference sample is indicative of CD, preferably of CD with ileal involvement (IC-CD or I-CD).

19. The method according to any of items 1 to 18, wherein the PHGII/PHGI ratio is determined and a significant deviation in the subject sample values with regard to said reference sample is indicative of CD, preferably of CD with colonic involvement (C-CD or IC-CD).

20. The method according to any of items 1 to 19, wherein said method further comprises detecting and/or quantifying one or more biomarkers of intestinal disease, preferably of IBD.

21. The method according to any of items 1 to 20, wherein said method further comprises combining the results of PHGI abundance, PHGII abundance and/or said further biomarkers detection and/or quantification with other indicators of intestinal disease, preferably of IBD.

22. The method according to any of items 1 to 21, wherein said method further comprises storing the method results in a data carrier, preferably wherein said data carrier is a computer readable medium.

23. Use of *Faecalibacterium prausnitzii* phylogroup I members (PHGI) abundance in an intestinal sample of a human subject as biomarker for the detection of intestinal disease.

24. The use according to item 23, for the screening, for the diagnosis, for monitoring progression, for monitoring relapses, and/or for monitoring postsurgical recurrence of an intestinal disease, and/or for determining efficacy of a treatment on an intestinal disease; preferably for the screening or diagnosis of an intestinal disease.

25. The use according to any of items 23 or 24, wherein PHGI abundance is used in combination with *Faecalibacterium prausnitzii* phylogroup II members (PHGII) abundance in an intestinal sample of said human subject, preferably wherein the ratio between the PHGII abundance and the PHGI abundance (PHGII/PHGI ratio) is determined.

26. The use according to any of items 23 to 25, wherein PHGI and/or PHGII abundance determination is performed by gene quantification with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

27. The use according to any of items 23 to 26, wherein PHGI and/or PHGII abundance determination is carried out by 16S rRNA gene quantification.

28. The use according to any of items 23 to 27, wherein said intestinal sample is a feces sample.

29. The use according to any of items 23 to 28, wherein said intestinal disease is IBD, preferably wherein said IBD is Ulcerative colitis (UC) or Crohn's disease (CD), more preferably wherein said IBD is CD.

30. A kit for detecting an intestinal disease according to a method of any of items 1 to 22, comprising:
    a reagent for determining the abundance of *Faecalibacterium prausnitzii* phylogroup I members (PHGI);
    optionally, a reagent for determining the abundance of *Faecalibacterium prausnitzii* phylogroup II members (PHGII); and
    instructions for use of said reagent(s) to determine the abundance levels of PHGI, and optionally PHGII, from a human intestinal sample, wherein preferably said intestinal sample is a feces sample.

31. The kit according to item 30, for the screening, for the diagnosis, for monitoring progression, for monitoring relapses, and/or for monitoring postsurgical recurrence of an intestinal disease, and/or for determining efficacy of a treatment on an intestinal disease; preferably for the screening or diagnosis of an intestinal disease.

32. The kit according to any of items 30 or 31, wherein said reagent for determining PHGI abundance is selected from the group consisting of:
  a pair of nucleic acid primers consisting of oligonucleotide sequences SEQ ID NO: 1 and SEQ ID NO: 2 or an oligonucleotide sequence with at least 75% identity thereof, and/or
  a probe consisting of oligonucleotide sequence SEQ ID NO: 3 or an oligonucleotide sequence with at least 75% of identity thereof.

33. The kit according to any of items 30 to 32, wherein said reagent for determining PHGII abundance is selected from the group consisting of:
  a pair of nucleic acid primers consisting of oligonucleotide sequences SEQ ID NO: 1 and SEQ ID NO: 2 or an oligonucleotide sequence with at least 75% identity thereof, and/or
  a probe consisting of oligonucleotide sequence SEQ ID NO: 4 or an oligonucleotide sequence with at least 75% identity thereof.

34. The kit according to any of items 30 to 33, further comprising a reference reagent for normalizing data, preferably wherein said reagent are primers and/or a probe for the quantification of total bacteria.

35. The kit according to any of items 30 to 34, wherein said intestinal disease is IBD, preferably wherein said IBD is Ulcerative colitis (UC) or Crohn's disease (CD), more preferably wherein said IBD is CD.

36. A nucleic acid sequence selected from the group consisting of SEQ ID NO: 1, SEQ ID NO: 2, SEQ ID NO: 3, and SEQ ID NO: 4 or an oligonucleotide sequence with at least 75% identity thereof.

37. A method for determining the abundance of *Faecalibacterium prausnitzii* phylogroup I members (PHGI) and/or the abundance of *Faecalibacterium prausnitzii* phylogroup II members (PHGII) in an intestinal sample from a subject wherein said determination is carried out by 16S rRNA gene quantification, wherein PHGI abundance determination is carried out by quantifying a *Faecalibacterium prausnitzii* 16S rRNA gene sequence comprising or consisting of SEQ ID NO: 3, and wherein PHGII abundance determination is carried out by quantifying a *Faecalibacterium prausnitzii* 16S rRNA gene sequence comprising or consisting of SEQ ID NO: 4.

38. The method according to item 37, wherein 16S rRNA gene quantification is carried out with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

39. The method according to any of items 37 or 38, wherein PHGI 16S rRNA gene quantification is performed with primers consisting of oligonucleotide sequences SEQ ID NO: 1 and SEQ ID NO: 2 or a sequence with at least 75% identity thereof; and/or a probe consisting of oligonucleotide sequence SEQ ID NO: 3 or a sequence with at least 75% identity thereof.

40. The method according to any of items 37 to 39, wherein PHGI 16S rRNA gene quantification is performed with primers consisting of oligonucleotide sequences SEQ ID NO: 1 and SEQ ID NO: 2, and a probe consisting of oligonucleotide sequence SEQ ID NO: 3.

41. The method according to any of items 37 to 40, wherein PHGII 16S rRNA gene quantification is performed with primers consisting of oligonucleotide sequences SEQ ID NO: 1 and SEQ ID NO: 2 or a sequence with at least 75% identity thereof; and/or a probe consisting of oligonucleotide sequence SEQ ID NO: 4 or a sequence with at least 75% identity thereof.

42. The method according to any of items 37 to 41, wherein PHGII 16S rRNA gene quantification is performed with primers consisting of oligonucleotide sequences SEQ ID NO: 1 and SEQ ID NO: 2, and a probe consisting of oligonucleotide sequence SEQ ID NO: 4.

43. The method according to any of items 37 to 42, wherein DNA is extracted from the intestinal sample prior to PHGI and PHGII gene quantification.

44. The method according to any of items 37 to 43, wherein the PHGI and/or PHGII abundance levels are normalized, preferably wherein normalization is carried out with respect to total bacteria quantification.

45. The method according to any of items 37 to 44, wherein said intestinal sample is a feces sample.

Items Related to the Method for the Differential Diagnosis of Inflammatory Bowel Disease (IBD) Phenotypes 1. A method for the differential diagnosis of inflammatory bowel disease (IBD) phenotypes in a human subject comprising the following steps:
  i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and
  ii. comparing the subject sample abundance of one or more of said target microorganisms and/or a mathematical combination thereof, with the corresponding values in a reference sample of the IBD phenotypes to be distinguished from to determine the IBD phenotype the subject is suffering from; wherein the subject sample presenting values significantly similar to one of said IBD phenotypes will be indicative that the subject is suffering from said IBD phenotype; and
  wherein said IBD phenotypes are defined by at least the combination of two, preferably three, of the following parameters:
    disease location;
    IBD type; and
    age at diagnosis,
  optionally, comprising the use of additional biomarkers for the definition of said IBD phenotypes.

2. The method according to item 1, wherein said IBD phenotypes are selected from the group consisting of:
  CD phenotypes defined by one or more, preferably all, of the following parameters:
    disease location;
    age at diagnosis; and
    behavior;
  UC phenotypes defined by one or more, preferably all, of the following parameters:
    disease location or extent; and
    severity.

3. The method according to any of items 1 or 2, wherein said IBD phenotypes are selected from the group consisting of:
  CD phenotypes consisting of ileal CD (I-CD), ileocolonic CD (IC-CD) and colonic CD (C-CD); and
  UC phenotypes consisting of ulcerative proctitis (UC-E1), distal colitis (UC-E2) and extensive UC or pancolitis (UC-E3).

4. The method according to any of items 1 to 3, wherein said target microorganism is selected from the group consisting of PHGI and PHGII.

5. The method according to any of items 1 to 4, wherein the ratio between the PHGII abundance and the PHGI abundance (PHGII/PHGI ratio) is determined; and the PHGII/PHGI ratio in said subject sample is compared with the PHGII/PHGI ratio in a reference sample.

6. The method according to any of items 1 to 5, wherein said IBD phenotypes are UC-E3 and C-CD and the subject sample values are compared with a UC-E3 positive reference sample and/or a C-CD positive reference sample, wherein the subject sample presenting values significantly similar to UC-E3 or C-CD will be indicative that the subject is suffering from said IBD phenotype.

7. The method according to item 6, wherein said human subject has previously been diagnosed of IBD with colonic involvement.

8. The method according to any of items 6 or 7, wherein said target microorganism is the PHGII.

9. A method for diagnosing C-CD in a human subject suffering from IBD with colonic involvement comprising the following steps:
  i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and
  ii. comparing the subject sample abundance levels with the levels in a reference sample, wherein a significant reduction of abundance levels in the subject sample with regard to said reference sample is indicative of C-CD,
  wherein preferably said target microorganism is the PHGII.

10. The method according to item 9, wherein said reference sample is a sample of a healthy subject and/or a sample of a patient with IBD in remission, preferably a sample of the same subject in remission.

11. The method according to any of items 1 to 5, wherein said IBD phenotypes are selected from the group consisting of I-CD, C-CD and IC-CD and the subject sample values are compared with an I-CD positive reference sample, a C-CD positive reference sample and/or a IC-CD positive reference sample, wherein the subject sample presenting values significantly similar to I-CD, C-CD or IC-CD will be indicative that the subject is suffering from said IBD phenotype.

12. The method according to item 11, for determining extension of the disease to the colonic area (IC-CD) in a human subject who has previously been diagnosed with I-CD.

13. The method according to item 12, wherein said target microorganism is the PHGII.

14. The method according to item 13, for determining extension of the disease to the ileal area (IC-CD) in a human subject who has previously been diagnosed with C-CD.

15. The method according to item 14, wherein said target microorganism is the PHGII.

16. A method for diagnosing IC-CD in a human subject suffering from I-CD or C-CD comprising the following steps:
  i. determining the abundance of a target microorganism in an intestinal sample from said subject, wherein said target microorganism is selected from the group consisting of *Faecalibacterium prausnitzii* members (total FP), *Faecalibacterium prausnitzii* phylogroup I members (PHGI) and *Faecalibacterium prausnitzii* phylogroup II members (PHGII); and
  ii. comparing the subject sample PHGII abundance levels with the levels in a reference sample from said subject at around diagnose of I-CD or C-CD, wherein a significant reduction of abundance levels in the subject sample with regard to said reference sample is indicative of IC-CD,
  wherein preferably, said target microorganism is the PHGII.

17. The method according to any of items 1 to 16, wherein said target microorganism abundance determination is performed by gene quantification with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

18. The method according to any of items 1 to 17, wherein said target microorganism abundance determination is carried out by 16S rRNA gene quantification.

19. The method according to any of items 1 to 18, wherein PHGI abundance determination is carried out by quantifying a *Faecalibacterium prausnitzii* 16S rRNA gene sequence comprising or consisting of SEQ ID NO: 3.

20. The method according to any of items 1 to 19, wherein PHGI 16S rRNA gene quantification is performed with primers consisting of oligonucleotide sequences SEQ ID NO: 1 and SEQ ID NO: 2 or a sequence with at least 75% identity thereof; and/or a probe consisting of oligonucleotide sequence SEQ ID NO: 3 or a sequence with at least 75% identity thereof.

21. The method according to any of items 1 to 20, wherein PHGI 16S rRNA gene quantification is performed with primers consisting of oligonucleotide sequences SEQ ID NO: 1 and SEQ ID NO: 2, and a probe consisting of oligonucleotide sequence SEQ ID NO: 3.

22. The method according to any of items 1 to 21, wherein PHGII abundance determination is carried out by quantifying a *Faecalibacterium prausnitzii* 16S rRNA gene sequence comprising or consisting of SEQ ID NO: 4.

23. The method according to any of items 1 to 22, wherein PHGII 16S rRNA gene quantification is performed with primers consisting of oligonucleotide sequences SEQ ID NO: 1 and SEQ ID NO: 2 or a sequence with at least 75% identity thereof; and/or a probe consisting of oligonucleotide sequence SEQ ID NO: 4 or a sequence with at least 75% identity thereof.

24. The method according to any of items 1 to 23, wherein PHGII 16S rRNA gene quantification is performed with primers consisting of oligonucleotide sequences SEQ ID NO: 1 and SEQ ID NO: 2, and a probe consisting of oligonucleotide sequence SEQ ID NO: 4.

25. The method according to any of items 1 to 24, wherein total FP 16S rRNA gene quantification is performed with primers consisting of oligonucleotide sequences SEQ ID NO: 5 and SEQ ID NO: 6 or a sequence with at least 75% identity thereof; and/or a probe consisting of oligonucleotide sequence SEQ ID NO: 7 or a sequence with at least 75% identity thereof.

26. The method according to any of items 1 to 25, wherein total FP 16S rRNA gene quantification is performed with primers consisting of oligonucleotide sequences SEQ ID NO: 5 and SEQ ID NO: 6, and a probe consisting of oligonucleotide sequence SEQ ID NO: 7.

27. The method according to any of items 1 to 26, wherein DNA is extracted from the intestinal sample prior to the target microorganism gene quantification.

28. The method according to any of items 1 to 27, wherein said intestinal sample is a feces sample.

29. The method according to any of items 1 to 28, wherein the target abundance levels are normalized, preferably wherein normalization is carried out with respect to total bacteria quantification.

30. The method according to any of items 1 to 29, wherein said method further comprises detecting and/or quantifying one or more biomarkers of intestinal disease, preferably of IBD.

31. The method according to any of items 1 to 30, wherein said method further comprises combining the results of the target microorganism quantification and/or said further biomarkers detection and/or quantification with clinical signs and/or symptoms which are independent predictors of IBD.

32. The method according to any of items 1 to 31, wherein said method further comprises storing the method results in a data carrier, preferably wherein said data carrier is a computer readable medium.

33. A method for the prognosis of inflammatory bowel disease (IBD) which comprises the determination of an IBD phenotype according to a method for the differential diagnosis of any of items 1 to 32 and establishing prognosis according to the determined IBD phenotype.

34. Use of *Faecalibacterium prausnitzii* members (total FP) abundance, *Faecalibacterium prausnitzii* phylogroup I members (PHGI) abundance and/or *Faecalibacterium prausnitzii* phylogroup II members (PHGII) abundance determined in an intestinal sample of a human subject; and/or a mathematical combination thereof as biomarker for the differential diagnosis of inflammatory bowel disease (IBD) phenotypes as defined in any of items 1 to 3.

35. The use according to item 34; wherein said IBD phenotypes are selected from the group consisting of:
Ulcerative Colitis (UC) phenotypes consisting of ulcerative proctitis (UC-E1), distal colitis (UC-E2) and extensive UC or pancolitis (UC-E3); and
Crohn's disease (CD) phenotypes consisting of ileal CD (I-CD), ileocolonic CD (IC-CD) and colonic CD (C-CD).

36. The use according to any of items 34 or 35, wherein the abundance of PHGI, the abundance of PHGII and/or a mathematical combination thereof is used as biomarker.

37. The use according to any of items 34 to 36, wherein a mathematical combination of PHGI and PHGII abundance is used as biomarker, preferably wherein the ratio between the PHGII and the PHGI abundance (PHGII/PHGI ratio) is used as biomarker.

38. The use according to any of items 34 to 37, wherein said target microorganism abundance determination is performed by gene quantification with a molecular method selected from the group consisting of quantitative Polymerase Chain Reaction (qPCR), PCR-pyrosequencing, fluorescence in-situ hybridization (FISH), microarrays, and PCR-ELISA, preferably quantification is performed by qPCR.

39. The use according to any of items 34 to 38, wherein said target microorganism abundance determination is carried out by 16S rRNA gene quantification.

40. The use according to any of items 34 to 39, wherein said intestinal sample is a feces sample.

41. A kit for the differential diagnosis of inflammatory bowel disease (IBD) phenotypes according to a method of any of items 1 to 33, comprising:
a reagent for determining the abundance of a target microorganism selected from the group consisting of *Faecalibacterium prausnitzii* members (total FP), *Faecalibacterium prausnitzii* phylogroup I members (PHGI), and *Faecalibacterium prausnitzii* phylogroup II members (PHGII); and
instructions for use of said reagent(s) to determine the abundance levels of said target microorganism from a human intestinal sample.

42. The kit according to item 41, wherein said intestinal sample is a feces sample.

43. The kit according to any of items 41 or 42, wherein said reagent for determining PHGI abundance is selected from the group consisting of:
a pair of nucleic acid primers consisting of oligonucleotide sequences SEQ ID NO: 1 and SEQ ID NO: 2 or an oligonucleotide sequence with at least 75% identity thereof, and/or
a probe consisting of oligonucleotide sequence SEQ ID NO: 3 or an oligonucleotide sequence with at least 75% of identity thereof.

44. The kit according to any of items 41 to 43, wherein said reagent for determining PHGII abundance is selected from the group consisting of:
a pair of nucleic acid primers consisting of oligonucleotide sequences SEQ ID NO: 1 and SEQ ID NO: 2 or an oligonucleotide sequence with at least 75% identity thereof, and/or
a probe consisting of oligonucleotide sequence SEQ ID NO: 4 or an oligonucleotide sequence with at least 75% identity thereof.

45. The kit according to any of items 41 to 44, wherein said reagent for determining total FP abundance is selected from the group consisting of:
a pair of nucleic acid primers consisting of oligonucleotide sequences SEQ ID NO: 5 and SEQ ID NO: 6 or an oligonucleotide sequence with at least 75% identity thereof, and/or
a probe consisting of oligonucleotide sequence SEQ ID NO: 7 or an oligonucleotide sequence with at least 75% identity thereof.

46. The kit according to any of items 41 to 45, further comprising a reference reagent for normalizing data, preferably wherein said reagent are primers and/or a probe for the quantification of total bacteria.

It is contemplated that any embodiment discussed in this specification can be implemented with respect to any method, kit, reagent, or use of the invention, and vice versa. It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of limits the scope of a claim to the specified materials or steps and those that do not materially affect the basic and novel characteristic(s) of the claimed invention. As used herein, the phrase "consisting of excludes any element, step, or ingredient not specified in the claim except for, e.g., impurities ordinarily associated with the element or limitation.

The term "or combinations thereof as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "around", "approximately" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

EXAMPLES

Example 1

Materials and Methods of *F. Prausnitzii* Phylogroups Quantification in Biopsy Samples 1. Patients, Clinical Data and Sampling.

A Spanish cohort consisting of 70 IBD (45 CD and 25 UC), 10 IBS, 20 CRC patients, and 31 H was enrolled (Table 13).

Subjects were recruited by the Gastroenterology Services of the Hospital Universitari Dr. Josep Trueta (Girona, Spain) and the Hospital Santa Caterina (Salt, Spain). Subjects were gender matched for all the groups. Concerning age, CD patients were younger than those in the H group (P<0.001), whereas CRC patients were significantly older than all the other groups (P≤0.019). IBD patients were diagnosed according to standard clinical, pathological and endoscopic criteria and categorized according to the Montreal classification (Silverberg et al., Can J Gastroenterol. 2005, 19 Suppl A:5-36). IBS patients were diagnosed according to Rome III criteria (available at <http://www.romecriteria.org/criteria/>). The diagnosis of CRC was established by colonoscopy and biopsy, and data correlated with high risk of developing this disease was recorded. The control group consisted of subjects undergoing colonoscopy for different reasons as rectorrhagia (N=9), colorectal cancer familial history (N=11), and abdominal pain (N=11). Clinically relevant data of all the patients was collected. None of the subjects received antimicrobial treatment for at least two months before colonoscopy.

Prior to colonoscopy, patients were subjected to cleansing of the gastrointestinal tract using Casenglicol® following manufacturer's guidelines. During routine endoscopy, up to three biopsy samples per patient were taken from different locations along the gut (distal ileum, colon, and rectum) following standard procedures. All biopsies were immediately placed in sterile tubes without any buffer and stored at −80° C. following completion of the whole endoscopic procedure and upon analysis.

This work was approved by the Ethics Committee of Clinical Research of the Hospital Universitari Dr. Josep Trueta (Girona, Spain) and the Institut d'Assistència Sanitària of Girona (Salt, Spain) on 24 Feb. 2009 and 21 Apr. 2009, respectively. Informed consent from the subjects was obtained before enrollment.

TABLE 13

Sample size and clinical characteristics of subjects.

| | Healthy* | Irritable bowel syndrome | IBD | | Colorectal cancer | P value[§] |
| | | | Crohn's disease | Ulcerative colitis | | |
| --- | --- | --- | --- | --- | --- | --- |
| N (patients) | 31 | 10 | 45 | 25 | 20 | |
| Age (mean years ± SD) | 48.1 ± 16.3 | 42.4 ± 11.4 | 33.5 ± 11.1 | 40.1 ± 15.8 | 58.6 ± 7.52 | <0.001[‡] |
| Male (N, %) | 16 (51.6%) | 2 (20.0%) | 26 (57.7%) | 16 (64.0%) | 14 (70.0%) | 0.605[†] |
| Active (N, %) | na | na | 28 (62.2%) | 20 (80.0%) | na | 0.059[†] |
| Previous surgery (N, %) | 0 | nd | 9 (20.0%) | 1 (4.0%) | nd | 0.049[†] |
| Smokers (N, %) | 0 | 0 | 8 (17.8%) | 2 (8.0%) | 5 (25.0%) | 0.327[†] |

TABLE 13-continued

Sample size and clinical characteristics of subjects.

| | | | IBD | | | |
|---|---|---|---|---|---|---|
| | Healthy* | Irritable bowel syndrome | Crohn's disease | Ulcerative colitis | Colorectal cancer | P value§ |
| Treatment (N, %)** | | | | | | 0.087† |
| No treatment | | | 12 (26.7%) | 13 (52.0%) | | |
| Mesalazine | na | na | 3 (6.7%) | 3 (12.0%) | na | |
| Moderate immunosuppressant | na | na | 16 (35.5%) | 3 (12.0%) | na | |
| Anti-TNFα (infliximab, adalimumab) | na | na | 10 (22.2%) | 4 (16.0%) | na | |
| CD Montreal classification | | | | | | |
| Age of diagnosis (N, %)** | | | | | | 0.257‡ |
| diag <16 y (A1) | na | na | 5 (11.1%) | 1 (4.0%) | nd | |
| diag 17-40 y (A2) | na | na | 33 (73.3%) | 13 (52.0%) | nd | |
| diag >41 y (A3) | na | na | 5 (11.1%) | 8 (32.0%) | nd | |
| Location (N, %) | | | | | | na |
| Ileal-CD (L1) | na | na | 19 (42.2%) | na | na | |
| Colonic-CD (L2) | na | na | 11 (24.4%) | na | na | |
| Ileocolonic-CD (L3) | na | na | 14 (31.1%) | na | na | |
| Behavior (N, %)** | | | | | | na |
| Non-stricturing, non-penetrating (B1) | na | na | 30 (66.7%) | na | na | |
| Stricturing (B2) | na | na | 9 (20.0%) | na | na | |
| UC classification (N, %)** | | | | | | na |
| Ulcerative proctitis (E1) | na | na | na | 6 (24.0%) | na | |
| Distal UC (E2) | na | na | na | 11 (44.0%) | na | |
| Extensive UC or ulcerative pancolitis (E3) | na | na | na | 6 (24.0%) | na | |
| IBS subtype (N, %)** | | | | | | na |
| Diarrhea predominant type | na | 2 (20.0%) | na | na | na | |
| Constipation predominant type | na | 2 (20.0%) | na | na | na | |
| CRC subtype (N, %)** | | | | | | na |
| Sporadic | na | na | na | na | 14 (70.0%) | |
| Hereditary*** | na | na | na | na | 3 (15.0%) | |

IBD, Inflammatory bowel disease;
IBS, Irritable bowel syndrome;
CRC, colorectal cancer;
TNF, tumor necrosis factor;
nd, not determined;
na, not applicable
*Controls consisted of subjects who underwent colonoscopy for different reasons: 9/31 rectorrhagia, 11/31 colorectal cancer familial history and 11/31 abdominal pain.
**Medical treatment at the time of sampling was available in 41/45 CD patients, and 23/25 UC patients; Age of disease onset was available for 43/45 CD patients, and 22/25 UC patients; Disease behavior at last follow-up before the time of sampling was available in 39/45 CD patients, and none had penetrating CD (B3); Maximal disease extent at the time of sampling was available in 23/25 UC patients; disease subtype was available in 4/10 Irritable bowel syndrome patients, and none had alternating predominant type; presence or absence of relatives with CRC could only be clearly tracked in 17/20 CRC patients.
***Patients were included within this category if a first grade relative has had also CRC.
§Groups were compared by non-parametric statistical tests, and p value ≤ 0.05 was considered significant;
†$\chi^2$ test,
‡Mann-Whitney U test 2. Sample Treatment and DNA Extraction.

Prior to DNA extraction, biopsies were subjected to two mild ultrasound wash cycles to discard transient and loosely attached bacteria as previously reported (34). DNA was extracted using the NucleoSpin® Tissue Kit (Macherey-Nagel GmbH &Co., Duren, Germany). The support protocol for Gram positive bacteria and the RNAse treatment step were carried out. Genomic DNA was eluted with 10 mM Tris-HCl (pH 7.4) and stored at −80° C. until use. DNA concentration and purity of the extracts were determined with a NanoDrop ND-100 spectrophotometer (NanoDrop Technologies, USA).

3. Primers and Hydrolysis Probes Design, and Set Up of a qPCR Assay for F. prausnitzii Phylogroups.

In order to simultaneously quantify both F. prausnitzii phylogroups, a qPCR assay consisting of a unique pair of species-specific primers for F. prausnitzii and two hydrolysis probes targeting each F. prausnitzii phylogroup was designed.

Sequences of the 16S rRNA gene from F. prausnitzii and from closely related Ruminococcaceae were recovered from GenBank (Table 14) and aligned using Clustal W (Thompson J D et al. Nucleic Acids Res. 1994; 22:4673-4680). Both primers and hydrolysis probes were manually designed, from consensus sequences (Table 14) specifically built for each purpose, following the guidelines set by Applied Biosystems (Foster City, Calif., USA) for the design of primers and probes for allelic discrimination, and further checked using the software Primer Express® version 3.0 (Applied Biosystems, Foster City, Calif., USA). Oligonucleotides were also evaluated using NetPrimer® software (PREMIER Biosoft International, California, USA) to check for primer-dimer structures, hairpins and possible cross dimer interactions. Resulting primers and probes are listed in Table 15.

TABLE 14

16S rRNA gene sequences used to perform oligonucleotide design. GenBank accession numbers have been indicated. Sequences from *F. prausnitzii* isolates, related sequences recovered via molecular methods and sequences of the same gene from *F. prausnitzii* close relatives have been included.

| Accession number | Characteristics |
|---|---|
| AJ413954*[1] | *Faecalibacterium prausnitzii* 16S rRNA gene, strain ATCC 27768 |
| X85022*[1] | *F. prausnitzii* DNA for 16S ribosomal RNA, strain ATCC 27766 |
| AY305307*[1] | Butyrate-producing bacterium M21/2 16S ribosomal RNA gene |
| HQ457025*[1] | *F. prausnitzii* strain S4L/4 16S ribosomal RNA gene |
| HQ457024*[1] | *F. prausnitzii* strain S3L/3 16S ribosomal RNA gene |
| AJ270469*[2] | Butyrate-producing bacterium A2-165 16S rRNA gene |
| AJ270470*[2] | Butyrate-producing bacterium L2-6 16S rRNA gene |
| JN037415*[2] | *F. prausnitzii* strain L2-15 16S ribosomal RNA gene |
| JN037416*[2] | *F. prausnitzii* strain L2-39 16S ribosomal RNA gene |
| JN037417*[2] | *F. prausnitzii* strain L2-61 16S ribosomal RNA gene |
| HQ457026*[2] | *F. prausnitzii* strain HTF-A 16S ribosomal RNA gene |
| HQ457027*[2] | *F. prausnitzii* strain HTF-B 16S ribosomal RNA gene |
| HQ457028*[2] | *F. prausnitzii* strain HTF-C 16S ribosomal RNA gene |
| HQ457029*[2] | *F. prausnitzii* strain HTF-E 16S ribosomal RNA gene |
| HQ457030*[2] | *F. prausnitzii* strain HTF-F 16S ribosomal RNA gene |
| HQ457031*[2] | *F. prausnitzii* strain HTF-I 16S ribosomal RNA gene |
| HQ457032*[2] | *F. prausnitzii* strain HTF-60C 16S ribosomal RNA gene |
| HQ457033*[2] | *F. prausnitzii* strain HTF-75H 16S ribosomal RNA gene |
| AY169429* | *Faecalibacterium prausnitzii* clone 1-84 16S ribosomal RNA gene, partial sequence |
| AY169430* | *Faecalibacterium prausnitzii* clone 1-88 16S ribosomal RNA gene, partial sequence |
| AY169427* | *Faecalibacterium prausnitzii* clone 1-79 16S ribosomal RNA gene, partial sequence |
| AF132237* | Uncultured bacterium adhufec13 16S ribosomal RNA gene, partial sequence[§] |
| AF132236* | Uncultured bacterium adhufec113 16S ribosomal RNA gene, partial sequence[§] |
| AF132246* | Uncultured bacterium adhufec218 16S ribosomal RNA gene, partial sequence[§] |
| AF132265* | Uncultured bacterium adhufec365 16S ribosomal RNA gene, partial sequence[§] |
| AY494671* | Uncultured *Faecalibacterium* sp. clone FIRM8 16S ribosomal RNA gene, partial sequence |
| EF205929* | Uncultured bacterium clone 46706[§] |
| EF205662* | Uncultured bacterium clone 58014[§] |
| EF206222* | Uncultured bacterium clone 56806[§] |
| EF206249* | Uncultured bacterium clone 57601[§] |
| EF205881* | Uncultured bacterium clone 35509[§] |
| EF205761* | Uncultured bacterium clone 59415[§] |
| EF205681* | Uncultured bacterium clone 58033[§] |
| X98011 | *Anaerofilum agile* 16S rRNA gene |
| X97852 | *Anaerofilum pentosovorans* 16S rRNA gene |
| L09177 | *Clostridium cellulosi* 16S ribosomal RNA (16S rRNA) gene |
| M59095 | *Clostridium leptum* 16S ribosomal RNA |
| AJ305238 | *Clostridium leptum*; DSM 753T |
| M59116 | *Clostridium sporosphaeroides* 16S ribosomal RNA |
| X66002 | *Clostridium sporosphaeroides*; DSM 1294 |
| X81125 | *Clostridium viride* 16S rRNA gene |
| L34618 | *Eubacterium desmolans* 16S ribosomal RNA |
| L34625 | *Eubacterium siraeum* 16S ribosomal RNA |
| AY445600 | *Ruminococcus albus* strain 7 16S ribosomal RNA gene, complete |
| AY445594 | *Ruminococcus albus* strain 8 16S ribosomal RNA gene, complete |
| AY445592 | *Ruminococcus albus* strain B199 16S ribosomal RNA gene, complete |
| AY445596 | *Ruminococcus albus* strain KF1 16S ribosomal RNA gene, complete |
| AY445602 | *Ruminococcus albus* strain RO13 16S ribosomal RNA gene, complete |
| X85099 | *Ruminococcus bromii* 16S rRNA gene |
| L76600 | *Ruminococcus bromii* small subunit ribosomal RNA (16S rDNA) gene |
| X85100 | *Ruminococcus callidus* 16S rRNA gene |
| L76596 | *Ruminococcus callidus* small subunit ribosomal RNA (16S rDNA) |
| AM915269 | *Ruminococcus flavefaciens* partial 16S rRNA gene, type strain C94T = ATCC19208 |
| AF030449 | *Ruminococcus flavefaciens* strain ATCC 49949 16S ribosomal RNA, partial sequence |
| AY445599 | *Ruminococcus flavefaciens* strain B146 16S ribosomal RNA gene, complete sequence |
| AY445597 | *Ruminococcus flavefaciens* strain FD1 16S ribosomal RNA gene, complete sequence |
| AY445595 | *Ruminococcus flavefaciens* strain JM1 16S ribosomal RNA gene, complete sequence |
| AY445593 | *Ruminococcus flavefaciens* strain C94 16S ribosomal RNA gene, complete sequence |

TABLE 14-continued 16S rRNA gene sequences used to perform oligonucleotide design. GenBank accession numbers have been indicated. Sequences from *F. prausnitzii* isolates, related sequences recovered via molecular methods and sequences of the same gene from *F. prausnitzii* close relatives have been included.

| Accession number | Characteristics |
|---|---|
| AY445603 | *Ruminococcus flavefaciens* strain LB4 16S ribosomal RNA gene, complete sequence |
| AY445601 | *Ruminococcus flavefaciens* strain JF1 16S ribosomal RNA gene, complete sequence |
| AY445598 | *Ruminococcus flavefaciens* strain R13e2 16S ribosomal RNA gene, complete sequence |

*Sequences used to obtain the *F. prausnitzii* 16S rRNA gene consensus sequence for oligonucleotides design
[1] Sequences used to obtain the *F. prausnitzii* phylogroup I 16S rRNA gene consensus sequence for specific hydrolysis probe design
[2] Sequences used to obtain the *F. prausnitzii* phylogroup II 16S rRNA gene consensus sequence for specific hydrolysis probe design

TABLE 15

16S rRNA-targeted primers and probes used in this study.

| Target | Name | Sequence 5'-3' | Reference | Total cycles | Denaturing (° C.; s) | Annealing and extension (° C.; s) |
|---|---|---|---|---|---|---|
| Bacteria | F_Bact 1369 | CGGTGAATACGTTCCCGG | (44) | 50 | 95; 15 | 60; 60 |
|  | R_Prok_1492 | TACGGCTACCTTGTTACGACTT |  |  |  |  |
|  | P_TM_1389F | 6FAM-CTTGTACACACCGCCCG TC-TAMRA |  |  |  |  |
| *F. prausnitzii* (total) | Fpra 428 F | TGTAAACTCCTGTTGTTGAGGAAGATAA | (18) | 40 | 95; 15 | 60; 60 |
|  | Fpra 583 R | GCGCTCCCTTTACACCCA |  |  |  |  |
|  | Fpra 493 PR | 6FAM-CAAGGAAGTGACGGCTA ACTACGTGCCAG-TAMRA |  |  |  |  |
| DNA IAC[b] | IAC F | TACGGATGAGGAGGACAAAGGA | (18) | 40 | 95; 15 | 60; 60 |
|  | IAC R | CACTTCGCTCTGATCCATTGG |  |  |  |  |
|  | IAC PR | VIC®-CGCCGCTATGGGCATCG CA-TAMRA |  |  |  |  |
| *E. Coli* | E. coli 395 F | CATGCCGCGTGTATGAAGAA | (43) | 40 | 95; 15 | 60; 60 |
|  | E. coli 490 R | CGGGTAACGTCAATGAGCAAA |  |  |  |  |
|  | E. coli 437 PR | 6FAM-TATTAACTTTACTCCCTTCCT CCCCGCTGAA-TAMRA |  |  |  |  |
| *F. prausnitzii* (phylo-groups) | Fpra 136F | CTCAAAGAGGGGGACAACAGTT | this study | 50 | 95; 15 | 64; 60 |
|  | Fpra 232R | GCCATCTCAAAGCGGATTG |  |  |  |  |
|  | PHG1 180PR | 6FAM-TAAGCCCACGACCCGGCATCG-BHQ1 |  |  |  |  |
|  | PHG2 180PR | JOE-TAAGCCCACRGCTCGGCATC-BHQ1 |  |  |  |  |

[a] Probe sequences are in bold. FAM™ (6-carboxyfluorescein), VIC® (6-carboxyrhodamine), JOE (4',5'-dichloro-2',7'-dimethoxy-5(6)-carboxyfluorescein), TAMRA™ (tetramethylrhodamine) BHQ1 (Black Hole Quencher 1).
[b] IAC, Internal Amplification Control; DNA IAC sequence: 5'TACGGATGAGGAGGACAAAGGACGCCGCTATGGGCATCGCACCAATGGATCAGAGCGAAGTG-3' (according to Ref. 18.).
[c] For all quantitative PCR, an initial step at 50° C. during 2 min was performed for amperase treatment. Also an initial denaturation step was set at 95° C. for 10 min. In quantitative PCR, annealing and extension steps were performed simultaneously.
(18) Lopez-Siles M, Martinez-Medina M, Busquets D, et al. Mucosa-associated *Faecalibacterium prausnitzii* and *Escherichia coli* co-abundance can distinguish Irritable Bowel Syndrome and Inflammatory Bowel Disease phenotypes. International Journal of Medical Microbiology. 2014; 304: 464-475
(43) Huijsdens X W, Linskens R K, Mak M, et al. Quantification of Bacteria Adherent to Gastrointestinal Mucosa by Real-Time PCR. J Clin Microbiol. 2002; 40: 4423-4427
(44) Furet J-P, Firmesse O, Gourmelon M, et al. Comparative assessment of human and farm animal faeca microbiota using real-time quantitative PCR. FEMS Microbiology Ecology. 2009; 68: 351-362

To determine the best reagent concentrations for the qPCR assay, experiments were performed using different primer and probe concentrations ranging from 50 to 900 nM. Those reagents concentrations that yield the maximum fluorescent signal and the lowest quantification cycle ($C_q$) value for $10^6$ copies/reaction of the target DNA were chosen as optimal, and have therefore been used for further quantification in samples (as described in the qPCR assays section below).

Oligonucleotides specificity was checked against the Ribosomal Database Project II (RDP) (Maidak B L, et al., Nucleic Acids Research. 2001; 29:173-174) and GenBank database through Seqmatch and BLAST (Altschul S F, et al. Nucleic Acids Research. 1997; 25:3389-3402), respectively. Coverages were evaluated using the SILVA Probe Match and Evaluation Tool—TestProbe 3.0 (available at http://www.arb-silva.de/search/testprobe/). Finally, in vitro inclusivity/exclusivity test was performed including 89 bacterial strains, nine of which were *F. prausnitzii* (Table 16).

Linearity, efficiency and detection limit of the assay were determined. To determine the confident quantification range of the assay, decaplicate ten-fold dilutions (ranging from $2 \times 10^8$ to 2 target gene copies per reaction) of a linearized plasmid containing either a single copy of the 16S rRNA gene of *F. prausnitzii* S3L/3 (phylogroup I) or *F. prausnitzii* DSM 17677 (phylogroup II) were used. The linear range for quantification was considered for those concentrations having a SD value lower than 0.34 between replicates. Regression analysis plotting the obtained Cq against the logarithm of the number of target genes in the reaction was also performed. The efficiency of the qPCR assay was calculated using the formula: Efficiency=$[10^{(-1/slope)}]-1$. As concerns to detection limit of the assay, a calibration curve of two-fold serial dilutions between 1 and 100 target copies of *F. prausnitzii* 16S rRNA gene was performed. Eight replicas of each dilution were assayed. Data was analyzed by a Probit test (Minitab® 14 Statistical Software, Pennsylvania, US), in which the ratio of positive/negative amplification events was plotted against the amount of target genes present per reaction.

4. Quantification Standards for qPCR.

Standard DNA templates from *F. prausnitzii* strain S3L/3 (phylogroup I), and *F. prausnitzii* DSM 17677 (phylogroup II) were prepared as genetic constructs after PCR amplification as previously reported (Lane D J. et al., E. Stackebrandt and M. Goodfellow (ed.)., John Willy and Sons; 1991; Weisburg W G, Barns S M, Pelletier D A, et al. J Bacteriol. 1991; 173:697-703), and subsequent insertion of the whole 16S rRNA gene into a pCR®4-TOPO® cloning plasmid (Invitrogen, CA, USA) following manufacturer's guidelines. After purification with the NucleoSpin® Plasmid (Macherey-Nagel GmbH&Co., Duren, Germany), plasmids were linearized with SpeI (*F. prausnitzii*) and quantified using Qubit™ Quantitation Platform (Invitrogen, Carlsbad, USA). Initial target concentration was inferred as previously reported (Lopez-Siles M, et al. International Journal of Medical Microbiology. 2014; 304:464-475). Standard curves were obtained from ten-fold serial dilutions of the titrated suspension of linearized plasmids, and ranged from 20 to $2 \times 10^8$ copies/reaction, which correspond to the linear dynamic range span for all the reactions. The standard curve built with *F. prausnitzii* DSM 17677 16S rRNA gene was used for both the total bacteria and the total faecali bacteria 16S rRNA gene quantification, and standard curves obtained from either phylogroup were intercalibrated using the total *F. prausnitzii* primers and probe set.

5. qPCR assays.

Previously reported 16S rDNA-targeting primers and probe were used for total *F. prausnitzii* (Lopez-Siles M, et al. International Journal of Medical Microbiology. 2014; 304: 464-475), and total bacteria (Furet J-P, et al. FEMS Microbiology Ecology. 2009; 68:351-362) quantifications, and amplification reactions were carried out as described previously (Lopez-Siles M, et al. International Journal of Medical Microbiology. 2014; 304:464-475). The novel assay for *F. prausnitzii* phylogroups quantification was carried out in a total volume of 20 µl reactions containing: 1×TaqMan® Universal PCR Master Mix 2× (Applied Biosystems, Foster City, Calif., USA), 900 nM of each primer, 300 nM of each probe, and up to 50 ng of genomic DNA template. All primers and probes used in this study as well as PCR conditions are detailed in Table 15. Total *F. prausnitzii*, and total bacteria primers and hydrolysis probes were purchased from Applied Biosystems (Foster City, Calif., USA), whereas primers and hydrolysis probes for *F. prausnitzii* phylogroups were acquired from Biomers (Ulm, Germany). The DNA of the internal amplification control (IAC) was synthesized by Bonsai technologies group (Alcobendas, Spain).

Samples were run in duplicate in the same plate. For data analysis, the mean of the duplicate quantifications was used. Duplicates were considered valid if the standard deviation between quantification cycles ($C_q$) was <0.34 (i.e. a difference of <10% of the quantity was tolerated). Quantification controls consisting of at least five reactions with a known number of target genes were performed to assess inter-run reproducibility. Inhibition was controlled on total *F. prausnitzii* quantification by adding $10^3$ copies of IAC template to each reaction. It was considered that there was no inhibition if the obtained $C_q$ was <0.34 different from those obtained when quantifying the IAC alone for any of the replicates. A no-template control consisting of a reaction without *F. prausnitzii* DNA as well as a non-amplification control which did not contain any DNA template (either bacterial or IAC) were also included in each run. Negative controls resulted in undetectable $C_q$ values in all cases.

All quantitative PCR were performed using a 7500 Real Time PCR system (Applied Biosystems, Foster City, Calif., USA). Data were collected and analyzed using the 7500 SDS system software version 1.4 (Applied Biosystems, Foster City, Calif., USA). All quantifications were done under average PCR efficiencies of 89.51±7.06%.

6. Data Normalization and Statistical Analysis.

As regards to qualitative analyses, absence of *F. prausnitzii* or its phylogroups was considered if no detection was obtained during the qPCR analysis, corresponding to samples that carried *F. prausnitzii* or the phylogroups below the detection limit (i. e. 106.6, 1.10 and 2.39 16S rRNA genes per reaction for total *F. prausnitzii*, phylogroup I and phylogroup II, respectively). Pearson's $\chi^2$ test was used to compare the prevalence of *F. prausnitzii* and its phylogroups between groups of patients and by IBD disease location.

Referring to quantitative analyses, total *F. prausnitzii*, and phylogroups copy numbers were normalized to the total bacteria 16S rRNA gene copies. Data is given as the $\log_{10}$ of the ratio between 16S rRNA gene copies of the target microorganism and million of total bacterial 16S rRNA genes detected in the same sample.

The non-parametric Kruskal-Wallis test was used to test differences in variables with more than two categories such as diagnostics, CD and UC disease location, and current medication. Pairwise comparisons of subcategories of these variables were analyzed using a Mann-Whitney U test. This test was also used to compare, within a subgroup of patients, variables with two categories such as activity (active CD and UC patients when CDAI>150 (Best, W. R., et al. Gastroenterology, 1976. 70(3): p. 439-44.) and a Mayo score >3 (Pineton de Chambrun, G., L. et al. Nat Rev Gastroenterol Hepatol, 2010. 7(1): p. 15-29.), respectively), and intestinal resection.

In addition, the receiver operating characteristic (ROC) curve analysis, a plot of the true positive rate (sensitivity) versus false positive rate (1−specificity), was applied to establish the usefulness of F. prausnitzii, and each phylogroup to distinguish amongst different intestinal disorders. The accuracy of discrimination was measured by the area under the ROC curve (AUC). An AUC approaching 1 indicates that the test is highly sensitive as well as highly specific whereas an AUC approaching 0.5 indicates that the test is neither sensitive nor specific.

All the statistical analyses were performed using the SPSS 15.0 statistical package (LEAD Technologies, Inc.). Significance levels were established for P values≤0.05.

Example 2

Features of the Novel Multiplex qPCR Assay for F. Prausnitzii Phylogroups I and II A novel oligonucleotide set was designed to quantify the two recently described F. prausnitzii phylogroups (Table 15). The in silico analysis of the oligonucleotide set of choice showed that primer Fpra 136F-Fpra 232R were specific for F. prausnitzii and targeted all the isolates available to date, whereas the probes PHG1 180PR and PHG2 180PR specifically matched phylogroups I and II, respectively. These results were confirmed in vitro by the inclusivity-exclusivity tests (Table 16). Coverage of the Fpra 136F-Fpra 232R primers set was 74.85% of the sequences in the SILVA datasets. PHG1 180PR probe targeted 20.50% of the Faecalibacterium sp. sequences whereas PHG2 180PR probe coverage was 38.80% of the Faecalibacterium sp. sequences in this database. Approximately 25% of all Faecalibacterium sequences available in SILVA dataset are not targeted in silico by any of these assays. This discrepancy could be due to the existence of other phylogroups and/or because different phylogroup probes do not include all members within each phylogroup. Our results are still valid however to compare between diseases in our study, as the same criteria for the definition of phylogroup members has been used, i.e., PHGI has been defined by specific hybridization with SEQ ID NO:3 and PHGII with SEQ ID NO:4.

For both reactions reliable quantification was possible over a linear range span of 7 logarithms, starting at 20 target genes per reaction ($R^2$=0.998), with an average efficiency of 85.68±3.23% for phylogroup I and 90.31±3.40% for the phylogroup II. The detection limits were 1.10 and 2.39 target genes for phylogroup I and phylogroup II, respectively.

TABLE 16

Growth conditions and source of the bacterial strains used in this study. The results obtained from the specificity tests are also included.

| Source of DNA information* | | | | | | | |
|---|---|---|---|---|---|---|---|
| Phylogeny | Strain/ source [1] | Growth [2] Media | T(° C.) | ng [3] | cnPCR | qPHG1 | qPHG2 |
| Firmicutes | | | | | | | |
| Faecalibacterium prausnitzii ATCC 27768[T] | ATCC 27768 | M2GSC | 37 | 10 | + | + | − |
| F. prausnitzii M21/2 | nd | M2GSC | 37 | 10 | + | + | − |
| F. prausnitzii S3L/3 | nd | M2GSC | 37 | 10 | + | + | − |
| F. prausnitzii S4L/4 | nd | M2GSC | 37 | 10 | + | + | − |
| F. prausnitzii A2-165 | DSM17677 | M2GSC | 37 | 10 | + | − | + |
| F. prausnitzii L2-15 | nd | M2GSC | 37 | 10 | + | − | + |
| F. prausnitzii L2-39 | nd | M2GSC | 37 | 10 | + | − | + |
| F. prausnitzii L2-6 | nd | M2GSC | 37 | 10 | + | − | + |
| F. prausnitzii L2-61 | nd | M2GSC | 37 | 10 | + | − | + |
| Anaerofilum agile | DSM4272 | nc | nc | 1.6 | + | − | − |
| Eubacterium siraeum | DSM15702 | nc | nc | 6.9 | + | − | − |
| Eubacterium halii | DSM17630 | nc | nc | 1 | + | − | − |
| Clostridium viride | DSM6836 | nc | nc | 10 | + | − | − |
| Clostridium leptum | DSM753 | nc | nc | 10 | + | − | − |
| Ruminococcus albus | DSM20455 | nc | nc | 10 | + | − | − |
| Clostridium acetobutylicum | CECT 979 | AN | 37 | 3.7 | + | − | − |
| Clostridium botulinum type E | CECT4611 | LiB | 37 | 10 | + | − | − |
| Bacillus cereus | NCTC11145 | AN | 30 | 10 | + | − | − |
| Bacillus megaterium | DSM319 | AN | 30 | 10 | + | − | − |
| Bacillus sp. | CECT 40 | AN | 30 | 10 | + | − | − |
| Bacillus subtilis | NCTC10400 | AN | 30 | 2.3 | + | − | − |
| Bacillus subtilis sups. spizizwnii | CECT 482 | AN | 30 | 10 | + | − | − |
| Listeria grayi | CECT931 | BHI | 37 | 10 | + | − | − |
| Listeria innocua | CECT910 | BHI | 37 | 10 | + | − | − |
| Paenibacillus polymyxa | DSM372 | BHI | 37 | 2.1 | + | − | − |
| Staphylococcus aureus | ATCC9144 | AN | 37 | 10 | + | − | − |
| Staphylococcus epidermidis | CECT 231 | AN | 37 | 10 | + | − | − |
| Enterococcus avium | CECT 968 | BHI | 37 | 10 | + | − | − |
| Enterococcus columbae | CECT 4798 | BHI | 37 | 10 | + | − | − |
| Enterococcus durans | CECT 411 | BHI | 37 | 10 | + | − | − |
| Enterococcus faecalis | CECT 481 | BHI | 37 | 10 | + | − | − |
| Enterococcus faecium | CECT 410 | BHI | 37 | 10 | + | − | − |

TABLE 16-continued

Growth conditions and source of the bacterial strains used in this study.
The results obtained from the specificity tests are also included.

Source of DNA information*

| Phylogeny | Strain/ source [1] | Growth [2] Media | T(° C.) | ng [3] | Specificity test information cnPCR | qPHG1 | qPHG2 |
|---|---|---|---|---|---|---|---|
| *Enterococcus gallinarum* | CECT 970 | BHI | 37 | 10 | + | − | − |
| *Enterococcus mundtii* | CECT 972 | BHI | 37 | 10 | + | − | − |
| *Lactobacillus acidophilus* | CECT 903 | MRS | 30 | 6.3 | + | − | − |
| *Lactococcus lactis* | CECT 185 | MRS | 30 | 3.8 | + | − | − |
| *Streptococcus agalactiae* | CECT 183 | BHI | 37 | 7.2 | + | − | − |
| *Streptococcus anginosus* | CECT 948 | BHI | 37 | 10 | + | − | − |
| *Streptococcus equi* subsp. *equi* | CECT 989 | BHI | 37 | 10 | + | − | − |
| *Streptococcus equinus* | CECT 213 | BHI | 37 | 10 | + | − | − |
| *Streptococcus intermedius* | CECT 803 | BHI | 37 | 10 | + | − | − |
| *Streptococcus mutans* | CECT 479 | BHI | 37 | 3.8 | + | − | − |
| *Streptococcus oralis* | CECT 907 | BHI | 37 | 10 | + | − | − |
| *Streptococcus pneumoniae* | CECT 993 | BHI | 37 | 10 | + | − | − |
| *Streptococcus pyogenes* | CECT 598 | BHI | 37 | 10 | + | − | − |
| *Streptococcus salivarus* | CECT 805 | BHI | 37 | 10 | + | − | − |
| *Streptococcus sanguinis* | CECT 480 | BHI | 37 | 5.5 | + | − | − |
| *Streptococcus sobrinus* | CECT 4034 | BHI | 37 | 6.5 | + | − | − |
| *Streptococcus suis* | CECT 958 | BHI | 37 | 10 | + | − | − |
| *Streptococcus thermophilus* | CECT 986 | BHI | 37 | 10 | + | − | − |
| *Streptococcus uberis* | CECT 994 | BHI | 37 | 10 | + | − | − |
| Actinobacteria | | | | | | | |
| *Corynebacterium bovis* | DSM20582 | MRS | 37 | 4.8 | + | − | − |
| *Kocuria rhizophila* | DSM348 | AN | 30 | 2.3 | + | − | − |
| *Micrococcus luteus* | CECT 241 | AN | 30 | 2.6 | + | − | − |
| *Mycobacterium phlei* | CECT 3009 | BHI | 37 | 10 | + | − | − |
| *Streptomyces griseus* | DSM40236 | PDA | 30 | 10 | + | − | − |
| *Bifidobacterium adolescentis* | CECT 5781 | AN | 37 | 0.4 | + | | |
| *Bifidobacterium breve* | CECT 4839 | AN | 37 | 2.0 | + | − | − |
| Bacteroidetes | | | | | | | |
| *Bacteroides fragilis* | DSM2151 | nc | nc | 10 | + | − | − |
| *Bacteroides uniformis* | DSM6597 | nc | nc | 10 | + | − | − |
| *Bacteroides vulgatus* | DSM1447 | nc | nc | 10 | + | − | − |
| Proteobacteria | | | | | | | |
| *Methylophilus methylotrophus* | DSM5691 | CZ | 30 | 10 | + | − | − |
| *Campylobacter jejuni* | DSM4688 | BA | 37 | 10 | + | − | − |
| *Citrobacter freundii* | CECT 401 | AN | 30 | 10 | + | − | − |
| *Enterobacter aerogenes* | CECT 684 | AN | 30 | 10 | + | − | − |
| *Enterobacter cloacae* | CECT 194 | AN | 30 | 10 | + | − | − |
| *Enterobacter sakazakii* | CECT 858 | AN | 30 | 10 | + | − | − |
| *Enterobacter sakazakii* | ATCC51329 | AN | 30 | 0.4 | + | − | − |
| *Enterobacter amnigenus* (*Sakazakii*) | CECT 4078 | AN | 37 | 10 | + | − | − |
| *Enterobacter gergoviae* (*Sakazakii*) | CECT 857 | AN | 37 | 10 | + | − | − |
| *Escherichia coli* | CECT 100 | AN | 37 | 10 | + | − | − |
| *Escherichia coli* | CECT 101 | AN | 37 | 10 | + | − | − |
| *Escherichia coli* | CECT 105 | AN | 37 | 10 | + | − | − |
| *Escherichia coli* | CECT 12242 | AN | 37 | 10 | + | − | − |
| *Escherichia coli* | CECT 831 | AN | 37 | 10 | + | − | − |
| *Escherichia coli* | CECT 4201 | AN | 37 | 10 | + | − | − |
| *Escherichia coli* | CECT 4084 | AN | 37 | 10 | + | − | − |
| *Escherichia coli* | CECT 405 | AN | 37 | 10 | + | − | − |
| *Escherichia coli* | ATCC10536 | AN | 37 | 10 | + | − | − |
| *Klebsiella pneumoniae* ssp. *pneumoniae* | CECT 143 | AN | 37 | 10 | + | − | − |
| *Proteus mirabilis* | CECT 170 | AN | 37 | 10 | + | − | − |
| *Salmonella* LT2 | CECT878 | AN | 37 | 10 | + | − | − |
| *Salmonella* TA98 | CECT880 | AN | 37 | 10 | + | − | − |
| *Serratia marcescens* | CECT846 | AN | 25 | 10 | + | − | − |
| *Shigella sonnei* | CECT457 | AN | 37 | 10 | + | − | − |

TABLE 16-continued

Growth conditions and source of the bacterial strains used in this study.
The results obtained from the specificity tests are also included.

| Phylogeny | Strain/source [1] | Growth [2] | | ng [3] | Specificity test information | | |
|---|---|---|---|---|---|---|---|
| | | Media | T(° C.) | | cnPCR | qPHG1 | qPHG2 |
| Pseudomonas aeruginosa | CECT 532 | AN | 30 | 10 | + | − | − |
| Pseudomonas fluorescens | CECT 378 | AN | 30 | 10 | + | − | − |
| Pseudomonas mendocina | CECT320 | AN | 30 | 10 | + | − | − |
| Pseudomonas putida | CECT 324 | AN | 30 | 4.1 | + | − | − |

*Specificity test with human Xsomal DNA (Eurogentec, Belgium) was also performed
[1] ATCC: American Type Culture Collection (Manassas, VA, USA); CECT: Colección Española de Cultivos Tipo (Valencia, Spain); DSMZ: Deutche Sammlung von Mikroorganismen and Zellkulturren (Braunschweig, Germany), NCTC: National Collection of Type Cultures (London, UK), nd: not deposited (stocks held by the authors, Rowett Institute of nutrition and Health, Aberdeen, United Kingdom).
[2] nc: not cultured. BHI (Brain Heart Infusion Broth), AN (Nutrient Agar), BA (Blood Agar), MRS (Man, Rogosa and Sharpe medium ), LiB(Liver Broth, CECT medium #15), CZ (Colby and Zathman medium, DSMZ medium #606), PDA (Potato Dextrose Agar), M2GSC (modified Med2 of Hobson, (1)).
[3] ng of genomic DNA used for the inclusivity/exclusivity test. When possible, 10 ng was used. The DNA was obtained from 1 ml of bacterial culture at the stationary growth phase or for nc strains, the dried culture directly obtained from the culture type collection was rehydrated with the appropriate buffer for DNA extraction and used for DNA purification.

Example 3

Prevalence of Mucosa-Associated F. Prausnitzii and Phylogroups I and II Along the Gut in Health and Disease Prevalence of F. prausnitzii and both phylogroups as calculated from positive determinations over total samples was analyzed by disease status considering all the data across all sites (FIG. 1). F. prausnitzii prevalence was lower in CD patients than in H (FIG. 1). CD patients with I-CD feature lower F. prausnitzii prevalence than those with E1, E2, E3 and C-CD. Prevalence values ranged from 81-100%, except for I-CD whose value was significantly lower (down to 68%, P≤0.046).

As far as the phylogroups are concerned, both were found to be less prevalent in CD patients (P<0.001) than in the H and CRC groups, particularly in those with ileal involvement (FIG. 1). For CRC and UC patients, the prevalence remained similar to H. Nevertheless phylogroup I showed a trend of lower values in ulcerative pancolitis, which did not reach statistical significance (P=0.053) probably due to the low number of samples processed. Similarly IBS patients only had reduced prevalence of phylogroup I in comparison to H subjects.

Figure 2:
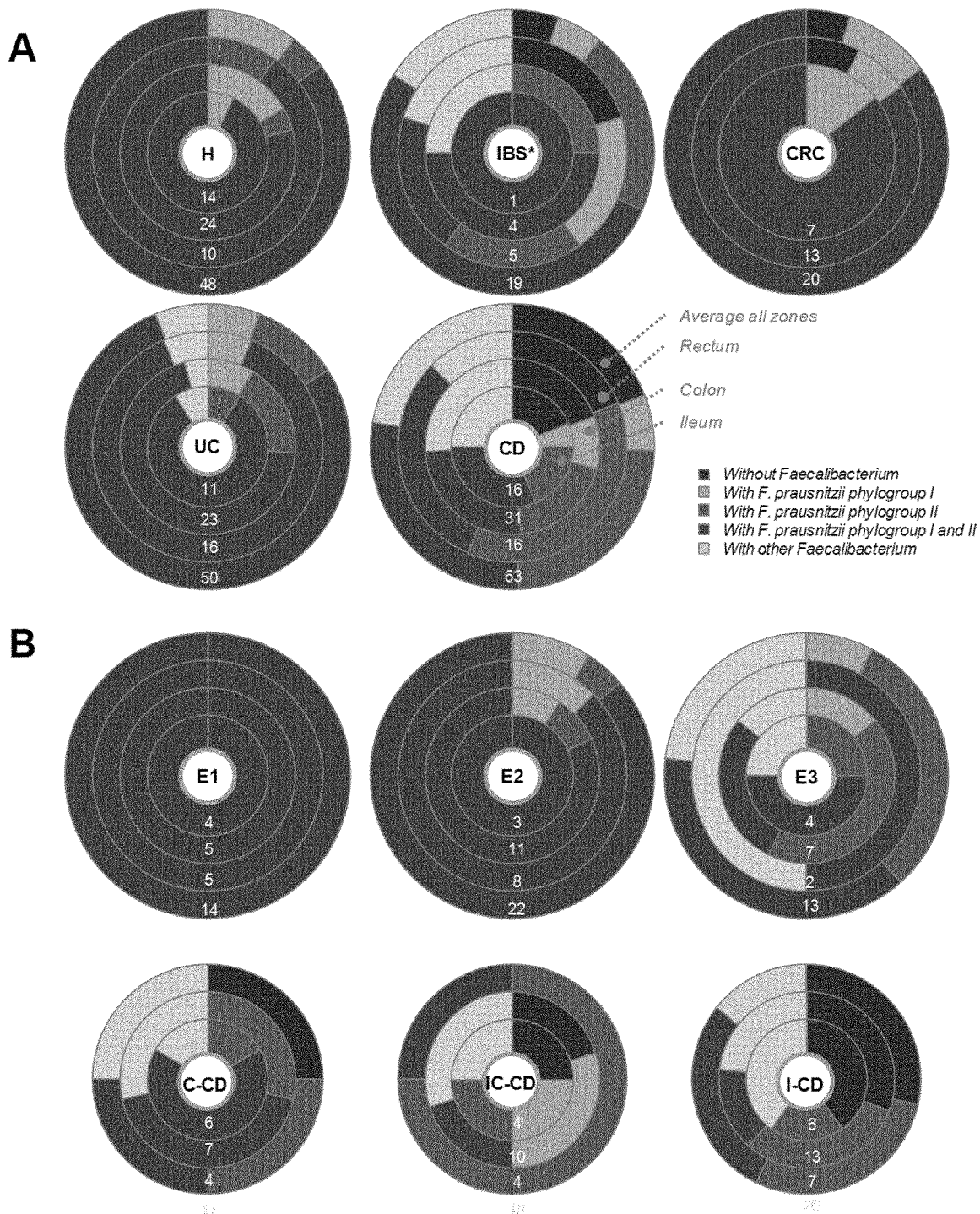
FIG. 2. Graphical representation of the prevalence of *F. prausnitzii*, *F. prausnitzii* phylogroup I and *F. prausnitzii* phylogroup II in each group of patients (A) categorized by disease and (B) categorized by IBD subtype. Both in A) and B) prevalence values along the gut have been represented (from inner to outer circles-ileum, colon and rectum) and also the corresponding prevalence pooling all the samples (outer circle). The following abbreviations have been used: H, control subjects; CRC, colorectal cancer; IBS, irritable bowel syndrome; UC, ulcerative colitis; CD, Crohn's disease; E1, ulcerative proctitis; E2, ulcerative left-sided colitis; E3, ulcerative pancolitis; C-CD, colonic CD; IC-CD, ileocolonic CD; and I-CD, ileal CD. Numbers in the sectors indicate the number of biopsies analysed. * Samples with uncertain location have been included in the average analysis of IBS patients.

Both phylogroups co-occurred in 85.4% and 85.0% of samples containing F. prausnitzii from H and CRC patients, respectively. Phylogroup I was exclusive in 10% of H and CRC subjects, whereas phylogroup II was found as the only representative in 4.2% of H subjects (FIG. 2A). In contrast, 16% of IBS, 6% of UC and 22% of CD patients with F. prausnitzii carried neither phylogroup I nor II, which suggests the existence of other phylogroups. Differences in prevalences were observed between IBD disease location. All the patients with less severe UC (i.e. E1 and E2) had one or both F. prausnitzii phylogroups, resembling H subjects, whereas none of the phylogroups were detected in 23.1% of ulcerative pancolitis patients despite having F. prausnitzii (FIG. 2B). Similarly, 22.2% of all CD patients did not show either of the phylogroups. Within CD patients, 47.1% of C-CD patients had both F. prausnitzii phylogroups whereas the presence of a unique phylogroup was more frequent (44.4% of IC-CD and 28.0% of I-CD patients) in those with ileal involvement. Remarkably whenever a single phylogroup was found in I-CD it always was the phylogroup II.

The majority of H and CRC subjects harbored both phylogroups far higher than the detectable level whereas IBS, and IBD patients feature a reduced prevalence of one of the phylogroups, particularly those with CD. Furthermore, phylogroup I and II were undetected in 16% of IBS and 22% of CD patients with F. prausnitzii. These results suggest an imbalance within the F. prausnitzii population in these diseases and suggest the existence of at least one more phylogroup.

Example 4

Abundances of Mucosa-Associated F. Prausnitzii and Phylogroups in Health and Disease The abundance of F. prausnitzii and its phylogroups from all the biopsies pooled together was compared amongst patients with different intestinal disorders and H subjects (Table 17). F. prausnitzii was less abundant in IBD and CRC patients as compared to healthy subjects (P<0.001), whereas IBS patients closely resembled the H group. As previously reported (Lopez-Siles M, et al. International Journal of Medical Microbiology. 2014; 304:464-475), within UC patients, those with E1 and E3 presented F. prausnitzii loads similar to H subjects, whereas those with E2 had abundances between CD patients and H subjects. In CD patients, those with ileal involvement presented the lowest levels of this bacterium, whereas C-CD patients were similar to UC (Table 17).

F. prausnitzii phylogroup I load was reduced in all the intestinal diseases analyzed in comparison to H subjects, except for IBS patients, probably due to the low number of patients included and the high dispersion of data. This reduction was particularly conspicuous in CD patients, who had values 1000 times lower than H subjects (P<0.001). When analyzing data by disease location, all CD patients showed this marked reduction of phylogroup I abundance, as well as those UC patients with E3 that resembled more to CD patients than to those with other UC disease location. In contrast, F. prausnitzii phylogroup II abundance was only significantly reduced in CD patients in comparison to H (P<0.001) (Table 17), particularly in those with ileal involvement (either I-CD or IC-CD), suggesting that in these patients the depletion of F. prausnitzii affects the overall faecali bacteria community.

TABLE 17

Abundances of mucosa-associated *F. prausnitzii* and its phylogroups in controls (H), Irritable Bowel Syndrome (IBS), Ulcerative Colitis (UC), and Crohn's disease (CD) patients. Disease locations of UC and CD patients are analyzed as independent groups.

| | n patients (n biopsies) | *F. prausnitzii*[*,§] | Phylogroup I[*,§] | Phylogroup II[*,§] |
|---|---|---|---|---|
| H | 31 (48) | 5.33 ± 0.58 [a] | 3.39 ± 0.87 [a] | 3.39 ± 1.51 [a] |
| IBS | 9 (19) | 5.29 ± 0.54 [a, b] | 2.53 ± 1.22 [a, b] | 2.72 ± 1.06 [a, b] |
| CRC | 20 (20) | 4.42 ± 0.58 [c] | 2.66 ± 0.91 [b] | 2.56 ± 1.14 [a, b] |
| UC | 25 (50) | 5.00 ± 0.62 [b] | 2.59 ± 1.24 [b] | 2.93 ± 0.99 [a] |
| Location | | | | |
| Ulcerative proctitis (E1) | 6 (14) | 5.09 ± 0.29 [a] | 2.76 ± 0.38 [a, b] | 3.22 ± 0.43 [a] |
| Distal UC (E2) | 11 (22) | 4.49 ± 0.59 [b] | 2.58 ± 1.15 [a, b] | 2.84 ± 0.93 [a, b] |
| Extensive UC or ulcerative pancolitis (E3) | 6 (10) | 5.34 ± 0.69 [a] | 0.95 ± 1.60 [b, c] | 3.13 ± 1.02 [a, b] |
| CD | 45 (63) | 4.26 ± 1.34 [c] | 0.71 ± 1.65 [c] | 1.54 ± 1.47 [c] |
| Location | | | | |
| Ileal-CD (L1) | 19 (25) | 3.97 ± 1.42 [c] | 0.43 ± 1.33 [c] | 1.14 ± 1.54 [b] |
| Colonic-CD (L2) | 11 (17) | 5.06 ± 1.07 [a, c] | 1.54 ± 1.71 [b, c] | 2.63 ± 1.51 [a, b] |
| Ileocolonic-CD (L3) | 14 (18) | 4.30 ± 1.12 [b, c] | 1.06 ± 1.72 [b, c] | 1.38 ± 1.54 [b] |

[*]Statistics were calculated separately for each variable (column). Groups of patients with similar abundances of *F. prausnitzii* or its phylogroups are indicated with the same superscript (a, b or c) whereas groups not sharing superscript are those with statistically different median abundance values ($P < 0.05$)
[§]Median $\log_{10}$ 16S rRNA gene copies/million bacterial 16S rRNA gene copies ± standard deviations Our data show that mucosa-associated *F. prausnitzii* loads are markedly reduced in CRC and CD patients, especially in those with ileal involvement. *F. prausnitzii* was below detection limits of the method (106.6 16S rRNA genes of *F. prausnitzii* per reaction) in 5% of CRC and 20% of CD patients. UC patients also featured a lower *F. prausnitzii* abundance than H subjects, but this depletion was four-times less prominent than the depletion observed in CD and CRC patients. Finally, abundance in IBS patients was similar to H subjects. Our study is in agreement with previous reports which found *F. prausnitzii* to be less abundant and/or prevalent in adult CD, UC and CRC. We have not observed depletion in *F. prausnitzii* load in IBS patients, although this observation could be biased by the small cohort size which also had not been classified by disease type.

In general terms, this quantitative analysis demonstrated that, while the depletion in phylogroup I abundance is a general feature in abnormal gut conditions, the depletion of *F. prausnitzii* phylogroup II seems to be specific to CD patients with ileal disease location.

Example 5

Figure 3:
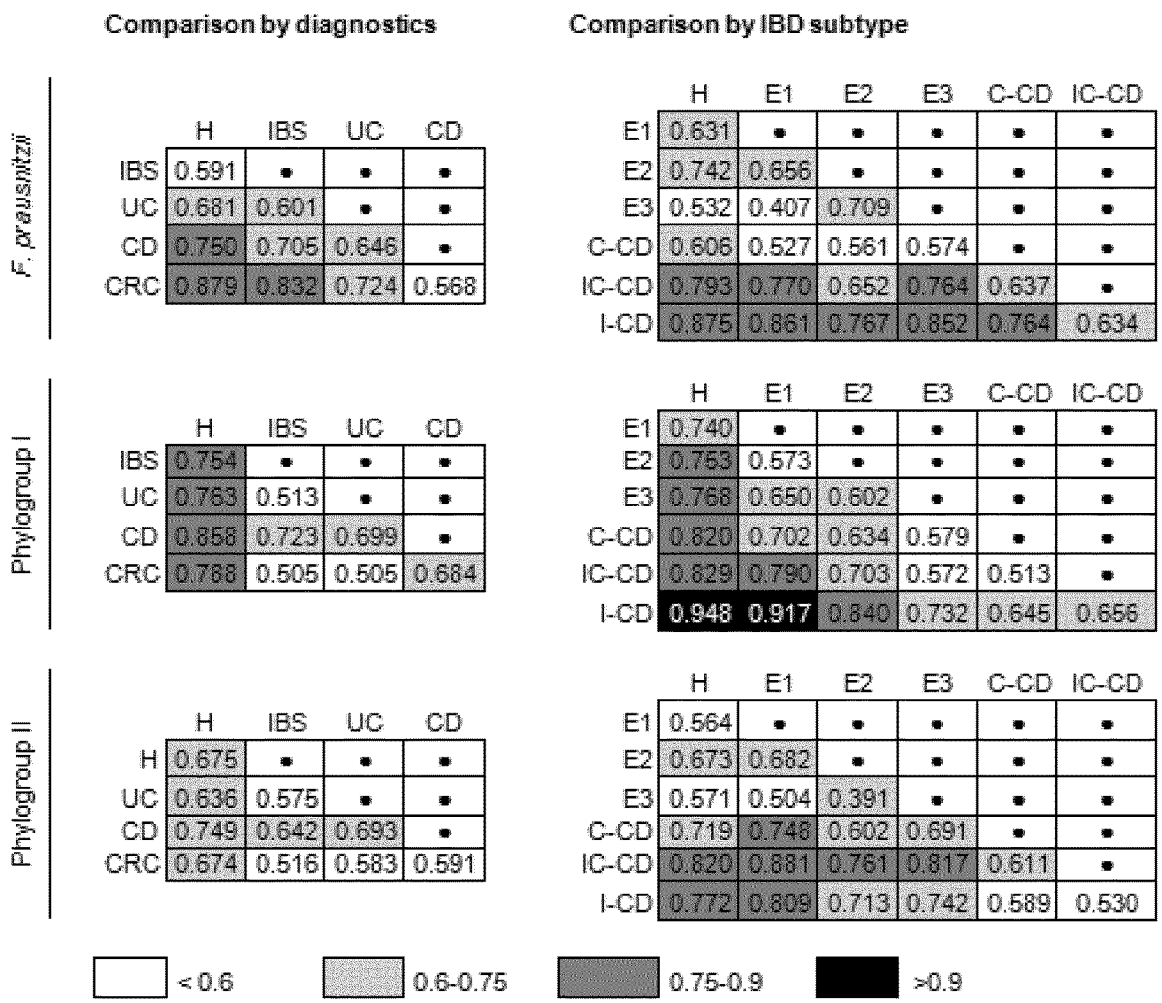
FIG. 3. Graphical representation as a heat map on the suitability of mucosa-associated *F. prausnitzii*, *F. prausnitzii* phylogroup I and *F. prausnitzii* phylogroup II abundances to be used as biomarkers to distinguish amongst different intestinal disorders and IBD subtypes (by location) determined by the area under the curve (AUC) obtained by receiver operating characteristic analysis (ROC curve). A test is considered to be a suitable discriminator if the AUC is from 0.6 to 0.75 (in light grey), to have a high discrimination if the AUC is from 0.75 to 0.9 (in dark grey) and to be an excellent discriminator if the AUC is from 0.9 to 1 (in black). The following abbreviations have been used: H, controls; IBD, inflammatory bowel disease; IBS, irritable bowel syndrome; UC, ulcerative colitis; CD, Crohn's disease; CRC, colorectal cancer; I-CD, ileal CD; IC-CD, ileocolonic CD, C-CD, colonic CD; E1, ulcerative proctitis, E2, distal UC; and E3, extensive UC or ulcerative pancolitis.

Usefulness of Mucosa-Associated *F. Prausnitzii* and Phylogroup Abundance as Diagnostic Biomarkers ROC curve analysis, applied to test the putative accuracy of total *F. prausnitzii* abundance as an indicator to differentiate between two groups of patients, confirmed that the reduction of this species load is a good discriminator for CRC patients from H and IBS patients, with AUC values greater than 0.8 (FIG. 3) with an 80% of specificity and above 70% of sensitivity at a set threshold. Good discrimination was also observed between CD and H patients, although for the same specificity values, sensitivity was reduced to 62%. Interestingly, phylogroup I abundance was a more accurate indicator to distinguish H from IBD subjects, than total *F. prausnitzii* abundance (FIG. 3). When comparing H subjects with UC more than 76.60% of sensitivity and above 57.14% of specificity at a set threshold were reached for all the disease locations but with the exception of ulcerative proctitis (E1). Specificity was improved up to 70% when considering exclusively E3 patients. In addition, phylogroup I abundance was a particularly accurate biomarker to distinguish H and CD patients (91.48% sensitivity, 73.02% specificity), especially those with I-CD in which 91.48% sensitivity and up to 88.00% of specificity could be reached. Although phylogroup II abundance can accurately discriminate H and CD subjects, AUC values were slightly lower than those obtained for phylogroup I, thus indicating that the latter is a more suitable biomarker for H status. In contrast, phylogroup II was a useful biomarker to discriminate within IBD subtypes as the best AUC values were obtained to distinguish between ulcerative pancolitis patients and those with CD with colonic involvement (phylogroup II AUC E3vsC-CD=0.817).

Figure 4:
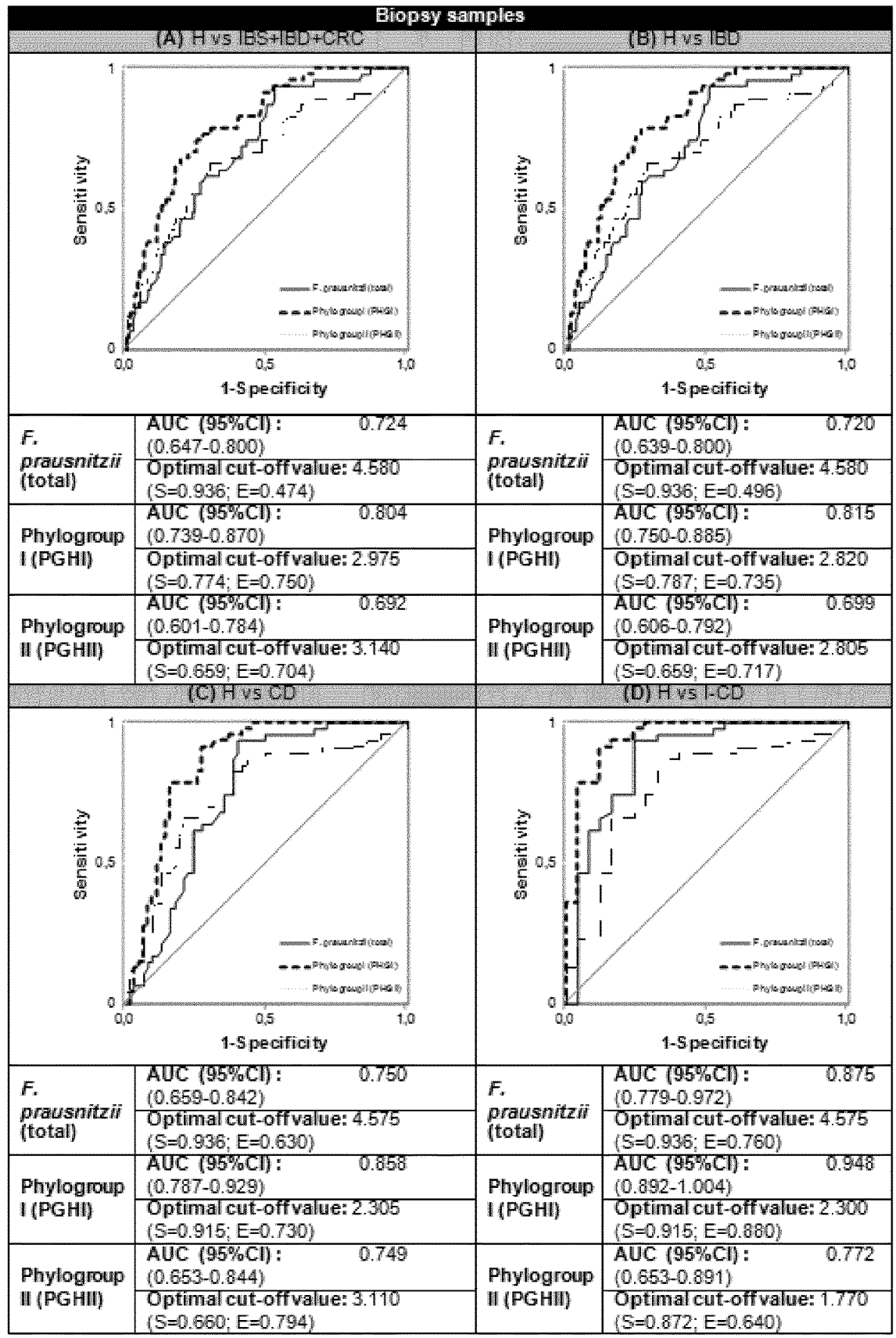
FIG. 4. Receiver operating characteristic (ROC) curves for mucosa-associated *F. prausnitzii*, *F. prausnitzii* phylogroup I (PHGI) and *F. prausnitzii* phylogroup II (PHGII) abundances for those group comparisons wherein PHGI shows to be the best discriminator between presence and absence of intestinal disease or disease subtype. A) H vs IBS+IBD+CRC; B).H vs IBD; C) H vs CD and D) H vs I-CD. In the Y axis is represented sensitivity and in the X axis 1−specificity. The following abbreviations have been used: H, controls; IBD, inflammatory bowel disease; IBS, irritable bowel syndrome; CD, Crohn's disease; CRC, colorectal cancer; and I-CD, ileal CD.
Figure 5:
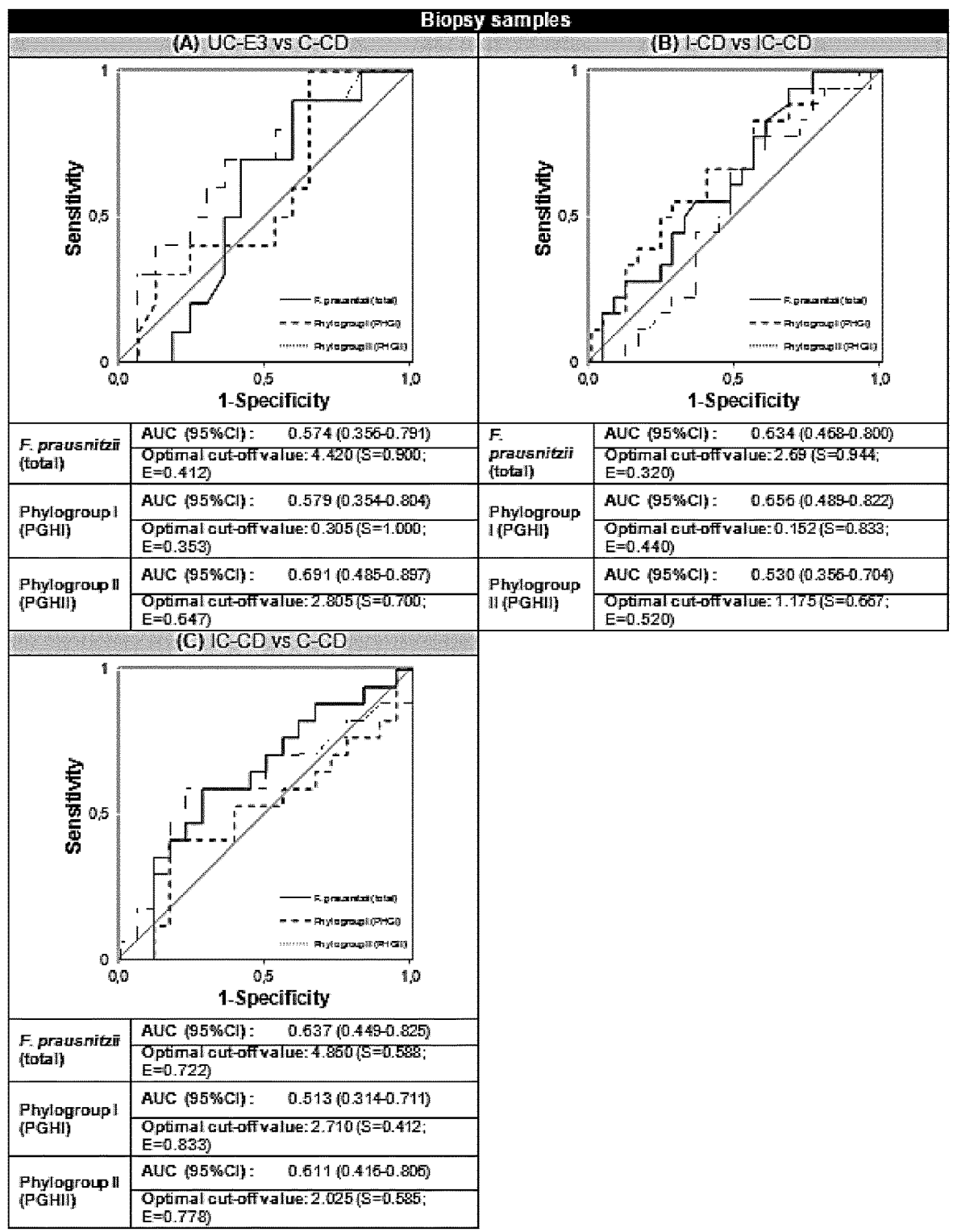
FIG. 5. Receiver operating characteristic (ROC) curves for mucosa-associated *F. prausnitzii*, *F. prausnitzii* phylogroup I (PHGI) and *F. prausnitzii* phylogroup II (PHGII) abundances for selected group comparisons for differential diagnosis of clinical interest. A) UC-E3 vs C-CD; B) I-CD vs IC-CD; and C) IC-CD vs C-CD. In the Y axis is represented sensitivity and in the X axis 1−specificity. The following abbreviations have been used: I-CD, ileal CD; IC-CD, ileocolonic CD, C-CD, colonic CD; and E3, extensive UC or ulcerative pancolitis.

FIG. 3 provides a heat map on the suitability of mucosa-associated *F. prausnitzii*, phylogroup I and phylogroup II abundances to be used as biomarkers to distinguish amongst different intestinal disorders and IBD subtypes (by location) determined by the area under the curve (AUC) obtained by receiver operating characteristic analysis (ROC curve). FIGS. 4 and 5 show the ROC curve, calculated AUC value and specificity and sensitivity values for the optimal cut-off point for selected group comparisons. Furthermore, Tables 29-35 at the end of the Examples section provide the ROC curve coordinates for those selected group comparisons.

In conclusion, it was found that mucosa-associated *F. prausnitzii* Phylogroup I (PHGI) abundance was a good biomarker of intestinal disease, notably of IBD, CD and I-CD, as PHGI abundance can accurately discriminate between H subjects and intestinal disease patients with an AUC for H vs IBS+IBD+CRC of 0.804. PHGI being also a better discriminator than total *F. prausnitzii* abundance (AUC: 0.724) or PHGII (AUC: 0.693). AUC of PHGI abundance for H+IBS vs IBD+CRC was of 0.753.

Furthermore, PHGI abundance was shown to discriminate between H subjects and IBD (UC+CD) patients with high accuracy (AUC: 0.816) and was better discriminator than total *F. prausnitzii* abundance (AUC: 0.720) or PHGII (AUC: 0.699).

In addition, PHGI abundance was a more accurate indicator than total *F. prausnitzii* load to distinguish H subjects from patients with CD (AUC: 0.858) with an 80% of specificity and 78% of sensitivity. Furthermore, sensitivity values as high as 91.48% could be reached, maintaining a good specificity of 73.02%. More specifically, PHGI abundance was shown to be a particularly good indicator of ileal location (I-CD) with a sensitivity of 91.48% a specificity of up to 88.00% could be reached. Accuracy values were also better than those obtained for total *F. prausnitzii* abundance and PHGII (PHGI AUC: 0.948 vs Total FP AUC: 0.875 and PHGII AUC: 0.772).

On the other hand, PHGII abundance showed a good discrimination capacity within IBD subtypes. In particular, it was shown to distinguish between ulcerative pancolitis patients (UC-E3) and those with CD with colonic involvement (C-CD) with high accuracy (E3 vs C-CD AUC of 0.691), these two disorders may present similar clinical manifestations and both are located in the colonic area. Due to differences in treatment and management between UC and CD it is of relevance an accurate discrimination between UC-E3 and C-CD. Furthermore, PHGII was found to be a suitable discriminator between C-CD and IC-CD (AUC: 0.611), and thus might be used as an indicator of the progression of the disease from the colonic to the ileal region.

Example 6

*F. Prausnitzii* and Phylogroup Abundances in Mucosa in Relation to Patients Clinical and Treatment Data 1. Disease Activity Status

*F. prausnitzii* and the abundance of the phylogroups did not differ between active and inactive UC patients (Table 18). Although no statistical significance was reached, active CD patients showed a marked reduction on phylogroup I abundance with respect to CD patients in remission (P=0.106).

TABLE 18

*F. prausnitzii* and its phylogroups abundance in IBD patients by disease activity status. Active CD and UC were defined by a CDAI of >150 (Best, W. R., et al. Gastroenterology, 1976. 70(3): p. 439-44.) and a Mayo score >3 (Pineton de Chambrun, G., L. et al. Nat Rev Gastroenterol Hepatol, 2010. 7(1): p. 15-29.), respectively.

| Diagnostics§ | N | *F. prausnitzii*\* | p-value | Phylogroup I\* | p-value | Phylogroup II\* | p-value |
|---|---|---|---|---|---|---|---|
| UC | | | | | | | |
| active | 41 | 4.80 ± 0.41 | 0.344 | 2.62 ± 1.32 | 0.720 | 2.92 ± 1.02 | 0.623 |
| inactive | 8 | 5.02 ± 0.66 | | 2.69 ± 0.78 | | 3.18 ± 0.87 | |
| CD | | | | | | | |
| active | 41 | 4.31 ± 1.10 | 0.507 | 0.61 ± 1.51 | 0.106 | 1.50 ± 1.63 | 0.624 |
| inactive | 22 | 4.25 ± 1.46 | | 1.36 ± 1.80 | | 1.69 ± 1.14 | |

\*Median $\log_{10}$ 16S rRNA gene copies/million bacterial 16S rRNA gene copies ± standard deviations
§UC, ulcerative colitis; CD, Crohn's disease The fact that *F. prausnitzii* abundance, including both phylogroups, seems to remain lower under remission suggest that this depletion may be occurring at early disease stages or even prior to disease onset, and remains altered over time even if there is endoscopic and clinical remission. Despite no statistically significant differences being observed, active CD patients presented a reduction of phylogroup I levels in comparison with inactive patients.

2. Intestinal Resection

*F. prausnitzii* abundance was reduced in those CD patients that underwent intestinal resection (Table 19). Interestingly, this could be attributable to lower phylogroup II abundance, that was 10-fold lower in resected CD patients than in those without intestinal surgery (P=0.001) whereas the phylogroup I load was only slightly lower between resected and non-resected patients.

TABLE 19

*F. prausnitzii* and its phylogroups abundance in inflammatory bowel disease patients depending on whether or not they have had intestinal resection during the course of the disease.

| Diagnostics§ | N | *F. prausnitzii*\* | p-value | Phylogroup I\* | p-value | Phylogroup II\* | p-value |
|---|---|---|---|---|---|---|---|
| UC | | | | | | | |
| non-resected | 43 | 4.85 ± 0.61 | 1.000 | 2.51 ± 1.21 | 0.136 | 2.92 ± 0.96 | 0.727 |
| resected | 1 | 4.91 | | 3.45 | | 2.68 | |

TABLE 19-continued

*F. prausnitzii* and its phylogroups abundance in inflammatory bowel disease patients depending on whether or not they have had intestinal resection during the course of the disease.

| Diagnostics[§] | N | F. prausnitzii* | p-value | Phylogroup I* | p-value | Phylogroup II* | p-value |
|---|---|---|---|---|---|---|---|
| CD | | | | | | | |
| non-resected | 41 | 4.86 ± 1.43 | 0.016 | 1.52 ± 1.84 | 0.379 | 2.11 ± 1.46 | 0.001 |
| resected | 13 | 3.74 ± 0.78 | | 0.45 ± 1.07 | | 0.65 ± 0.84 | |

*Median $\log_{10}$ 16S rRNA gene copies/million bacterial 16S rRNA gene copies ± standard deviations
[§]UC, ulcerative colitis; CD, Crohn's disease Lower numbers of *F. prausnitzii* were detected in resected CD patients. This reduction is also replicated with phylogroups counts. In this case nevertheless, statistical significant differences were only achieved for phylogroup II, probably because the depletion is more striking 3. Medication Finally, as far as therapies are concerned, data were analyzed taking into account the medication of the patients at the time of sampling (Table 20). No differences in *F. prausnitzii* or in phylogroup abundances were observed between medications within any IBD. However, those CD patients who received no treatment or mesalazine had higher *F. prausnitzii* loads than those patients under moderate immunosuppressants or anti-tumor necrosis factor. No medication was associated with the recovery of normal levels of these bacterial indicators.

In general terms, we have observed that the used medication does not restore the levels of mucosa-associated *F. prausnitzii* or its phylogroups, which is in agreement with a previous report (Lopez-Siles M, et al. International Journal of Medical Microbiology. 2014; 304:464-475).

4. Disease Duration

Concerning disease duration, no statistically significant correlation was found between time from disease onset and *F. prausnitzii* and phylogroup abundances (Table 21).

TABLE 21

Spearman correlation coefficients and significance between years since disease onset and *F. prausnitzii* phylogroups abundances in fecal samples in Ulcerative Colitis (UC), and Crohn's disease (CD) patients.

| | | F. prausnitzii | | Phylogroup I | | Phylogroup II | |
|---|---|---|---|---|---|---|---|
| Patients | N | Coef correl | p-value | Coef correl | p-value | Coef correl | p-value |
| UC | 46 | 0.076 | 0.616 | 0.225 | 0.133 | 0.015 | 0.922 |
| CD | 61 | -0.013 | 0.919 | 0.119 | 0.359 | -0.056 | 0.671 |

* Median $\log_{10}$ 16S rRNA gene copies/million bacterial 16S rRNA gene copies ± standard deviations
[§]UC, ulcerative colitis; CD, Crohn's disease

TABLE 20

*F. prausnitzii* and its phylogroups abundances (median $\log_{10}$ 16S rRNA gene copies/million bacterial 16S rRNA gene copies ± standard deviations) in inflammatory bowel disease by medication at sampling.

| Diagnostics[§] | N | F. prausnitzii* | p-value | Phylogroup I* | p-value | Phylogroup II* | p-value |
|---|---|---|---|---|---|---|---|
| UC | | | | | | | |
| No treatment | 25 | 4.95 ± 0.65 | | 2.51 ± 1.32 | | 2.93 ± 1.03 | |
| Mesalazine | 6 | 5.02 ± 0.33 | 0.904 | 2.53 ± 0.84 | 0.806 | 3.31 ± 0.98 | 0.832 |
| moderate immunosuppresants | 9 | 4.56 ± 0.58 | | 2.75 ± 0.41 | | 2.85 ± 0.71 | |
| Anti-tumor necrosis factor | 7 | 4.44 ± 0.83 | | 3.16 ± 1.93 | | 2.92 ± 1.07 | |
| CD | | | | | | | |
| No treatment | 21 | 4.86 ± 1.66 | | 0.69 ± 2.04 | | 2.70 ± 1.71 | |
| Mesalazine | 3 | 5.10 ± 0.41 | 0.225 | 1.71 ± 1.67 | 0.854 | 2.63 ± 1.89 | 0.738 |
| moderate immunosuppressants | 19 | 4.01 ± 0.95 | | 0.71 ± 1.45 | | 1.23 ± 1.48 | |
| Anti-tumor necrosis factor | 16 | 4.01 ± 1.43 | | 0.67 ± 1.48 | | 1.49 ± 1.18 | |

*Median $\log_{10}$ 16S rRNA gene copies/million bacterial 16S rRNA gene copies ± standard deviations
[§]UC, ulcerative colitis; CD, Crohn's disease

Example 7

Materials and Methods of *F. Prausnitzii* Phylogroups Quantification in Faecal Samples 1. Patients, Clinical Data and Sampling.

A Spanish cohort consisting of 20 IBD (12 CD and 8 UC) and 12 H was enrolled (Table 22). Subjects were recruited by the Gastroenterology Services of the Hospital Universitari Dr. Josep Trueta (Girona, Spain) (Salt, Spain). Subjects were age and gender matched for all the groups. IBD patients were diagnosed according to standard clinical, pathological and endoscopic criteria and categorized according to the Montreal classification (Silverberg et al., Can J Gastroenterol. 2005, 19 Suppl A:5-36). Clinically relevant data of all the patients was collected. None of the subjects received antimicrobial treatment for at least one month before sample collection.

Each subject provided a faecal sample, which was collected at the Gastroenterology Services of the Hospital Universitari Dr. Josep Trueta in less than 24 h after deposition. All samples were homogenized, aliquoted to 2 ml tubes and stored at −80° C. until use.

This work was approved by the Ethics Committee of Clinical Research of the Hospital Universitari Dr. Josep Trueta (Girona, Spain) and the Institut d'Assistència Sanitària of Girona (Salt, Spain) on January 2015. Informed consent from the subjects was obtained before enrollment.

2. Sample Treatment and DNA Extraction.

DNA was extracted from 200 mg-500 mg of fecal sample using the NucleoSpin® Soil Kit (Macherey-Nagel GmbH &Co., Duren, Germany). SL1 (700 µl) and Enhancer SX (150 µl) were added to each sample in order to improve DNA recovery. Afterwards, DNA was extracted and purified following the instructions from the manufacturer. Genomic DNA was eluted with 10 mM Tris-HCl (pH 7.4) and stored at −80° C. until use. DNA concentration and purity of the extracts were determined with a NanoDrop ND-100 spectrophotometer (NanoDrop Technologies, USA).

3. qPCR Assays.

qPCR assays were conducted as detailed in Example 1.

4. Data Normalization and Statistical Analysis.

Data normalization and statistical analyses were conducted as detailed in Example 1.

Example 8

Prevalence of Fecal *F. Prausnitzii* Phylogroups I and II in Health and Disease Prevalence of *F. prausnitzii* phylogroups as calculated from positive determinations over total samples was analyzed both by disease status and by disease location (Table 23). Both phylogroups were found to be less prevalent in CD patients than in H subjects, particularly in those with I-CD. Interestingly, whereas C-CD patients had a lower prevalence

TABLE 22

Sample size and clinical characteristics of subjects.

|  | Healthy | Crohn's disease | Ulcerative colitis | p value[§] |
| --- | --- | --- | --- | --- |
| N (patients) | 12 | 12 | 8 |  |
| Age (mean years ± SD) | 42.8 ± 18.6 | 39.5 ± 13.8 | 54.3 ± 17.2 | 0.223[‡] |
| Male (N, %) | 5 (41.7%) | 7 (58.3%) | 4 (50.0%) | 0.547[†] |
| Active (N, %) | na | 6 (50.0%) | 2 (25.0%) | 0.502[†] |
| Previous surgery (N, %) | 0 | 4 (50.0%) | 1 (12.5%) | 0.457[†] |
| Smokers (N, %) | 3 (25.0%) | 2 (24.0%) | 0 | 0.005[†] |
| Treatment (N, %)** |  |  |  | 0.569[†] |
| No treatment |  | 2 (16.7%) | 0 |  |
| Mesalazine | na | 0 | 0 |  |
| Moderate immunosuppressant | na | 3 (25.0%) | 1 (12.5%) |  |
| Anti-TNFα (infliximab, adalimumab) | na | 7 (58.3%) | 4 (25.0%) |  |
| CD Montreal classification* |  |  |  |  |
| Age of diagnosis (N, %)** |  |  |  | 0.319[‡] |
| diag <16 y (A1) | na | 2 (16.7%) | 0 |  |
| diag 17-40 y (A2) | na | 7 (58.3%) | 2 (25.0%) |  |
| diag >41 y (A3) | na | 3 (25.0%) | 3 (37.5%) |  |
| Location (N, %) |  |  |  | na |
| Ileal-CD (L1) | na | 6 (50.0%) | na |  |
| Colonic-CD (L2) | na | 3 (25.0%) | na |  |
| Ileocolonic-CD (L3) | na | 3 (25.0%) | na |  |
| UC classification (N, %)** |  |  |  | na |
| Ulcerative proctitis (E1) | na | na | 0 |  |
| Distal UC (E2) | na | na | 3 (37.5%) |  |
| Extensive UC or ulcerative pancolitis (E3) | na | na | 1 (12.5%) |  |

IBD, Inflammatory bowel disease;
TNF, tumor necrosis factor;
nd, not determined;
na, not applicable,
nd, not determined
**Medical treatment at the time of sampling was available in 5/8 UC patients; Age of disease onset was available for 5/8 UC patients; Disease behavior at last follow-up before the time of sampling was not determined for any patient; Maximal disease extent at the time of sampling was available in 4/8 UC patients;
[§]Groups were compared by non-parametric statistical tests, and p value ≤ 0.05 was considered significant
[†]$\chi^2$ test:
[‡]Mann-Whitney U test of phylogroup I, those with IC-CD featured less prevalence of phylogroup II. In contrast, UC patients only had lower prevalence of phylogroup II with respect to H subjects, and this was only observed in those patients with E2. Additional assays with a larger cohort of patients should preferably be carried out in order to confirm the observed trends.

TABLE 23

Prevalence of *F. prausnitzii* phylogroups by diagnostics and IBD subtype.

| % | Phylogroup I | | Phylogroup II | |
|---|---|---|---|---|
| | absence | presence | absence | presence |
| H | 0 | 100 | 0 | 100 |
| UC | 0 | 100 | 33 | 67 |
| CD | 17 | 83 | 25 | 75 |
| p-value | | 0.200 | | 0.122 |
| C-CD | 33 | 67 | 0 | 100 |
| IC-CD | 0 | 100 | 33 | 67 |
| I-CD | 17 | 83 | 33 | 67 |
| p-value | | 0.549 | | 0.513 |
| E2-Distal UC | 0 | 100 | 33 | 67 |
| E3-Pancolitis | 0 | 100 | 0 | 100 |
| p-value | | nd | | 0.505 |

In contrast to results in biopsy samples, all IBD patients carried at least one of the *F. prausnitzii* phylogroups. Both phylogroups co-occurred in all the samples from H, and in the majority of IBD patients (75% of UC and 66.7% of CD). Phylogroup I was exclusive in 25% of CD (two I-CD and one IC-CD) and 25% of UC (an E2 patient an another whose disease location could not be determined), whereas phylogroup II was found as the only representative in a CD patient (8.3% of CD subjects).

Example 9

Abundance of Fecal *F. Prausnitzii* Phylogroups in Health and Disease

The abundance of *F. prausnitzii* phylogroups from fecal samples was compared amongst patients with different intestinal disorders and H subjects (Table 24). *F. prausnitzii* phylogroup I load was reduced in all IBD patients analyzed in comparison to H subjects. This reduction was particularly conspicuous in CD patients, who had values 186 times lower than H subjects. However, the observed differences were not statistically supported, probably due to the low number of patients included and the high dispersion of data. When analyzing data by disease location, all CD patients showed this marked reduction of phylogroup I abundance. UC patients featured intermediate values between H and CD patients, and it cannot be determined if as observed in biopsies, those with E3 resembled more to CD patients than to those with other UC disease location as only a subject with this disease location was included in this study. *F. prausnitzii* phylogroup II abundance was also reduced in IBD patients in comparison to H (Table 24), particularly in those with colonic involvement (either C-CD or IC-CD), suggesting that in feces these patients the depletion of *F. prausnitzii* affects the overall faecali bacteria community. These results are in contrast with those observed in biopsy samples, where a reduction of phylogroup II was observed only in patients with ileal involvement. Further analysis including a higher number of subjects with each disease location should be conducted to validate these observations. This could be explained either by a different distribution of this phylogroup between feces/mucosa or because inflammatory processes affect differently according to disease location.

TABLE 24

Abundances of faecal *F. prausnitzii* phylogroups in controls (H), Ulcerative Colitis (UC), and Crohn's disease (CD) patients. Disease locations of UC and CD patients are analyzed as independent groups.

| | n patients | Phylogroup I[§] | Phylogroup II[§] |
|---|---|---|---|
| H | 12 | 4.43 ± 0.66 | 3.19 ± 0.77 |
| UC | 8 | 3.15 ± 2.36 | 2.04 ± 1.98 |
| Location | | | |
| Distal UC (E2) | 3 | 3.36 ± 2.41 | 1.82 ± 1.88 |
| Extensive UC or ulcerative pancolitis (E3) | 1 | 4.25 | 3.17 |
| CD | 12 | 2.16 ± 2.21 | 1.97 ± 1.61 |
| Location | | | |
| Ileal-CD (L1) | 6 | 2.06 ± 3.08 | 3.39 ± 1.55 |
| Colonic-CD (L2) | 3 | 2.00 ± 1.92 | 1.49 ± 1.18 |
| Ileocolonic-CD (L3) | 3 | 2.29 ± 2.33 | 1.49 ± 1.60 |
| p-value | | 0.068 | 0.233 |

[§]Median $\log_{10}$ 16S rRNA gene copies/million bacterial 16S rRNA gene copies ± standard deviations Interestingly, we observed that for H and UC patients there is an imbalance of both phylogroups abundances, where phylogroup II outnumbers by a factor of 10 phylogroup I quantity. In contrast CD patients featured similar abundances of both phylogroups. This is not in line with results observed in biopsy samples, in which we found that in H, CRC and IBS subjects the abundance of the two phylogroups was similar, whereas in IBD patients phylogroup II outnumbered phylogroup I.

Here we have corroborated that in fecal samples differences in *F. prausnitzii* phylogroups loads exist between IBD locations. For instance, phylogroup II abundance is particularly compromised in patients with distal UC in comparison to those with ulcerative pancolitis. In addition, this phylogroup also allowed to differentiate I-CD patients from those with colonic involvement.

Example 10

Usefulness of Fecal *F. Prausnitzii* Phylogroups Abundance as Diagnostic Biomarkers ROC curve analysis, applied to test the putative accuracy of *F. prausnitzii* phylogroups abundance in feces as an indicator to differentiate between two groups of patients, confirmed that the reduction of phylogroup I load is a good discriminator for CD patients from H (especially those with ileal involvement), with AUC values greater than 0.75 (FIG. 6) with an 80% of specificity and above 58% of sensitivity at a set threshold. Similar values were obtained to discriminate between CD and UC entities, and the discrimination was excellent between IC-CD and E3, with AUC values greater than 0.9. In contrast, the discrimination capacity between H and UC patients for this indicator was lower in comparison to the results observed in biopsies.

Phylogroup II abundance could also discriminate H from IBD subjects, but was not appropriate to distinguish UC from CD patients. Whereas in biopsies we observed that AUC values from phylogroup II were slightly lower than those obtained for phylogroup I, the abundance of this indicator in feces was an excellent biomarker to distinguish E3 patients form those with CD with colonic involvement (either C-CD or IC-CD) (AUC=1.000).

Figure 6:
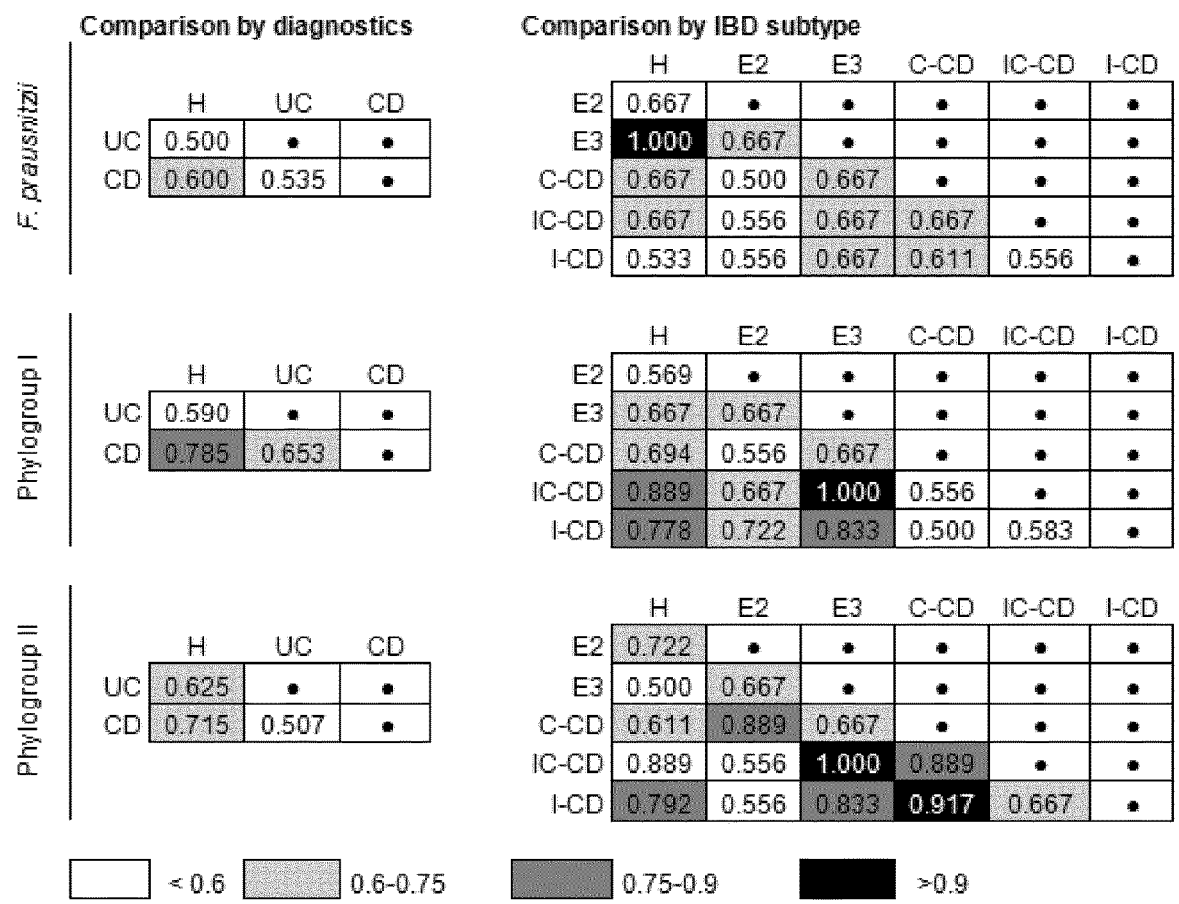
FIG. 6. Graphical representation as a heat map on the suitability of *F. prausnitzii*, *F. prausnitzii* phylogroup I and *F. prausnitzii* phylogroup II abundances in feces to be used as biomarkers to distinguish amongst different IBD diagnostics and IBD subtypes (by location) determined by the area under the curve (AUC) obtained by receiver operating characteristic analysis (ROC curve). A test is considered to be a suitable discriminator if the AUC is from 0.6 to 0.75 (in light grey), to have a high discrimination if the AUC is from 0.75 to 0.9 (in dark grey) and to be an excellent discriminator if the AUC is from 0.9 to 1 (in black). The following abbreviations have been used: H, controls; IBD, inflammatory bowel disease; IBS, irritable bowel syndrome; UC, ulcerative colitis; CD, Crohn's disease; CRC, colorectal cancer; I-CD, ileal CD; IC-CD, ileocolonic CD, C-CD, colonic CD; E1, ulcerative proctitis, E2, distal UC; and E3, extensive UC or ulcerative pancolitis.
Figure 7:
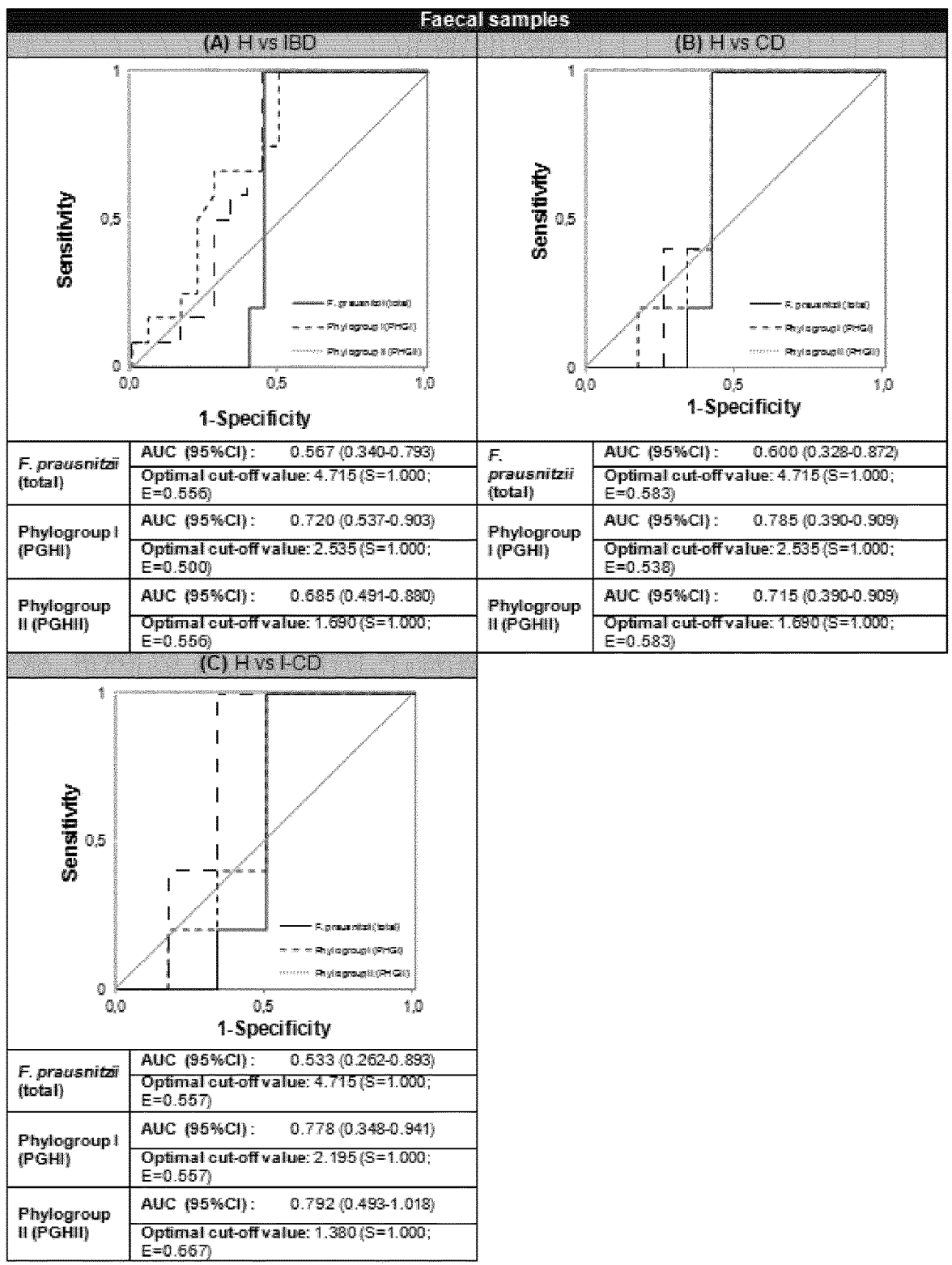
FIG. 7. Receiver operating characteristic (ROC) curves for *F. prausnitzii*, *F. prausnitzii* phylogroup I (PHGI) and *F. prausnitzii* phylogroup II (PHGII) abundances in feces for selected group comparisons of IBD disease and disease subtype. A).H vs IBD; C) H vs CD and D) H vs I-CD. In the Y axis is represented sensitivity and in the X axis 1-specificity. The following abbreviations have been used: H, controls; IBD, inflammatory bowel disease; IBS, irritable bowel syndrome; CD, Crohn's disease; CRC, colorectal cancer; and I-CD, ileal CD.
Figure 8:
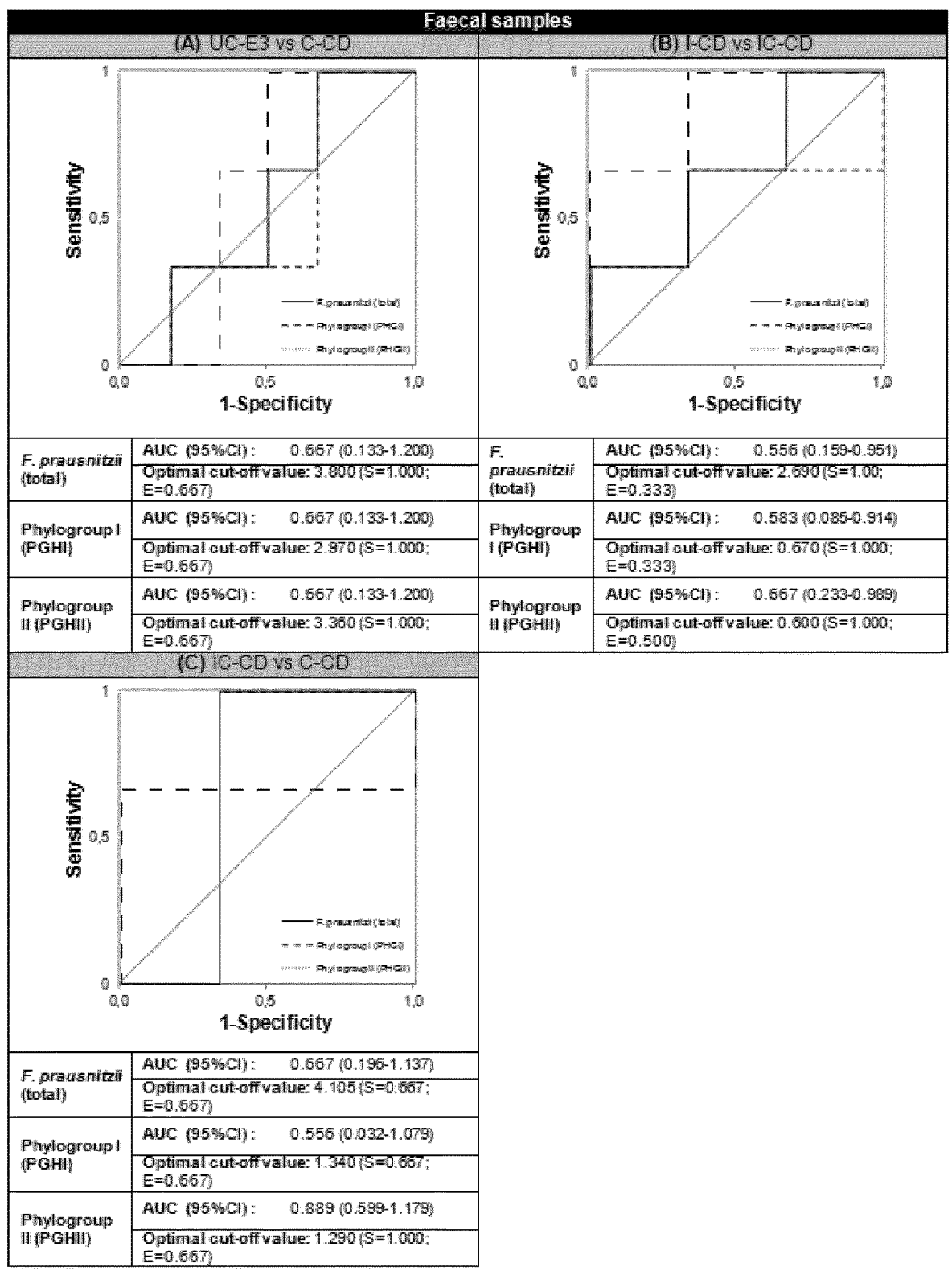
FIG. 8. Receiver operating characteristic (ROC) curves for *F. prausnitzii*, *F. prausnitzii* phylogroup I (PHGI) and *F. prausnitzii* phylogroup II (PHGII) abundances in feces for selected group comparisons for differential diagnosis of clinical interest. A) IC-CD vs I-CD; B). IC-CD vs C-CD; and C) UC-E3 vs C-CD. In the Y axis is represented sensitivity and in the X axis 1–specificity. The following abbreviations have been used: I-CD, ileal CD; IC-CD, ileocolonic CD, C-CD, colonic CD; and E3, extensive UC or ulcerative pancolitis.

FIG. 6 provides a heat map on the suitability of *F. prausnitzii*, phylogroup I and phylogroup II abundances in feces to be used as biomarkers to distinguish amongst different IBD diagnostics and IBD subtypes (by location) determined by the area under the curve (AUC) obtained by receiver operating characteristic analysis (ROC curve). FIGS. 7 and 8 show the ROC curve, calculated AUC value and specificity and sensitivity values for the optimal cut-off point for selected group comparisons. Furthermore, Tables 35-41 at the end of the Examples section provide the ROC curve coordinates for those selected group comparisons.

In conclusion, PHGI abundance was confirmed as a good biomarker in feces for diagnosis of IBD, showing a good discrimination capacity between H subjects and IBD patients with an AUC of 0.720, and in particular for the diagnosis of CD with an AUC of 0.785. PHGII abundance also shows a good correlation with CD, however the accuracy value (AUC: 0.715) is slightly lower than that obtained with PHGI abundance. Accordingly, PHGI abundance was confirmed as a good biomarker for detection of IBD and, in particular for detection of CD, in feces samples.

On the other hand, the value of PHGII abundance as biomarker for differential diagnosis between patients suffering from ulcerative pancolitis patients (UC-E3) and those with CD with colonic involvement (C-CD) has been confirmed in feces (AUC: 0.667), although the accuracy values are slightly lower than those obtained for mucosa samples.

In addition, it was confirmed that PHGII was a good discriminator between C-CD and IC-CD (AUC: 0.889), which suggests its potential value in determining extension of the disease to the ileal area (IC-CD) in a human subject who has previously been diagnosed with C-CD. Furthermore, despite ROC AUC values being slightly lower, PHGII was also pointed out as a suitable discriminator between I-CD and IC-CD (AUC: 0.667), and might be a useful biomarker for determining extension of the disease to the colonic area (IC-CD) in a human subject who has previously been diagnosed with I-CD.

Example 11

*F. Prausnitzii* Phylogroups Abundances in Feces in Relation to Patients' Clinical and Treatment Data 1. Disease Activity Status

*F. prausnitzii* phylogroups abundances did not differ between active and inactive IBD patients (Table 25). In contrast to results observed in biopsies, active IBD patients had higher abundances than inactive. Although no statistical significance was reached, inactive UC patients showed a marked reduction on phylogroup I abundance with respect to UC patients in remission (P=0.068).

TABLE 25

*F. prausnitzii* phylogroups abundance in inflammatory bowel disease patients by disease activity status. Active CD and UC were defined by a CDAI of >150 (Best, W. R., et al. Gastroenterology, 1976. 70(3): p. 439-44.) and a Mayo score >3 (Pineton de Chambrun, G., L. et al. Nat Rev Gastroenterol Hepatol, 2010. 7(1): p. 15-29.), respectively.

| Diagnostics[§] | N | Phylogroup I* | p-value | Phylogroup II* | p-value |
|---|---|---|---|---|---|
| UC | | | | | |
| Active | 2 | 4.99 ± 0.15 | 0.064 | 2.76 ± 1.97 | 0.355 |
| Inactive | 4 | 2.43 ± 2.43 | | 1.69 ± 2.17 | |
| CD | | | | | |
| Active | 6 | 2.96 ± 2.51 | 0.423 | 1.29 ± 1.86 | 0.937 |
| Inactive | 6 | 1.00 ± 1.97 | | 1.81 ± 1.49 | |

*Median $\log_{10}$ 16S rRNA gene copies/million bacterial 16S rRNA gene copies ± standard deviations
[§]UC. ulcerative colitis; CD. Crohn's disease 2. Intestinal Resection

*F. prausnitzii* phylogroups abundance was reduced in those CD patients that underwent intestinal resection (Table 26), which is in line with results observed in biopsies. Interestingly, this could be attributable to lower numbers of both phylogroups. However, these results were not statistically supported probably because of the low number of patients and the high dispersion of data.

TABLE 26

*F. prausnitzii* phylogroups abundance in inflammatory bowel disease patients depending on whether or not they have had intestinal resection during the course of the disease.

| Diagnostics[§] | N | Phylogroup I* | p-value | Phylogroup II* | p-value |
|---|---|---|---|---|---|
| UC | | | | | |
| non-resected | 5 | 4.38 ± 2.57 | 1.000 | 1.36 ± 2.12 | 1.000 |
| resected | 1 | 4.25 | | 3.17 | |
| CD | | | | | |
| non-resected | 8 | 2.85 ± 2.23 | 0.368 | 2.22 ± 1.69 | 0.368 |
| resected | 4 | 0.77 ± 2.13 | | 0.82 ± 1.29 | |

*Median $\log_{10}$ 16S rRNA gene copies/million bacterial 16S rRNA gene copies ± standard deviations
[§]UC, ulcerative colitis; CD, Crohn's disease 3. Disease Duration Concerning disease duration, no statistically significant correlation was found between time since disease onset and *F. prausnitzii* phylogroups abundances (Table 27), which is in line with results obtained in biopsy samples.

TABLE 27

Spearman correlation coefficients and significance between years since disease onset and *F. prausnitzii* phylogroups abundances in fecal samples in Ulcerative Colitis (UC), and Crohn's disease (CD) patients.

| Patients | N | Phylogroup I Coef correl | p-value | Phylogroup II Coef correl | p-value |
|---|---|---|---|---|---|
| UC | 6 | 0.154 | 0.805 | 0.667 | 0.219 |
| CD | 12 | −0.127 | 0.695 | −0.281 | 0.376 |

* Median $\log_{10}$ 16S rRNA gene copies/million bacterial 16S rRNA gene copies ± standard deviations
§ UC, ulcerative colitis; CD, Crohn's disease

4. Medication at Sampling

Finally, as far as therapies are concerned, data were analyzed taking into account the medication of the patients at the time of sampling (Table 28). No differences in *F. prausnitzii* phylogroups abundances were observed between medications within any disease. In contrast to biopsy, no trends between medications were observed in CD patients. Interestingly, UC patients with anti-tumor necrosis factor had similar abundances of both phylogroups in feces, to that observed in H subjects.

TABLE 28

*F. prausnitzii* phylogroups abundances (median log10 16S rRNA gene copies/million bacterial 16S rRNA gene copies ± standard deviations) in inflammatory

| Diagnostics§ | N | Phylogroup I* | p-value | Phylogroup II* | p-value |
|---|---|---|---|---|---|
| UC | | | | | |
| moderate immunosuppresants | 1 | −0.30 | 0.157 | −0.53 | 0.157 |
| Anti-tumor necrosis factor | 4 | 4.63 ± 0.40 | | 3.53 ± 1.26 | |
| CD | | | | | |
| No treatment | 2 | 1.71 ± 3.54 | 0.528 | 2.01 ± 1.46 | 0.891 |
| moderate immunosuppresants | 3 | 0.80 ± 2.54 | | 1.60 ± 1.03 | |
| Anti-tumor necrosis factor | 7 | 1.69 ± 2.01 | | 0.66 ± 2.00 | |

*Median $\log_{10}$ 16S rRNA gene copies/million bacterial 16S rRNA gene copies ± standard deviations
§ UC, ulcerative colitis; CD, Crohn's disease Finally, as regards to clinical data of the patients, we have observed that in feces both phylogroups loads remain lower under remission, which is in agreement with our results in biopsies. However, subsequent studies on larger cohorts of patients are needed to corroborate these observations, and follow up studies would also be interesting to determine their potential usefulness as a prognostic biomarker in feces.

In agreement with previous studies lower numbers of *F. prausnitzii* were detected in resected CD patients (Sokol, H., et al, Proc. Natl. Acad. Sci. USA, 2008. 105(43): p. 16731-16736; Lopez-Siles, M., et al. International Journal of Medical Microbiology, 2014. 304(3-4): p. 464-475.) Our results about phylogroups load are in agreement with those observed in biopsies. In this case however, statistical significant differences were not achieved, probably because the small cohort of subjects engaged.

In general terms, we have observed that the used medication does not restore the levels of fecal *F. prausnitzii* phylogroups in feces of CD patients, which is in agreement with our observations based on biopsies.

TABLE 29

ROC curve coordinates in mucosa-associated samples for H vs IBS + IBD + CRC

| *F. prausnitzii* (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.99342105 | 1 | 0.99342105 | 0.9787234 | 1 |
| 1 | 0.98684211 | 1 | 0.98684211 | 0.95744681 | 1 |
| 1 | 0.98026316 | 1 | 0.98026316 | 0.95744681 | 0.99342105 |
| 1 | 0.97368421 | 1 | 0.97368421 | 0.95744681 | 0.98684211 |
| 1 | 0.96710526 | 1 | 0.96710526 | 0.95744681 | 0.98026316 |
| 1 | 0.96052632 | 1 | 0.96052632 | 0.95744681 | 0.97368421 |
| 1 | 0.95394737 | 1 | 0.95394737 | 0.95744681 | 0.96710526 |
| 1 | 0.94736842 | 1 | 0.94736842 | 0.95744681 | 0.96052632 |
| 1 | 0.94078947 | 1 | 0.94078947 | 0.93617021 | 0.96052632 |
| 1 | 0.93421053 | 1 | 0.93421053 | 0.93617021 | 0.95394737 |
| 1 | 0.92763158 | 1 | 0.92763158 | 0.93617021 | 0.94736842 |
| 1 | 0.92105263 | 1 | 0.92105263 | 0.93617021 | 0.94078947 |
| 1 | 0.90131579 | 1 | 0.91447368 | 0.93617021 | 0.93421053 |
| 1 | 0.89473684 | 1 | 0.90789474 | 0.91489362 | 0.92763158 |
| 1 | 0.88815789 | 1 | 0.90131579 | 0.91489362 | 0.91447368 |
| 1 | 0.88157895 | 1 | 0.89473684 | 0.91489362 | 0.90789474 |
| 1 | 0.875 | 1 | 0.88815789 | 0.91489362 | 0.90131579 |
| 1 | 0.86842105 | 1 | 0.88157895 | 0.91489362 | 0.89473684 |
| 0.9787234 | 0.86842105 | 1 | 0.875 | 0.91489362 | 0.88815789 |
| 0.9787234 | 0.86184211 | 1 | 0.86842105 | 0.91489362 | 0.86842105 |
| 0.9787234 | 0.85526316 | 1 | 0.86184211 | 0.91489362 | 0.86184211 |
| 0.9787234 | 0.84868421 | 1 | 0.85526316 | 0.91489362 | 0.85526316 |
| 0.9787234 | 0.84210526 | 1 | 0.84210526 | 0.91489362 | 0.84868421 |

TABLE 29-continued

ROC curve coordinates in mucosa-associated samples for H vs IBS + IBD + CRC

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 0.9787234 | 0.83552632 | 1 | 0.83552632 | 0.91489362 | 0.84210526 |
| 0.95744681 | 0.82894737 | 1 | 0.82894737 | 0.91489362 | 0.83552632 |
| 0.95744681 | 0.82236842 | 1 | 0.82236842 | 0.91489362 | 0.82894737 |
| 0.95744681 | 0.81578947 | 1 | 0.81578947 | 0.91489362 | 0.81578947 |
| 0.95744681 | 0.80921053 | 1 | 0.80921053 | 0.91489362 | 0.80921053 |
| 0.95744681 | 0.80263158 | 1 | 0.80263158 | 0.89361702 | 0.80921053 |
| 0.95744681 | 0.78947368 | 1 | 0.79605263 | 0.89361702 | 0.79605263 |
| 0.95744681 | 0.77631579 | 1 | 0.78947368 | 0.89361702 | 0.78289474 |
| 0.95744681 | 0.76973684 | 1 | 0.78289474 | 0.89361702 | 0.76973684 |
| 0.95744681 | 0.75 | 1 | 0.77631579 | 0.89361702 | 0.76315789 |
| 0.95744681 | 0.74342105 | 1 | 0.76973684 | 0.89361702 | 0.75657895 |
| 0.95744681 | 0.73684211 | 1 | 0.76315789 | 0.89361702 | 0.75 |
| 0.95744681 | 0.72368421 | 1 | 0.75657895 | 0.89361702 | 0.73684211 |
| 0.95744681 | 0.71052632 | 1 | 0.75 | 0.89361702 | 0.73026316 |
| 0.95744681 | 0.70394737 | 1 | 0.74342105 | 0.89361702 | 0.72368421 |
| 0.95744681 | 0.69078947 | 1 | 0.73684211 | 0.89361702 | 0.71710526 |
| 0.95744681 | 0.67763158 | 1 | 0.73026316 | 0.89361702 | 0.71052632 |
| 0.95744681 | 0.67105263 | 1 | 0.72368421 | 0.89361702 | 0.70394737 |
| 0.95744681 | 0.66447368 | 1 | 0.71710526 | 0.89361702 | 0.68421053 |
| 0.93617021 | 0.66447368 | 1 | 0.71052632 | 0.89361702 | 0.67763158 |
| 0.93617021 | 0.65789474 | 1 | 0.70394737 | 0.89361702 | 0.67105263 |
| 0.93617021 | 0.65131579 | 1 | 0.69736842 | 0.89361702 | 0.66447368 |
| 0.93617021 | 0.63815789 | 1 | 0.69078947 | 0.87234043 | 0.66447368 |
| 0.93617021 | 0.63157895 | 1 | 0.68421053 | 0.87234043 | 0.65789474 |
| 0.93617021 | 0.625 | 1 | 0.67763158 | 0.87234043 | 0.65131579 |
| 0.93617021 | 0.61842105 | 1 | 0.67105263 | 0.87234043 | 0.64473684 |
| 0.93617021 | 0.61184211 | 1 | 0.66447368 | 0.87234043 | 0.63815789 |
| 0.93617021 | 0.59868421 | 0.9787234 | 0.66447368 | 0.87234043 | 0.63157895 |
| 0.93617021 | 0.56578947 | 0.9787234 | 0.65789474 | 0.87234043 | 0.625 |
| 0.93617021 | 0.55921053 | 0.9787234 | 0.65131579 | 0.87234043 | 0.61842105 |
| 0.93617021 | 0.54605263 | 0.9787234 | 0.64473684 | 0.85106383 | 0.61842105 |
| 0.93617021 | 0.53947368 | 0.9787234 | 0.63815789 | 0.85106383 | 0.61184211 |
| 0.93617021 | 0.53289474 | 0.9787234 | 0.63157895 | 0.85106383 | 0.60526316 |
| 0.93617021 | 0.52631579 | 0.95744681 | 0.63157895 | 0.82978723 | 0.60526316 |
| 0.91489362 | 0.52631579 | 0.95744681 | 0.61842105 | 0.82978723 | 0.59868421 |
| 0.89361702 | 0.52631579 | 0.95744681 | 0.60526316 | 0.82978723 | 0.59210526 |
| 0.87234043 | 0.51973684 | 0.95744681 | 0.59868421 | 0.82978723 | 0.58552632 |
| 0.87234043 | 0.51315789 | 0.95744681 | 0.59210526 | 0.82978723 | 0.57894737 |
| 0.87234043 | 0.5 | 0.95744681 | 0.58552632 | 0.82978723 | 0.57236842 |
| 0.85106383 | 0.5 | 0.95744681 | 0.57894737 | 0.80851064 | 0.55921053 |
| 0.82978723 | 0.49342105 | 0.93617021 | 0.57894737 | 0.78723404 | 0.55921053 |
| 0.80851064 | 0.47368421 | 0.93617021 | 0.57236842 | 0.76595745 | 0.55921053 |
| 0.78723404 | 0.47368421 | 0.93617021 | 0.56578947 | 0.76595745 | 0.55263158 |
| 0.76595745 | 0.47368421 | 0.93617021 | 0.55921053 | 0.74468085 | 0.55263158 |
| 0.74468085 | 0.46710526 | 0.93617021 | 0.55263158 | 0.74468085 | 0.54605263 |
| 0.74468085 | 0.45394737 | 0.93617021 | 0.54605263 | 0.74468085 | 0.53289474 |
| 0.74468085 | 0.44736842 | 0.93617021 | 0.53947368 | 0.74468085 | 0.52631579 |
| 0.74468085 | 0.44078947 | 0.93617021 | 0.53289474 | 0.74468085 | 0.51973684 |
| 0.74468085 | 0.43421053 | 0.93617021 | 0.52631579 | 0.74468085 | 0.51315789 |
| 0.74468085 | 0.42763158 | 0.91489362 | 0.51973684 | 0.74468085 | 0.50657895 |
| 0.72340426 | 0.42763158 | 0.91489362 | 0.51315789 | 0.74468085 | 0.49342105 |
| 0.72340426 | 0.42105263 | 0.91489362 | 0.50657895 | 0.74468085 | 0.48684211 |
| 0.72340426 | 0.41447368 | 0.91489362 | 0.5 | 0.74468085 | 0.48026316 |
| 0.72340426 | 0.40789474 | 0.91489362 | 0.49342105 | 0.70212766 | 0.48026316 |
| 0.68085106 | 0.40789474 | 0.91489362 | 0.48684211 | 0.70212766 | 0.46710526 |
| 0.68085106 | 0.40131579 | 0.89361702 | 0.48684211 | 0.70212766 | 0.46052632 |
| 0.68085106 | 0.39473684 | 0.87234043 | 0.48684211 | 0.70212766 | 0.45394737 |
| 0.68085106 | 0.38815789 | 0.87234043 | 0.48026316 | 0.70212766 | 0.44736842 |
| 0.65957447 | 0.375 | 0.85106383 | 0.48026316 | 0.70212766 | 0.44078947 |
| 0.63829787 | 0.35526316 | 0.82978723 | 0.47368421 | 0.70212766 | 0.43421053 |
| 0.63829787 | 0.34868421 | 0.82978723 | 0.45394737 | 0.70212766 | 0.42763158 |
| 0.63829787 | 0.33552632 | 0.82978723 | 0.44736842 | 0.70212766 | 0.42105263 |
| 0.63829787 | 0.32894737 | 0.82978723 | 0.43421053 | 0.70212766 | 0.41447368 |
| 0.61702128 | 0.32894737 | 0.82978723 | 0.42105263 | 0.70212766 | 0.40789474 |
| 0.61702128 | 0.31578947 | 0.82978723 | 0.41447368 | 0.68085106 | 0.39473684 |
| 0.61702128 | 0.30921053 | 0.82978723 | 0.40789474 | 0.68085106 | 0.38815789 |
| 0.61702128 | 0.30263158 | 0.82978723 | 0.40131579 | 0.68085106 | 0.38157895 |
| 0.61702128 | 0.28947368 | 0.80851064 | 0.39473684 | 0.68085106 | 0.375 |
| 0.61702128 | 0.28289474 | 0.78723404 | 0.39473684 | 0.68085106 | 0.36184211 |
| 0.59574468 | 0.26973684 | 0.78723404 | 0.38815789 | 0.68085106 | 0.35526316 |
| 0.59574468 | 0.26315789 | 0.78723404 | 0.375 | 0.68085106 | 0.34868421 |
| 0.57446809 | 0.26315789 | 0.78723404 | 0.36842105 | 0.68085106 | 0.34210526 |
| 0.55319149 | 0.26315789 | 0.78723404 | 0.36184211 | 0.68085106 | 0.33552632 |
| 0.55319149 | 0.24342105 | 0.78723404 | 0.35526316 | 0.65957447 | 0.33552632 |

TABLE 29-continued

ROC curve coordinates in mucosa-associated samples for H vs IBS + IBD + CRC

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 0.4893617 | 0.24342105 | 0.78723404 | 0.34210526 | 0.65957447 | 0.32894737 |
| 0.4893617 | 0.23684211 | 0.78723404 | 0.33552632 | 0.65957447 | 0.31578947 |
| 0.46808511 | 0.23684211 | 0.78723404 | 0.32236842 | 0.65957447 | 0.30921053 |
| 0.46808511 | 0.19736842 | 0.78723404 | 0.30921053 | 0.65957447 | 0.29605263 |
| 0.44680851 | 0.19078947 | 0.78723404 | 0.30263158 | 0.63829787 | 0.29605263 |
| 0.42553191 | 0.19078947 | 0.76595745 | 0.30263158 | 0.61702128 | 0.27631579 |
| 0.40425532 | 0.19078947 | 0.76595745 | 0.28947368 | 0.59574468 | 0.27631579 |
| 0.40425532 | 0.18421053 | 0.76595745 | 0.27631579 | 0.59574468 | 0.26973684 |
| 0.40425532 | 0.17105263 | 0.74468085 | 0.26973684 | 0.59574468 | 0.26315789 |
| 0.38297872 | 0.15789474 | 0.74468085 | 0.26315789 | 0.59574468 | 0.25657895 |
| 0.38297872 | 0.14473684 | 0.74468085 | 0.25657895 | 0.55319149 | 0.25657895 |
| 0.36170213 | 0.13815789 | 0.74468085 | 0.25 | 0.55319149 | 0.25 |
| 0.34042553 | 0.13815789 | 0.72340426 | 0.25 | 0.55319149 | 0.24342105 |
| 0.34042553 | 0.13157895 | 0.70212766 | 0.25 | 0.55319149 | 0.23026316 |
| 0.34042553 | 0.125 | 0.70212766 | 0.24342105 | 0.53191489 | 0.22368421 |
| 0.29787234 | 0.125 | 0.70212766 | 0.23684211 | 0.5106383 | 0.22368421 |
| 0.27659574 | 0.11842105 | 0.70212766 | 0.22368421 | 0.5106383 | 0.21710526 |
| 0.27659574 | 0.11184211 | 0.68085106 | 0.22368421 | 0.4893617 | 0.21710526 |
| 0.25531915 | 0.11184211 | 0.68085106 | 0.21052632 | 0.46808511 | 0.21052632 |
| 0.23404255 | 0.09868421 | 0.68085106 | 0.20394737 | 0.46808511 | 0.20394737 |
| 0.23404255 | 0.09210526 | 0.68085106 | 0.19736842 | 0.46808511 | 0.19736842 |
| 0.21276596 | 0.08552632 | 0.65957447 | 0.19736842 | 0.46808511 | 0.19078947 |
| 0.21276596 | 0.07894737 | 0.65957447 | 0.19078947 | 0.46808511 | 0.17763158 |
| 0.19148936 | 0.07894737 | 0.65957447 | 0.17763158 | 0.42553191 | 0.17105263 |
| 0.17021277 | 0.07236842 | 0.63829787 | 0.17763158 | 0.42553191 | 0.15789474 |
| 0.17021277 | 0.06578947 | 0.59574468 | 0.17763158 | 0.40425532 | 0.15131579 |
| 0.17021277 | 0.05921053 | 0.57446809 | 0.17105263 | 0.38297872 | 0.15131579 |
| 0.17021277 | 0.05263158 | 0.55319149 | 0.17105263 | 0.38297872 | 0.13815789 |
| 0.14893617 | 0.05263158 | 0.55319149 | 0.16447368 | 0.36170213 | 0.13815789 |
| 0.14893617 | 0.04605263 | 0.55319149 | 0.15789474 | 0.36170213 | 0.13157895 |
| 0.14893617 | 0.03947368 | 0.53191489 | 0.15789474 | 0.36170213 | 0.125 |
| 0.14893617 | 0.03289474 | 0.53191489 | 0.15131579 | 0.36170213 | 0.11842105 |
| 0.12765957 | 0.03289474 | 0.53191489 | 0.14473684 | 0.34042553 | 0.11184211 |
| 0.10638298 | 0.02631579 | 0.5106383 | 0.14473684 | 0.31914894 | 0.11184211 |
| 0.08510638 | 0.02631579 | 0.5106383 | 0.13157895 | 0.31914894 | 0.09868421 |
| 0.06382979 | 0.02631579 | 0.4893617 | 0.13157895 | 0.29787234 | 0.09868421 |
| 0.06382979 | 0.01973684 | 0.4893617 | 0.125 | 0.27659574 | 0.09868421 |
| 0.06382979 | 0.01315789 | 0.4893617 | 0.11842105 | 0.27659574 | 0.09210526 |
| 0.04255319 | 0.00657895 | 0.46808511 | 0.11842105 | 0.25531915 | 0.09210526 |
| 0.0212766 | 0.00657895 | 0.46808511 | 0.11184211 | 0.25531915 | 0.07894737 |
| 0 | 0.00657895 | 0.44680851 | 0.11184211 | 0.23404255 | 0.07236842 |
| 0 | 0 | 0.42553191 | 0.11184211 | 0.23404255 | 0.05921053 |
| | | 0.40425532 | 0.11184211 | 0.23404255 | 0.05263158 |
| | | 0.38297872 | 0.11184211 | 0.19148936 | 0.05263158 |
| | | 0.38297872 | 0.10526316 | 0.17021277 | 0.05263158 |
| | | 0.38297872 | 0.09210526 | 0.17021277 | 0.04605263 |
| | | 0.38297872 | 0.08552632 | 0.14893617 | 0.04605263 |
| | | 0.38297872 | 0.07894737 | 0.12765957 | 0.04605263 |
| | | 0.36170213 | 0.07236842 | 0.12765957 | 0.03947368 |
| | | 0.36170213 | 0.06578947 | 0.12765957 | 0.03289474 |
| | | 0.34042553 | 0.06578947 | 0.12765957 | 0.02631579 |
| | | 0.31914894 | 0.06578947 | 0.12765957 | 0.01973684 |
| | | 0.29787234 | 0.06578947 | 0.12765957 | 0.01315789 |
| | | 0.27659574 | 0.06578947 | 0.10638298 | 0.00657895 |
| | | 0.27659574 | 0.05263158 | 0.08510638 | 0.00657895 |
| | | 0.25531915 | 0.05263158 | 0.06382979 | 0.00657895 |
| | | 0.25531915 | 0.04605263 | 0.04255319 | 0.00657895 |
| | | 0.21276596 | 0.04605263 | 0.04255319 | 0 |
| | | 0.21276596 | 0.03947368 | 0.0212766 | 0 |
| | | 0.19148936 | 0.03947368 | 0 | 0 |
| | | 0.19148936 | 0.03289474 | | |
| | | 0.17021277 | 0.03289474 | | |
| | | 0.14893617 | 0.03289474 | | |
| | | 0.14893617 | 0.02631579 | | |
| | | 0.12765957 | 0.02631579 | | |
| | | 0.12765957 | 0.01973684 | | |
| | | 0.08510638 | 0.01973684 | | |
| | | 0.08510638 | 0.01315789 | | |
| | | 0.04255319 | 0.01315789 | | |
| | | 0.04255319 | 0.00657895 | | |
| | | 0.0212766 | 0.00657895 | | |
| | | 0 | 0.00657895 | | |
| | | 0 | 0 | | |

TABLE 30

ROC curve coordinates in mucosa-associated samples for H vs IBD.

| *F. prausnitzii* (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.99115044 | 1 | 0.99115044 | 0.9787234 | 1 |
| 1 | 0.98230088 | 1 | 0.98230088 | 0.95744681 | 1 |
| 1 | 0.97345133 | 1 | 0.97345133 | 0.95744681 | 0.99115044 |
| 1 | 0.96460177 | 1 | 0.96460177 | 0.95744681 | 0.98230088 |
| 1 | 0.95575221 | 1 | 0.95575221 | 0.95744681 | 0.97345133 |
| 1 | 0.94690265 | 1 | 0.94690265 | 0.95744681 | 0.96460177 |
| 1 | 0.9380531 | 1 | 0.9380531 | 0.95744681 | 0.95575221 |
| 1 | 0.92920354 | 1 | 0.92920354 | 0.95744681 | 0.94690265 |
| 1 | 0.92035398 | 1 | 0.92035398 | 0.93617021 | 0.94690265 |
| 1 | 0.91150442 | 1 | 0.91150442 | 0.93617021 | 0.9380531 |
| 1 | 0.90265487 | 1 | 0.90265487 | 0.93617021 | 0.92920354 |
| 1 | 0.87610619 | 1 | 0.89380531 | 0.93617021 | 0.92035398 |
| 1 | 0.86725664 | 1 | 0.88495575 | 0.93617021 | 0.91150442 |
| 1 | 0.85840708 | 1 | 0.87610619 | 0.91489362 | 0.90265487 |
| 1 | 0.84955752 | 1 | 0.86725664 | 0.91489362 | 0.88495575 |
| 1 | 0.84070796 | 1 | 0.85840708 | 0.91489362 | 0.87610619 |
| 1 | 0.83185841 | 1 | 0.84955752 | 0.91489362 | 0.86725664 |
| 0.9787234 | 0.83185841 | 1 | 0.84070796 | 0.91489362 | 0.84070796 |
| 0.9787234 | 0.82300885 | 1 | 0.83185841 | 0.91489362 | 0.83185841 |
| 0.9787234 | 0.81415929 | 1 | 0.82300885 | 0.91489362 | 0.82300885 |
| 0.9787234 | 0.80530973 | 1 | 0.81415929 | 0.91489362 | 0.81415929 |
| 0.9787234 | 0.79646018 | 1 | 0.80530973 | 0.91489362 | 0.79646018 |
| 0.95744681 | 0.79646018 | 1 | 0.78761062 | 0.91489362 | 0.78761062 |
| 0.95744681 | 0.78761062 | 1 | 0.77876106 | 0.89361702 | 0.78761062 |
| 0.95744681 | 0.77876106 | 1 | 0.7699115 | 0.89361702 | 0.77876106 |
| 0.95744681 | 0.7699115 | 1 | 0.76106195 | 0.89361702 | 0.76106195 |
| 0.95744681 | 0.75221239 | 1 | 0.75221239 | 0.89361702 | 0.75221239 |
| 0.95744681 | 0.74336283 | 1 | 0.74336283 | 0.89361702 | 0.74336283 |
| 0.95744681 | 0.73451327 | 1 | 0.73451327 | 0.89361702 | 0.73451327 |
| 0.95744681 | 0.71681416 | 1 | 0.72566372 | 0.89361702 | 0.72566372 |
| 0.95744681 | 0.7079646 | 1 | 0.71681416 | 0.89361702 | 0.71681416 |
| 0.95744681 | 0.69911504 | 1 | 0.7079646 | 0.89361702 | 0.7079646 |
| 0.95744681 | 0.68141593 | 1 | 0.69911504 | 0.89361702 | 0.69911504 |
| 0.95744681 | 0.66371681 | 1 | 0.69026549 | 0.89361702 | 0.69026549 |
| 0.95744681 | 0.6460177 | 1 | 0.68141593 | 0.89361702 | 0.67256637 |
| 0.95744681 | 0.63716814 | 1 | 0.67256637 | 0.89361702 | 0.66371681 |
| 0.93617021 | 0.63716814 | 1 | 0.66371681 | 0.89361702 | 0.65486726 |
| 0.93617021 | 0.62831858 | 1 | 0.65486726 | 0.89361702 | 0.6460177 |
| 0.93617021 | 0.61061947 | 1 | 0.6460177 | 0.87234043 | 0.6460177 |
| 0.93617021 | 0.60176991 | 1 | 0.63716814 | 0.87234043 | 0.63716814 |
| 0.93617021 | 0.59292035 | 1 | 0.62831858 | 0.87234043 | 0.62831858 |
| 0.93617021 | 0.5840708 | 1 | 0.61946903 | 0.87234043 | 0.61946903 |
| 0.93617021 | 0.57522124 | 1 | 0.61061947 | 0.87234043 | 0.61061947 |
| 0.93617021 | 0.53982301 | 1 | 0.60176991 | 0.87234043 | 0.60176991 |
| 0.93617021 | 0.53097345 | 0.9787234 | 0.60176991 | 0.87234043 | 0.59292035 |
| 0.93617021 | 0.52212389 | 0.9787234 | 0.59292035 | 0.85106383 | 0.59292035 |
| 0.93617021 | 0.51327434 | 0.9787234 | 0.5840708 | 0.85106383 | 0.5840708 |
| 0.93617021 | 0.50442478 | 0.9787234 | 0.57522124 | 0.82978723 | 0.5840708 |
| 0.91489362 | 0.50442478 | 0.9787234 | 0.56637168 | 0.82978723 | 0.57522124 |
| 0.89361702 | 0.50442478 | 0.95744681 | 0.56637168 | 0.82978723 | 0.56637168 |
| 0.87234043 | 0.49557522 | 0.95744681 | 0.55752212 | 0.82978723 | 0.55752212 |
| 0.87234043 | 0.48672566 | 0.95744681 | 0.54867257 | 0.82978723 | 0.54867257 |
| 0.85106383 | 0.48672566 | 0.95744681 | 0.53982301 | 0.80851064 | 0.53982301 |
| 0.82978723 | 0.47787611 | 0.95744681 | 0.53097345 | 0.78723404 | 0.53982301 |
| 0.80851064 | 0.46902655 | 0.95744681 | 0.52212389 | 0.76595745 | 0.53982301 |
| 0.78723404 | 0.46902655 | 0.93617021 | 0.52212389 | 0.74468085 | 0.53982301 |
| 0.76595745 | 0.46902655 | 0.93617021 | 0.51327434 | 0.74468085 | 0.53097345 |
| 0.74468085 | 0.46017699 | 0.93617021 | 0.50442478 | 0.74468085 | 0.52212389 |
| 0.74468085 | 0.44247788 | 0.93617021 | 0.49557522 | 0.74468085 | 0.51327434 |
| 0.74468085 | 0.43362832 | 0.93617021 | 0.48672566 | 0.74468085 | 0.49557522 |
| 0.72340426 | 0.43362832 | 0.91489362 | 0.47787611 | 0.74468085 | 0.48672566 |
| 0.72340426 | 0.42477876 | 0.91489362 | 0.46902655 | 0.74468085 | 0.47787611 |
| 0.72340426 | 0.4159292 | 0.91489362 | 0.46017699 | 0.70212766 | 0.47787611 |
| 0.68085106 | 0.4159292 | 0.91489362 | 0.45132743 | 0.70212766 | 0.46902655 |
| 0.68085106 | 0.40707965 | 0.91489362 | 0.44247788 | 0.70212766 | 0.46017699 |
| 0.68085106 | 0.39823009 | 0.89361702 | 0.44247788 | 0.70212766 | 0.45132743 |
| 0.65957447 | 0.38938053 | 0.87234043 | 0.44247788 | 0.70212766 | 0.44247788 |
| 0.63829787 | 0.37168142 | 0.87234043 | 0.43362832 | 0.70212766 | 0.43362832 |
| 0.63829787 | 0.36283186 | 0.85106383 | 0.43362832 | 0.70212766 | 0.42477876 |
| 0.63829787 | 0.3539823 | 0.82978723 | 0.42477876 | 0.70212766 | 0.4159292 |
| 0.63829787 | 0.34513274 | 0.82978723 | 0.39823009 | 0.70212766 | 0.40707965 |
| 0.61702128 | 0.34513274 | 0.82978723 | 0.38053097 | 0.70212766 | 0.39823009 |
| 0.61702128 | 0.32743363 | 0.82978723 | 0.37168142 | 0.68085106 | 0.39823009 |

TABLE 30-continued

ROC curve coordinates in mucosa-associated samples for H vs IBD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 0.61702128 | 0.31858407 | 0.82978723 | 0.36283186 | 0.68085106 | 0.38938053 |
| 0.61702128 | 0.30973451 | 0.80851064 | 0.3539823 | 0.68085106 | 0.38053097 |
| 0.61702128 | 0.30088496 | 0.78723404 | 0.3539823 | 0.68085106 | 0.37168142 |
| 0.61702128 | 0.2920354 | 0.78723404 | 0.33628319 | 0.68085106 | 0.36283186 |
| 0.59574468 | 0.27433628 | 0.78723404 | 0.32743363 | 0.68085106 | 0.3539823 |
| 0.59574468 | 0.26548673 | 0.78723404 | 0.31858407 | 0.68085106 | 0.34513274 |
| 0.57446809 | 0.26548673 | 0.78723404 | 0.30088496 | 0.68085106 | 0.33628319 |
| 0.55319149 | 0.26548673 | 0.78723404 | 0.2920354 | 0.68085106 | 0.32743363 |
| 0.55319149 | 0.25663717 | 0.78723404 | 0.27433628 | 0.65957447 | 0.32743363 |
| 0.4893617 | 0.25663717 | 0.78723404 | 0.26548673 | 0.65957447 | 0.30973451 |
| 0.46808511 | 0.25663717 | 0.76595745 | 0.26548673 | 0.65957447 | 0.30088496 |
| 0.46808511 | 0.22123894 | 0.76595745 | 0.25663717 | 0.65957447 | 0.28318584 |
| 0.44680851 | 0.21238938 | 0.76595745 | 0.24778761 | 0.63829787 | 0.28318584 |
| 0.42553191 | 0.21238938 | 0.74468085 | 0.24778761 | 0.61702128 | 0.26548673 |
| 0.40425532 | 0.21238938 | 0.74468085 | 0.23893805 | 0.59574468 | 0.26548673 |
| 0.40425532 | 0.20353982 | 0.72340426 | 0.23893805 | 0.59574468 | 0.25663717 |
| 0.40425532 | 0.19469027 | 0.70212766 | 0.23893805 | 0.59574468 | 0.24778761 |
| 0.38297872 | 0.18584071 | 0.70212766 | 0.2300885 | 0.55319149 | 0.24778761 |
| 0.38297872 | 0.16814159 | 0.70212766 | 0.22123894 | 0.55319149 | 0.23893805 |
| 0.36170213 | 0.15929204 | 0.68085106 | 0.22123894 | 0.55319149 | 0.2300885 |
| 0.34042553 | 0.15929204 | 0.68085106 | 0.21238938 | 0.53191489 | 0.22123894 |
| 0.34042553 | 0.15044248 | 0.68085106 | 0.20353982 | 0.5106383 | 0.22123894 |
| 0.34042553 | 0.14159292 | 0.65957447 | 0.20353982 | 0.5106383 | 0.21238938 |
| 0.29787234 | 0.14159292 | 0.65957447 | 0.19469027 | 0.4893617 | 0.21238938 |
| 0.27659574 | 0.13274336 | 0.65957447 | 0.17699115 | 0.46808511 | 0.20353982 |
| 0.27659574 | 0.12389381 | 0.63829787 | 0.17699115 | 0.46808511 | 0.19469027 |
| 0.25531915 | 0.12389381 | 0.59574468 | 0.17699115 | 0.46808511 | 0.18584071 |
| 0.23404255 | 0.10619469 | 0.57446809 | 0.16814159 | 0.46808511 | 0.16814159 |
| 0.21276596 | 0.09734513 | 0.55319149 | 0.16814159 | 0.42553191 | 0.16814159 |
| 0.21276596 | 0.08849558 | 0.55319149 | 0.15929204 | 0.42553191 | 0.15929204 |
| 0.19148936 | 0.08849558 | 0.53191489 | 0.15929204 | 0.40425532 | 0.15044248 |
| 0.17021277 | 0.07964602 | 0.53191489 | 0.15044248 | 0.38297872 | 0.15044248 |
| 0.17021277 | 0.07079646 | 0.53191489 | 0.14159292 | 0.38297872 | 0.13274336 |
| 0.17021277 | 0.0619469 | 0.5106383 | 0.14159292 | 0.36170213 | 0.13274336 |
| 0.14893617 | 0.0619469 | 0.5106383 | 0.12389381 | 0.36170213 | 0.12389381 |
| 0.14893617 | 0.05309735 | 0.4893617 | 0.12389381 | 0.36170213 | 0.11504425 |
| 0.14893617 | 0.04424779 | 0.46808511 | 0.12389381 | 0.34042553 | 0.10619469 |
| 0.12765957 | 0.04424779 | 0.46808511 | 0.11504425 | 0.31914894 | 0.10619469 |
| 0.10638298 | 0.03539823 | 0.44680851 | 0.11504425 | 0.31914894 | 0.09734513 |
| 0.08510638 | 0.03539823 | 0.42553191 | 0.11504425 | 0.29787234 | 0.09734513 |
| 0.06382979 | 0.03539823 | 0.40425532 | 0.11504425 | 0.27659574 | 0.09734513 |
| 0.06382979 | 0.02654867 | 0.38297872 | 0.11504425 | 0.25531915 | 0.09734513 |
| 0.06382979 | 0.01769912 | 0.38297872 | 0.09734513 | 0.25531915 | 0.08849558 |
| 0.04255319 | 0.00884956 | 0.38297872 | 0.08849558 | 0.23404255 | 0.07964602 |
| 0.0212766 | 0.00884956 | 0.38297872 | 0.07964602 | 0.23404255 | 0.0619469 |
| 0 | 0.00884956 | 0.36170213 | 0.07964602 | 0.23404255 | 0.05309735 |
| 0 | 0 | 0.36170213 | 0.07079646 | 0.19148936 | 0.05309735 |
| | | 0.34042553 | 0.07079646 | 0.17021277 | 0.05309735 |
| | | 0.31914894 | 0.07079646 | 0.17021277 | 0.04424779 |
| | | 0.29787234 | 0.07079646 | 0.14893617 | 0.04424779 |
| | | 0.27659574 | 0.07079646 | 0.12765957 | 0.04424779 |
| | | 0.27659574 | 0.05309735 | 0.12765957 | 0.03539823 |
| | | 0.25531915 | 0.05309735 | 0.12765957 | 0.02654867 |
| | | 0.25531915 | 0.04424779 | 0.12765957 | 0.01769912 |
| | | 0.21276596 | 0.04424779 | 0.10638298 | 0.00884956 |
| | | 0.21276596 | 0.03539823 | 0.08510638 | 0.00884956 |
| | | 0.19148936 | 0.03539823 | 0.06382979 | 0.00884956 |
| | | 0.17021277 | 0.03539823 | 0.04255319 | 0.00884956 |
| | | 0.14893617 | 0.03539823 | 0.04255319 | 0 |
| | | 0.14893617 | 0.02654867 | 0.0212766 | 0 |
| | | 0.12765957 | 0.02654867 | 0 | 0 |
| | | 0.12765957 | 0.01769912 | | |
| | | 0.08510638 | 0.01769912 | | |
| | | 0.04255319 | 0.01769912 | | |
| | | 0.04255319 | 0.00884956 | | |
| | | 0.0212766 | 0.00884956 | | |
| | | 0 | 0.00884956 | | |
| | | 0 | 0 | | |

TABLE 31

ROC curve coordinates in mucosa-associated samples for H vs CD.

| *F. prausnitzii* (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.98412698 | 1 | 0.98412698 | 0.9787234 | 1 |
| 1 | 0.96825397 | 1 | 0.96825397 | 0.95744681 | 1 |
| 1 | 0.95238095 | 1 | 0.95238095 | 0.95744681 | 0.98412698 |
| 1 | 0.93650794 | 1 | 0.93650794 | 0.95744681 | 0.96825397 |
| 1 | 0.92063492 | 1 | 0.92063492 | 0.95744681 | 0.95238095 |
| 1 | 0.9047619 | 1 | 0.9047619 | 0.95744681 | 0.93650794 |
| 1 | 0.88888889 | 1 | 0.88888889 | 0.95744681 | 0.92063492 |
| 1 | 0.87301587 | 1 | 0.87301587 | 0.95744681 | 0.9047619 |
| 1 | 0.85714286 | 1 | 0.85714286 | 0.93617021 | 0.9047619 |
| 1 | 0.84126984 | 1 | 0.84126984 | 0.93617021 | 0.88888889 |
| 1 | 0.82539683 | 1 | 0.82539683 | 0.93617021 | 0.87301587 |
| 1 | 0.77777778 | 1 | 0.80952381 | 0.93617021 | 0.85714286 |
| 1 | 0.76190476 | 1 | 0.79365079 | 0.91489362 | 0.84126984 |
| 1 | 0.74603175 | 1 | 0.77777778 | 0.91489362 | 0.80952381 |
| 1 | 0.73015873 | 1 | 0.76190476 | 0.91489362 | 0.79365079 |
| 1 | 0.71428571 | 1 | 0.74603175 | 0.91489362 | 0.77777778 |
| 0.9787234 | 0.71428571 | 1 | 0.73015873 | 0.91489362 | 0.74603175 |
| 0.9787234 | 0.6984127 | 1 | 0.71428571 | 0.91489362 | 0.73015873 |
| 0.9787234 | 0.68253968 | 1 | 0.6984127 | 0.91489362 | 0.71428571 |
| 0.9787234 | 0.66666667 | 1 | 0.68253968 | 0.91489362 | 0.6984127 |
| 0.95744681 | 0.66666667 | 1 | 0.66666667 | 0.89361702 | 0.6984127 |
| 0.95744681 | 0.65079365 | 1 | 0.65079365 | 0.89361702 | 0.68253968 |
| 0.95744681 | 0.63492063 | 1 | 0.63492063 | 0.89361702 | 0.65079365 |
| 0.95744681 | 0.61904762 | 1 | 0.61904762 | 0.89361702 | 0.63492063 |
| 0.95744681 | 0.6031746 | 1 | 0.6031746 | 0.89361702 | 0.61904762 |
| 0.95744681 | 0.58730159 | 1 | 0.58730159 | 0.89361702 | 0.6031746 |
| 0.95744681 | 0.57142857 | 1 | 0.57142857 | 0.89361702 | 0.58730159 |
| 0.95744681 | 0.53968254 | 1 | 0.55555556 | 0.89361702 | 0.57142857 |
| 0.95744681 | 0.50793651 | 1 | 0.53968254 | 0.89361702 | 0.55555556 |
| 0.95744681 | 0.49206349 | 1 | 0.52380952 | 0.89361702 | 0.53968254 |
| 0.93617021 | 0.49206349 | 1 | 0.50793651 | 0.89361702 | 0.52380952 |
| 0.93617021 | 0.47619048 | 1 | 0.49206349 | 0.89361702 | 0.50793651 |
| 0.93617021 | 0.46031746 | 1 | 0.47619048 | 0.89361702 | 0.49206349 |
| 0.93617021 | 0.44444444 | 1 | 0.46031746 | 0.87234043 | 0.49206349 |
| 0.93617021 | 0.42857143 | 1 | 0.44444444 | 0.87234043 | 0.47619048 |
| 0.93617021 | 0.41269841 | 0.9787234 | 0.44444444 | 0.87234043 | 0.46031746 |
| 0.93617021 | 0.3968254 | 0.9787234 | 0.42857143 | 0.87234043 | 0.44444444 |
| 0.91489362 | 0.3968254 | 0.9787234 | 0.41269841 | 0.87234043 | 0.42857143 |
| 0.89361702 | 0.3968254 | 0.95744681 | 0.3968254 | 0.85106383 | 0.42857143 |
| 0.87234043 | 0.38095238 | 0.95744681 | 0.38095238 | 0.85106383 | 0.41269841 |
| 0.85106383 | 0.38095238 | 0.95744681 | 0.36507937 | 0.82978723 | 0.41269841 |
| 0.82978723 | 0.38095238 | 0.93617021 | 0.36507937 | 0.82978723 | 0.3968254 |
| 0.80851064 | 0.38095238 | 0.93617021 | 0.34920635 | 0.82978723 | 0.38095238 |
| 0.78723404 | 0.38095238 | 0.93617021 | 0.33333333 | 0.80851064 | 0.38095238 |
| 0.76595745 | 0.38095238 | 0.93617021 | 0.31746032 | 0.78723404 | 0.38095238 |
| 0.74468085 | 0.38095238 | 0.91489362 | 0.3015873 | 0.76595745 | 0.38095238 |
| 0.74468085 | 0.34920635 | 0.91489362 | 0.28571429 | 0.74468085 | 0.38095238 |
| 0.72340426 | 0.34920635 | 0.91489362 | 0.26984127 | 0.74468085 | 0.36507937 |
| 0.68085106 | 0.34920635 | 0.89361702 | 0.26984127 | 0.74468085 | 0.34920635 |
| 0.68085106 | 0.33333333 | 0.87234043 | 0.26984127 | 0.70212766 | 0.34920635 |
| 0.65957447 | 0.31746032 | 0.85106383 | 0.26984127 | 0.70212766 | 0.33333333 |
| 0.63829787 | 0.3015873 | 0.82978723 | 0.26984127 | 0.70212766 | 0.31746032 |
| 0.63829787 | 0.28571429 | 0.82978723 | 0.25396825 | 0.70212766 | 0.3015873 |
| 0.63829787 | 0.26984127 | 0.80851064 | 0.25396825 | 0.70212766 | 0.28571429 |
| 0.61702128 | 0.26984127 | 0.78723404 | 0.25396825 | 0.68085106 | 0.28571429 |
| 0.61702128 | 0.25396825 | 0.78723404 | 0.23809524 | 0.68085106 | 0.26984127 |
| 0.61702128 | 0.23809524 | 0.78723404 | 0.22222222 | 0.68085106 | 0.25396825 |
| 0.59574468 | 0.23809524 | 0.78723404 | 0.20634921 | 0.65957447 | 0.25396825 |
| 0.57446809 | 0.23809524 | 0.78723404 | 0.19047619 | 0.65957447 | 0.22222222 |
| 0.55319149 | 0.23809524 | 0.78723404 | 0.15873016 | 0.65957447 | 0.20634921 |
| 0.4893617 | 0.23809524 | 0.76595745 | 0.15873016 | 0.63829787 | 0.20634921 |
| 0.46808511 | 0.23809524 | 0.74468085 | 0.15873016 | 0.61702128 | 0.19047619 |
| 0.46808511 | 0.22222222 | 0.72340426 | 0.15873016 | 0.59574468 | 0.19047619 |
| 0.44680851 | 0.20634921 | 0.70212766 | 0.15873016 | 0.55319149 | 0.19047619 |
| 0.42553191 | 0.20634921 | 0.68085106 | 0.15873016 | 0.55319149 | 0.17460317 |
| 0.40425532 | 0.20634921 | 0.65957447 | 0.15873016 | 0.53191489 | 0.17460317 |
| 0.38297872 | 0.19047619 | 0.65957447 | 0.14285714 | 0.5106383 | 0.17460317 |
| 0.36170213 | 0.17460317 | 0.63829787 | 0.14285714 | 0.4893617 | 0.17460317 |
| 0.34042553 | 0.17460317 | 0.59574468 | 0.14285714 | 0.46808511 | 0.15873016 |
| 0.34042553 | 0.15873016 | 0.57446809 | 0.12698413 | 0.46808511 | 0.14285714 |
| 0.29787234 | 0.15873016 | 0.55319149 | 0.12698413 | 0.46808511 | 0.12698413 |
| 0.27659574 | 0.15873016 | 0.53191489 | 0.12698413 | 0.42553191 | 0.12698413 |
| 0.25531915 | 0.15873016 | 0.53191489 | 0.12698413 | 0.40425532 | 0.12698413 |

TABLE 31-continued

ROC curve coordinates in mucosa-associated samples for H vs CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 0.23404255 | 0.14285714 | 0.5106383 | 0.12698413 | 0.38297872 | 0.12698413 |
| 0.21276596 | 0.12698413 | 0.5106383 | 0.11111111 | 0.36170213 | 0.12698413 |
| 0.19148936 | 0.12698413 | 0.4893617 | 0.11111111 | 0.36170213 | 0.11111111 |
| 0.17021277 | 0.11111111 | 0.46808511 | 0.11111111 | 0.34042553 | 0.0952381 |
| 0.17021277 | 0.0952381 | 0.44680851 | 0.11111111 | 0.31914894 | 0.0952381 |
| 0.14893617 | 0.0952381 | 0.42553191 | 0.11111111 | 0.29787234 | 0.0952381 |
| 0.14893617 | 0.07936508 | 0.40425532 | 0.11111111 | 0.27659574 | 0.0952381 |
| 0.12765957 | 0.07936508 | 0.38297872 | 0.11111111 | 0.25531915 | 0.0952381 |
| 0.10638298 | 0.06349206 | 0.38297872 | 0.0952381 | 0.23404255 | 0.0952381 |
| 0.08510638 | 0.06349206 | 0.36170213 | 0.0952381 | 0.23404255 | 0.07936508 |
| 0.06382979 | 0.06349206 | 0.36170213 | 0.07936508 | 0.23404255 | 0.06349206 |
| 0.06382979 | 0.04761905 | 0.34042553 | 0.07936508 | 0.19148936 | 0.06349206 |
| 0.06382979 | 0.03174603 | 0.31914894 | 0.07936508 | 0.17021277 | 0.06349206 |
| 0.04255319 | 0.01587302 | 0.29787234 | 0.07936508 | 0.14893617 | 0.06349206 |
| 0.0212766 | 0.01587302 | 0.27659574 | 0.07936508 | 0.12765957 | 0.06349206 |
| 0 | 0.01587302 | 0.27659574 | 0.06349206 | 0.12765957 | 0.04761905 |
| 0 | 0 | 0.25531915 | 0.06349206 | 0.12765957 | 0.03174603 |
| | | 0.21276596 | 0.06349206 | 0.10638298 | 0.01587302 |
| | | 0.19148936 | 0.06349206 | 0.08510638 | 0.01587302 |
| | | 0.17021277 | 0.06349206 | 0.06382979 | 0.01587302 |
| | | 0.14893617 | 0.06349206 | 0.04255319 | 0.01587302 |
| | | 0.14893617 | 0.04761905 | 0.04255319 | 0 |
| | | 0.12765957 | 0.04761905 | 0.0212766 | 0 |
| | | 0.12765957 | 0.03174603 | 0 | 0 |
| | | 0.08510638 | 0.03174603 | | |
| | | 0.04255319 | 0.03174603 | | |
| | | 0.04255319 | 0.01587302 | | |
| | | 0.0212766 | 0.01587302 | | |
| | | 0 | 0.01587302 | | |
| | | 0 | 0 | | |

TABLE 32

ROC curve coordinates in mucosa-associated samples for H vs I-CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.96 | 1 | 0.96 | 0.9787234 | 1 |
| 1 | 0.92 | 1 | 0.92 | 0.95744681 | 1 |
| 1 | 0.88 | 1 | 0.88 | 0.95744681 | 0.96 |
| 1 | 0.84 | 1 | 0.84 | 0.95744681 | 0.92 |
| 1 | 0.8 | 1 | 0.8 | 0.95744681 | 0.88 |
| 1 | 0.76 | 1 | 0.76 | 0.93617021 | 0.88 |
| 1 | 0.72 | 1 | 0.72 | 0.93617021 | 0.84 |
| 1 | 0.68 | 1 | 0.68 | 0.93617021 | 0.8 |
| 1 | 0.6 | 1 | 0.64 | 0.91489362 | 0.76 |
| 1 | 0.56 | 1 | 0.6 | 0.91489362 | 0.72 |
| 0.9787234 | 0.56 | 1 | 0.56 | 0.91489362 | 0.68 |
| 0.9787234 | 0.52 | 1 | 0.52 | 0.91489362 | 0.64 |
| 0.95744681 | 0.52 | 1 | 0.48 | 0.91489362 | 0.6 |
| 0.95744681 | 0.48 | 1 | 0.44 | 0.89361702 | 0.6 |
| 0.95744681 | 0.44 | 1 | 0.4 | 0.89361702 | 0.56 |
| 0.95744681 | 0.4 | 1 | 0.36 | 0.89361702 | 0.52 |
| 0.95744681 | 0.36 | 1 | 0.32 | 0.89361702 | 0.48 |
| 0.95744681 | 0.32 | 1 | 0.28 | 0.89361702 | 0.44 |
| 0.93617021 | 0.32 | 0.9787234 | 0.28 | 0.89361702 | 0.4 |
| 0.93617021 | 0.28 | 0.9787234 | 0.24 | 0.87234043 | 0.4 |
| 0.93617021 | 0.24 | 0.95744681 | 0.24 | 0.87234043 | 0.36 |
| 0.91489362 | 0.24 | 0.93617021 | 0.24 | 0.85106383 | 0.36 |
| 0.89361702 | 0.24 | 0.93617021 | 0.2 | 0.82978723 | 0.36 |
| 0.87234043 | 0.24 | 0.93617021 | 0.16 | 0.82978723 | 0.32 |
| 0.85106383 | 0.24 | 0.91489362 | 0.16 | 0.80851064 | 0.32 |
| 0.82978723 | 0.24 | 0.91489362 | 0.12 | 0.78723404 | 0.32 |
| 0.80851064 | 0.24 | 0.89361702 | 0.12 | 0.76595745 | 0.32 |
| 0.78723404 | 0.24 | 0.87234043 | 0.12 | 0.74468085 | 0.32 |
| 0.76595745 | 0.24 | 0.85106383 | 0.12 | 0.74468085 | 0.28 |
| 0.74468085 | 0.24 | 0.82978723 | 0.12 | 0.70212766 | 0.28 |
| 0.74468085 | 0.16 | 0.80851064 | 0.12 | 0.68085106 | 0.28 |

TABLE 32-continued

ROC curve coordinates in mucosa-associated samples for H vs I-CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 0.72340426 | 0.16 | 0.78723404 | 0.12 | 0.68085106 | 0.24 |
| 0.68085106 | 0.16 | 0.78723404 | 0.08 | 0.65957447 | 0.24 |
| 0.65957447 | 0.12 | 0.78723404 | 0.04 | 0.65957447 | 0.2 |
| 0.63829787 | 0.12 | 0.76595745 | 0.04 | 0.65957447 | 0.16 |
| 0.61702128 | 0.12 | 0.74468085 | 0.04 | 0.63829787 | 0.16 |
| 0.61702128 | 0.08 | 0.72340426 | 0.04 | 0.61702128 | 0.16 |
| 0.59574468 | 0.08 | 0.70212766 | 0.04 | 0.59574468 | 0.16 |
| 0.57446809 | 0.08 | 0.68085106 | 0.04 | 0.55319149 | 0.16 |
| 0.55319149 | 0.08 | 0.65957447 | 0.04 | 0.53191489 | 0.16 |
| 0.4893617 | 0.08 | 0.63829787 | 0.04 | 0.5106383 | 0.16 |
| 0.46808511 | 0.08 | 0.59574468 | 0.04 | 0.4893617 | 0.16 |
| 0.46808511 | 0.04 | 0.57446809 | 0.04 | 0.46808511 | 0.16 |
| 0.44680851 | 0.04 | 0.55319149 | 0.04 | 0.46808511 | 0.12 |
| 0.42553191 | 0.04 | 0.53191489 | 0.04 | 0.42553191 | 0.12 |
| 0.40425532 | 0.04 | 0.5106383 | 0.04 | 0.40425532 | 0.12 |
| 0.38297872 | 0.04 | 0.4893617 | 0.04 | 0.38297872 | 0.12 |
| 0.36170213 | 0.04 | 0.46808511 | 0.04 | 0.36170213 | 0.12 |
| 0.34042553 | 0.04 | 0.44680851 | 0.04 | 0.34042553 | 0.12 |
| 0.29787234 | 0.04 | 0.42553191 | 0.04 | 0.31914894 | 0.12 |
| 0.27659574 | 0.04 | 0.40425532 | 0.04 | 0.29787234 | 0.12 |
| 0.25531915 | 0.04 | 0.38297872 | 0.04 | 0.27659574 | 0.12 |
| 0.23404255 | 0.04 | 0.36170213 | 0.04 | 0.25531915 | 0.12 |
| 0.21276596 | 0.04 | 0.36170213 | 0 | 0.23404255 | 0.12 |
| 0.19148936 | 0.04 | 0.34042553 | 0 | 0.23404255 | 0.08 |
| 0.17021277 | 0.04 | 0.31914894 | 0 | 0.23404255 | 0.04 |
| 0.14893617 | 0.04 | 0.29787234 | 0 | 0.19148936 | 0.04 |
| 0.12765957 | 0.04 | 0.27659574 | 0 | 0.17021277 | 0.04 |
| 0.10638298 | 0.04 | 0.25531915 | 0 | 0.14893617 | 0.04 |
| 0.08510638 | 0.04 | 0.21276596 | 0 | 0.12765957 | 0.04 |
| 0.06382979 | 0.04 | 0.19148936 | 0 | 0.12765957 | 0 |
| 0.04255319 | 0.04 | 0.17021277 | 0 | 0.10638298 | 0 |
| 0.0212766 | 0.04 | 0.14893617 | 0 | 0.08510638 | 0 |
| 0 | 0.04 | 0.12765957 | 0 | 0.06382979 | 0 |
| 0 | 0 | 0.08510638 | 0 | 0.04255319 | 0 |
| | | 0.04255319 | 0 | 0.0212766 | 0 |
| | | 0.0212766 | 0 | 0 | 0 |
| | | 0 | 0 | | |

TABLE 33

ROC curve coordinates in mucosa-associated samples for E3 vs C-CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.94117647 | 1 | 0.94117647 | 1 | 0.94117647 |
| 1 | 0.88235294 | 1 | 0.88235294 | 1 | 0.88235294 |
| 1 | 0.82352941 | 1 | 0.82352941 | 1 | 0.82352941 |
| 0.9 | 0.82352941 | 1 | 0.76470588 | 0.9 | 0.76470588 |
| 0.9 | 0.76470588 | 1 | 0.70588235 | 0.9 | 0.70588235 |
| 0.9 | 0.70588235 | 1 | 0.64705882 | 0.9 | 0.64705882 |
| 0.9 | 0.64705882 | 0.9 | 0.64705882 | 0.9 | 0.58823529 |
| 0.9 | 0.58823529 | 0.8 | 0.64705882 | 0.8 | 0.58823529 |
| 0.8 | 0.58823529 | 0.7 | 0.64705882 | 0.8 | 0.52941176 |
| 0.7 | 0.58823529 | 0.6 | 0.64705882 | 0.7 | 0.52941176 |
| 0.7 | 0.52941176 | 0.6 | 0.58823529 | 0.7 | 0.47058824 |
| 0.7 | 0.47058824 | 0.5 | 0.58823529 | 0.7 | 0.41176471 |
| 0.7 | 0.41176471 | 0.5 | 0.52941176 | 0.7 | 0.35294118 |
| 0.6 | 0.41176471 | 0.4 | 0.52941176 | 0.6 | 0.35294118 |
| 0.5 | 0.41176471 | 0.4 | 0.47058824 | 0.6 | 0.29411765 |
| 0.5 | 0.35294118 | 0.4 | 0.41176471 | 0.5 | 0.29411765 |
| 0.4 | 0.35294118 | 0.4 | 0.35294118 | 0.5 | 0.23529412 |
| 0.3 | 0.35294118 | 0.4 | 0.23529412 | 0.4 | 0.23529412 |
| 0.2 | 0.29411765 | 0.3 | 0.23529412 | 0.4 | 0.17647059 |
| 0.2 | 0.23529412 | 0.3 | 0.17647059 | 0.4 | 0.11764706 |
| 0.1 | 0.23529412 | 0.3 | 0.11764706 | 0.3 | 0.11764706 |
| 0.1 | 0.17647059 | 0.2 | 0.11764706 | 0.3 | 0.05882353 |
| 0 | 0.17647059 | 0.1 | 0.05882353 | 0.2 | 0.05882353 |

TABLE 33-continued

ROC curve coordinates in mucosa-associated samples for E3 vs C-CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 0 | 0.11764706 | 0 | 0.05882353 | 0.1 | 0.05882353 |
| 0 | 0.05882353 | 0 | 0 | 0 | 0.05882353 |
| 0 | 0 | | | 0 | 0 |

TABLE 34

ROC curve coordinates in mucosa-associated samples for I-CD vs IC-CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.96 | 1 | 0.96 | 1 | 0.96 |
| 1 | 0.92 | 0.94444444 | 0.96 | 1 | 0.92 |
| 1 | 0.88 | 0.94444444 | 0.92 | 0.94444444 | 0.92 |
| 1 | 0.84 | 0.94444444 | 0.88 | 0.94444444 | 0.88 |
| 1 | 0.8 | 0.94444444 | 0.84 | 0.94444444 | 0.84 |
| 1 | 0.76 | 0.94444444 | 0.8 | 0.94444444 | 0.8 |
| 0.94444444 | 0.76 | 0.94444444 | 0.76 | 0.88888889 | 0.8 |
| 0.94444444 | 0.72 | 0.88888889 | 0.76 | 0.88888889 | 0.76 |
| 0.94444444 | 0.68 | 0.88888889 | 0.72 | 0.83333333 | 0.76 |
| 0.88888889 | 0.68 | 0.88888889 | 0.68 | 0.83333333 | 0.72 |
| 0.83333333 | 0.6 | 0.83333333 | 0.68 | 0.77777778 | 0.72 |
| 0.77777778 | 0.6 | 0.83333333 | 0.64 | 0.77777778 | 0.68 |
| 0.77777778 | 0.56 | 0.83333333 | 0.6 | 0.77777778 | 0.64 |
| 0.72222222 | 0.56 | 0.83333333 | 0.56 | 0.77777778 | 0.6 |
| 0.66666667 | 0.56 | 0.77777778 | 0.56 | 0.72222222 | 0.6 |
| 0.66666667 | 0.52 | 0.72222222 | 0.56 | 0.72222222 | 0.56 |
| 0.61111111 | 0.52 | 0.66666667 | 0.56 | 0.66666667 | 0.56 |
| 0.61111111 | 0.48 | 0.66666667 | 0.52 | 0.66666667 | 0.52 |
| 0.55555556 | 0.48 | 0.66666667 | 0.48 | 0.66666667 | 0.48 |
| 0.55555556 | 0.44 | 0.66666667 | 0.44 | 0.61111111 | 0.48 |
| 0.55555556 | 0.4 | 0.66666667 | 0.4 | 0.55555556 | 0.48 |
| 0.55555556 | 0.36 | 0.61111111 | 0.4 | 0.5 | 0.48 |
| 0.5 | 0.32 | 0.55555556 | 0.4 | 0.5 | 0.44 |
| 0.44444444 | 0.32 | 0.55555556 | 0.36 | 0.44444444 | 0.44 |
| 0.44444444 | 0.28 | 0.55555556 | 0.32 | 0.44444444 | 0.4 |
| 0.38888889 | 0.28 | 0.55555556 | 0.28 | 0.44444444 | 0.36 |
| 0.33333333 | 0.28 | 0.5 | 0.28 | 0.38888889 | 0.36 |
| 0.33333333 | 0.24 | 0.5 | 0.24 | 0.33333333 | 0.36 |
| 0.27777778 | 0.24 | 0.44444444 | 0.24 | 0.27777778 | 0.36 |
| 0.27777778 | 0.16 | 0.38888889 | 0.24 | 0.22222222 | 0.36 |
| 0.27777778 | 0.12 | 0.38888889 | 0.2 | 0.22222222 | 0.32 |
| 0.22222222 | 0.12 | 0.38888889 | 0.16 | 0.22222222 | 0.28 |
| 0.22222222 | 0.08 | 0.33333333 | 0.16 | 0.16666667 | 0.28 |
| 0.16666667 | 0.08 | 0.33333333 | 0.12 | 0.16666667 | 0.24 |
| 0.16666667 | 0.04 | 0.27777778 | 0.12 | 0.11111111 | 0.2 |
| 0.11111111 | 0.04 | 0.22222222 | 0.12 | 0.11111111 | 0.16 |
| 0.05555556 | 0.04 | 0.16666667 | 0.12 | 0.05555556 | 0.16 |
| 0 | 0.04 | 0.16666667 | 0.08 | 0.05555556 | 0.12 |
| 0 | 0 | 0.16666667 | 0.04 | 0 | 0.12 |
| | | 0.11111111 | 0.04 | 0 | 0.08 |
| | | 0.11111111 | 0 | 0 | 0.04 |
| | | 0.05555556 | 0 | 0 | 0 |

TABLE 35

ROC curve coordinates in mucosa-associated samples for C-CD vs IC-CD.

| *F. prausnitzii* (total) | | Phylogroup I (PHGI) | | Phylogroup II (PHGII) | |
| --- | --- | --- | --- | --- | --- |
| Sensitivity | 1-Specificity | Sensitivity | 1-Specificity | Sensitivity | 1-Specificity |
| 1 | 1 | 1 | 1 | 1 | 1 |
| 1 | 0.94444444 | 1 | 0.94444444 | 0.94117647 | 1 |
| 0.94117647 | 0.94444444 | 0.94117647 | 0.94444444 | 0.88235294 | 1 |
| 0.94117647 | 0.88888889 | 0.88235294 | 0.94444444 | 0.88235294 | 0.94444444 |
| 0.94117647 | 0.83333333 | 0.82352941 | 0.94444444 | 0.88235294 | 0.88888889 |
| 0.88235294 | 0.83333333 | 0.82352941 | 0.88888889 | 0.82352941 | 0.83333333 |
| 0.88235294 | 0.77777778 | 0.76470588 | 0.88888889 | 0.82352941 | 0.77777778 |
| 0.88235294 | 0.72222222 | 0.76470588 | 0.83333333 | 0.76470588 | 0.77777778 |
| 0.88235294 | 0.66666667 | 0.76470588 | 0.77777778 | 0.76470588 | 0.72222222 |
| 0.82352941 | 0.66666667 | 0.70588235 | 0.77777778 | 0.70588235 | 0.66666667 |
| 0.82352941 | 0.61111111 | 0.70588235 | 0.72222222 | 0.70588235 | 0.61111111 |
| 0.76470588 | 0.61111111 | 0.64705882 | 0.72222222 | 0.70588235 | 0.55555556 |
| 0.76470588 | 0.55555556 | 0.64705882 | 0.66666667 | 0.70588235 | 0.5 |
| 0.70588235 | 0.55555556 | 0.58823529 | 0.66666667 | 0.64705882 | 0.5 |
| 0.70588235 | 0.5 | 0.58823529 | 0.61111111 | 0.58823529 | 0.5 |
| 0.64705882 | 0.5 | 0.58823529 | 0.55555556 | 0.58823529 | 0.44444444 |
| 0.64705882 | 0.44444444 | 0.52941176 | 0.55555556 | 0.58823529 | 0.38888889 |
| 0.58823529 | 0.44444444 | 0.52941176 | 0.5 | 0.58823529 | 0.33333333 |
| 0.58823529 | 0.38888889 | 0.52941176 | 0.44444444 | 0.58823529 | 0.27777778 |
| 0.58823529 | 0.33333333 | 0.52941176 | 0.38888889 | 0.58823529 | 0.22222222 |
| 0.58823529 | 0.27777778 | 0.47058824 | 0.38888889 | 0.52941176 | 0.22222222 |
| 0.52941176 | 0.27777778 | 0.41176471 | 0.38888889 | 0.47058824 | 0.22222222 |
| 0.47058824 | 0.27777778 | 0.41176471 | 0.33333333 | 0.47058824 | 0.16666667 |
| 0.47058824 | 0.22222222 | 0.41176471 | 0.27777778 | 0.41176471 | 0.16666667 |
| 0.41176471 | 0.22222222 | 0.41176471 | 0.22222222 | 0.35294118 | 0.16666667 |
| 0.41176471 | 0.16666667 | 0.41176471 | 0.16666667 | 0.29411765 | 0.16666667 |
| 0.35294118 | 0.16666667 | 0.35294118 | 0.16666667 | 0.29411765 | 0.11111111 |
| 0.35294118 | 0.11111111 | 0.23529412 | 0.16666667 | 0.23529412 | 0.11111111 |
| 0.29411765 | 0.11111111 | 0.17647059 | 0.16666667 | 0.17647059 | 0.11111111 |
| 0.23529412 | 0.11111111 | 0.11764706 | 0.16666667 | 0.17647059 | 0.05555556 |
| 0.17647059 | 0.11111111 | 0.11764706 | 0.11111111 | 0.11764706 | 0.05555556 |
| 0.11764706 | 0.11111111 | 0.05882353 | 0.11111111 | 0.05882353 | 0.05555556 |
| 0.05882353 | 0.11111111 | 0 | 0.11111111 | 0.05882353 | 0 |
| 0 | 0.11111111 | 0 | 0.05555556 | 0 | 0 |
| 0 | 0.05555556 | 0 | 0 | | |
| 0 | 0 | | | | |

TABLE 36

ROC curve coordinates in faecal samples for comparison H vs IBD.

| *F. prausnitzii* (total) | | Phylogroup I (PHGI) | | Phylogroup II (PHGII) | |
| --- | --- | --- | --- | --- | --- |
| Sensitivity | 1-Specificity | Sensitivity | 1-Specificity | Sensitivity | 1-Specificity |
| 1 | 1 | 1 | 1 | 1 | 1 |
| 1 | 0.95 | 1 | 0.94444444 | 1 | 0.94444444 |
| 1 | 0.9 | 1 | 0.88888889 | 1 | 0.88888889 |
| 1 | 0.85 | 1 | 0.83333333 | 1 | 0.83333333 |
| 1 | 0.8 | 1 | 0.77777778 | 1 | 0.77777778 |
| 1 | 0.75 | 1 | 0.72222222 | 1 | 0.72222222 |
| 1 | 0.7 | 1 | 0.66666667 | 1 | 0.66666667 |
| 1 | 0.65 | 1 | 0.61111111 | 1 | 0.61111111 |
| 1 | 0.6 | 1 | 0.55555556 | 1 | 0.55555556 |
| 1 | 0.55 | 1 | 0.5 | 1 | 0.5 |
| 1 | 0.5 | 0.91666667 | 0.5 | 1 | 0.44444444 |
| 1 | 0.45 | 0.83333333 | 0.5 | 0.91666667 | 0.44444444 |
| 0.8 | 0.45 | 0.75 | 0.5 | 0.83333333 | 0.44444444 |
| 0.6 | 0.45 | 0.75 | 0.44444444 | 0.75 | 0.44444444 |
| 0.4 | 0.45 | 0.66666667 | 0.44444444 | 0.66666667 | 0.44444444 |
| 0.2 | 0.45 | 0.66666667 | 0.38888889 | 0.66666667 | 0.38888889 |
| 0.2 | 0.4 | 0.66666667 | 0.33333333 | 0.58333333 | 0.38888889 |
| 0 | 0.4 | 0.66666667 | 0.27777778 | 0.58333333 | 0.33333333 |
| 0 | 0.35 | 0.58333333 | 0.27777778 | 0.5 | 0.33333333 |
| 0 | 0.3 | 0.5 | 0.22222222 | 0.5 | 0.27777778 |
| 0 | 0.25 | 0.41666667 | 0.22222222 | 0.41666667 | 0.27777778 |
| 0 | 0.15 | 0.33333333 | 0.22222222 | 0.33333333 | 0.27777778 |
| 0 | 0.1 | 0.25 | 0.22222222 | 0.25 | 0.27777778 |
| 0 | 0.05 | 0.25 | 0.16666667 | 0.16666667 | 0.27777778 |
| 0 | 0 | 0.16666667 | 0.16666667 | 0.16666667 | 0.22222222 |

TABLE 36-continued

ROC curve coordinates in faecal samples for comparison H vs IBD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| | | 0.16666667 | 0.11111111 | 0.16666667 | 0.16666667 |
| | | 0.16666667 | 0.05555556 | 0.08333333 | 0.16666667 |
| | | 0.08333333 | 0.05555556 | 0.08333333 | 0.05555556 |
| | | 0.08333333 | 0 | 0.08333333 | 0 |
| | | 0 | 0 | 0 | 0 |

TABLE 37

ROC curve coordinates in faecal samples for comparison H vs CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.91666667 | 1 | 0.91666667 | 1 | 0.91666667 |
| 1 | 0.83333333 | 1 | 0.83333333 | 1 | 0.83333333 |
| 1 | 0.75 | 1 | 0.75 | 1 | 0.75 |
| 1 | 0.66666667 | 1 | 0.66666667 | 1 | 0.66666667 |
| 1 | 0.58333333 | 1 | 0.58333333 | 1 | 0.58333333 |
| 1 | 0.5 | 1 | 0.5 | 1 | 0.5 |
| 1 | 0.41666667 | 1 | 0.41666667 | 1 | 0.41666667 |
| 0.8 | 0.41666667 | 0.8 | 0.41666667 | 0.8 | 0.41666667 |
| 0.6 | 0.41666667 | 0.6 | 0.41666667 | 0.6 | 0.41666667 |
| 0.4 | 0.41666667 | 0.4 | 0.41666667 | 0.4 | 0.41666667 |
| 0.2 | 0.41666667 | 0.4 | 0.33333333 | 0.4 | 0.33333333 |
| 0.2 | 0.33333333 | 0.2 | 0.33333333 | 0.4 | 0.25 |
| 0 | 0.33333333 | 0.2 | 0.25 | 0.2 | 0.25 |
| 0 | 0.25 | 0.2 | 0.16666667 | 0 | 0.25 |
| 0 | 0.16666667 | 0 | 0.16666667 | 0 | 0.16666667 |
| 0 | 0.08333333 | 0 | 0.08333333 | 0 | 0.08333333 |
| 0 | 0 | 0 | 0 | 0 | 0 |

TABLE 38

ROC curve coordinates in faecal samples for comparison H vs I-CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.83333333 | 1 | 0.83333333 | 1 | 0.83333333 |
| 1 | 0.66666667 | 1 | 0.66666667 | 1 | 0.66666667 |
| 1 | 0.5 | 1 | 0.5 | 1 | 0.5 |
| 0.8 | 0.5 | 0.8 | 0.5 | 1 | 0.33333333 |
| 0.6 | 0.5 | 0.6 | 0.5 | 0.8 | 0.33333333 |
| 0.4 | 0.5 | 0.4 | 0.5 | 0.6 | 0.33333333 |
| 0.2 | 0.5 | 0.4 | 0.33333333 | 0.4 | 0.33333333 |
| 0.2 | 0.33333333 | 0.2 | 0.33333333 | 0.4 | 0.16666667 |
| 0 | 0.33333333 | 0.2 | 0.16666667 | 0.2 | 0.16666667 |
| 0 | 0.16666667 | 0 | 0.16666667 | 0 | 0.16666667 |
| 0 | 0 | 0 | 0 | 0 | 0 |

TABLE 39

ROC curve coordinates in faecal samples for comparison C-CD vs E3-UC.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.66666667 | 1 | 0.66666667 | 0.66666667 | 1 |
| 1 | 0.33333333 | 1 | 0.33333333 | 0.66666667 | 0 |
| 0 | 0.33333333 | 0 | 0.33333333 | 0.33333333 | 0 |
| 0 | 0 | 0 | 0 | 0 | 0 |

TABLE 40

ROC curve coordinates in faecal samples for comparison I-CD vs IC-CD.

| F. prausnitzii (total) | | Phylogroup I (PHGI) | | Phylogroup II (PHGII) | |
|---|---|---|---|---|---|
| Sensitivity | 1-Specificity | Sensitivity | 1-Specificity | Sensitivity | 1-Specificity |
| 1 | 1 | 1 | 1 | 1 | 1 |
| 1 | 0.83333333 | 1 | 0.83333333 | 1 | 0.83333333 |
| 1 | 0.66666667 | 1 | 0.66666667 | 1 | 0.66666667 |
| 0.66666667 | 0.66666667 | 0.66666667 | 0.66666667 | 1 | 0.5 |
| 0.66666667 | 0.5 | 0.33333333 | 0.66666667 | 0.66666667 | 0.5 |
| 0.33333333 | 0.5 | 0.33333333 | 0.5 | 0.66666667 | 0.33333333 |
| 0.33333333 | 0.33333333 | 0.33333333 | 0.33333333 | 0.33333333 | 0.33333333 |
| 0.33333333 | 0.16666667 | 0.33333333 | 0.16666667 | 0 | 0.33333333 |
| 0 | 0.16666667 | 0 | 0.16666667 | 0 | 0.16666667 |
| 0 | 0 | 0 | 0 | 0 | 0 |

TABLE 41

ROC curve coordinates in faecal samples for comparison C-CD vs IC-CD.

| F. prausnitzii (total) | | Phylogroup I (PHGI) | | Phylogroup II (PHGII) | |
|---|---|---|---|---|---|
| Sensitivity | 1- Specificity | Sensitivity | 1-Specificity | Sensitivity | 1-Specificity |
| 1 | 1 | 1 | 1 | 1 | 1 |
| 1 | 0.66666667 | 0.66666667 | 1 | 1 | 0.66666667 |
| 0.66666667 | 0.66666667 | 0.66666667 | 0.66666667 | 1 | 0.33333333 |
| 0.66666667 | 0.33333333 | 0.66666667 | 0.33333333 | 0.66666667 | 0.33333333 |
| 0.33333333 | 0.33333333 | 0.33333333 | 0.33333333 | 0.66666667 | 0 |
| 0.33333333 | 0 | 0.33333333 | 0 | 0.33333333 | 0 |
| 0 | 0 | 0 | 0 | 0 | 0 |

Example 12

Material and Methods of Total *F. Prausnitzii, F. Prausnitzii* Phylogroups and *E. Coli* Quantification in Fecal Samples 1. Patients, Clinical Data and Sampling Eleven (11) healthy subjects and twenty-three (23) patients diagnosed of inflammatory bowel disease (IBD); 10 diagnosed of Crohn disease (CD) and 13 diagnosed of Ulcerative Colitis (UC) were recruited by the Gastroenterology Service of the Hospital Universitari Dr. Josep Trueta (Girona, Spain). From those volunteers, sixty-seven (67) fecal samples (26 CD, 30 UC, 11 Healthy) were obtained during different times along their treatment. (Table 42).

Subjects recruited as IBD patients were diagnosed according to standard clinical, pathological and endoscopic criteria and categorized according to the Montreal classification (Silverberg et al., Can J Gastroenterol. 2005, 19 Suppl A:5-36). The control group consisted of healthy subjects without any known gastrointestinal disorder, was recruited according to clinical standards. Clinically relevant data (as for example, age, sex, calprotectin levels or years of disease) from all the patients was also collected. All of them signed up the corresponding informed consent. Exclusion criteria included: antimicrobial treatment within one month before colonoscopy and prior surgery.

TABLE 42

Clinical and sampling data of the studied subjects

| | Total | | Healthy | | CD | | UC | |
|---|---|---|---|---|---|---|---|---|
| | Samples | Patients | Samples | Patients | Samples | Patients | Samples | Patients |
| N | 67 | 34 | 11 | 11 | 26 | 10 | 30 | 13 |
| Age (mean years ± SD) | 51.5 ± 18.98 | 50.7 ± 18.19 | 31.4 ± 2.98 | 31.4 ± 2.98 | 45.2 ± 18.6 | 46 ± 20.06 | 56.9 ± 17.86 | 54.4 ± 16.48 |
| Sex (% Male) | 31 (46.26%) | 17 (50%) | 5 (45.45%) | 5 (45.45%) | 9 (34.61%) | 3 (33%) | 17 (56.6%) | 9 (69.23%) |
| Anti-TNF Treatment | | | na | na | 7 (26.92%) | | 6 (20%) | |

This work was approved by the Ethics Committee of Clinical Research of the Hospital Universitari Dr. Josep Trueta (Girona, Spain) and the Institut d'Assistència Sanitària of Girona (Salt, Spain) on 18 May 2016.

2. Sample Collection, Preservation and Storage

Each subject contributed with fecal samples, which were collected at the Gastroenterology Service of the Hospital Universitari Dr. Josep Trueta in less than 24 h after deposition. All samples from all subjects were homogenized, aliquoted into 10 ml tubes and stored at −80° C. until use.

3. Sample Treatment and DNA Extraction

DNA was extracted using NucleoSpin® Soil Kit (Macherey-Nagel GmbH &Co., Duren, Germany). Briefly, 30-70 mg of fecal sample were placed in a Nucleospin bead-tube. 700 µl of SL1 and 150 µl of Enhancer (SX) were added to each sample in order to improve DNA recovery. Afterwards, DNA was extracted and purified following the instructions from the manufacturer. Genomic DNA was eluted with 100 µl of elution buffer and stored at −20° C. until use. DNA concentration of the extracts was determined with a Qubit fluorimeter (Invitrogen detection Technologies, USA) using Qubit dsDNA High Sensitivity Assay Kit. Prior to qPCR analysis, DNA concentration was adjusted to 8 ng/µl with free DNA water.

4. Quantitative Real-Time PCR (qPCR) of DNA Extracted from Fecal Samples

DNA from fecal samples was analysed by quantitative real-time PCR. More specifically, we assessed the quantity of Total *Faecalibacterium prausnitzii* (FT), *Faecalibacterium prausnitzii* phylogroup I (PHGI), *Faecalibacterium prausnitzii* phylogroup II (PHGII) and *Escherichia coli* (EC). The bacterial sequences were quantified using a quantitative real time PCR with Taqman probe-based assays. Primers and qPCR conditions were as described in Example 1.

Samples were run in duplicate in the same plate. For data analysis, the mean of the duplicate quantifications was used. Bacterial abundances for each sample were expressed as Ct normalized to total DNA concentration, where the Ct (cycle threshold) is defined as the number of q-PCR cycles required for the fluorescent signal to cross the threshold. Ct levels are inversely proportional to the logarithm of target nucleic acid concentration in the sample. The real time assays undergo 40 cycles of amplification.

Methodological differences were introduced with regards to Example 1. Bacteria copy number were not normalized to the total bacteria 16S rRNA gene copies, but Ct were normalized to total DNA concentration. The novel assay for FT, PHGI, PHGII and EC was composed of GoTaq qPCR Master Mix 2× (Promega, Wisconsin, USA) instead of Taqman Universal PCR Master Mix (Applied Biosystems, Foster City, Calif., USA). All bacteria primers were purchased from Macrogen (Seoul, Korea). And all quantitative PCR were performed using AriaMx PCR System (Stratagene by Agilent, Santa Clara, Calif., USA), and analyzed using the AriaMx Software version 1.2 (Stratagene by Agilent, Santa Clara, Calif., USA).

All the differences introduced were validated and none differences between the methods were observed.

5. Methods of Statistical Analysis

Statistical normal distribution of the data was analyzed through Kolmorov-Smirnov test. According to whether there was a statistical normal distribution of the data or not, an adequate statistical test to compare the following groups was used. Normal t-test was used to compare groups distributed normally whereas Mann-Whitney non-parametric test was used to compare groups without normal distribution. Analyzed groups were: Healthy vs CD, Healthy vs UC and CD vs UC, and different locations of both diseases: ileal (I), ileocolonic (IC) and colonic (C) for CD and distal (E2) and extensive (E3) for UC.

For these groups, analyzed variables were:
the quantification expressed in Ct of the four bacterial sequences described herein corresponding to Total *F. prausnitzii* (FT), phylogroup I (PHGI), phylogroup II (PHGII) and *E. coli*; and
the ratio of the quantification of these four bacterial sequences.

The different ratios between Total *F. prausnitzii*, phylogroup I, phylogroup II and *E. coli* have been obtained by subtracting the quantification levels of a first sequence by the quantification levels of a second sequence.

In addition, the receiver operating characteristic (ROC) curve analysis, a plot of the true positive rate (sensitivity) versus false positive rate (1−specificity), was performed to evaluate the usefulness of *F. prausnitzii*, and each phylogroup to differentiate amongst different intestinal disorders. The accuracy of discrimination was measured by the area under the ROC curve (AUC). While, an AUC approaching 1 indicates that the test is highly sensitive as well as highly specific, an AUC approaching 0.5 indicates that the test is neither sensitive nor specific. Sensitivity and specificity values are expressed in percent (%).

All the statistical analyses were performed using SPSS 15.0 statistical package (LEAD Technologies, Inc.). Significance levels were established for P values≤0.05. The graphics were performed using GraphPad Prism 6.

Example 13

Prevalence of Fecal *F. Prausnitzii* Phylogroups I and II in Health and Disease

Prevalence of *F. prausnitzii* phylogroups as calculated from positive determinations over total samples was analyzed both by disease status (CD and UC) and by disease location (ileal (I), ileocolonic (IC) and colonic (C) for CD and distal (E2) and extensive (E3) for UC) (Table 43). Both phylogroups were less prevalent in CD patients than in healthy individuals, but phylogroup I was significantly more reduced than phylogroup II. Interestingly, phylogroup I had lower prevalence in C-CD samples than I-CD and IC-CD while phylogroup II reduction was exclusive for C-CD.

In contrast to Example 8, UC patients only had lower prevalence of phylogroup I when compared to healthy individuals. This lower prevalence was exclusive for Extensive UC compared to Distal UC.

TABLE 43

Prevalence of *F. prausnitzii* phylogroups by diagnostics and IBD subtype.

|  | PHGI | | PHGII | |
|---|---|---|---|---|
| % | Absence | Presence | Absence | Presence |
| H | 0 | 100 | 0 | 100 |
| UC | 10 | 90 | 0 | 100 |
| CD | 31 | 69 | 8 | 92 |
| p-value | 0.030* | | 0.204 | |
| I-CD | 17 | 83 | 0 | 100 |
| IC-CD | 21 | 79 | 0 | 100 |
| C-CD | 80 | 20 | 40 | 60 |
| p-value | 0.033* | | 0.009** | |
| E2-Distal UC | 0 | 100 | 0 | 100 |
| E3-Extensive UC | 19 | 81 | 0 | 100 |
| p-value | 0.180 | | nd | | different IBD by separately (H vs CD, H vs UC) (Table 44; FIGS. 9A to 9E). Healthy subjects were also compared to IBD (considering both CD and UC patients together) (FIGS. 9F to 9I).

Figure 9:
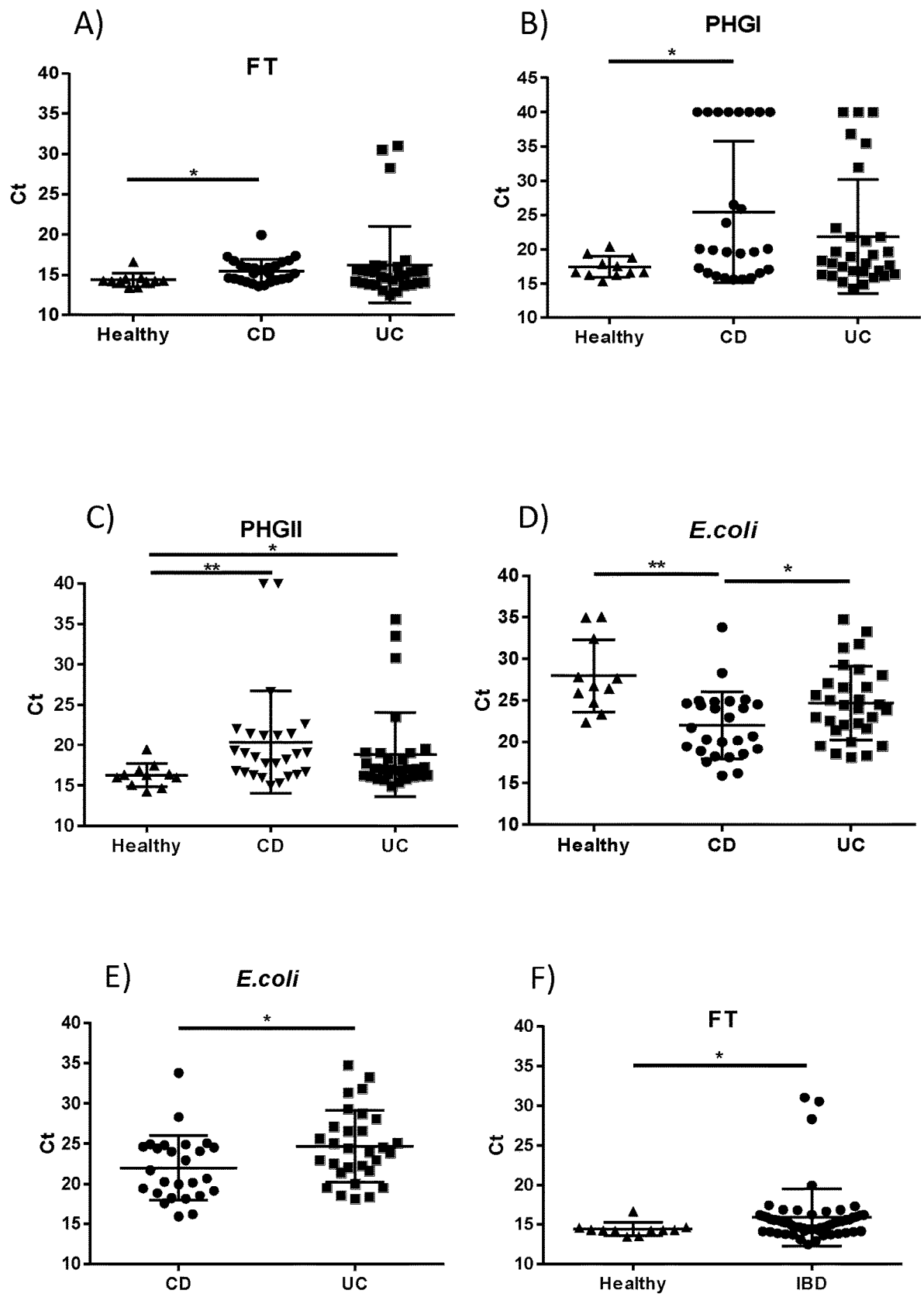
FIG. 9. Graphs representing abundances of fecal Total *F. prausnitzii* (FT), phylogroups (PHGI and PHGII) and *E. coli* (EC) in healthy (H), Ulcerative Colitis (UC) and Crohn's Disease (CD) patients (expressed in Ct).
Figure 9:
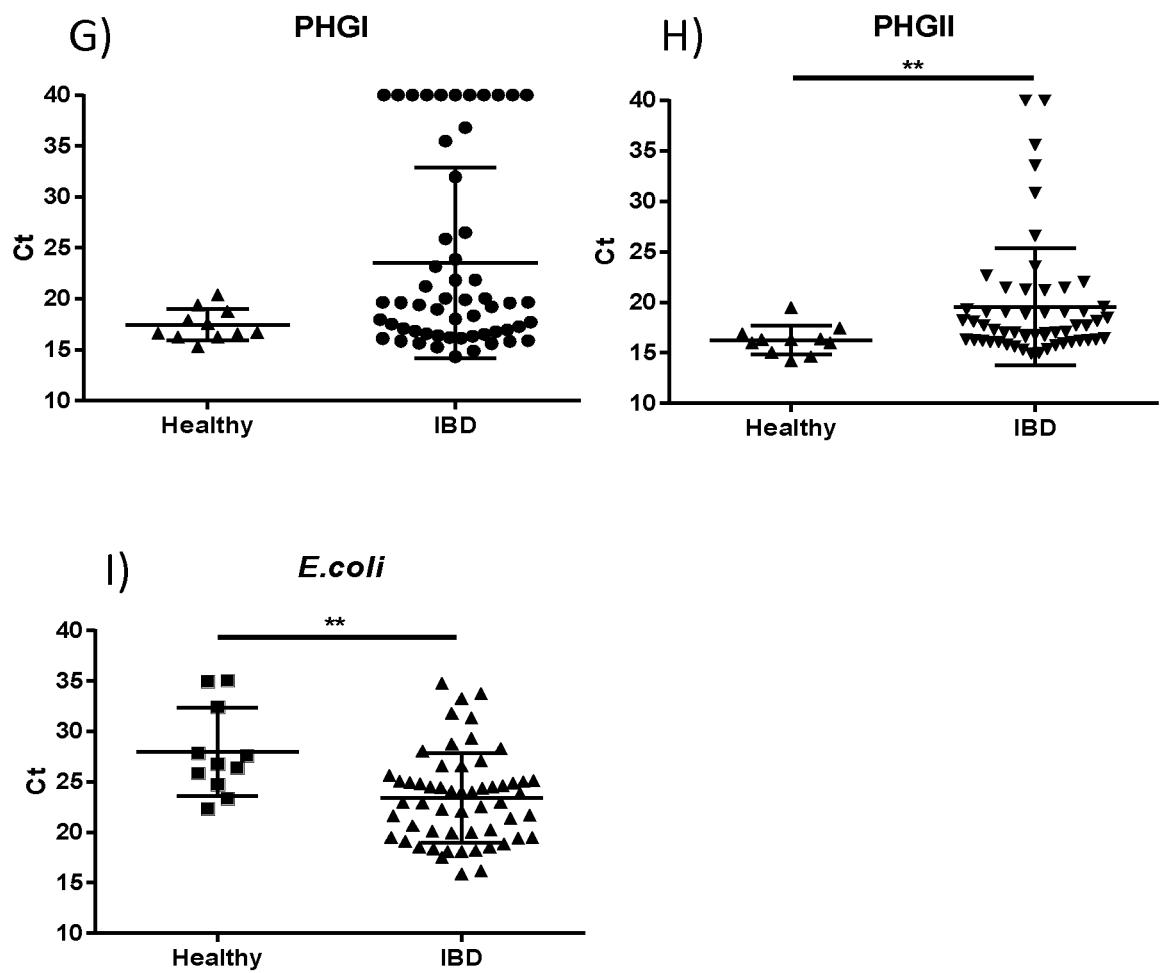

Total *F. prausnitzii* load was reduced in IBD patients analyzed in comparison to H subjects (FIG. 9A). While in CD patients the observed differences were statistically different, in UC patients the differences were not statistically supported.

*F. prausnitzii* PHGI and PHGII Ct were increased, so its abundances were reduced in IBD patients in comparison to H (FIGS. from 9B and 9C). While, PHGI abundance was significantly decreased just in CD patients (FIG. 9C), PHGII abundance was decreased in both CD and UC patients (FIG. 9C).

*E. coli* abundance was significantly increased in IBD in comparison to H subjects (FIG. 9D). This increase was particularly marked in CD patients. Furthermore, *E. coli* abundance was significantly increased in CD patients compared to UC patients (FIG. 9E).

As was expected, when comparing H to IBD disease, both total *F. prausnitzii* and its phylogroups abundance were reduced in IBD patients (FIGS. 9F to 9H), while *E. coli* load was increased (FIG. 9I).

In conclusion, in CD patients the microbiological profile is characterized by a decrease of FT, PHGI and PHGII abundance and an increase of *E. coli*. For UC patients, microbiological profile is defined by a decrease of PHGII and an increase of *E. coli*.

TABLE 44

Abundance of fecal Total *Faecalibacterium prausnitzii* (FT), phylogroup I (PHGI), phylogroup II (PHGII) and *Escherichia coli* (EC) in controls (H), Ulcerative Colitis (UC), and Crohn's disease (CD) patients. Disease locations of CD patients had been analyzed as independent groups.

|  | n Samples | FT | PHGI | PHGII | EC |
|---|---|---|---|---|---|
| H | 11 | 14.39 ± 0.83 | 17.45 ± 1.54 | 16.26 ± 0.95 | 27.98 ± 4.37 |
| UC | 30 | 16.24 ± 4.78 | 21.85 ± 8.28 | 18.84 ± 5.23 | 24.69 ± 4.45 |
| CD | 26 | 15.49 ± 1.44 | 25.44 ± 10.3 | 20.4 ± 6.37 | 21.98 ± 4.06 |
| p-value H vs CD | | 0.014* | 0.045* | 0.004** | 0.001*** |
| H vs UC | | 0.206 | 0.172 | 0.050* | 0.047* |
| CD vs UC | | 0.297 | 0.201 | 0.116 | 0.021* |
| H vs IBD | | 0.048* | 0.069 | 0.009** | 0.007** |

*p-value < 0.05
**p-value < 0.01
***p-value < 0.001

Example 14

Figure 10:
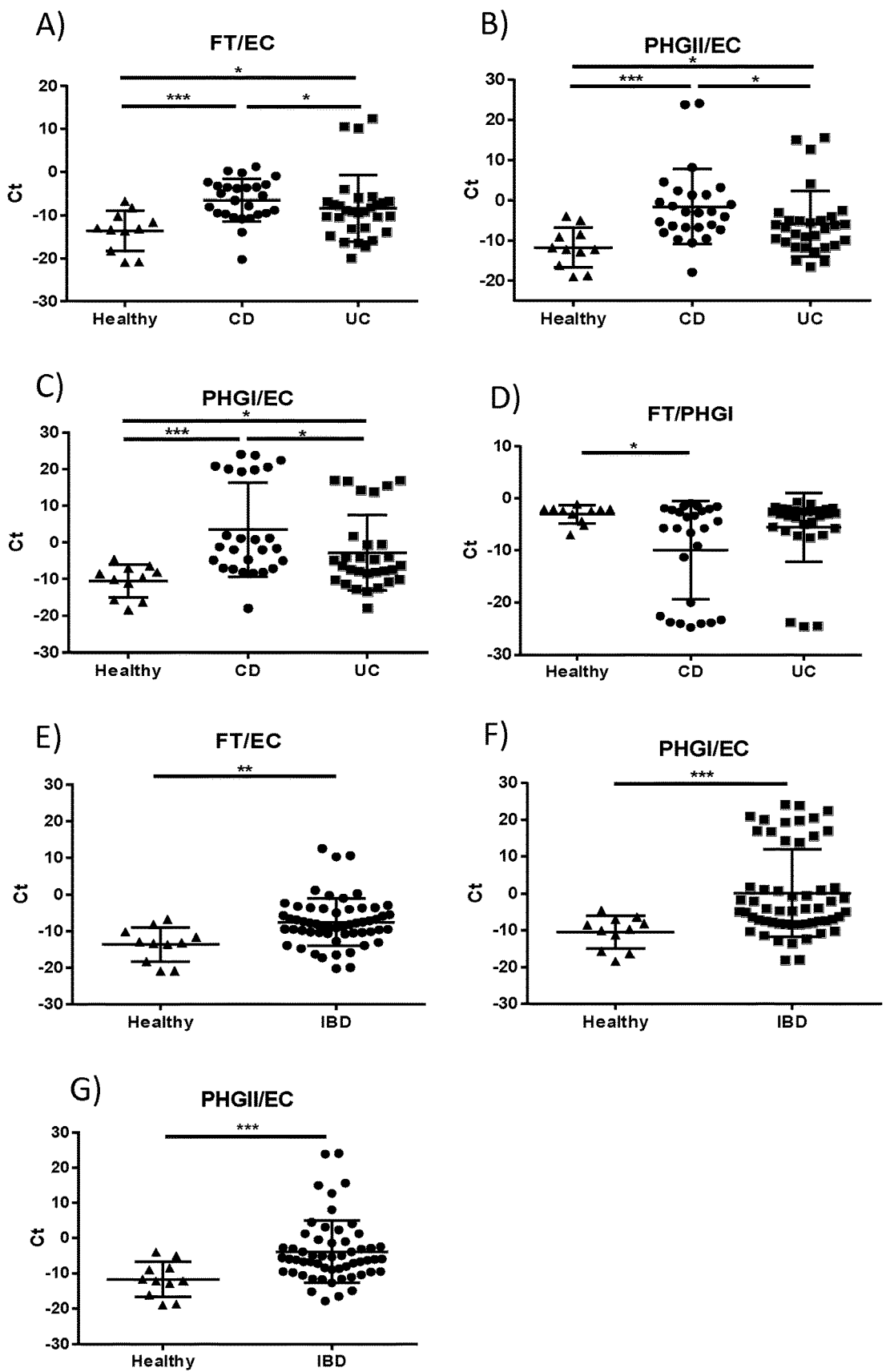
FIG. 10. Graphs representing bacterial abundances by biomarkers ratios.

Abundance of Fecal Total *F. Prausnitzii*, Phylogroups and *E. Coli* in Health and Disease The abundance of the biomarkers from fecal samples was compared amongst healthy subjects (H) and patients with Biomarkers ratios were also compared between healthy and both CD and UC samples (Table 45). Ratios FT/EC, PHGI/EC and PHGII/EC were significantly increased in IBD samples compared to health. Moreover, significant differences were also observed for the three ratios amongst CD, UC and healthy individuals (FIG. 10A, FIG. 10B and FIG. 10C). FT/PHGI ratio was also significantly increased in CD compared to healthy samples (FIG. 10D). Finally, statistically differences were not observed in PHGI/PHGII and FT/PHGI ratios amongst the three groups.

Moreover, when contrasting H ratios with IBD ratios, significant differences were also observed in ratios FT/EC, PHGI/EC and PHGII/EC (FIG. 10E to 10G).

In conclusion, due to the differences observed when comparing CD or UC with H or between them, we may conclude that IBD samples are represented by changes in FT/EC, PHGI/EC and PHGII/EC counts in the fecal microbiological profile, and changes in FT/PHGI is exclusive for UC samples.

TABLE 45

Bacterial abundances represented by ratio of different bacterial markers (expressed in Ct)

|  | FT/EC | PHGI/PHGII | PHGI/EC | PHGII/EC | FT/PHGI | FT/PHGII |
|---|---|---|---|---|---|---|
| CD | −6.49 ± 4.88 | 5.04 ± 9.46 | 3.47 ± 12.87 | −1.58 ± 9.29 | −9.95 ± 9.43 | −4.91 ± 5.96 |
| UC | −8.38 ± 7.67 | 3.01 ± 7.54 | −2.84 ± 10.29 | −5.85 ± 8.09 | −5.54 ± 6.62 | −2.60 ± 1.82 |
| Healthy | −13.58 ± 4.68 | 1.19 ± 2.25 | −10.53 ± 4.43 | −11.72 ± 4.98 | −3.06 ± 1.74 | −1.87 ± 0.81 |
| p-value H vs CD | 0.043* | 0.522 | 0.017* | 0.017* | 0.189 | 0.305 |
| H vs UC | 0.000*** | 0.398 | 0.000*** | 0.000*** | 0.052* | 0.101 |
| CD vs UC | 0.027* | 0.988 | 0.021* | 0.025* | 0.234 | 0.147 |
| H vs IBD | 0.002** | 0.680 | 0.001** | 0.001** | 0.093 | 0.092 |

*p-value < 0.05
**p-value < 0.01
***p-value < 0.001

Example 15

Figure 11:
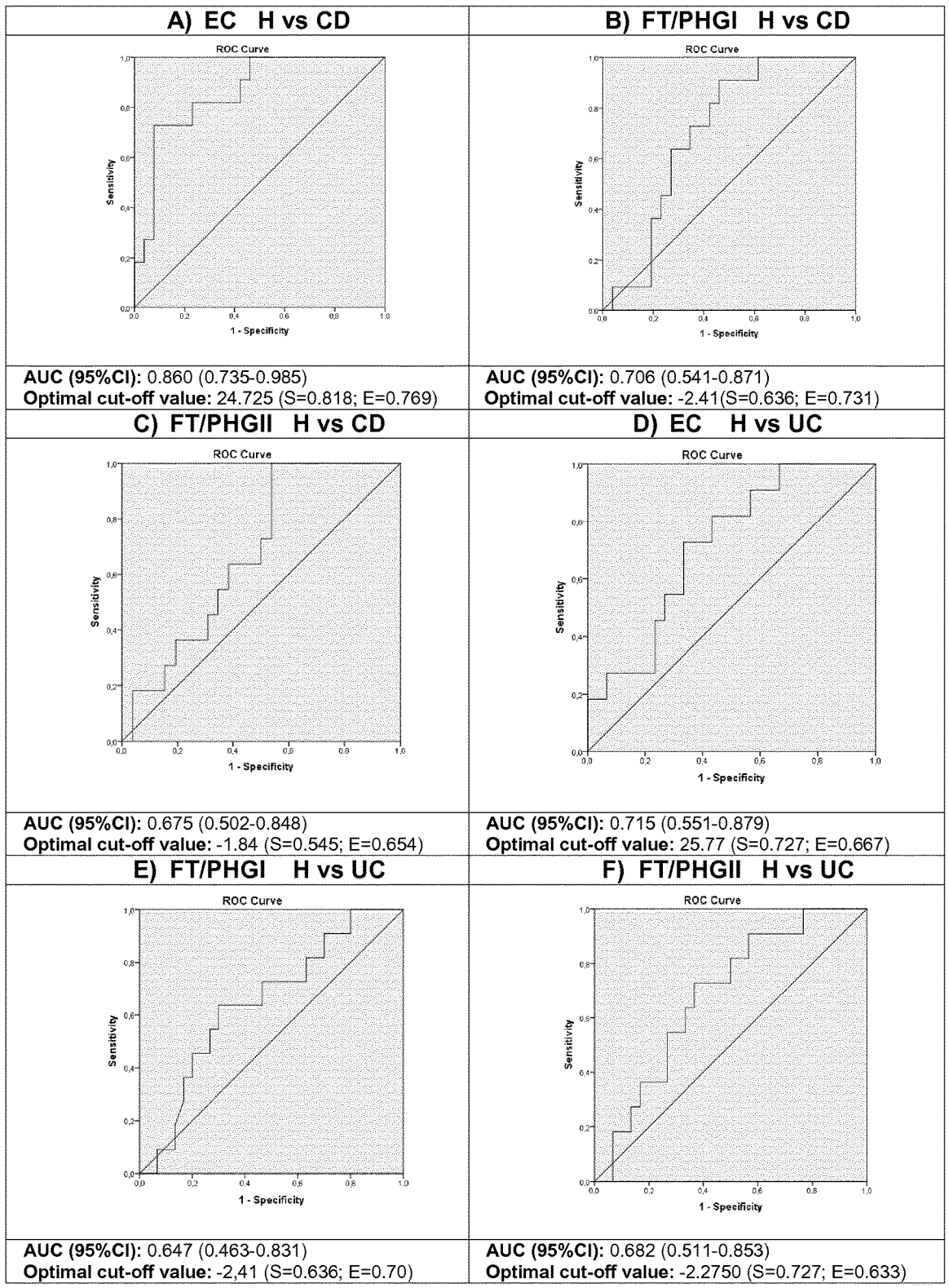
FIG. 11. Graphs representing ROC curve analysis of fecal Total *F. prausnitzii* (FT), phylogroups (PHGI and PHGII) and *E. coli* (EC) in healthy (H), Ulcerative Colitis (UC) and Crohn's Disease (CD) patients.
Figure 11:
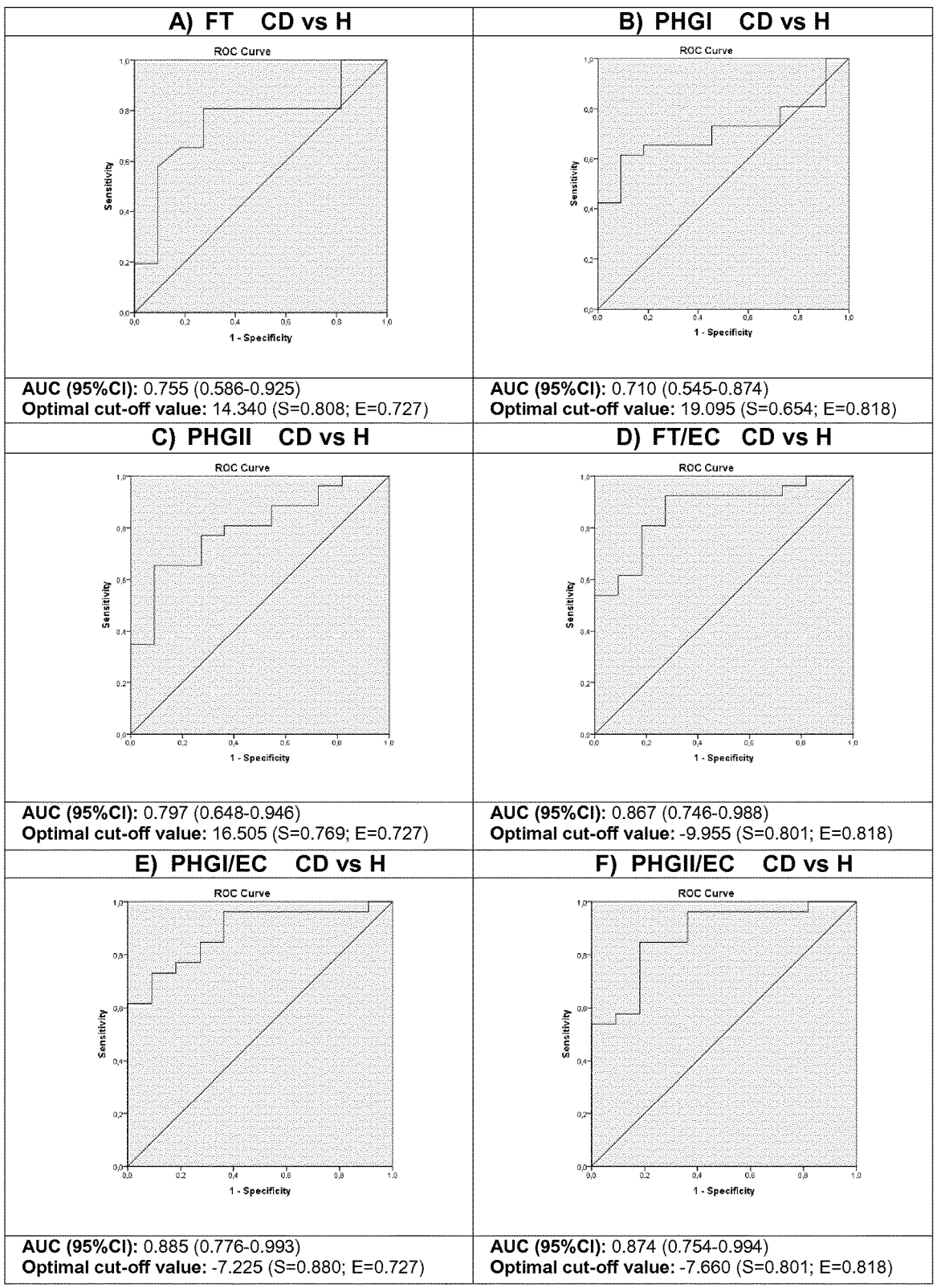
Figure 11:
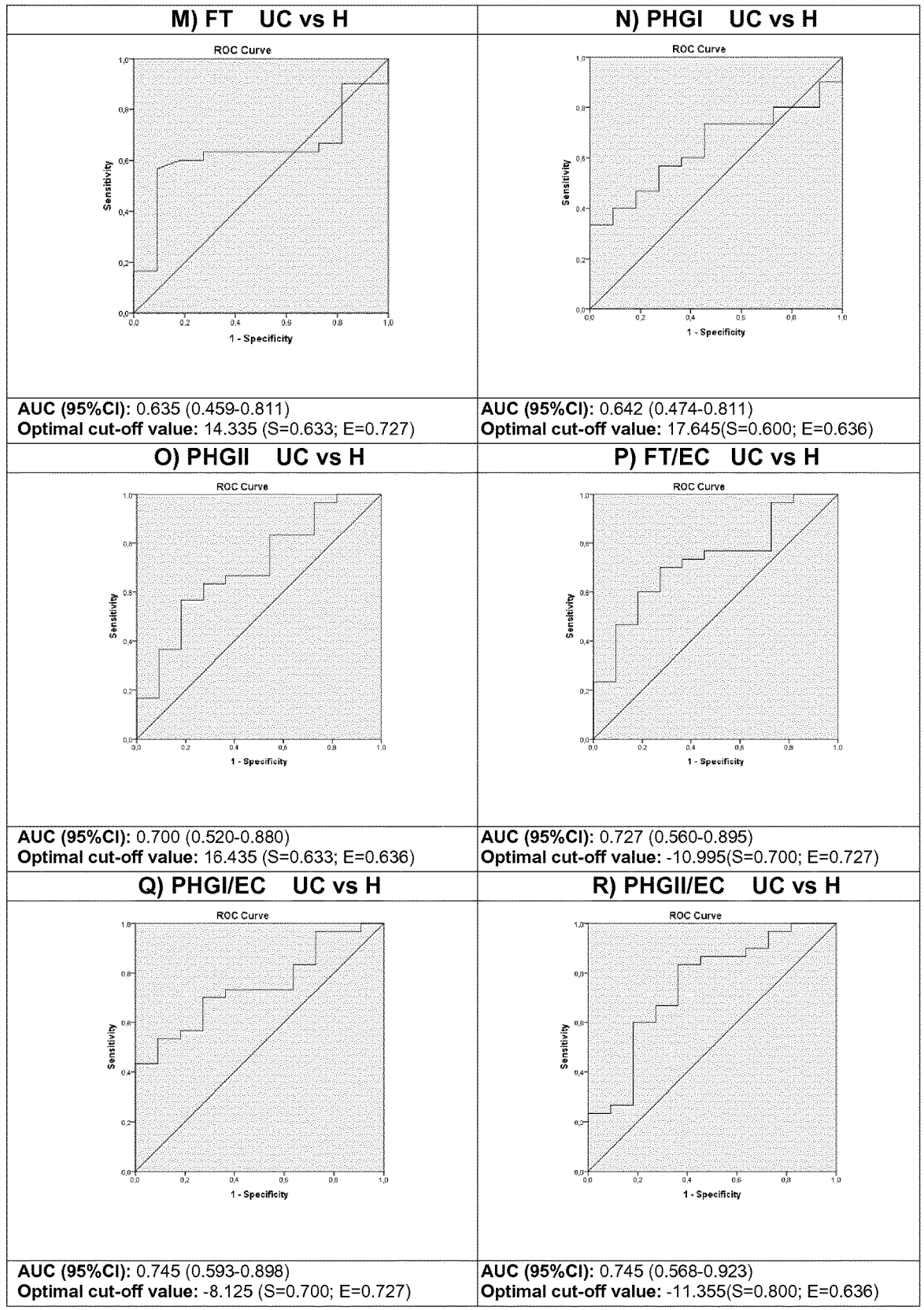
Figure 11:
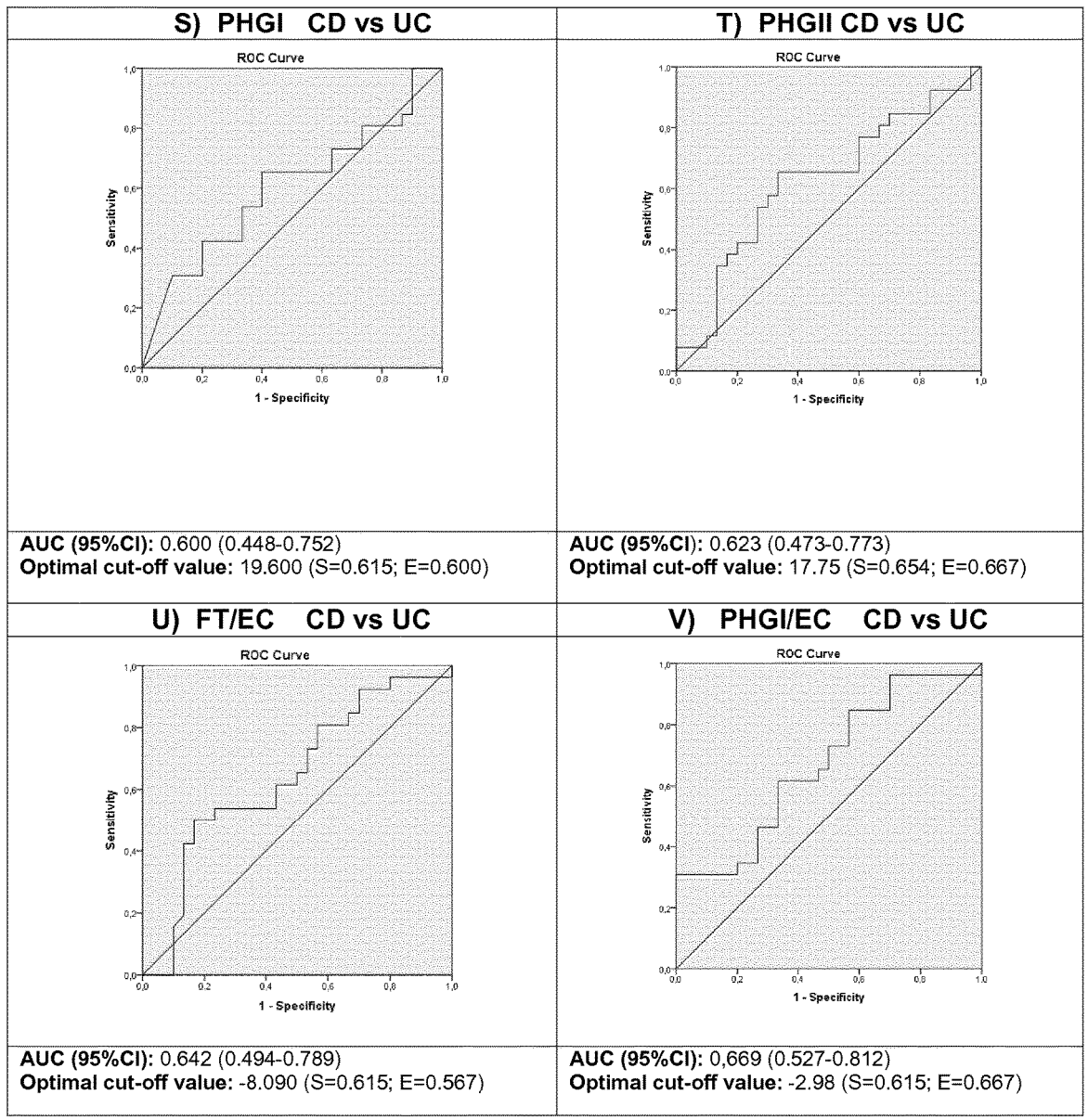
Figure 11:
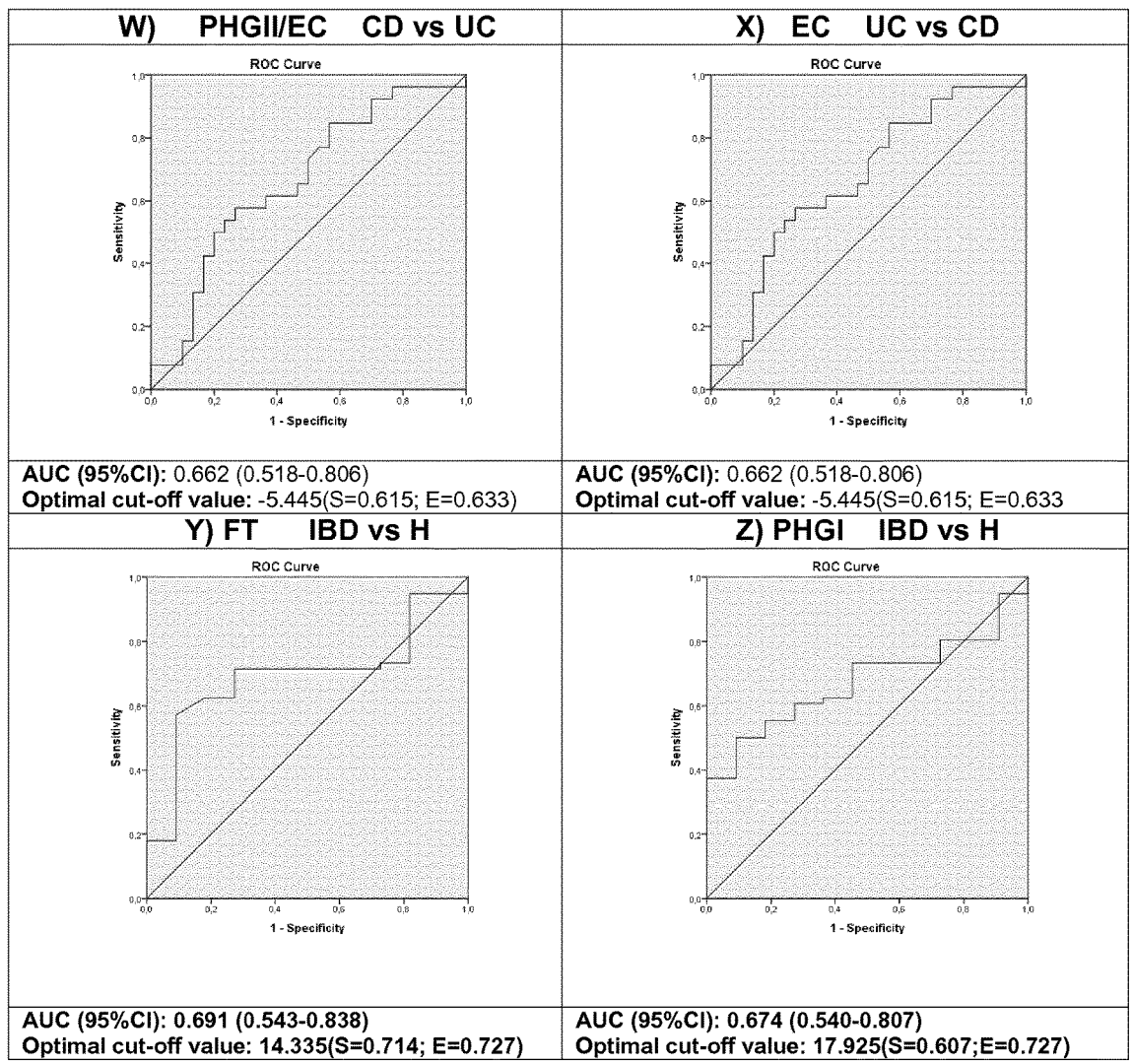
Figure 11:
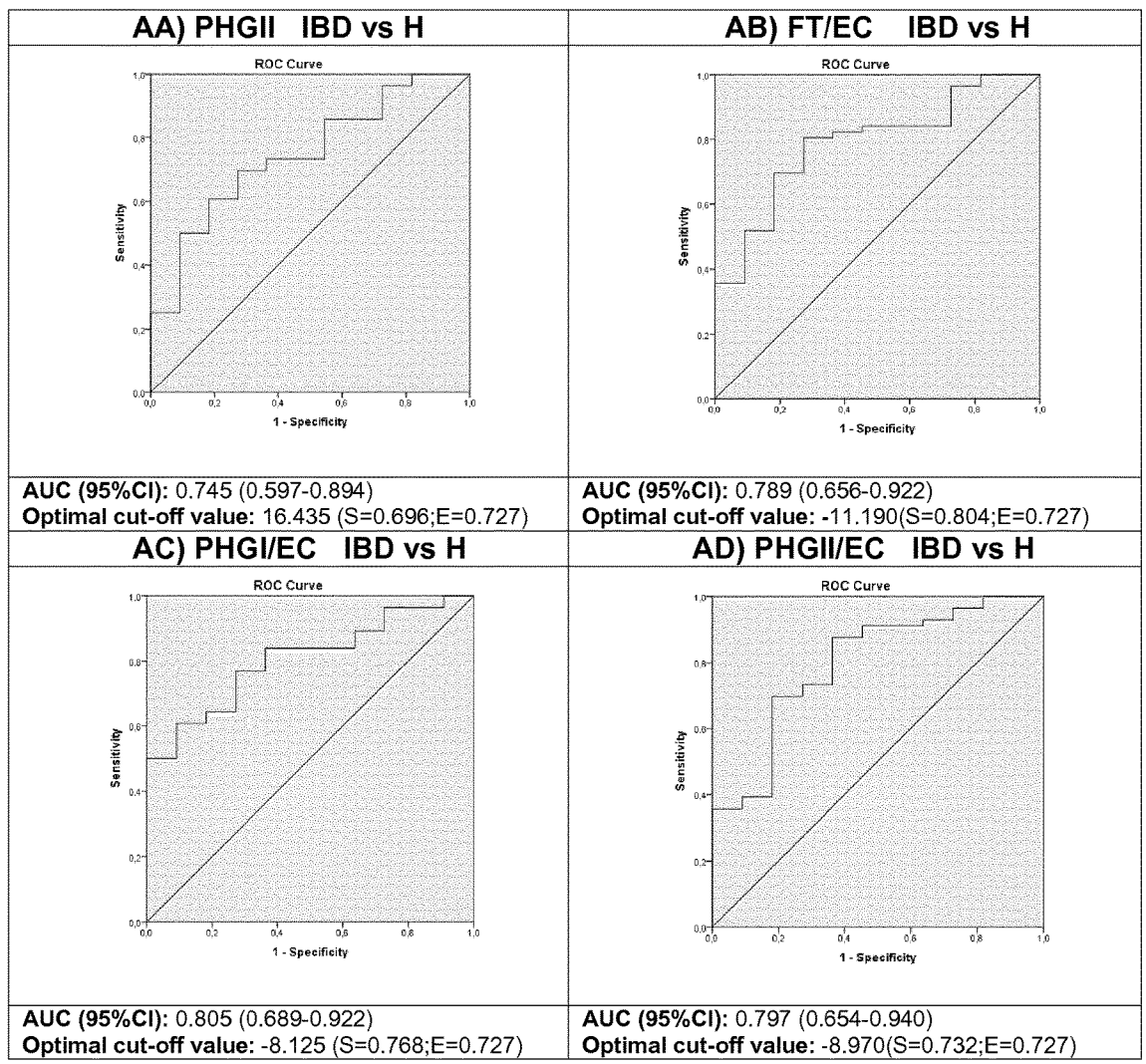

Usefulness of Fecal *F. Prausnitzii* Phylogroups Abundance as Diagnostic Biomarkers ROC curve analysis was performed to test the putative accuracy of fecal *F. prausnitzii* total, its phylogroups and *E. coli* abundance as indicators to differentiate between two groups of patients. Results are provided in FIG. 11.

The microbiological profile which best discriminate the healthy digestive status is composed by *E. coli* (HvsCD-AUC:0.860, with an 81.8 of sensitivity and 76.9 of specificity, FIG. 11A; HvsUC-AUC:0.715, with an 72.7 of sensitivity and 66.7 of specificity, FIG. 11D), FT/PHGI (HvsCD-AUC:0.706, with an 63.6 of sensitivity and 73.1 of specificity, FIG. 11B; HvsUC-AUC:0.647, with an 63.6 of sensitivity and 70 of specificity, FIG. 11E) and FT/PHGII (HvsCD-AUC:0.675, with an 54.5 of sensitivity and 65.4 of specificity, FIG. 11C; HvsUC-AUC:0.682 with an 72.7 of sensitivity and 63.3 of specificity, FIG. 11F). FIGS. from 11A to 11F describe the performance of bacterial biomarker defining healthy individuals.

Several markers were confirmed as good discriminators for CD patients, with AUC values greater than 0.70 (FIGS. 11G to 11L). More specifically, Total *F. prausnitzii* (AUC: 0.755, with an 80.8 of sensitivity and 72.7 of specificity, FIG. 11G), *F. prausnitzii* phylogroup I (AUC:0.710 with an 65.4 of sensitivity and 81.8 of specificity, FIG. 11H), *F. prausnitzii* phylogroup II (AUC:0.797 with an 76.9 of sensitivity and 72.7 of specificity, FIG. 11I), FT/EC (AUC: 0.867 with an 80.1 of sensitivity and 81.8 of specificity, FIG. 11J), PHGI/EC (AUC:0.885 with an 88 of sensitivity and 72.7 of specificity, FIG. 11K) and PHGII/EC (AUC:0.874 with an 80.1 of sensitivity and 81.8 of specificity, FIG. 11L).

The same markers were confirmed as good discriminators for UC, but in contrast, the marker's capacity of discrimination was lower in comparison to the results observed in CD patients with AUC between 0.745 and 0.635 (FIGS. 11M to 11R): Total *F. prausnitzii* (AUC:0.635, with an 63.3 of sensitivity and 72.7 of specificity, FIG. 11M), *F. prausnitizii* phylogroup I (AUC:0.642 with an 60 of sensitivity and 63.6 of specificity, FIG. 11N), *F. prausnitizii* phylogroup II (AUC:0.700 with an 63.3 of sensitivity and 63.6 of specificity, FIG. 11O), FT/EC (AUC:0.727 with an 70 of sensitivity and 72.7 of specificity, FIG. 11P), PHGI/EC (AUC: 0.745 with an 70 of sensitivity and 72.7 of specificity, FIG. 11Q) and PHGII/EC (AUC:0.745 with an 80 of sensitivity and 63.6 of specificity, FIG. 11R).

Finally, to discriminate between CD and UC diseases, two markers and three ratios were found to be good discriminators with AUC between 0.600 and 0.669 (FIGS. 11S to 11X):

*F. prausnitizii* phylogroup I (AUC:0.600 with an 61.5 of sensitivity and 60 of specificity, FIG. 11S), *F. prausnitizii* phylogroup II (AUC:0.623 with an 65.4 of sensitivity and 66.7 of specificity, FIG. 11T), *E. coli* (AUC:0.672 with an 60 of sensitivity and 57.7 of specificity, FIG. 11U), FT/EC (AUC:0.642 with an 61.5 of sensitivity and 56.7 of specificity, FIG. 11V), PHGI/EC (AUC:0.669 with an 61.5 of sensitivity and 66.7 of specificity, FIG. 11W) and PHGII/EC (AUC:0.662 with an 61.5 of sensitivity and 63.3 of specificity, FIG. 11X).

Furthermore, to distinguish between H and IBD (both CD and UC diseases together), three markers and three ratios proved to be good discriminators with AUC between 0.674 and 0.805 (FIGS. 11Y to 11AD): Total *F. prausnitizii* (AUC: 0.691 with an 71.4 of sensitivity and 72.7 of specificity, FIG. 11Y), *F. prausnitizii* phylogroup I (AUC:0.674 with an 60.7 of sensitivity and 72.7 of specificity, FIG. 11Z), *F. prausnitizii* phylogroup II (AUC:0.745 with an 69.6 of sensitivity and 72.7 of specificity, FIG. 11AA), FT/EC (AUC:0.789 with an 80.4 of sensitivity and 72.7 of specificity, FIG. 11AB), PHGI/EC (AUC:0.805 with an 76.8 of sensitivity and 72.7 of specificity, FIG. 11AC) and PHGII/EC (AUC: 0.797 with an 73.2 of sensitivity and 72.7 of specificity, FIG. 11AD).

In conclusion, the best discriminators were found to be the ratios FT/EC, PHGI/EC and PHGII/EC for CD disease, with AUC values above 0.850 and sensitivities and specificities over 80%.

With regards to UC, even though marker's capacity of discrimination was lower, the best discriminators proved to be the ratios PHGI/EC and PHGII/EC with AUC values of 0.745 and sensitivities over 70%.

The following Figures provide the ROC curve, AUC value and specificity and sensitivity values for the optimal cut-off point for all the markers described above.

Example 16

Abundance of Total *F. Prausnitzii*, Phylogroups and *E. Coli* in CD with Different Lesion Location and its Usefulness as Biomarkers for Differential Diagnosis by Disease Location/Extension Example 16.1. Abundance CD samples were analyzed by disease location, ileal (I-CD), colonic (C-CD) and ileocolonic (IC-CD) locations were studied.

Figure 12:
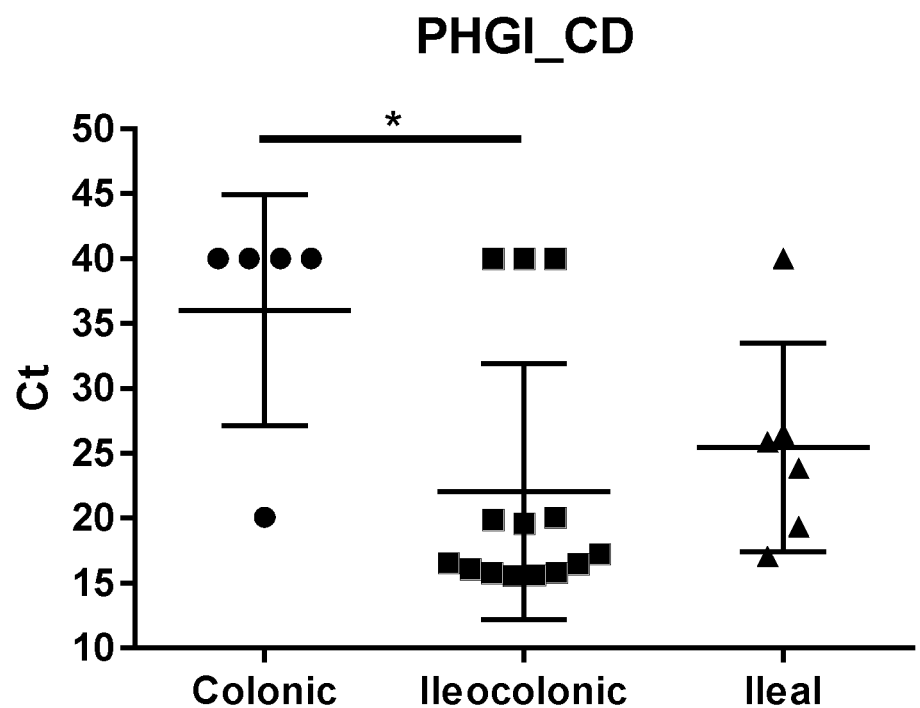
FIG. 12. *Faecalibacterium prausnitzii* phylogroup I (PHGI) and phylogroup II (PHGII) abundance in samples of colonic, ileocolonic and ileal locations of CD patients.
Figure 12:
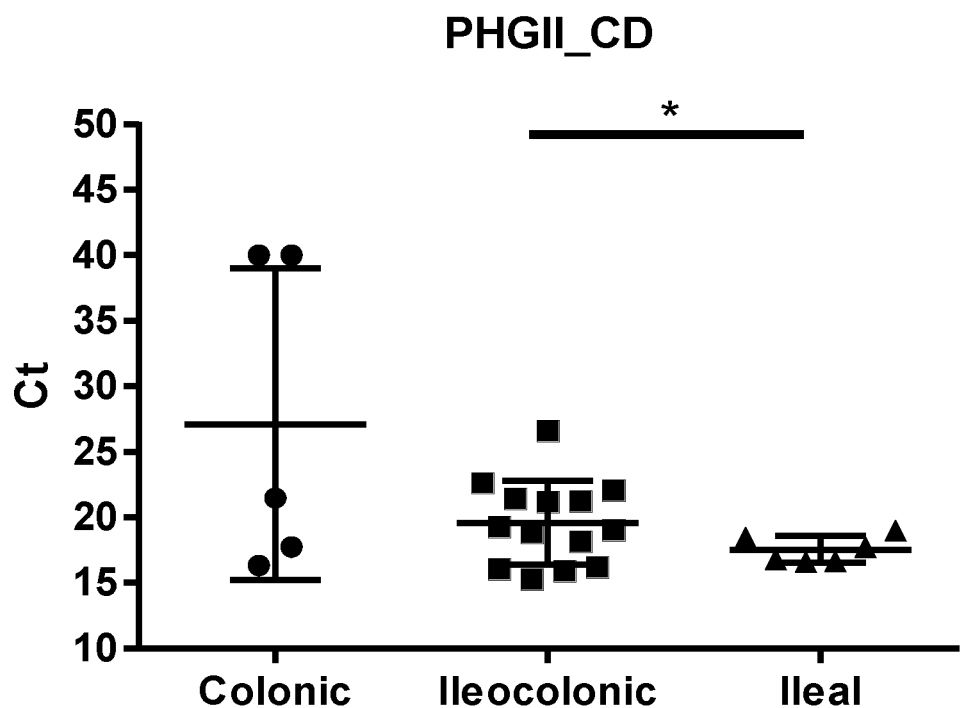

Total *F. prausnitzii* and phylogroup I (PHGI) abundances were significantly decreased in patients with inflammation located in the colon, while PHGII was significantly increased in ileal location. (Table 46, FIG. 12).

TABLE 46

Abundance of fecal Total *Faecalibacterium prausnitzii* (FT), phylogroup I (PHGI), phylogroup II (PHGII) and *Escherichia coli* (EC) in colon, ileocolonic and ileal locations.

|  | n Samples | FT | PHGI | PHGII | EC |
|---|---|---|---|---|---|
| Colonic-CD | 5 | 16.77 ± 2.08 | 36.01 ± 8.91 | 27.12 ± 11.91 | 20 ± 5.02 |
| Ileocolonic-CD | 14 | 15 ± 1.04 | 22.07 ± 9.84 | 19.60 ± 3.19 | 22.09 ± 4.29 |
| Ileal-CD | 6 | 15.84 ± 1.02 | 25.46 ± 8.03 | 17.56 ± 1.02 | 22.92 ± 2.82 |
| p-value | C-CD vs IC-CD | 0.046* | 0.026* | 0.055 | 1.00 |
|  | IC-CD vs I-CD | 0.583 | 1.00 | 0.046* | 1.00 |
|  | C-CD vs I-CD | 0.745 | 0.222 | 0.032* | 0.774 |

*p-value < 0.05
**p-value < 0.01
***p-value < 0.001

Figure 13:
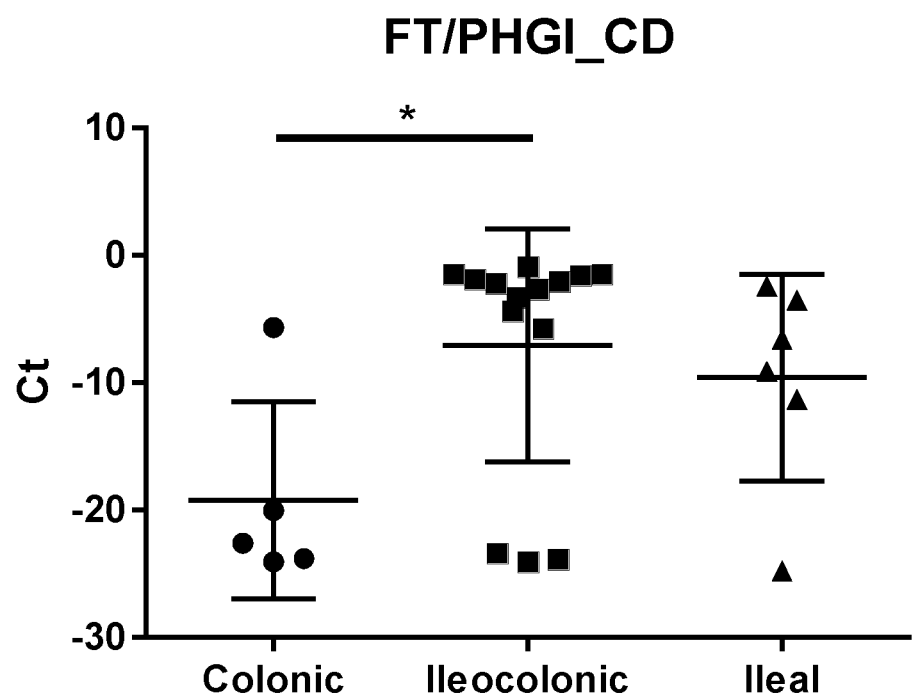
FIG. 13. Ratios of FT/PHGI and FT/PHGII abundance in samples of colonic, ileocolonic and ileal locations of CD patients.
Figure 13:
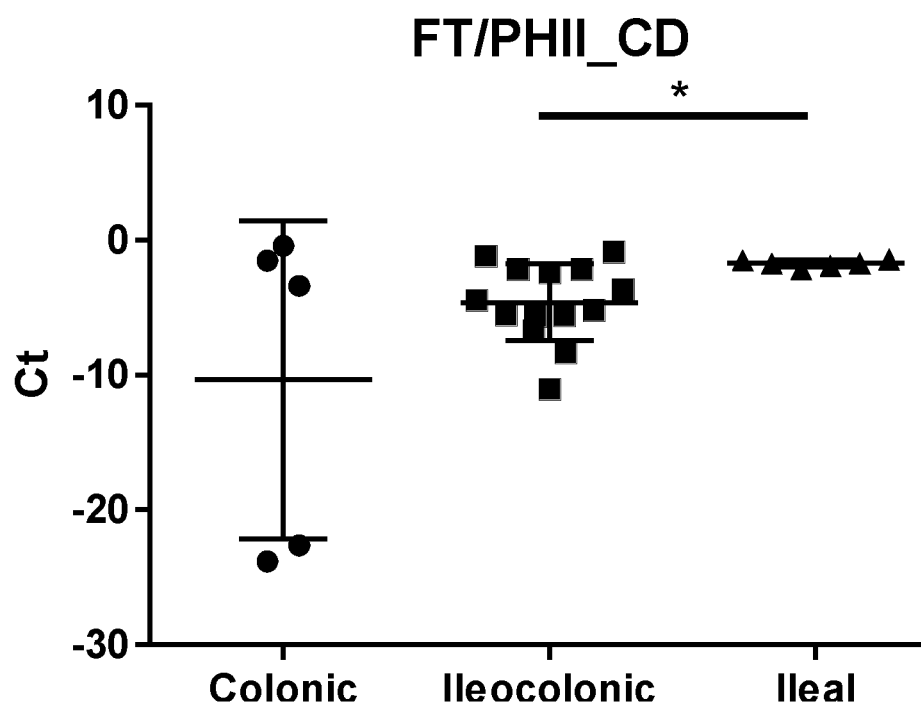

Ratios within the markers were also compared by the different locations studied. FT/PHGI and PHGI/EC showed significant differences when comparing colonic and ileocolonic locations, whereas FT/PHGII showed significant differences between colonic and ileal locations (Table 47, FIG. 13).

TABLE 47

Bacterial abundances represented by ratio of different bacterial markers (expressed in Ct)

|  | FT/EC | PHGI/PHGII | PHGI/EC | PHGII/EC | FT/PHGI | FT/PHGII |
|---|---|---|---|---|---|---|
| Colonic-CD | −3.23 ± 6.24 | 8.89 ± 11.31 | 16.01 ± 13.69 | 7.12 ± 15.94 | −19.25 ± 7.74 | −10.35 ± 11.80 |
| Ileocolonic-CD | −7.10 ± 4.99 | 2.47 ± 9.45 | −0.02 ± 12.29 | −2.49 ± 6.59 | −7.07 ± 9.15 | −4.60 ± 2.86 |
| Ileal-CD | −7.08 ± 2.75 | 7.90 ± 8.35 | 2.54 ± 8.85 | −5.36 ± 2.77 | −9.62 ± 8.14 | −1.72 ± 0.27 |
| p-value C-CD vs IC-CD | 0.420 | 0.635 | 0.05* | 0.128 | 0.040* | 0.171 |
| IC-CD vs I-CD | 1.00 | 0.775 | 1.00 | 1.00 | 1.00 | 0.882 |
| C-CD vs I-CD | 0.609 | 1.00 | 0.223 | 0.076 | 0.242 | 0.005* |

*p-value < 0.05
**p-value < 0.01
***p-value < 0.001

Example 16.2 Usefulness

ROC curve analysis was performed to test the putative accuracy of fecal *F. prausnitzii* total, its phylogroups and *E. coli* abundance as well as the ratios thereof as indicators to differentiate between different disease locations.

Ileal Location in CD Patients

Figure 14:
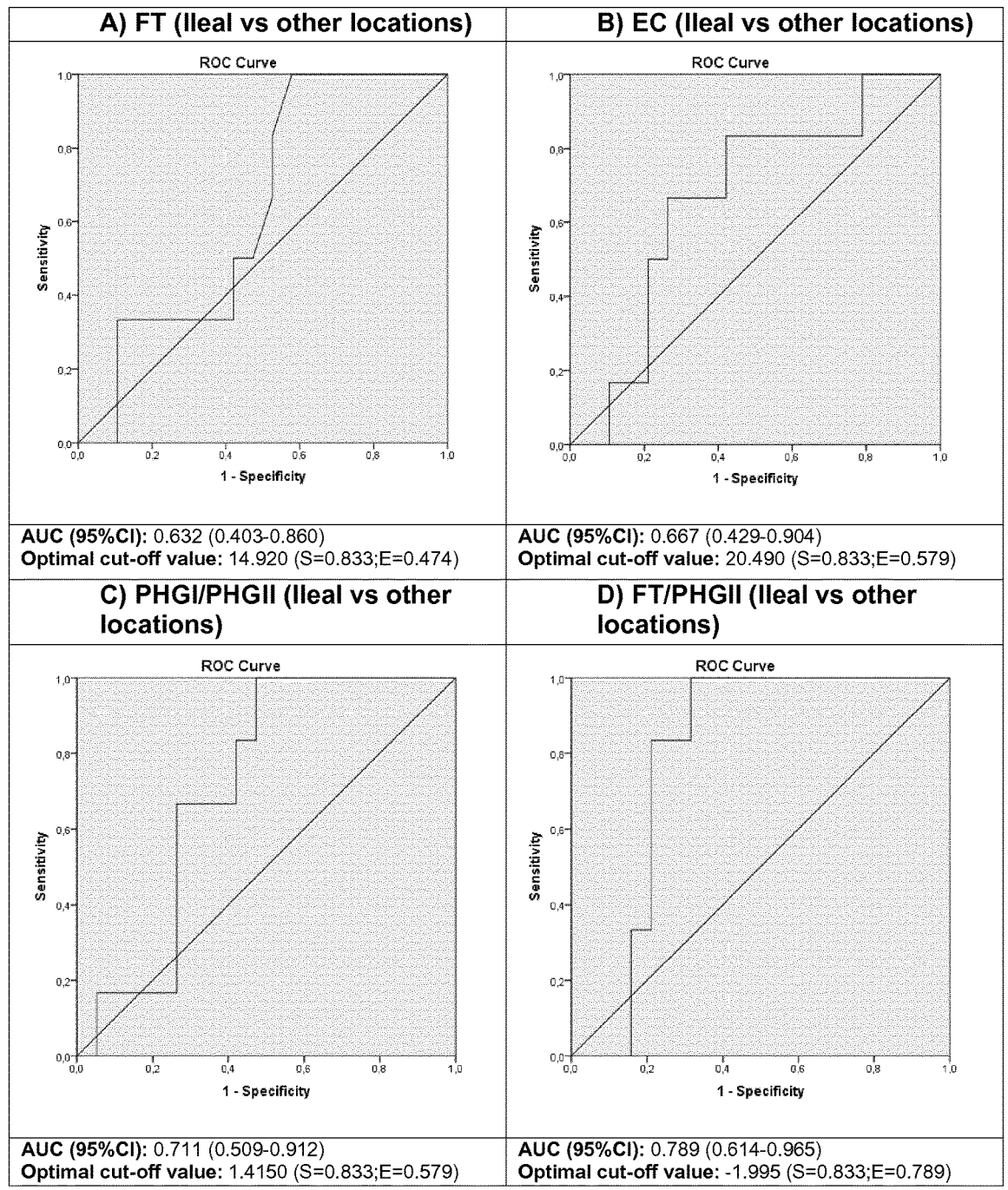
FIG. 14. Graphs representing ROC curve analysis of faecal Total *F. prausnitzii* (FT), phylogroups (PHGI and PHGII) and *E. coli* (EC) in ileal location in Crohn's Disease (CD) patients.

As we can observe in FIG. 14, four markers were confirmed as good discriminators for ileal location in CD patients, with AUC between 0.632 and 0.789. More specifically, Total *F. prausnitzii* (AUC:0.632, with an 83.3 of sensitivity and 47.4 of specificity, FIG. 14A), *E. coli* (AUC: 0.667, with an 83.3 of sensitivity and 57.9 of specificity, FIG. 14B), PHGI/PHGII (AUC:0.711, with an 83.3 of sensitivity and 57.9 of specificity, FIG. 14C) and FT/PHGII (AUC:0.789, with an 83.3 of sensitivity and 78.9 of specificity, FIG. 14D).

Ileocolonic Location in CD Patients

Figure 15:
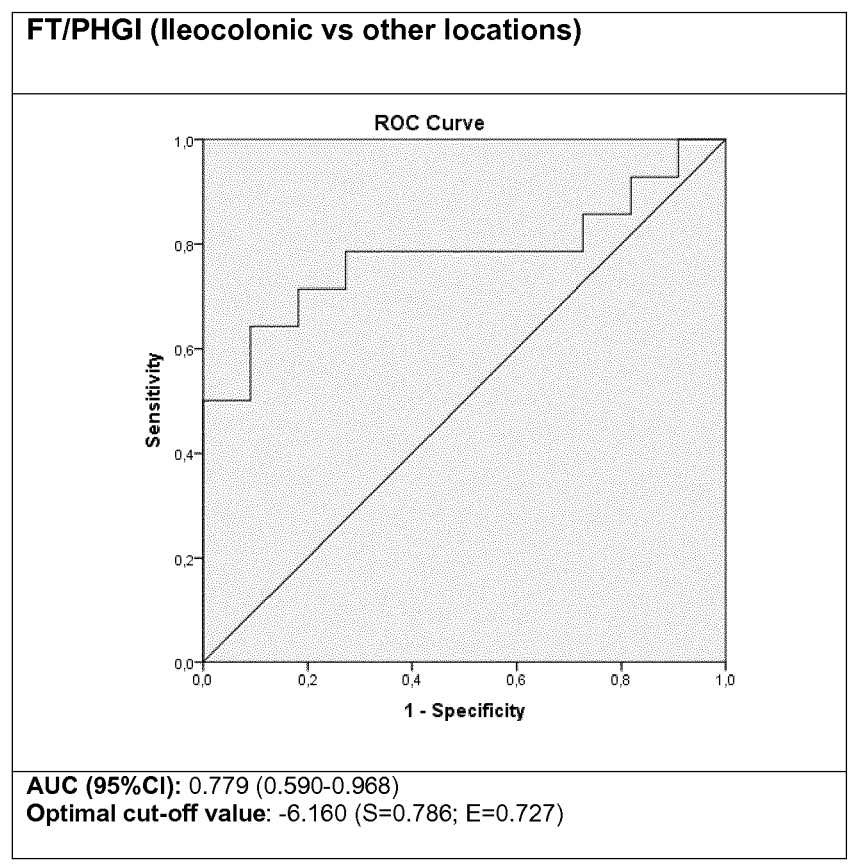
FIG. 15. Graph representing ROC curve analysis of fecal Total *F. prausnitzii* (FT), and phylogroup I (PHGI) in ileocolonic location in Crohn's Disease (CD) patients.

Regarding to ileocolonic location, just one marker was confirmed as good discriminator, FT/PHGI with and AUC of 0.779, a sensitivity of 78.6 and a specificity of 72.7 (FIG. 15).

Colonic Location in CD Patients

Figure 16:
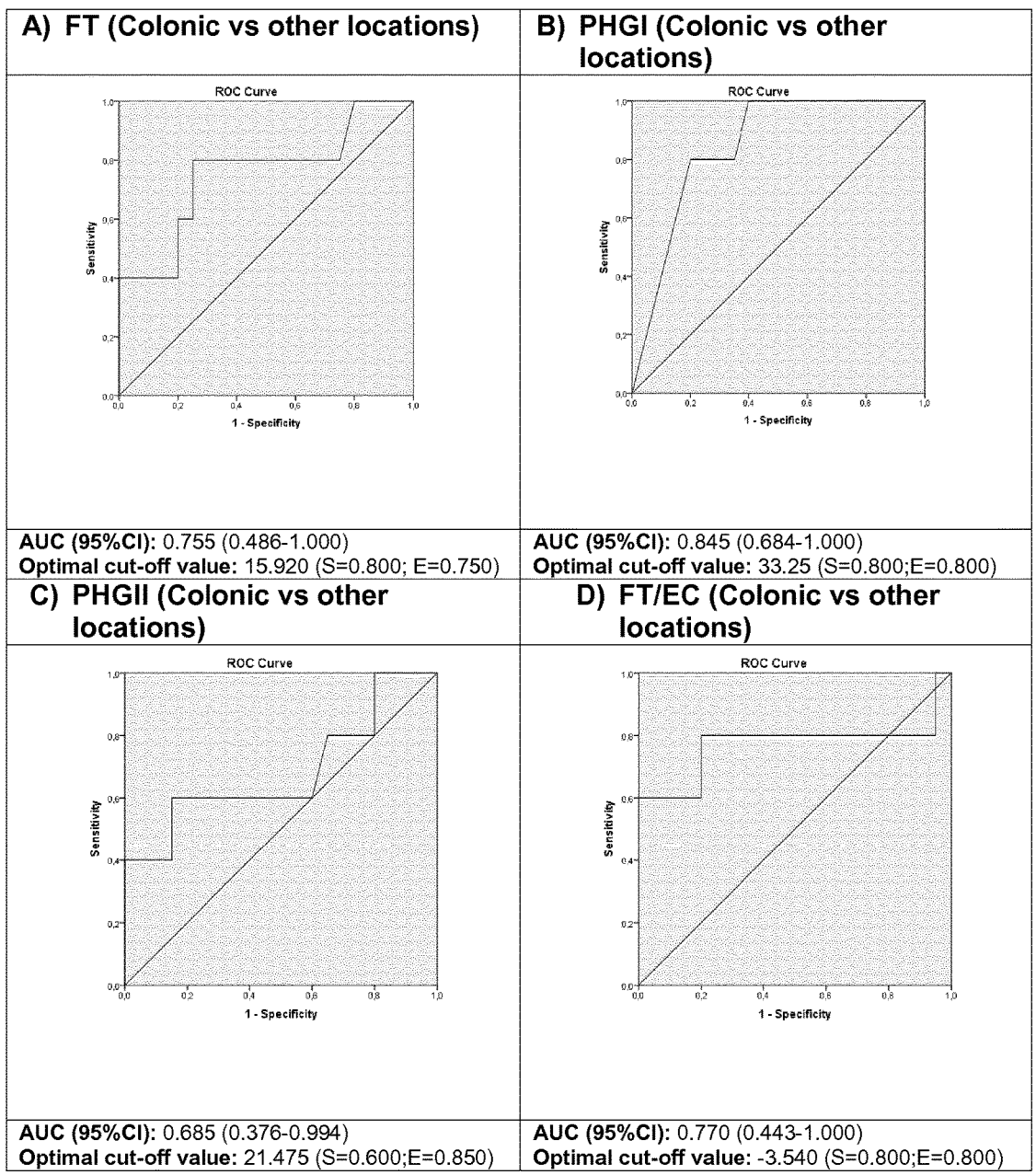
FIG. 16. Graphs representing ROC curve analysis of faecal Total *F. prausnitzii* (FT) and phylogroups (PHGI and PHGII) in colonic location in Crohn's Disease (CD) patients.
Figure 16:
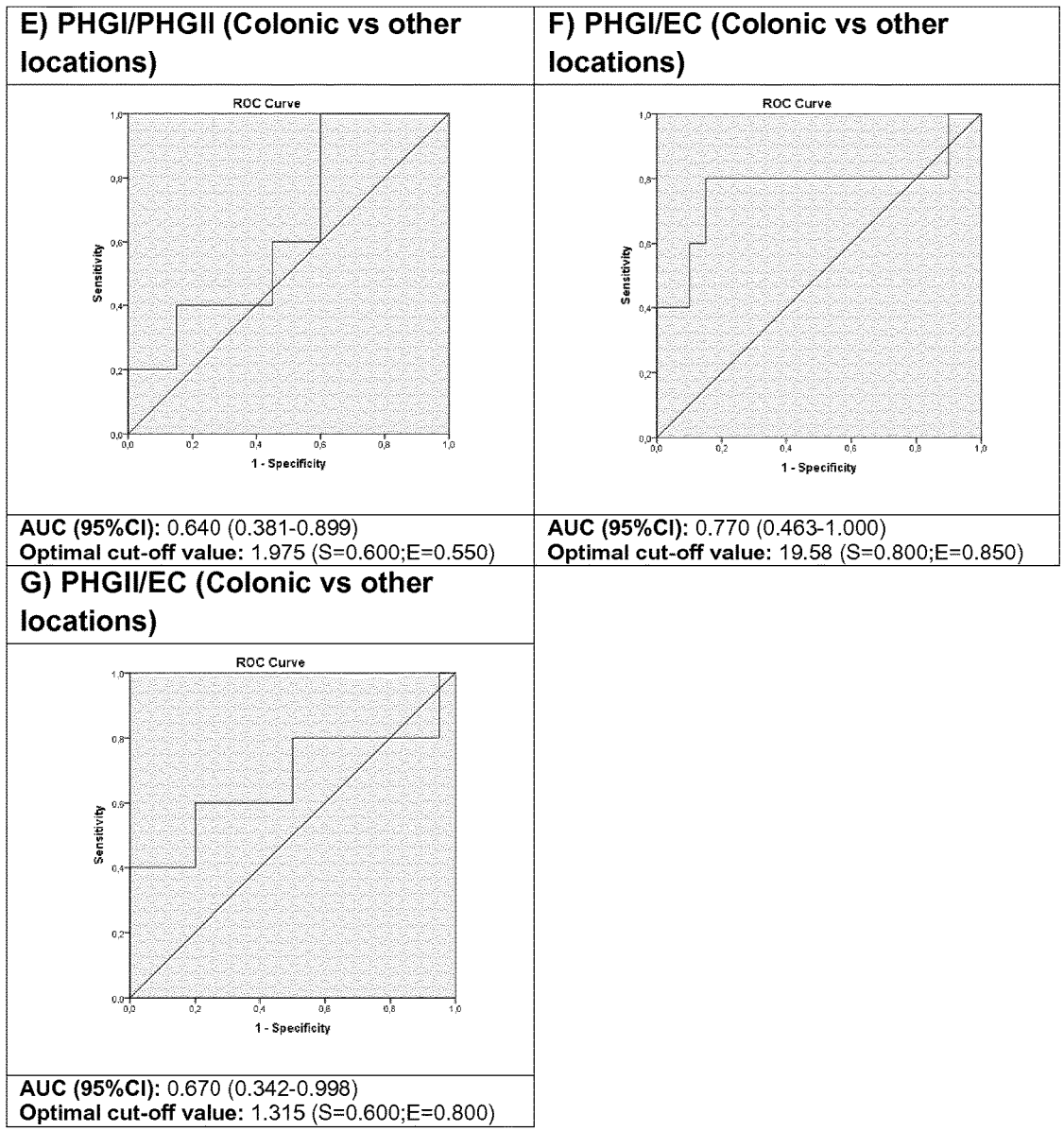

Finally, for colonic location in CD patients, seven markers were confirmed as good discriminators (FIG. 16). More specifically, Total *F. prausnitzii* (AUC:0.755, with an 80.0 of sensitivity and 75.0 of specificity, FIG. 16A), PHGI (AUC: 0.845, with an 80.0 of sensitivity and 80.0 of specificity, FIG. 16B), PHGII (AUC:0.685, with an 60.0 of sensitivity and 85.0 of specificity, FIG. 16C), FT/EC (AUC:0.770, with an 80.0 of sensitivity and 80.0 of specificity, FIG. 16D), PHGI/PHGII (AUC:0.640, with an 60.0 of sensitivity and 55.0 of specificity, FIG. 16E), PHGI/EC (AUC:0.770, with an 80.0 of sensitivity and 85.0 of specificity, FIG. 16F) and PHGII/EC (AUC:0.670, with an 60.0 of sensitivity and 80.0 of specificity, FIG. 16G).

Example 17

Abundance of Total *F. Prausnitzii*, Phylogroups and *E. Coli* in C-CD and UC and its Usefulness as Biomarkers for Differential Diagnosis Between C-CD and UC Differential diagnose between colonic CD and UC is relevant in clinical practice. We have thus compared the bacterial markers and ratios between these two groups. Lower abundance for *F. prausnitzii* phylogroup I and II and *E. coli* is observed in CD patients with colonic lesion when compared to UC patients (Table 48). With regards to the ratios, PHGI/EC, PHGII/EC and FT/PHGI show significant differences between these two groups (Table 49).

TABLE 48

Abundance of fecal Total *Faecalibacterium prausnitzii* (FT), phylogroup I (PHGI), phylogroup II (PHGII) and *Escherichia coli* (EC) in colonic CD location and UC patients.

|  | FT | PHGI | PHGII | Ecoli |
|---|---|---|---|---|
| Colonic-CD | 16.7 ± 2.08 | 36.01 ± 8.91 | 27.12 ± 11.90 | 20.0 ± 5.07 |
| UC | 16.3 ± 4.78 | 21.84 ± 8.27 | 18.83 ± 5.22 | 24.68 ± 4.45 |
| p-value | 0.724 | 0.020* | 0.054* | 0.048* |

TABLE 49

Bacterial abundances represented by ratio of different bacterial markers (expressed in Ct).

|  | FT/EC | PHGI/PHGII | PHGI/EC | PHGII/EC | FT/PHGI | FT/PHGII |
|---|---|---|---|---|---|---|
| Colonic-CD | −3.23 ± 6.23 | 8.89 ± 11.31 | 16.01 ± 13.69 | 7.12 ± 15.94 | −19.24 ± 7.74 | −10.35 ± 11.79 |
| UC | −8.38 ± 7.66 | 3.01 ± 7.53 | −2.83 ± 10.29 | −5.85 ± 8.09 | −5.54 ± 6.62 | −2.59 ± 1.82 |
| p-value | 0.069 | 0.369 | 0.08* | 0.043* | 0.013* | 0.345 |

Figure 17:
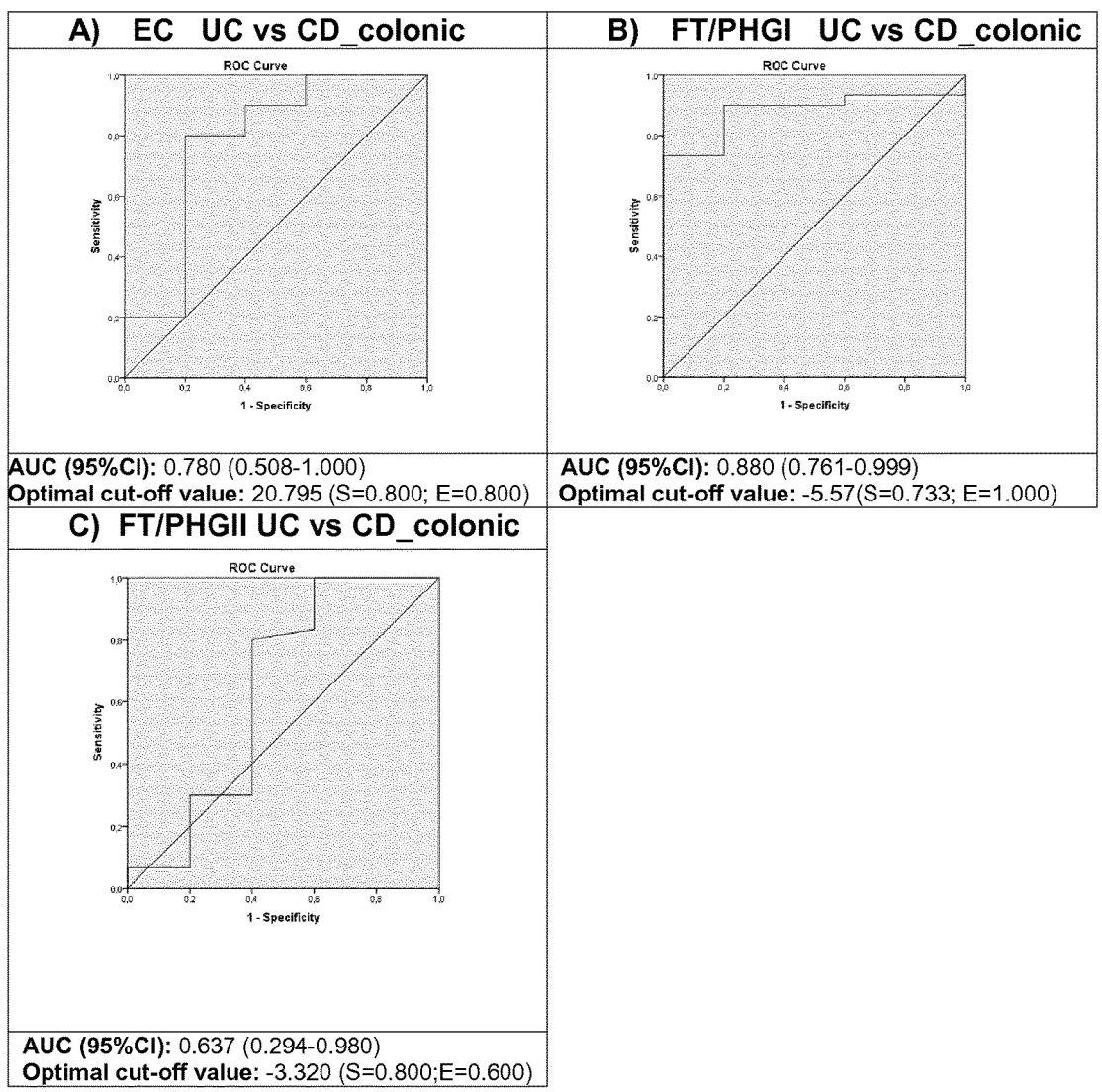
FIG. 17. Graphs representing ROC curve analysis of bacterial markers and ratios to discriminate UC patients.

ROC curve analysis was performed to test the putative accuracy of fecal *F. prausnitzii* total, its phylogroups and *E. coli* abundance and its ratios as indicators to differentiate between CD patients with colonic lesions and UC patients. As we can observe in FIG. 17, three markers were confirmed as good discriminators for UC, with AUC between 0.637 and 0.880. More specifically, *E. coli* (AUC:0.780, with an 80 of sensitivity and 80 of specificity, FIG. 17A), FT/PHGI (AUC:0.880, with an 73.3 of sensitivity and 100 of specificity, FIG. 17B), FT/PHGII (AUC:0.637, with an 80 of sensitivity and 60 of specificity, FIG. 17C).

Figure 18:
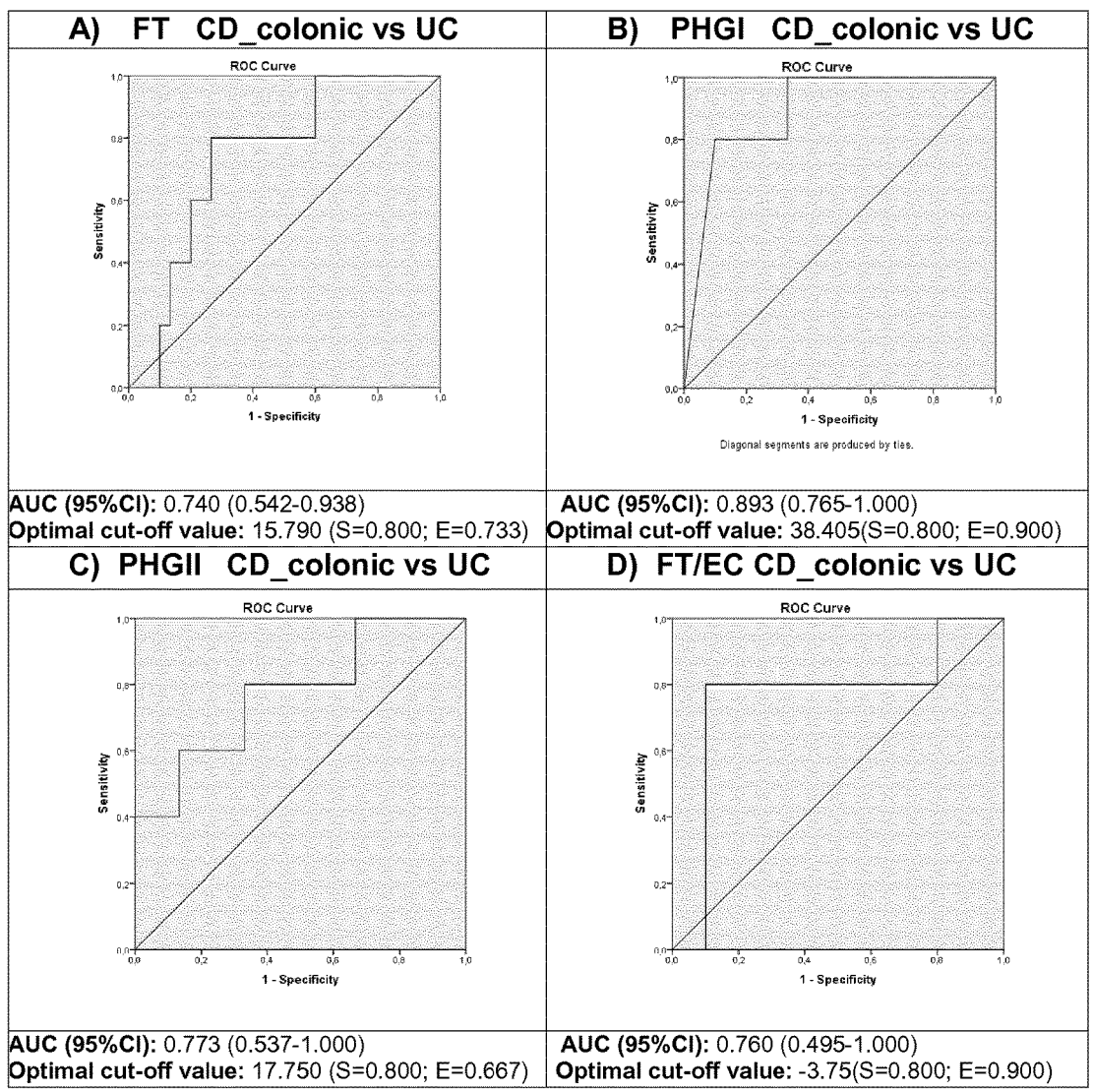
FIG. 18. Graphs representing ROC curve analysis of bacterial markers and ratios in colonic location in Crohn's Disease (CD) patients.
Figure 18:
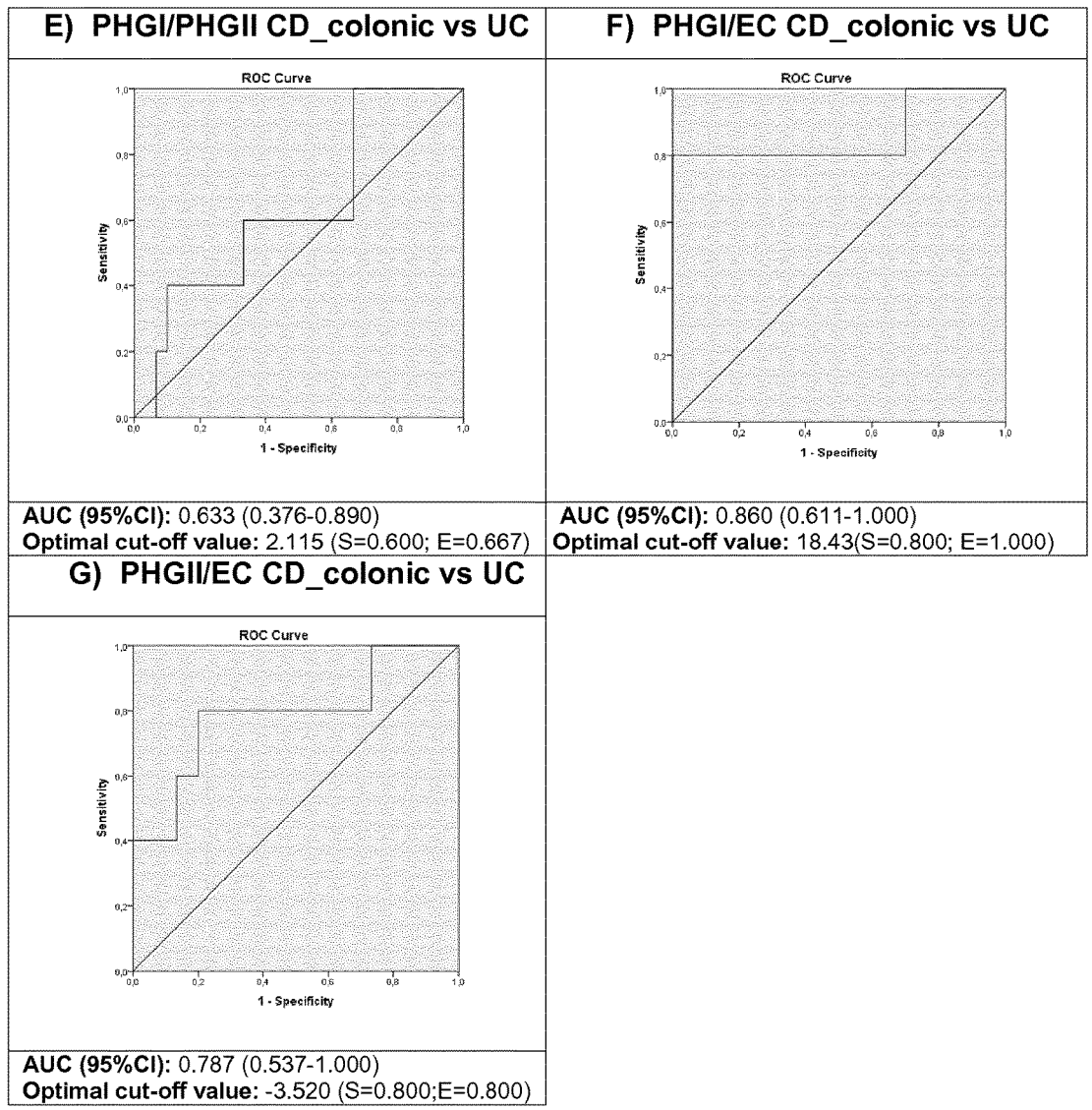

To discriminate colonic location CD patients seven markers were relevant: FT (AUC:0.740, with an 80 of sensitivity and 73.3 of specificity, FIG. 18A), PHGI (AUC:0.83, with an 80 of sensitivity and 90 of specificity, FIG. 18B), PHGII (AUC:0.773, with an 80 of sensitivity and 66.7 of specificity, FIG. 18C), FT/EC (AUC:0.760, with an 80 of sensitivity and 90 of specificity, FIG. 18D), PHGI/PHGII (AUC:0.663, with an 60 of sensitivity and 66.7 of specificity, FIG. 18E), PHGI/EC (AUC:0.860, with an 80 of sensitivity and 100 of specificity, FIG. 18F), PHGII/EC (AUC:0.787, with an 80 of sensitivity and 80 of specificity, FIG. 18G).

In conclusion, the best markers for differential diagnose between UC and colonic lesion in CD patients are: EC, PHGI, FT/PHGI, PHGI/EC and PHGII/EC.

Example 18

Figure 19:
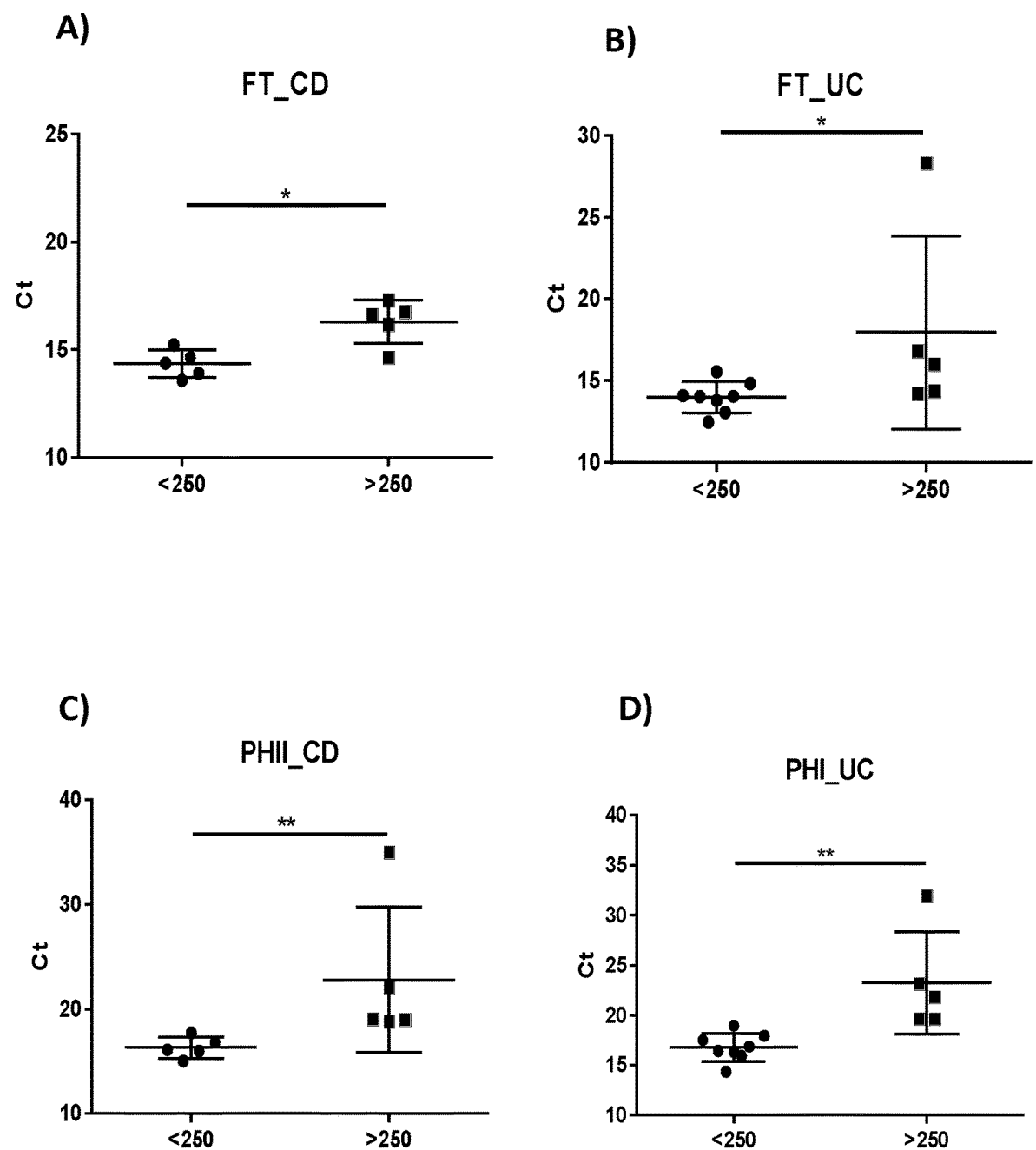
FIG. 19. Total *Faecalibacterium prausnitzii* (FT), phylogroup I (PHI) and phylogroup II (PHII) in CD and UC patients between different ranges of calprotectin.

Bacterial Biomarkers Abundance and its Usefulness in Determining Disease Activity in Crohn Disease and Ulcerative Colitis Example 18.1 Abundance The abundance of the biomarkers from fecal samples was compared in CD and UC patients according to whether or not calprotectin values were lower or greater than 250 µg/g. Calprotectin concentration is as a non-invasive marker of inflammation of the intestinal mucosa that it is usually used as reference marker for the determination of IBD disease activity, namely values of calprotectin greater than 250 µg/g have been regarded as a sign of high level of inflammatory response (Table 50). Total *F. prausnitzii* and phylogroups load was significantly reduced in the group with calprotectin levels over 250 µg/g, however, while FT was reduced in both CD and UC (FIGS. 19A and 19B), PHGII abundance was just reduced in CD patients (FIG. 19C) and PHGI in UC patients (FIG. 19D). Moreover, *E. coli* abundance did not show significant differences.

In conclusion, total *F. prausnitzii* has been found to be a marker of active disease (i.e., associated with calprotectin values of over 250 µg/g). Furthermore, interestingly, while PHGI appears to be a marker exclusive for active UC, PHGII has been found to be a marker exclusive for active CD.

TABLE 50

Abundance of faecal Total *Faecalibacterium prausnitzii* (FT), phylogroup I (PHGI), phylogroup II (PHGII) and *Escherichia coli* (EC) in CD and UC patients between different ranges of calprotectin

|  | Group | Condition(µg/g calprotectin) | FT | PHGI | PHGII | EC |
|---|---|---|---|---|---|---|
| Mean | CD | <250 | 14.35 ± 0.64 | 18.60 ± 2.04 | 16.32 ± 1.03 | 25.92 ± 5.55 |
|  |  | >250 | 16.29 ± 1.00 | 27.25 ± 9.81 | 22.81 ± 6.95 | 20.88 ± 4.00 |
|  | UC | <250 | 13.99 ± 0.96 | 16.79 ± 1.41 | 16.86 ± 0.91 | 28.51 ± 4.90 |
|  |  | >250 | 17.95 ± 5.90 | 23.26 ± 5.09 | 20.26 ± 6.07 | 25.31 ± 5.73 |
| p-value | CD | <250->250 | 0.024* | 0.595 | 0.008* | 0.222 |
|  | UC | <250->250 | 0.019* | 0.002* | 0.284 | 0.333 |

Figure 20:
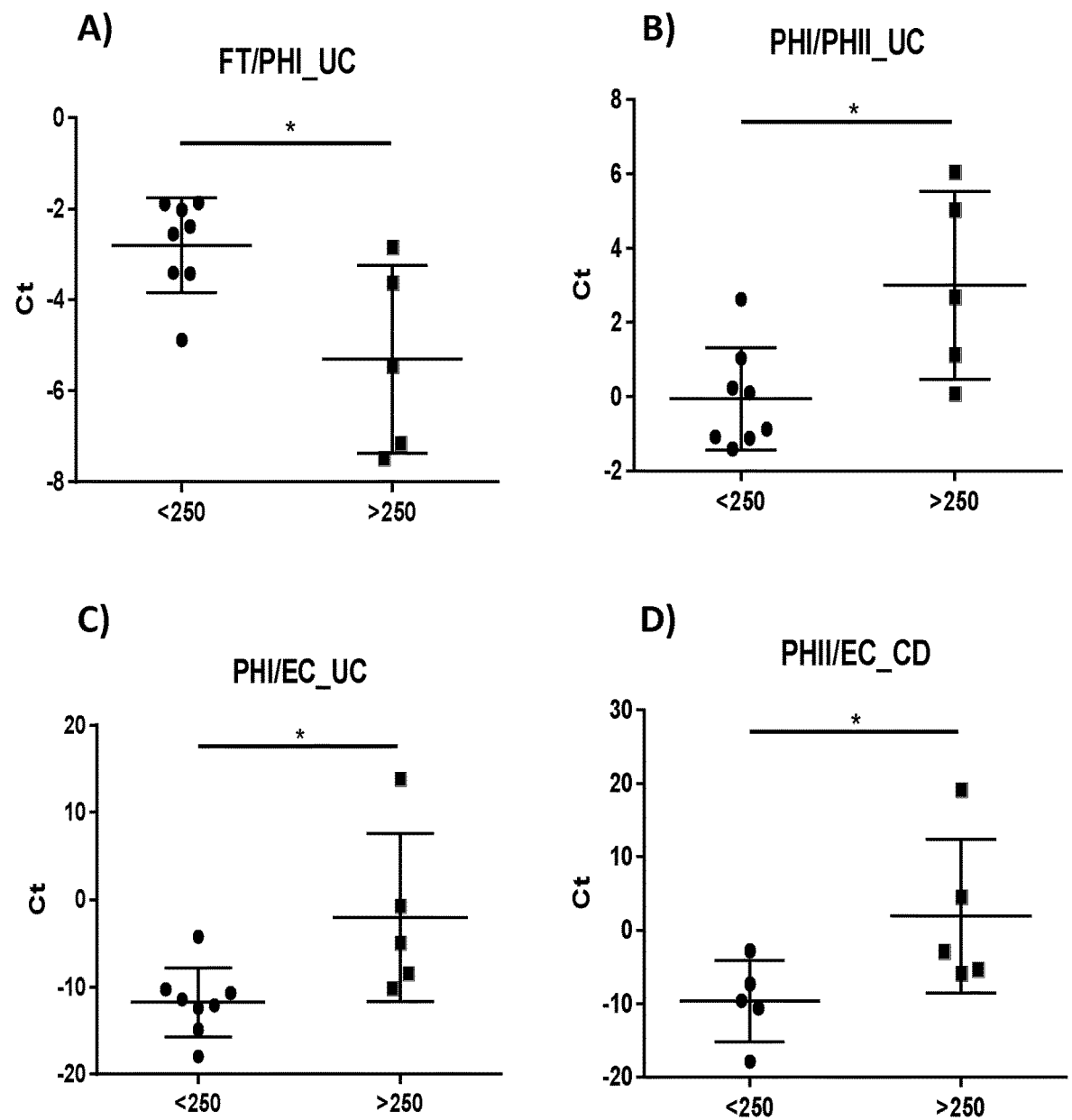
FIG. 20. Graphs of ratios FT/PHI, PHI/PHII, PHI/EC and PHII/EC in CD and UC patients between calprotectin over or under 250 µg/g.

Ratios, FT/EC, FT/PHGI, FT/PHGII, PHGI/PHGII, PHGI/EC and PHGII/EC were also compared in CD and UC patients according to calprotectin values (Table 51). Regarding CD patients just the ratio PHGII/EC showed a trend to increase significantly (FIG. 20D), while in UC patients, three markers were significantly represented, FT/PHGI (FIG. 20A), PHGI/PHGII (FIG. 20B) and PHGI/EC (FIG. 20C). These data are in agreement with the above results, studying the markers independently, where active CD disease was represented by PHGII and active UC was represented by PHGI.

TABLE 51

Ratios of FT/EC, FT/PHGI, FT/PHGII, PHGI/EC and PHGII/EC in CD and UC patients between calprotectin over or under 250 µg/g

| | Group | Condition | FT/EC | FT/PHGI | FT/PHGII | PHGI/PHGII | PHGI/EC | PHGII/EC |
|---|---|---|---|---|---|---|---|---|
| Mean | CD | <250 | −11.58 ± 6.12 | −4.25 ± 1.91 | −1.97 ± 1.03 | 2.27 ± 2.31 | −7.33 ± 6.90 | −9.60 ± 5.50 |
| | | >250 | −4.59 ± 4.24 | −2.95 ± 12.7 | −6.51 ± 7.06 | −3.56 ± 10.6 | −1.64 ± 13.36 | 1.92 ± 10.4 |
| | UC | <250 | −14.52 ± 4.22 | −2.80 ± 1.05 | −2.87 ± 1.09 | −0.07 ± 1.37 | −11.72 ± 3.93 | −11.65 ± 4.32 |
| | | >250 | −7.36 ± 10.6 | −5.31 ± 2.07 | −2.31 ± 0.56 | 3.00 ± 2.53 | −2.06 ± 9.60 | −5.05 ± 10.7 |
| p-value | CD | <250->250 | 0.095 | 0.841 | 0.222 | 0.309 | 0.548 | 0.056* |
| | UC | <250->250 | 0.222 | 0.019* | 0.222 | 0.029* | 0.011* | 0.284 |

Moreover, correlations between calprotectin concentration and the different markers and its ratios in CD and UC patients were studied by a Spearman Correlation. As was expected, FT was positively correlated with calprotectin concentration both in CD and UC, furthermore, while PHGI was also positively correlated with fecal calprotectin in UC patients, PHGII showed a positive tendency to correlate in CD (Table 52). As far as ratios is concerned, only trends were observed (Table 52).

TABLE 52

Spearman correlation between calprotectin concentration and abundance and ratios of faecal Total *Faecalibacterium prausnitzii* (FT), phylogroup I (PHGI), phylogroup II (PHGII) and *Escherichia coli* (EC) in CD and UC patients

| Patients | N = 10 | FT | PHGI | PHGII | EC |
|---|---|---|---|---|---|
| CD | Coef correlation | 0.659 | 0.375 | 0.620 | −0.401 |
| | p-value | 0.038* | 0.286 | 0.056* | 0.250 |

| | RATIOS | FT/EC | FT/PHGI | FT/PHGII | PHGI/PHGII | PHGI/EC | PHGII/EC |
|---|---|---|---|---|---|---|---|
| | Coef correlation | 0.474 | −0.207 | −0.122 | −0.128 | 0.407 | 0.584 |
| | p-value | 0.166 | 0.567 | 0.738 | 0.725 | 0.243 | 0.077 |

| Patients | N = 13 | FT | PHGI | PHGII | EC |
|---|---|---|---|---|---|
| UC | Coef correlation | 0.586 | 0.667 | 0.210 | −0.238 |
| | p-value | 0.035* | 0.013* | 0.491 | 0.434 |

| | RATIOS | FT/EC | FT/PHGI | FT/PHGII | PHGI/PHGII | PHGI/EC | PHGII/EC |
|---|---|---|---|---|---|---|---|
| | Coef correlation | 0.309 | −0.514 | 0.409 | 0.541 | 0.536 | 0.287 |
| | p-value | 0.304 | 0.072 | 0.165 | 0.056 | 0.059 | 0.341 |

Example 18.2 Usefulness

Afterwards, ROC curve analysis was performed to test the putative accuracy of fecal *F. prausnitzii* total, its phylogroups, *E. coli* abundance and their ratios as indicators to differentiate between calprotectin levels under and over 250 µg/g.

Figure 21:
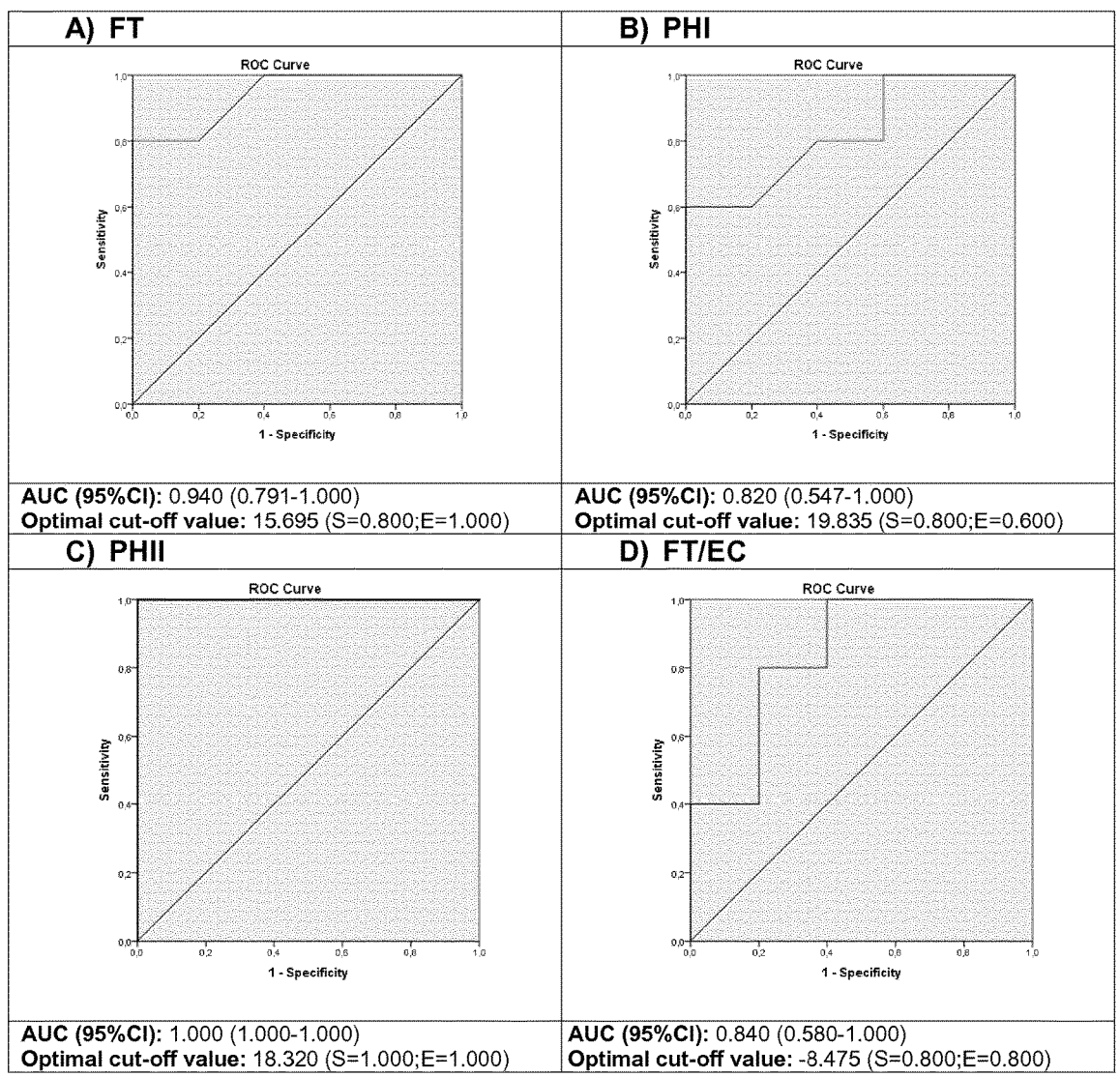
FIG. 21. Graphs of ROC curve analysis in CD patients with calprotectin values over 250 µg/g.
Figure 21:
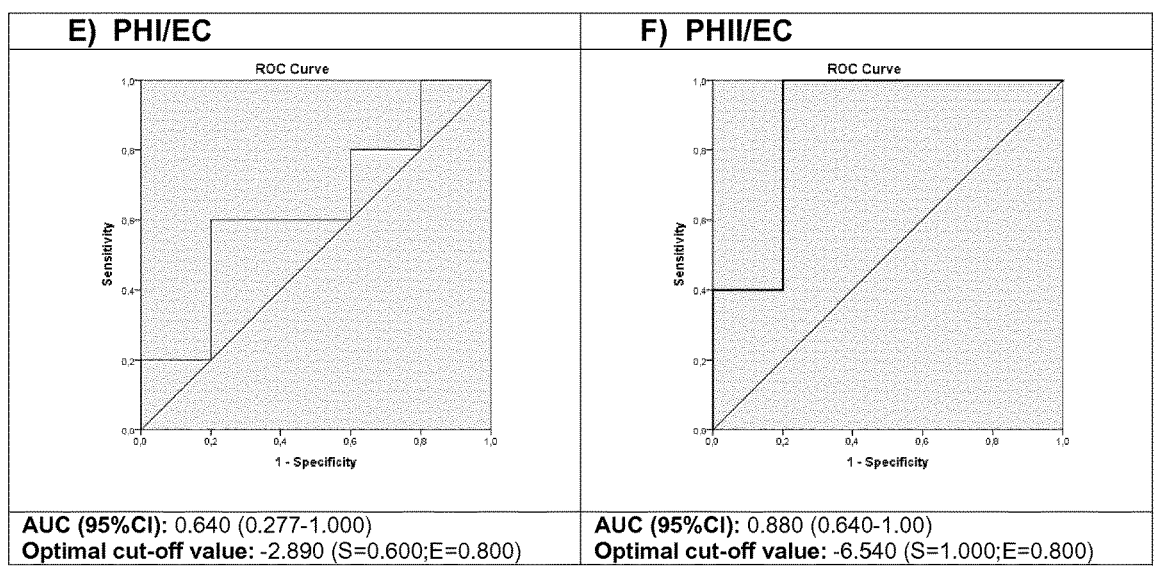

Different markers were confirmed as good discriminators for CD disease (FIG. 21), more concretely: Total *F. prausnitzii* (AUC:0.940, with an 80 of sensitivity and 100 of specificity, FIG. 21A), *F. prausnitizii* phylogroup I (AUC: 0.820 with an 80 of sensitivity and 60 of specificity, FIG. 21B), *F. prausnitizii* phylogroup II (AUC:1.000 with an 100 of sensitivity and 100 of specificity, FIG. 21C), FT/EC (AUC:0.840 with an 80 of sensitivity and 80 of specificity, FIG. 21D), PHGI/EC (AUC:0.640 with an 60 of sensitivity and 80 of specificity, FIG. 21E) and PHGII/EC (AUC:0.880 with an 100 of sensitivity and 80 of specificity, FIG. 21F).

Figure 22:
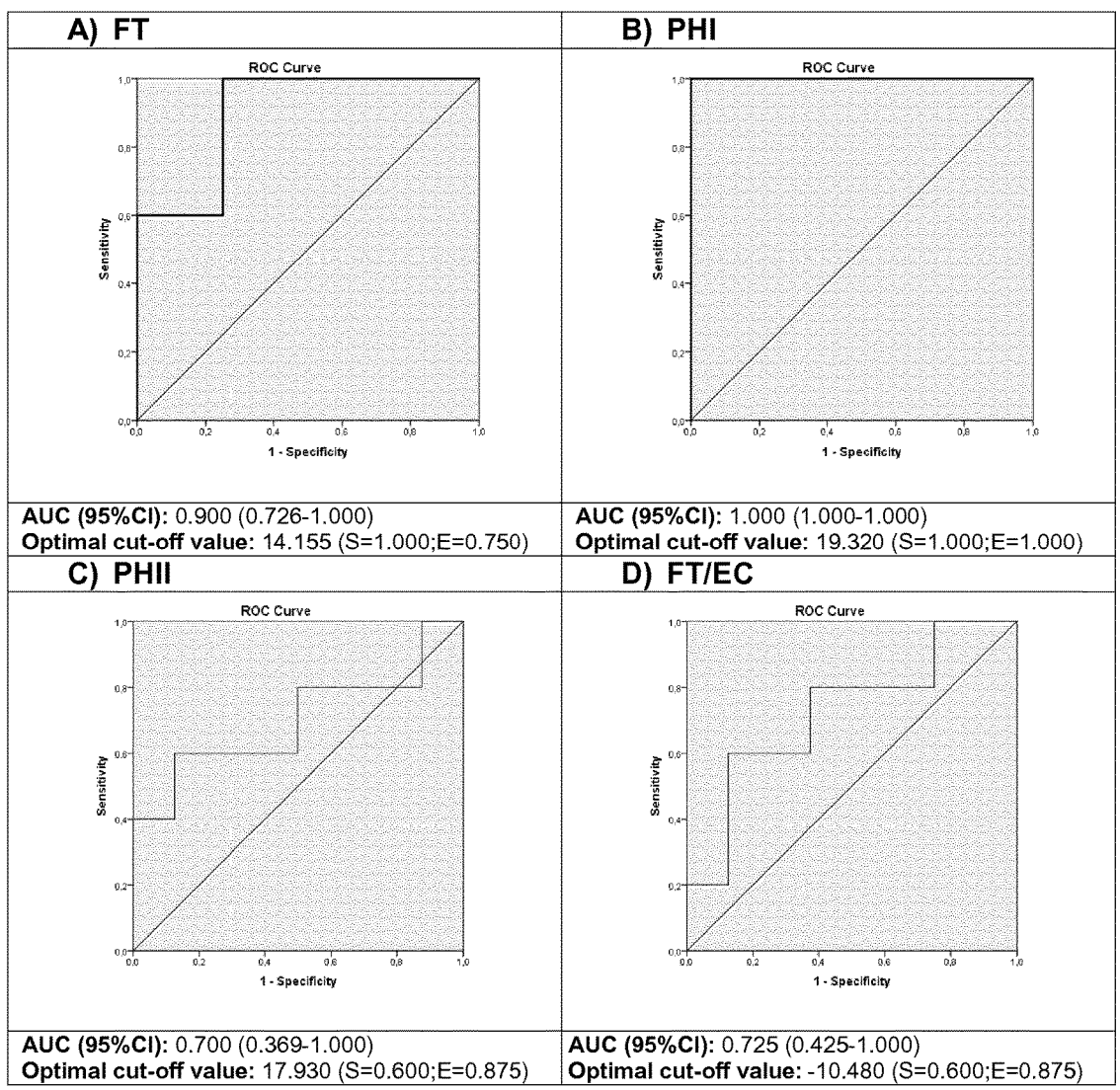
FIG. 22. Graphs of ROC curve analysis in UC patients with calprotectin values over 250 µg/g.
Figure 22:
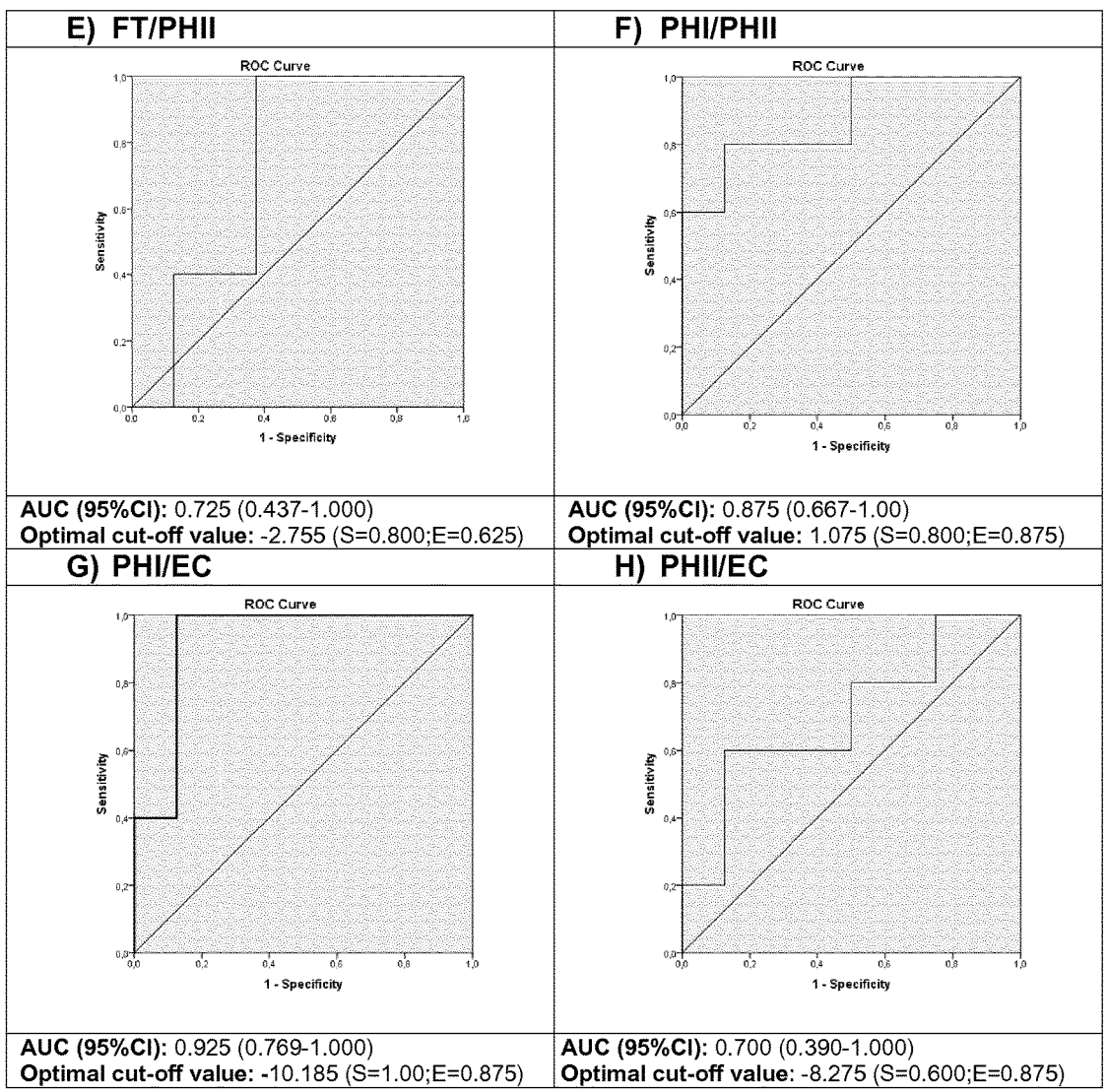

Furthermore, as regards to UC, several markers were validated as good discriminators (FIG. 22): Total *F. prausnitzii* (AUC:0.900, with an 100 of sensitivity and 75 of specificity, FIG. 22A), *F. prausnitizii* phylogroup I (AUC: 1.000 with an 100 of sensitivity and 100 of specificity, FIG. 22B), *F. prausnitizii* phylogroup II (AUC:0.700 with an 60 of sensitivity and 87.5 of specificity, FIG. 22C), FT/EC (AUC:0.725 with an 60 of sensitivity and 87.5 of specificity, FIG. 22D), FT/PHGII (AUC:0.725 with an 80 of sensitivity and 62.5 of specificity, FIG. 22E), PHGI/PHGII (AUC: 0.825 with an 80 of sensitivity and 87.5 of specificity, FIG. 22F), PHGI/EC (AUC:0.925 with an 100 of sensitivity and 87.5 of specificity, FIG. 22G) and PHGII/EC (AUC:0.700 with an 60 of sensitivity and 807.5 of specificity, FIG. 22H).

It is important to emphasize, that although some of the markers are common discriminators for both diseases, PHII for CD and PHI for UC disease appear to be perfect discriminators for calprotectin levels over 250 µg/g, being the AUC of 1.000 and both the sensitivity and specificity of 100% (FIGS. 21C and 22B, respectively).

Example 19

Bacterial Biomarkers Abundance and its Usefulness for Disease Monitoring in Crohn's Disease and Ulcerative Colitis Patients Fecal samples were collected from 8 Crohn's disease (CD) patients and 7 Ulcerative colitis (UC) patients (with more than 6 months of diagnose) at two different time points in clinical practice checkups (T0 and T1). Disease activity was defined in terms of inflammatory response and the inflammatory activity was followed up in both groups of patients by measuring the concentration of fecal calprotectin. Levels of fecal calprotectin above 250 μg/g were considered as high level of inflammatory response and levels under 250 μg/g were considered as a non-inflammatory response.

For each of these groups of patients, two subgroups were defined only considering its calprotectin measures independently of the treatment:

(+) Increased inflammatory activity: patients with an increase of fecal calprotectin levels over 250 μg/g between the two-time point samples.

(−) Decreased inflammatory activity: patients with a decreased of fecal calprotectin levels under 250 μg/g between the two-time point samples.

Abundances of Total *Faecalibacterium prausnitzii* (FT), phylogroup I (PHGI), phylogroup II (PHGII) and *Escherichia coli* (EC) were analyzed in the two-time point samples and compared according to its inflammatory activity evolution.

In CD patients with different inflammatory activity evolution, non-statistical differences were observed in bacterial markers abundances (Table 53) and ratios (Table 54).

In contrast, UC presented statistically significant differences for FT and PHGI (Table 55) were observed. The abundances of these two markers were significantly reduced in patients presenting an increase of inflammatory activity during the monitoring period. Similarly, ratio FT/PHGI also presented significant differences in UC patients with an evolution of increased inflammatory activity (Table 56).

In order to test the correlation between two-time point samples (Table 57), both Pearson and Spearman correlation test were performed. Significant correlation was detected in UC patients for FT and a tendency was observed in PHGII/EC.

In conclusion, determination of bacterial markers abundance and its ratios can be relevant for the follow up of UC patients, especially FT, PHGI and FT/PHGI.

TABLE 53

Abundances of bacterial markers in two-time point sample (T0 and T1) in Crohn's disease patients (CD) with different inflammatory evolution according calprotectin measure: increased inflammatory activity (+) and decreased inflammatory activity (−).

| Calprotectin | FT T0 | FT T1 | PHGI T0 | PHGI T1 | PHGII T0 | PHGII T1 | EC T0 | EC T1 |
|---|---|---|---|---|---|---|---|---|
| + | 16.60 | 15.91 | 40.00 | 40.00 | 22.07 | 21.46 | 17.57 | 19.13 |
|   | 16.75 | 14.15 | 20.07 | 15.64 | 18.88 | 16.25 | 21.72 | 22.97 |
| Average | 16.67 ± 0.10 | 15.03 ± 1.24 | 30.04 ± 14.1 | 27.82 ± 17.22 | 20.47 ± 2.25 | 18.86 ± 3.68 | 19.64 ± 2.93 | 21.05 ± 2.71 |
| P-Value | 0.180 | | ns | | 0.180 | | 0.180 | |
| − | 16.17 | 17.40 | 40.00 | 40.00 | 40.00 | 40.00 | 15.91 | 16.18 |
|   | 14.38 | 13.72 | 15.86 | 15.60 | 22.66 | 19.31 | 24.03 | 20.30 |
|   | 17.30 | 16.81 | 23.87 | 25.92 | 19.01 | 18.49 | 25.08 | 24.83 |
|   | 14.17 | 15.22 | 19.92 | 19.60 | 15.31 | 16.08 | 24.97 | 18.85 |
|   | 14.53 | 13.58 | 16.57 | 15.81 | 18.19 | 15.96 | 24.92 | 33.82 |
|   | 19.96 | 14.38 | 40.00 | 20.07 | 21.49 | 17.76 | 20.16 | 28.31 |
| Average | 16.09 ± 2.25 | 15.19 ± 1.61 | 26.04 ± 11.18 | 22.83 ± 9.21 | 22.78 ± 8.82 | 21.27 ± 9.27 | 22.51 ± 3.74 | 23.72 ± 6.58 |
| P-Value | ns | | ns | | 0.138 | | ns | |

TABLE 54

Ratios of bacterial markers in two-time point sample (T0 and T1) in Crohn's disease patients (UC) with different inflammatory evolution according calprotectin measure: increased inflammatory activity (+) and decreased inflammatory activity (−).

| Calprotectin | FT/EC T0 | FT/EC T1 | FT/PHGI T0 | FT/PHGI T1 | FT/PHGII T0 | FT/PHGII T1 |
|---|---|---|---|---|---|---|
| + | −0.97 | −3.22 | −23.40 | −24.09 | −5.47 | −5.55 |
|   | −4.97 | −8.82 | −3.32 | −1.49 | −2.13 | −2.10 |
| Average | −2.97 ± 2.82 | −6.02 ± 3.95 | −13.36 ± 14.1 | −12.79 ± 15.98 | −3.80 ± 2.36 | −3.83 ± 2.43 |
| P-Value | 0.180 | | ns | | ns | |
| − | 0.26 | 1.22 | −23.83 | −22.60 | −23.83 | −22.60 |
|   | −9.65 | −6.58 | −1.48 | −1.88 | −8.28 | −5.59 |
|   | −7.78 | −8.02 | −6.57 | −9.11 | −1.71 | −1.68 |
|   | −10.80 | −3.63 | −5.75 | −4.38 | −1.14 | −0.86 |
|   | −10.39 | −20.24 | −2.04 | −2.23 | −3.66 | −2.38 |
|   | −0.20 | −13.93 | −20.04 | −5.69 | −1.53 | −3.38 |
| Average | −6.43 ± 5.10 | −8.53 ± 7.60 | −9.95 ± 9.56 | −7.65 ± 7.78 | −6.69 ± 8.80 | −6.08 ± 8.25 |
| P-Value | ns | | ns | | 0.250 | |

TABLE 54-continued

Ratios of bacterial markers in two-time point sample (T0 and T1) in Crohn's disease patients (UC) with different inflammatory evolution according calprotectin measure: increased inflammatory activity (+) and decreased inflammatory activity (−).

| Calprotectin | EC/PHGI | | EC/PHGII | | PHGI/PHGII | |
|---|---|---|---|---|---|---|
| | T0 | T1 | T0 | T1 | T0 | T1 |
| + | −22.43 | −20.87 | −4.50 | −2.33 | 17.93 | 18.54 |
| | 1.65 | 7.33 | 2.84 | 6.72 | 1.19 | −0.61 |
| Average | −10.39 ± 17 | −6.77 ± 19.9 | −0.83 ± 5.19 | 2.20 ± 6.39 | 9.56 ± 11.83 | 8.96 ± 13.5 |
| P-Value | 0.180 | | 0.180 | | ns | |
| − | −24.09 | −23.82 | −24.09 | −23.82 | 0.00 | 0.00 |
| | 8.17 | 4.70 | 1.37 | 0.99 | −6.80 | −3.71 |
| | 1.21 | −1.09 | 6.07 | 6.34 | 4.86 | 7.43 |
| | 5.05 | −0.75 | 9.66 | 2.77 | 4.61 | 3.52 |
| | 8.35 | 18.01 | 6.73 | 17.86 | −1.62 | −0.15 |
| | −19.84 | 8.24 | −1.33 | 10.55 | 18.51 | 2.31 |
| Average | −3.52 ± 14.6 | 0.88 ± 13.9 | −0.26 ± 12.3 | 2.45 ± 14.2 | 3.26 ± 8.6 | 1.57 ± 3.79 |
| P-Value | ns | | ns | | ns | |

TABLE 55

Abundances of bacterial markers in two-time point sample (T0 and T1) in ulcerative colitis patients (UC) with different inflammatory evolution according calprotectin measure: increased inflammatory activity (+) and decreased inflammatory activity (−).

| Calprotectin | FT | | PHGI | | PHGII | | EC | |
|---|---|---|---|---|---|---|---|---|
| | T0 | T1 | T0 | T1 | T0 | T1 | T0 | T1 |
| + | 16.16 | 16.83 | 16.78 | 19.66 | 19.04 | 19.58 | 22.99 | 24.55 |
| | 14.04 | 15.65 | 15.92 | 17.71 | 17.04 | 19.03 | 28.76 | 25.15 |
| | 12.47 | 12.90 | 14.33 | 15.27 | 15.42 | 16.11 | 18.35 | 21.67 |
| | 28.32 | 30.57 | 31.95 | 36.81 | 30.83 | 35.62 | 18.11 | 20.02 |
| | 13.85 | 16.22 | 14.88 | 40 | 23.55 | 17.10 | 19.53 | 22.98 |
| Average | 16.97 ± 6.48 | 18.43 ± 6.94 | 18.77 ± 7.42 | 25.89 ± 11.58 | 21.18 ± 6.19 | 21.49 ± 8.02 | 21.55 ± 4.47 | 22.87 ± 2.09 |
| P-Value | 0.043* | | 0.043* | | ns | | ns | |
| − | 15.34 | 14.03 | 18.36 | 16.41 | 19.10 | 17.29 | 31.83 | 27.11 |
| | 30.02 | 15.52 | 33.77 | 21.21 | 33.07 | 17.03 | 32.36 | 19.51 |
| Average | 22.68 ± 10.4 | 14.78 ± 1.05 | 26.06 ± 10.9 | 18.81 ± 3.39 | 26.08 ± 9.88 | 17.16 ± 0.18 | 32.09 ± 0.37 | 23.31 ± 5.37 |
| P-Value | 0.180 | | 0.180 | | 0.180 | | 0.180 | |

TABLE 56

Ratios of bacterial markers in two-time point sample (T0 and T1) in ulcerative colitis patients (UC) with different inflammatory evolution according calprotectin measure: increased inflammatory activity (+) and decreased inflammatory activity (−).

| Calprotectin | FT/EC | | FT/PHGI | | FT/PHGII | |
|---|---|---|---|---|---|---|
| | T0 | T1 | T0 | T1 | T0 | T1 |
| + | −6.83 | −7.72 | −0.62 | −2.83 | −2.88 | −2.75 |
| | −14.72 | −9.50 | −1.88 | −2.06 | −3.00 | −3.38 |
| | −5.88 | −8.77 | −1.86 | −2.37 | −2.95 | −3.21 |
| | 10.21 | 10.55 | −3.63 | −6.24 | −2.51 | −5.05 |
| | −5.68 | −6.76 | −1.03 | −23.78 | −9.70 | −0.88 |
| Average | −4.58 ± 9.07 | −4.44 ± 8.44 | −1.80 ± 1.15 | −7.46 ± 9.27 | −4.21 ± 3.07 | −3.05 ± 1.49 |
| P-Value | ns | | 0.043* | | ns | |
| − | −16.49 | −13.08 | −3.02 | −2.38 | −3.76 | −3.26 |
| | −2.34 | −3.99 | −3.75 | −5.69 | −3.05 | −1.51 |
| Average | −9.42 ± 10 | −8.54 ± 6.42 | −3.39 ± 0.51 | −4.04 ± 2.34 | −3.41 ± 0.50 | −2.39 ± 1.23 |
| P-Value | ns | | ns | | 0.180 | |

| Calprotectin | EC/PHGI | | EC/PHGII | | PHGI/PHGII | |
|---|---|---|---|---|---|---|
| | T0 | T1 | T0 | T1 | T0 | T1 |
| + | 6.21 | 4.89 | 3.95 | 4.97 | −2.26 | 0.08 |
| | 12.84 | 7.44 | 11.72 | 6.12 | −1.12 | −1.32 |

TABLE 56-continued

Ratios of bacterial markers in two-time point sample (T0 and T1) in ulcerative colitis
patients (UC) with different inflammatory evolution according calprotectin measure:
increased inflammatory activity (+) and decreased inflammatory activity (−).

|         |             |              |             |             |              |             |
|---------|-------------|--------------|-------------|-------------|--------------|-------------|
|         | 4.02        | 6.40         | 2.93        | 5.56        | −1.09        | −0.84       |
|         | −13.84      | −16.79       | −12.72      | −15.60      | 1.12         | 1.19        |
|         | 4.65        | −17.02       | −4.02       | 5.88        | −8.67        | 22.90       |
| Average | 2.78 ± 9.92 | −3.02 ± 12.7 | 0.37 ± 9.20 | 1.39 ± 9.50 | −2.40 ± 3.71 | 4.40 ± 10.4 |
| P-Value | 0.138       |              | ns          |             | 0.138        |             |
| −       | 13.47       | 10.70        | 12.73       | 9.82        | −0.74        | −0.88       |
|         | −1.41       | −1.70        | −0.71       | 2.48        | 0.70         | 4.18        |
| Average | 6.03 ± 10.5 | 4.50 ± 8.76  | 6.01 ± 9.50 | 6.15 ± 5.19 | −0.02 ± 1.01 | 1.65 ± 3.57 |
| P-Value | 0.180       |              | ns          |             | ns           |             |

TABLE 57

Pearson and Spearman correlation between abundance and ratios of bacterial markers in two-time point
sample (T0 and T1) in Crohn's disease patient (CD) with different inflammatory evolution according
calprotectin measure: increased inflammatory activity (+) and decreased inflammatory activity (−).

| CD           | N = 8               | FT     | PHGI    | PHGII    | EC       |          |
|--------------|---------------------|--------|---------|----------|----------|----------|
| Calprotectin | Coef. Correlation   | −0.167 | 0.335   | −0.137   | 0.214    |          |
|              | P-value             | 0.692  | 0.417   | 0.746    | 0.611    |          |
| CD           | N = 8               | FT/EC  | FT/PHGI | FT/PHGII | PHGI/PHGII | PHGI/EC | PHGII/EC |
| Calprotectin | Coef. Correlation   | −0.210 | 0.132   | −0.164   | −0.165   | −0.218   | −0.199   |
|              | P-value             | 0.618  | 0.756   | 0.697    | 0.697    | 0.604    | 0.636    |
| UC           | N = 7               | FT     | PHGI    | PHGII    | EC       |          |
| Calprotectin | Coef. Correlation   | 0.786  | 0.643   | −0.084   | 0.660    |          |
|              | P-value             | 0.036* | 0.119   | 0.857    | 0.106    |          |
| UC           | N = 7               | FT/EC  | FT/PHGI | FT/PHGII | PHGI/PHGII | PHGI/EC | PHGII/EC |
| Calprotectin | Coef. Correlation   | −0.139 | −0.214  | 0.000    | 0.286    | 0.429    | −0.748   |
|              | P-value             | 0.766  | 0.645   | 1.000    | 0.535    | 0.337    | 0.053    |

Example 20

Bacterial Biomarkers Abundance and its Usefulness in the Prediction of Treatment Efficacy in Crohn's Disease and Ulcerative Colitis Fecal samples of 4 Crohn's disease (CD) and 3 Ulcerative colitis (UC) patients with active disease in terms of inflammatory response and naïve to biological treatment were collected. Its inflammatory response (measured by calprotectin concentration) to biological treatment (anti-TNF agents) was recorded and patients were grouped according to their response to treatment:

Responders: Subjects showing a decrease of calprotectin levels below 250 µg/G after biological treatment induction.*

Non-responders: Subjects showing an increase of calprotectin levels after biological induction.*

*Induction: Time period where different treatment dosage are given to achieve the therapeutic dose.

The abundance of fecal Total *F. prausnitzii*, phylogroup I, phylogroup II and *E. coli* of these patients before biological treatment were studied in order to determine the potential of treatment efficacy prediction of these bacterial markers (Table 16). Either in CD or UC patients, differences between responders and non-responders were no significantly different, probable due to the low number of subjects included in the study.

Figure 23:
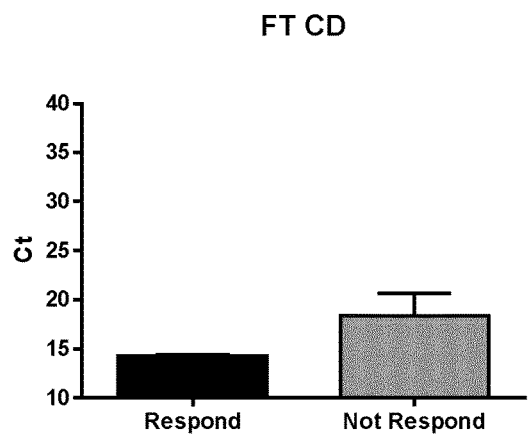
FIG. 23. Abundances of total *Faecalibacterium prausnitzii* (FT), phylogroup I (PHI), phylogroup II (PHII) and *E. coli* in responders and non-responders CD and UC patients.
Figure 23:
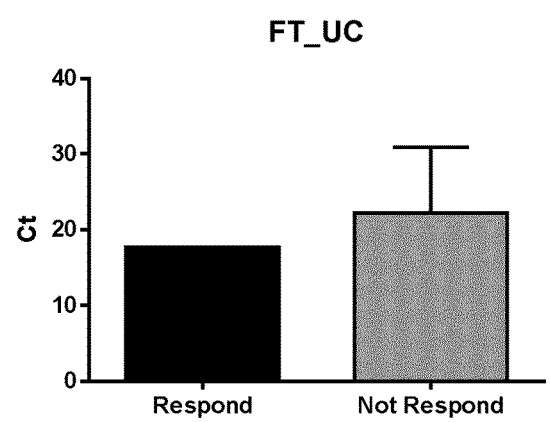
Figure 23:
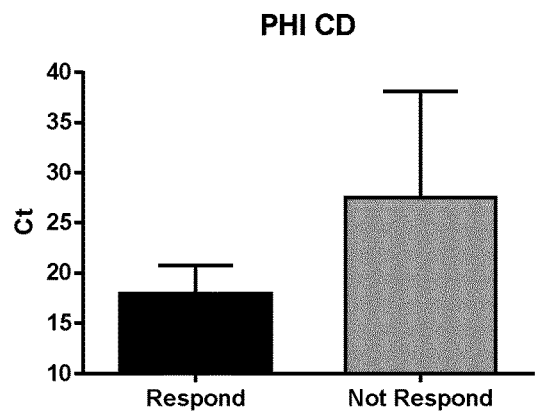
Figure 23:
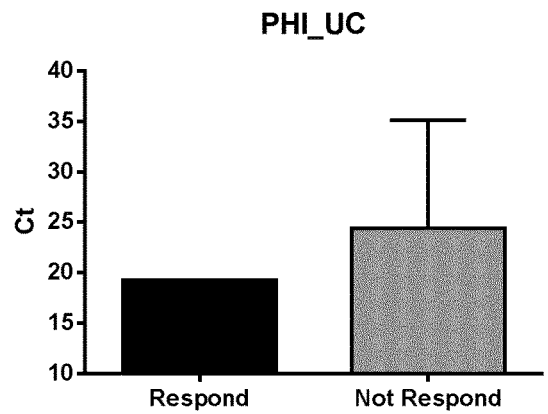
Figure 23:
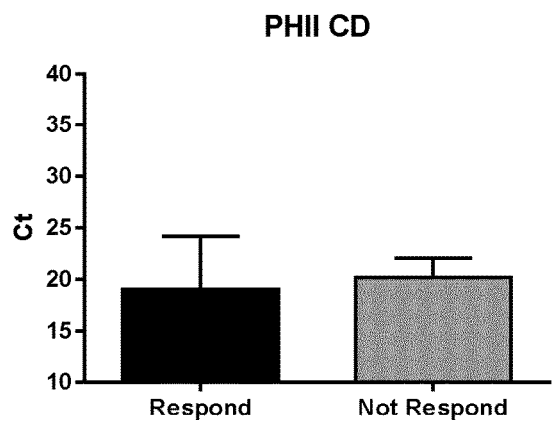
Figure 23:
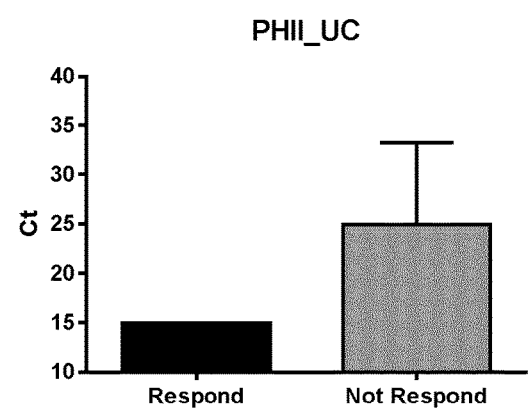
Figure 23:
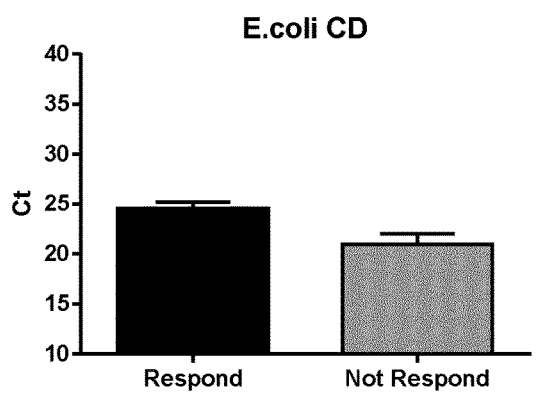
Figure 23:
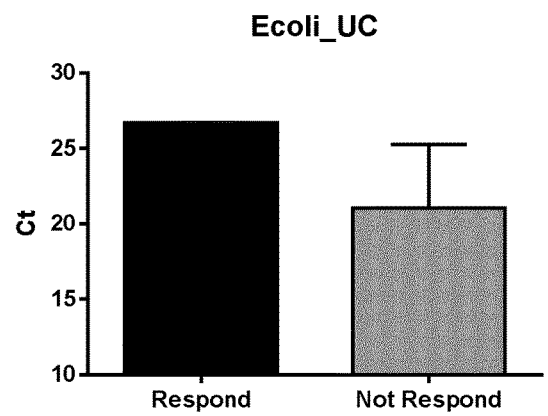

Nonetheless, tendencies were observed (FIG. 23). FT Ct of CD and UC were 28.57% and 26.58% increased in non-responders compared to responders. PHGI Ct were also increased in UC and CD (26.80% and 53.94%, respectively). PHGII Ct were 66.82% increased in non-responders of UC.

On contrast, EC Ct were reduced in non-responders of UC and CD (−20.91% and 14.53%, respectively).

CD non-responder subjects were found to be characterized by a microbiological profile with low load of FT and PHGI, and high load of EC. UC non-responders were characterized by low load of FT and PHGII, and high load of EC.

TABLE 58

Abundance of fecal Total *Faecalibacterium prausnitzii* (FT), phylogroup I (PHGI), phylogroup II (PHGII) and *Escherichia coli* (EC) in CD and UC patients between responders and non-responders

| | Group | Condition | FT | PHGI | PHGII | EC |
|---|---|---|---|---|---|---|
| Mean | CD | Responders | 14.28 ± 0.15 | 17.89 ± 2.87 | 18.99 ± 5.20 | 24.50 ± 0.67 |
| | | Non-Responders | 18.36 ± 2.27 | 27.54 ± 10.56 | 20.19 ± 1.85 | 20.94 ± 1.10 |
| | UC | Responders | 17.57 (n = 1) | 19.22 (n = 1) | 14.95 (n = 1) | 26.64 (n = 1) |
| | | Non-Responders | 22.24 ± 8.60 | 24.37 ± 10.73 | 24.94 ± 8.34 | 21.07 ± 4.19 |
| % Dif. | CD | NR − R (%) | 28.57 | 53.94 | 6.32 | −14.53 |
| | UC | NR − R (%) | 26.58 | 26.80 | 66.82 | −20.91 |

Figure 24:
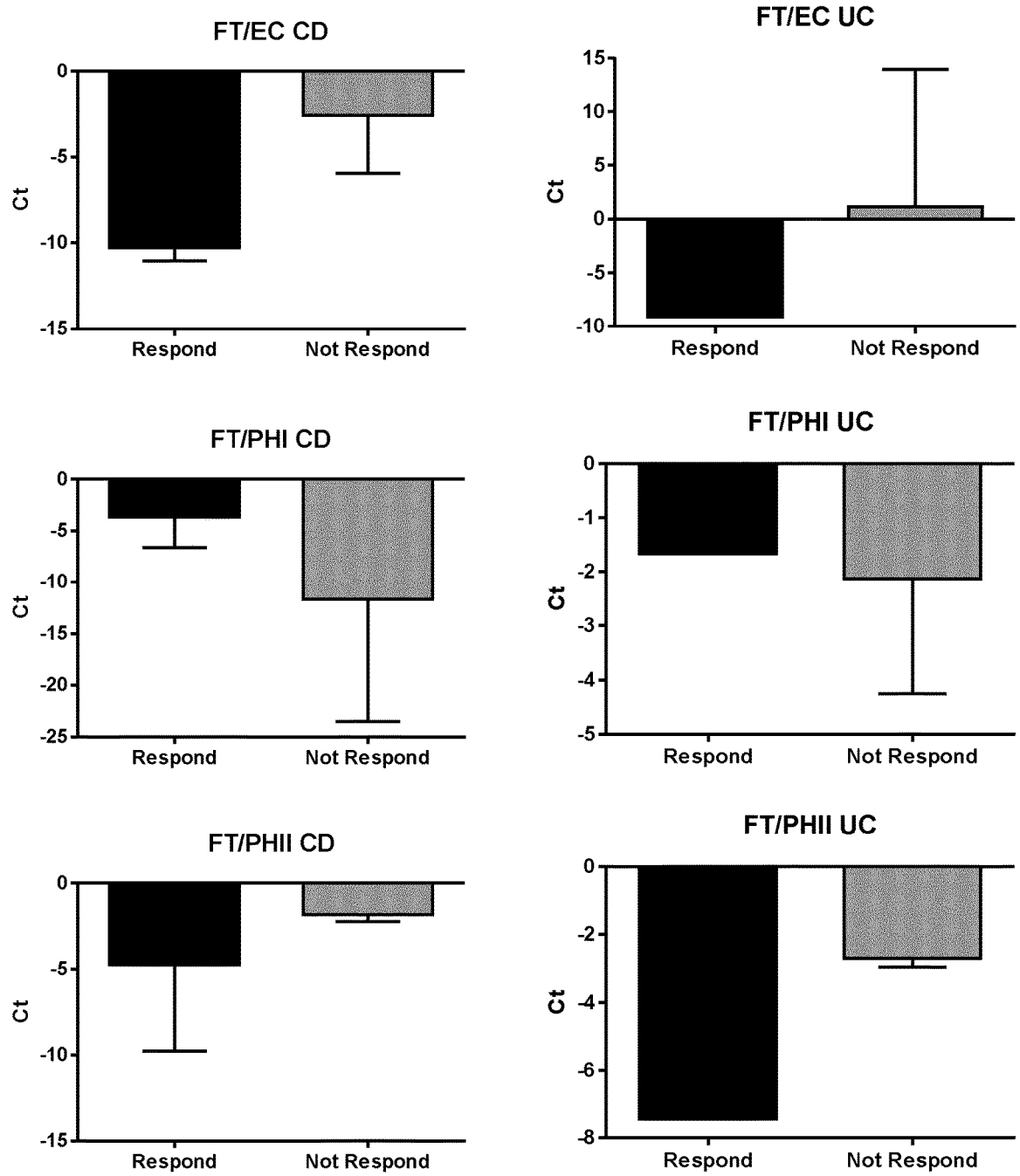
FIG. 24. FT/EC, FT/PHI, FT/PHII, PHI/PHII, PHI/EC and PHII/EC ratios in CD and UC patients subclassified as responders and non-responders.
Figure 24:
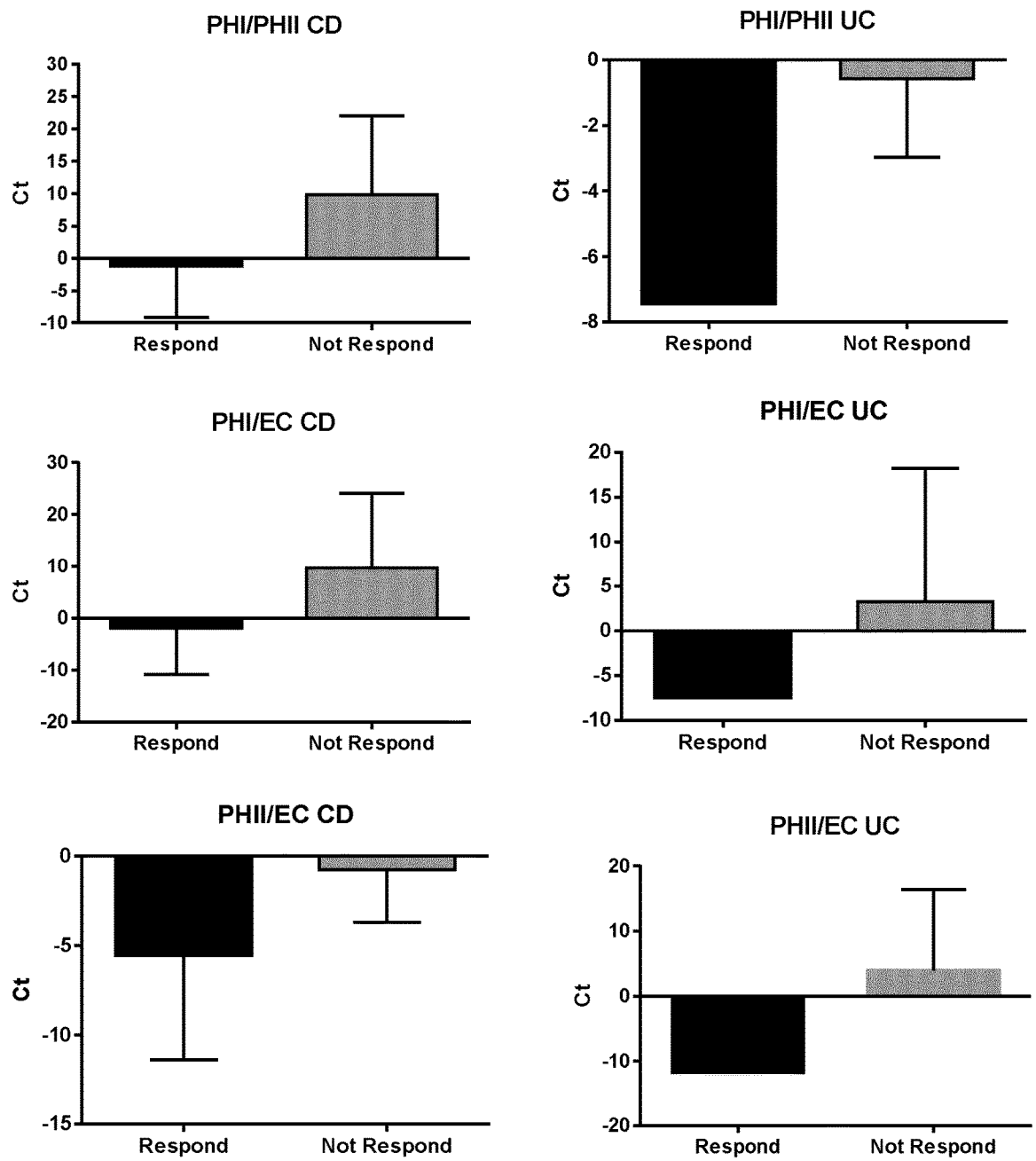

Ratios between the abundance of fecal Total *F. prausnitzii*, phylogroup I, phylogroup II and *E. coli* were also calculated: FT/EC, FT/PHGI, FT/PHGII, PHGI/PHGII, PHGI/EC and PHGII/EC (Table 59). Once again due to the small sample size, just tendencies were observed. More marked differences were seen in UC, where FT/EC, FT/PHGII and PHGI/PHGII ratios tended to increase in non-responder subjects, whereas in non-responder CD patients only the FT/EC ratio tended to increase (FIG. 24).

phylogroups' load could predict the inflammatory response in both UC and CD patients under anti-TNF treatment.

Concluding that, it is likely that, improved calprotectin values are associated with improved microbial status, being the markers' values in responders patients closer to those observed in a healthy condition.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of

TABLE 59

FT/EC, FT/PHGI, FT/PHGII, PHGI/PHGII, PHGI/EC and PHGII/EC ratios in CD and UC patients sub classified as responders and non-responders

| | Group | Condition | FT/EC | FT/PHGI | FT/PHGII | PHGI/PHGII | PHGI/EC | PHGII/EC |
|---|---|---|---|---|---|---|---|---|
| Mean | CD | Responders | −10.23 ± 0.81 | −3.62 ± 3.02 | −4.71 ± 5.05 | −1.10 ± 8.07 | −1.78 ± 9.04 | −5.52 ± 5.86 |
| | | Non-Responders | −2.59 ± 3.37 | −11.68 ± 11.8 | −1.83 ± 0.41 | 9.85 ± 12.3 | 9.60 ± 14.5 | −0.76 ± 2.95 |
| | UC | Responders | −9.07 | −1.65 | −7.42 | −7.42 | −7.42 | −11.69 |
| | | | (n = 1) | (n = 1) | (n = 1) | (n = 1) | (n = 19) | (n = 1) |
| | | Non-Responders | 1.17 ± 12.8 | −2.13 ± 2.13 | −2.70 ± 0.26 | −0.57 ± 2.40 | 3.30 ± 14.9 | 3.87 ± 12.5 |

Despite the small number of patients studied, interesting trends have been observed between patients whose calprotectin levels respond to a biological treatment versus those who not.

In Example 2, abundance of fecal Total *F. prausnitzii*, phylogroups and *E. coli* in health and disease was determined. It was shown that *E. coli* abundance was increased both in CD and UC patients, whereas PHGII was diminished and FT and PHGI were decreased in CD patients, all when compared to healthy patients.

We have observed in the present example, that an increased *E. coli*'s abundance either a decreased FT and its the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An in vitro method for determining the abundance of one or more of (a) *Faecalibacterium prausnitzii* phylogroup I members (PHGI) and (b) *Faecalibacterium prausnitzii* phylogroup II members (PHGII) in an intestinal sample from a subject by quantitative Polymerase Chain Reaction (qPCR) comprising *F. prausnitzii* 16S rRNA gene amplification comprising using:
   (i) *F. prausnitzii* species-specific 16S rRNA gene primers; and
   (ii) (a) a PHGI-specific probe consisting of the nucleotide sequence of SEQ ID NO:3 for determining the abundance of PHGI; and/or
   (b) a PHGII-specific probe consisting of the nucleotide sequence of SEQ ID NO:4 for determining the abundance of PHGII.

2. The method of claim 1, wherein the intestinal sample from the subject comprises a fecal sample, and wherein the method further comprises comparing: (a) a value selected from: (i) PHGII abundance; (ii) PHGI and/or PHGII abundance; and/or (iii) a ratio of PHGII abundance to *E. coli* (EC) abundance in the subject sample; with (b) a corresponding values in a reference sample, wherein a significant deviation in the subject sample value with regard to the corresponding value in the reference sample is indicative of inflammatory bowel disease (IBD).

3. The method according to claim 2, wherein the reference sample is a healthy subject sample.

4. The method according to claim 2, wherein the reference sample is a previous sample of the same subject.

5. The method according to claim 1, wherein PHGI abundance determination is performed with a forward primer with at least 75% identity to SEQ ID NO: 1, a reverse primer with at least 75% identity to SEQ ID NO: 2, and the PHGI-specific probe consisting of the nucleotide sequence of SEQ ID NO:3.

6. The method according to claim 1, wherein PHGII abundance determination is performed with: a forward primer comprising the nucleotide sequence of SEQ ID NO: 1, a reverse primer comprising the nucleotide sequence of SEQ ID NO: 2; and the PHGII-specific probe consisting of the nucleotide sequence of SEQ ID NO: 4.

7. The method according to claim 1, wherein the PHGI and/or PHGII abundance levels are normalized, wherein normalization is carried out (i) with respect to total bacteria quantification or (ii) by DNA concentration.

8. The method according to claim 1, wherein the intestinal sample from the subject is a feces sample.

9. The method according to claim 1, wherein the method further comprises detecting and/or quantifying one or more additional biomarkers of intestinal disease and optionally comprises combining the results of PHGI abundance, PHGII abundance and/or additional biomarkers of intestinal disease.

10. The method of claim 1, further comprising determining the abundance of PHGI and PHGII in the intestinal sample from the subject.

11. The method of claim 1, wherein the intestinal sample from the subject is a fecal sample, and wherein the method further comprises comparing:
    (a) the PHGII abundance in the subject sample; with
    (b) a corresponding value in a reference sample,
    wherein a significant deviation in the PHGII abundance in the subject sample value with regard to the corresponding value in the reference sample is indicative of inflammatory bowel disease (IBD).

12. The method of claim 1, wherein the intestinal sample from the subject is a fecal sample, the method further comprises comparing:
    (a) a value selected from:
    (1) the PHGII abundance, or
    (2) the PHGI and PHGII abundance in the subject sample; with
    (b) a corresponding value in a reference sample,
    wherein a significant deviation in the subject sample value with regard to the corresponding value in the reference sample is indicative of inflammatory bowel disease (IBD).

13. The method of claim 1, wherein the intestinal sample from the subject comprises a fecal sample, and wherein the method further comprises comparing:
    (a) a value selected from:
    (1) the PHGII abundance,
    (2) a ratio of the PHGII abundance to *E. coli* (EC) abundance, in the subject sample; with
    (b) a corresponding value in a reference sample,
    wherein a significant deviation in the subject sample value with regard to the corresponding value in the reference sample is indicative of inflammatory bowel disease (IBD).

14. The method of claim 1, wherein the intestinal sample from the subject comprises a fecal sample, and wherein the method further comprises comparing:
    (a) the PHGII abundance in the subject sample with
    (b) a corresponding value in a reference sample,
    wherein a decrease in the PHGII abundance in the subject sample with regard to the corresponding value in the reference sample is indicative of IBD.

15. The method of claim 1, wherein the PHGII abundance is determined by quantitative PCR on the intestinal sample from the subject, wherein the intestinal sample is a feces sample, and is expressed as a Ct value, and wherein the method further comprises comparing: (a) the PHGII Ct value with (b) a cut-off Ct value, wherein an increase in the PHGII Ct value in the feces sample of the subject with respect to the cut-off Ct value is indicative of IBD.

* * * * *

UNITED STATES PATENT AND TRADEMARK OFFICE
CERTIFICATE OF CORRECTION

| | |
|---|---|
| PATENT NO. | : 11,299,788 B2 |
| APPLICATION NO. | : 15/751805 |
| DATED | : April 12, 2022 |
| INVENTOR(S) | : Mireia Lopez Siles |

It is certified that error appears in the above-identified patent and that said Letters Patent is hereby corrected as shown below:

On the Title Page

Item (71) Applicants:
"Fundoado Institut D'Investigacio."
Should read:
--Fundacio Institut D'Investigacio--

In the Claims

Column 148, Claim 9, Line 16:
"abundance and/or additional biomarkers"
Should read:
--abundance and/or the additional biomarkers--

Signed and Sealed this
Eighth Day of October, 2024

Katherine Kelly Vidal
*Director of the United States Patent and Trademark Office*